(12) United States Patent
Takahashi et al.

(10) Patent No.: US 7,619,092 B2
(45) Date of Patent: *Nov. 17, 2009

(54) PIPERIDINE COMPOUNDS

(75) Inventors: Masami Takahashi, Osaka (JP);
Tsutomu Miyake, Hyogo (JP);
Yasunori Moritani, Osaka (JP);
Hidetoshi Asai, Ibaraki (JP); Taketoshi Ishii, Tokyo (JP); Rikako Kono, Saitama (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 559 days.

This patent is subject to a terminal disclaimer.

(21) Appl. No.: 10/515,845

(22) PCT Filed: May 29, 2003

(86) PCT No.: PCT/JP03/06720

§ 371 (c)(1),
(2), (4) Date: Jun. 13, 2005

(87) PCT Pub. No.: WO03/099787

PCT Pub. Date: Dec. 4, 2003

(65) Prior Publication Data

US 2005/0239829 A1  Oct. 27, 2005

Related U.S. Application Data

(60) Provisional application No. 60/395,342, filed on Jul. 12, 2002, provisional application No. 60/409,595, filed on Sep. 11, 2002.

(30) Foreign Application Priority Data

May 29, 2002 (JP) ............................... 2002-155744
Aug. 28, 2002 (JP) ............................... 2002-248755

(51) Int. Cl.
*C07D 211/30* (2006.01)
*A61K 31/445* (2006.01)

(52) U.S. Cl. ...................................... 546/225; 514/317
(58) Field of Classification Search .................. 514/317; 546/225

See application file for complete search history.

(56) References Cited

U.S. PATENT DOCUMENTS 5,310,743 A  5/1994 Schilling et al.
5,459,270 A * 10/1995 Williams et al. ............ 546/152
2007/0112029 A1* 5/2007 Takahashi et al. ............ 514/317

FOREIGN PATENT DOCUMENTS

| WO | WO 97/24324 A1 | 7/1997 |
|----|----|----|
| WO | WO 02/32867 A1 | 4/2002 |
| WO | 03066589 A1 | 8/2003 |
| WO | WO 03/066589 A1 | 8/2003 |
| WO | WO 03/066621 A1 | 8/2003 |
| WO | WO 03/066635 A1 | 8/2003 |

OTHER PUBLICATIONS

John Daintith, A Dictionary of Chemistry, 5th Edition, 2004, Oxford University Press, p. 296.*
F. Z. Dorwald "Side Reactions in Organic Synthesis: A Guide to Successful Synthesis Design" 2005, Wiley-VCH Verlag GmbH & KGaA, Wienheim.*
Monterde et al Tetrahedron: Asymmetry 2001, 12, 525-528.*

* cited by examiner

*Primary Examiner*—Rita J Desai
*Assistant Examiner*—John Mabry

(57) ABSTRACT

The present invention provides a novel piperidine compound of the formula [I]: wherein Ring A represents an optionally substituted benzene ring, Ring B represents an optionally substituted benzene ring, $R_1$ represents an optionally substituted alkyl group, an optionally substituted hydroxyl group, etc., or a group of the formula: (a) wherein $R_{11}$ and $R_{12}$ are the same or different, and each represents hydrogen atom, a substituted carbonyl group, a substituted sulfonyl group, an optionally substituted alkyl group, etc., $R_2$ represents hydrogen atom, etc., Z represents oxygen atom or a group represented by —N($R_3$)—, $R_3$ represents hydrogen atom or an alkyl group, etc., $R_4$ represents hydrogen atom or an alkyl group, etc., or a pharmaceutically acceptable salt thereof.

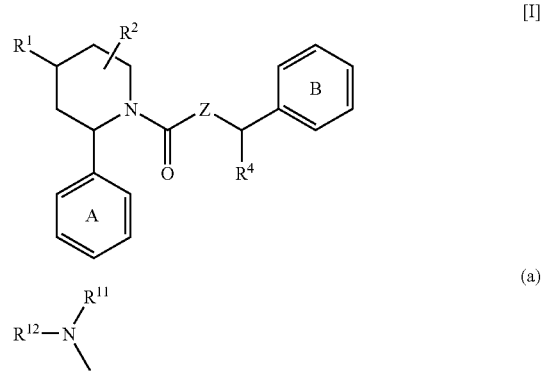

7 Claims, No Drawings

PIPERIDINE COMPOUNDS

TECHNICAL FIELD

The present invention relates to a novel piperidine compound having excellent tachykinin receptor antagonistic action.

BACKGROUND ART

Tachykinin is a general name for a group of neuropeptides, and there have been known substance P (hereinafter referred to as SP), neurokinin-A, and neurokinin-B in mammals. These peptides are known to exhibit a various kinds of biological activities by binding their corresponding receptors which exist in vivo (neurokinin-1, neurokinin-2, neurokinin-3). Among them, SP is one of those which have the longest history in the neuropeptides, and have been studied in detail. Its existence was confirmed in an extract of horse intestinal tube in 1931, and it was a peptide comprising 11 amino acids, whose structure was determined in 1971.

SP exists widely in peripheral nervous system, and it has physiological activities such as vasodilation action, vascular permeability promoting action, smooth muscle contracting action, hypertarachia (neuronal excitement) action, salivation action, diuretic action, immunological action, etc., as well as a function of neurotransmitter of the primary sensory neuron. Specifically, it is known that SP released from the terminus of posterior horn of spinal cord upon pain impulse transfers pain information to the secondary neuron, and that SP released from the peripheral terminus induces an inflammatory reaction in the receptor. From these facts, SP is considered to be involved in various diseases (for example, pain, inflammation, allergy, thamuria, incontinence of urine, respiratory disease, mental illness, depression, uneasiness, emesis, etc.), and also, SP is considered to be involved in Alzheimer type dementia [Review: Physiological Reviews, vol. 73, pp. 229-308 (1993), Journal of Autonomic Pharmacology, vol. 13, pp. 23-93 (1993)].

Currently, as a therapeutic agent for the above-mentioned various diseases (especially for emesis, depression, urination disorder, etc.), there have not been discovered yet any compound having an excellent tachykinin receptor antagonistic action (specifically, SP receptor antagonistic action), and at the same time, having sufficiently satisfying safety, sustainability (metabolism, dynamics in vivo, and absorption), etc. Therefore, a compound has been sought for which has an excellent tachykinin receptor antagonistic action, and has sufficiently satisfying clinical effect as the therapeutic agent.

Accordingly, an object of the present invention is to provide a compound having excellent tachykinin receptor antagonistic action, and having a clinical satisfying effect in terms of safety, sustainability (metabolism, dynamics in vivo and absorption), etc.

SUMMARY OF THE INVENTION

The present invention relates to a piperidine compound represented by the formula [I]:

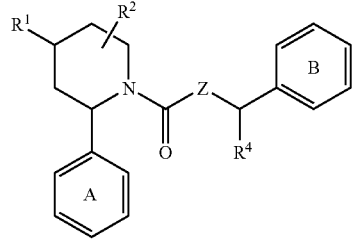

wherein Ring A represents an optionally substituted benzene ring, Ring B represents an optionally substituted benzene ring, $R^1$ represents an optionally substituted alkyl group, an optionally substituted hydroxyl group, a substituted thiol group, a substituted carbonyl group, a substituted sulfinyl group, a substituted sulfonyl group, or a group represented by the formula:

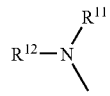

wherein $R^{11}$ and $R^{12}$ are the same or different and each is hydrogen atom, a substituted carbonyl group, a substituted sulfonyl group, an optionally substituted alkyl group or a heterocyclic group containing 1 to 4 atom(s) selected from nitrogen atom, oxygen atom and sulfur atom as a hetero atom, wherein the heterocyclic group is optionally substituted, and the nitrogen atom contained in the heterocyclic group is optionally oxidized, or $R^{11}$ and $R^{12}$ are taken together, with an adjacent nitrogen atom, to form a heterocyclic group selected from piperidino group, azacycloheptyl group, pyrrolidino group, imidazolidinyl group, hexahydropyrimidinyl group, thiazolidyl group, morpholino group, triazolyl group, tetrazolyl group and purinyl group, wherein the heterocyclic group is optionally substituted, and the nitrogen atom contained in the heterocyclic group is optionally oxidized, $R^2$ represents hydrogen atom, an optionally substituted hydroxyl group, an optionally substituted amino group, an optionally substituted alkyl group, a substituted carbonyl group or a halogen atom, Z represents oxygen atom or a group represented by —N($R^3$)—, wherein $R^3$ represents hydrogen atom or an optionally substituted alkyl group, $R^4$ represents hydrogen atom or an optionally substituted alkyl group, or a pharmaceutically acceptable salt thereof.

In the present invention, Ring A represents an optionally substituted benzene ring, and a substituent of the benzene ring is exemplified by an alkyl group, a halogen atom, cyano group, optionally protected hydroxyl or alkoxy group. Ring A may have 1 to 3 of these substituent(s) which is (are) the same or different.

In the present invention, Ring B represents an optionally substituted benzene ring, and a substituent of the benzene ring is exemplified by a trihalogenoalkyl group, a halogen atom, a cyano group, a phenyl group, a heterocyclic group containing 1 to 4 atom(s) selected from nitrogen atom, oxygen atom and sulfur atom as hetero atom, an alkyl group, an optionally protected hydroxyl or an alkoxy group. Ring B may have 1 to 3 of these substituent(s) which are the same or different.

A preferred example of Ring A and Ring B in the compound of the present invention is exemplified by a compound wherein Ring A is a benzene ring of the formula:

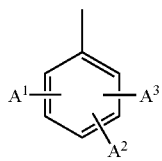

and Ring B is a benzene ring of the formula:

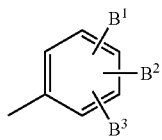

wherein $A^1$, $A^2$ and $A^3$ are the same or different, and each is hydrogen atom, a halogen atom, an alkyl group, an optionally protected hydroxyl or alkoxy group, $B^1$, $B^2$ and $B^3$ are the same or different, and each is hydrogen atom, a trihalogenoalkyl group, a halogen atom, a cyano group, a phenyl group, a heterocyclic group containing 1 to 4 atom(s) selected from nitrogen atom, oxygen atom and sulfur atom as hetero atom, an alkyl group, an optionally protected hydroxyl or an alkoxy group. The trihalogenoalkyl group is exemplified by a trifluoromethyl group or a trichloromethyl group, etc. The heterocyclic group is exemplified by a tetrazolyl group, etc.

In the present invention, a protecting group of the optionally protected hydroxyl group is exemplified by a conventional protection group such as an optionally substituted arylalkyl group, an optionally substituted silyl group and an acyl group. In the above, preferred are an arylalkyl group such as benzyl group and phenethyl group, a substituted silyl group such as tert-butyldimethylsilyl group and tert-butyldiphenylsilyl group, and an acyl group such as formyl group, acetyl group, propionyl group, malonyl group, acryloyl group and benzoyl group.

In the present invention, $R^1$ is an optionally substituted alkyl group, an optionally substituted hydroxyl group, a substituted thiol group, a substituted carbonyl group, a substituted sulfinyl group, a substituted sulfonyl group, or a group represented by the formula:

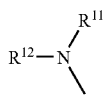

wherein $R^{11}$ and $R^{12}$ are the same or different, and each is hydrogen atom, a substituted carbonyl group, a substituted sulfonyl group, an optionally substituted alkyl group or a heterocyclic group containing 1 to 4 atom(s) selected from nitrogen atom, oxygen atom and sulfur atom as a hetero atom, wherein the heterocyclic group is optionally substituted, and the nitrogen atom contained in the heterocyclic group is optionally oxidized, or $R^{11}$ and $R^{12}$ are taken together, with an adjacent nitrogen atom, to form a heterocyclic group selected from piperidino group, azacycloheptyl group, pyrrolidino group, imidazolidinyl group, hexahydropyrimidinyl group, thiazolidyl group, morpholino group, triazolyl group, tetrazolyl group and purinyl group, wherein the heterocyclic group is optionally substituted, and the nitrogen atom contained in the heterocyclic group is optionally oxidized.

In the above, $R^1$ is preferably an optionally substituted alkyl group, an optionally substituted hydroxyl group, a substituted thiol group, a substituted carbonyl group, a substituted sulfinyl group, a substituted sulfonyl group, or a group represented by the formula:

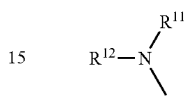

wherein $R^{11}$ and $R^{12}$ are the same or different, and each is hydrogen atom, a substituted carbonyl group, a substituted sulfonyl group, an optionally substituted alkyl group or a heterocyclic group containing 1 to 4 atom(s) selected from nitrogen atom, oxygen atom and sulfur atom as a hetero atom, wherein the heterocyclic group is optionally substituted, and the nitrogen atom contained in the heterocyclic group is optionally oxidized, further preferably is an optionally substituted alkyl group, an optionally substituted hydroxyl group, a substituted thiol group, a substituted carbonyl group, a substituted sulfinyl group, a substituted sulfonyl group, or a group represented by the formula:

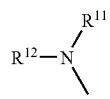

wherein $R^{11}$ is a substituted carbonyl group, a substituted sulfonyl group or a heterocyclic group containing 1 to 4 atom(s) selected from nitrogen atom, oxygen atom and sulfur atom as a hetero atom, wherein the heterocyclic group is optionally substituted, and the nitrogen atom contained in the heterocyclic group is optionally oxidized, and $R^{12}$ is hydrogen atom, an optionally substituted alkyl group, a substituted carbonyl group, a substituted sulfonyl group or a heterocyclic group containing 1 to 4 atom(s) selected from nitrogen atom, oxygen atom and sulfur atom as a hetero atom, wherein the heterocyclic group is optionally substituted, and the nitrogen atom contained in the heterocyclic group is optionally oxidized.

In the present invention, the substituent of the optionally substituted alkyl group of $R^1$ is exemplified by an alkoxycarbonyl group, a morpholinocarbonyl group, a pyridylaminocarbonyl group, a morpholinoaminocarbonyl group, a piperidinocarbonyl group substituted by an alkoxyphenyl group, a dialkylaminocarbonyl group, hydroxyl group, a hydroxyalkylaminocarbonyloxy group or an alkylpiperazinocarbonyl group.

In the present invention, the substituent of the optionally substituted hydroxyl group of $R^1$ is exemplified by (1) a substituted carbonyl group,
(2) a substituted sulfinyl group,
(3) a substituted sulfonyl group or
(4) an optionally substituted alkyl group.

The substituent of the substituted carbonyl group in the above (1) is exemplified by an optionally substituted alkyl group, an optionally substituted alkoxy group, a substituted amino group, a monocyclic heterocyclic group having 1 to 2 atom(s) selected from nitrogen atom and oxygen atom as a hetero atom (the monocyclic heterocyclic group is optionally substituted). The substituent of the optionally substituted alkyl group is exemplified by hydroxyl group. The substituent of the optionally substituted alkoxy group is exemplified by an alkoxy group, hydroxyl group or a halogen atom. The substituent of the substituted amino group is exemplified by an alkyl group substituted by a group selected from a halogen atom, a dialkylamino group, piperidinyl group, morpholino group, a carboxyl group, a morpholinocarbonyl group, a dialkylaminocarbonyl group, an alkylaminocarbonyl group, an alkanoylamino group, an alkylthio group, an alkoxy group, an alkylsulfonyl group, an alkanoyloxy group and hydroxyl group; piperidinyl group substituted by a hydroxyalkanoyl group or an alkoxyalkanoyl group; or a dialkylamionsulfonyl group. The monocyclic heterocyclic group is exemplified by morpholino group, piperazinyl group, imidazolyl group, thiomorpholino group, piperidino group, furyl group, tetrahydrothiazolinyl group or pirrolidinyl group. The substituent of the monocyclic heterocyclic group is exemplified by an alkyl group which may be substituted by hydroxyl group, an alkoxycarbonyl group, a carboxyl group, hydroxyalkylaminocarbonyl group, alkoxyalkylaminocarbonyl group, alkylthioalkylaminocarbonyl group, alkylsulfinylalkylaminocarbonyl group, an alkylsulfonylalkylaminocarbonyl group or morpholino group, an oxo group or hydroxyl group.

The substituent of the substituted sulfinyl group in the above (2) is exemplified by an alkyl group or thienyl group.

The substituent of the substituted sulfonyl group in the above (3) is exemplified by an alkyl group or thienyl group.

The substituent of the optionally substituted alkyl group in the above (4) is exemplified by an optionally substituted hydroxyl group, a dialkylamino group or a monocyclic heterocyclic group having 1 to 4 atom(s) selected from sulfur atom, nitrogen atom and oxygen atom as a hetero atom (the monocyclic heterocyclic group is optionally substituted). The substituent of the optionally substituted hydroxyl group is exemplified by an alkyl group, an alkylsulfonyl group or tetrahydropyranyl group. The monocyclic heterocyclic group is exemplified by pyridyl group, piperidinyl group, morpholino group, isoxazolyl group, triazolyl group, tetrazolyl group or pirrolidinyl group. The substituent of the monocyclic heterocyclic group is exemplified by an alkyl group or a phenyl group.

In the present invention, the substituent of the substituted thiol group of $R^1$ is exemplified by a substituted phenyl group, a substituted carbonyl group or an optionally substituted alkyl group. The substituent of the substituted phenyl group is exemplified by hydroxyl group. The substituent of a substituted carbonyl group is exemplified by an alkyl group. The substituent of the optionally substituted alkyl group is exemplified by an alkylaminocarbonyl group, a dialkylaminocarbonyl group an alkoxycarbonylamino group, hydroxyalkanoylamino group, a morpholinocarbonylamino group, a hydroxyalkylaminocarbonylamino group, an alkanoyloxy group or hydroxyl group.

In the present invention, the substituent of the substituted carbonyl group of $R^1$ is exemplified by hydroxyl group, an alkoxy group, an optionally substituted amino group or a monocyclic heterocyclic group having 1 to 4 atom(s), selected from sulfur atom, nitrogen atom and oxygen atom as a hetero atom(s) (the monocyclic heterocyclic group is optionally substituted). The substituent of the optionally substituted amino group is exemplified by (a) group(s) selected from pyridyl group optionally substituted by hydroxyl group (s), pyrimidyl group, an alkylpyrido group, pyrazinyl group, and an alkyl group optionally substituted by hydroxyl group or cyano group. The monocyclic heterocyclic group is exemplified by piperidino group, piperazino group, morpholino group, thiomorpholino group or pyrrolidino group. The substituent of the monocyclic heterocyclic group is exemplified by an alkyl group, hydroxyl group, an oxo group, pyrimidyl group, pyrazinyl group, an alkylsulfonyl group, an alkanoyl group or hydroxyalkyl group.

In the present invention, the substituent of the substituted sulfinyl group of $R^1$ is exemplified by hydroxyl group or an optionally substituted alkyl group. The substituent of the optionally substituted alkyl group is exemplified by hydroxyl group.

In the present invention, the substituent of the substituted sulfonyl group of $R^1$ is exemplified by an optionally substituted alkyl group. The substituent of the optionally substituted alkyl group is exemplified by hydroxyl group or an alkanoyloxy group.

In the present invention, when $R^1$ is a group of the formula:

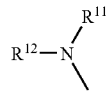

(1) the substituent of the substituted carbonyl of $R^{11}$ and $R^{12}$ is exemplified by an optionally substituted alkyl group, an optionally substituted alkoxy group, an optionally substituted aryl group, a substituted amino group or a heterocyclic group containing 1 to 4 atom(s) selected from nitrogen atom, oxygen atom and sulfur atom as a hetero atom, wherein the heterocyclic group is optionally substituted, and the nitrogen atom contained in the heterocyclic group is optionally oxidized. The substituent of the optionally substituted alkyl group is exemplified by an alkylaminocarbonyl group, a dialkylaminocarbonyl group wherein the alkyl moiety thereof is optionally substituted by hydroxyl group, an aminocarbonyl group, an alkoxycarbonylamino group, an alkanoylamino group, an amino group substituted by an alkoxycarbonyl group and an alkyl group, an amino group substituted by an alkanoyl group and an alkyl group, an alkoxy group, a halogen atom, tetrazolyl group, pyridyl group, furyl group, hydroxyl group, an alkylthio group, 2-oxopyrrolidino group, 2-aminothiazolyl group, 2-thiol-4-akylthiazolyl group, 2,2-dialkyl-1,3-dioxolanyl group, a cycloalkyl group, an alkylsulfinyl group, an alkylsulfonyl group, thienyl group, 5-methyl-2,4(1H, 3H)pyrimidinedione group, an amino group or a dialkylamino group. The substituent of the optionally substituted aryl group is exemplified by nitro group or an amino group, and the aryl group is exemplified by phenyl group, naphthyl group, phenanthryl group or anthracenyl group. The substituent of the substituted amino group is exemplified by an alkyl group optionally substituted by a group selected from a halogen atom, an alkoxy group and hydroxyl group, and the amino group is mono-substituted or di-substituted. The heterocyclic group is exemplified by a saturated or unsaturated monocyclic or bicyclic aromatic heterocyclic group, such as thienyl group, furyl group, tetrahydrofuryl group, pyranyl group, pyrrolyl group, imidazolyl group, pyrazolyl group, isothiazolyl group, isoxazolyl group, pyridyl group, pyrazinyl group, pyrimidinyl group, pyridazinyl group, pirrolidinyl group, pyrrolinyl group, imidazolidinyl group, imidazolinyl group, pyrazolidinyl group, pyrazolinyl group, piperidyl group, piperazinyl group, morpholinyl group, thiomorpholinyl group, benzothienyl group, benzofuryl group, isobenzofuranyl group, chromenyl group, indolyl group, isoindolyl group, indazolyl group, purinyl group, quinolizinyl group, naphthyridinyl group, quinoxalinyl group, cinnolinyl group, quinolyl group, isoquinolyl group, benzothiazolyl group, benzisothiazolyl group, quinazolinyl group, phthalazinyl group, benzoxazolyl group, benzimidazolyl group, pteridinyl group, pyridopyrimidinyl group, isochromanyl group, chromanyl group, indolinyl group, isoindolinyl group, tetrahydroquinolyl group, tetrahydroisoquinolyl group, tetrahydroquinoxalinyl group, dihydrophthalazinyl group, etc. Among these heterocyclic groups, pyridyl group, pirrolidinyl group, piperazinyl group, quinolyl group, piperidinyl group, pyrimidyl group, thiazolyl group, pyrazinyl group, morpholino group, thiomorpholino group, indolyl group, cinnolinyl group, furyl group, tetrahydrofuryl group, thienyl group, etc. are preferably used. The substituent of the heterocyclic group is exemplified by a dialkylamino group, an alkoxycarbonyl group, morpholinoalkyl group, a hydroxyalkyl group, an alkyl group, benzyloxy group, an alkoxycarbonyl group, an alkanoyl group, hydroxyl group, an oxo group or formyl group.

(2) The substituent of the substituted sulfonyl group of $R^{11}$ and $R^{12}$ is exemplified by an optionally substituted alkyl group, cyanophenyl group, a dialkylamino group, or alkenyl group. The substituent of the the optionally substituted alkyl group is exemplified by a halogen atom, hydroxyl group, a dialkylamino group optionally substituted by hydroxyl group, morpholino group, piperidino group or 4-methylpiperazino group.

(3) The substituent of the optionally substituted alkyl group of $R^{11}$ and $R^{12}$ is exemplified by a dialkylaminocarbonyl group, an alkoxy group, a dialkylamino group, cyano group, morpholino group, pyridyl group or a halogen atom.

(4) The heterocyclic group containing 1 to 4 atom(s) selected from nitrogen atom, oxygen atom and sulfur atom as a hetero atom of $R^{11}$ and $R^{12}$ is exemplified by a saturated or unsaturated monocyclic or bicyclic aromatic heterocyclic group, such as thienyl group, furyl group, pyranyl group, pyrrolyl group, imidazolyl group, pyrazolyl group, isothiazolyl group, isoxazolyl group, pyridyl group, pyrazinyl group, pyrimidinyl group, pyridazinyl group, pirrolidinyl group, pyrrolinyl group, imidazolidinyl group, imidazolinyl group, pyrazolidinyl group, pyrazolinyl group, piperidyl group, piperazinyl group, morpholinyl group, benzothienyl group, benzofuryl group, isobenzofuranyl group, chromenyl group, indolyl group, isoindolyl group, indazolyl group, purinyl group, quinolizinyl group, naphthyridinyl group, quinoxalinyl group, cinnolinyl group, quinolyl group, isoquinolyl group, benzothiazolyl group, benzisothiazolyl group, quinazolinyl group, phthalazinyl group, benzoxazolyl group, benzimidazolyl group, pteridinyl group, pyridopyrimidinyl group, isochromanyl group, chromanyl group, indolinyl group, isoindolinyl group, tetrahydroquinolyl group, tetrahydroisoquinolyl group, tetrahydroquinoxalinyl group, dihydrophthalazinyl group. Of these heterocyclic groups, pyridyl group, pyrrolyl group, piperazinyl group, quinolyl group, piperidinyl group, pyrimidyl group, thiazolyl group, pyrazinyl group, morpholino group, indolyl group, cinnolinyl group, furyl group, thienyl group, etc. are preferably used. The substituent of the heterocyclic group is exemplified by a dialkylamino group, an alkoxycarbonyl group, an alkyl group, an alkoxy group, hydroxyl group, a halogen atom etc.

Further, when $R^{11}$ and $R^{12}$ form a bond at the termini thereof, to form a heterocyclic group, with an adjacent nitrogen atom, selected from piperidino group, azacycloheptyl group, pyrrolidino group, imidazolidinyl group, hexahydropyrimidinyl group, thiazolidyl group, morpholino group, triazolyl group, tetrazolyl group and purinyl group, the substituent of the heterocyclic group is exemplified by an alkyl group substituted by an alkoxy group or hydroxyl group, piperidinyl group, alkoxyphenyl group, an alkanoyl group, hydroxyl group, an oxo group and an amino group.

When the nitrogen atom of the heterocyclic group is oxidized, the oxidized nitrogen atom means a state where the nitrogen atom is cationized, which is exemplified by N-oxomorpholino group or N-alkylmorpholinio group.

In the present invention, $R^2$ represents hydrogen atom, an optionally substituted hydroxyl group, an optionally substituted amino group, an optionally substituted alkyl group, a substituted carbonyl group or a halogen atom.

In the present invention, the substituent of the optionally substituted hydroxyl group of $R^2$ is exemplified by an alkyl group.

In the present invention, the substituent of the optionally substituted amino group of $R^2$ is exemplified by an alkyl group.

In the present invention, the substituent of the optionally substituted alkyl group of $R^2$ is exemplified by an alkoxy group.

In the present invention, the substituent of the substituted carbonyl group of $R^2$ is exemplified by hydroxyl group, an alkoxy group or alkylamino group.

In the present invention, Z is exemplified by an oxygen atom or a group of —$N(R^3)$—.

In the present invention, $R^3$ is exemplified by hydrogen atom or an optionally substituted alkyl group. The substituent of the optionally substituted alkyl group of $R^3$ is exemplified by hydroxyl group, an alkanoyl group, a halogen atom, an alkoxy group or an alkylamino group.

In the present invention, $R^4$ is exemplified by hydrogen atom or an optionally substituted alkyl group. The substituent of the optionally substituted alkyl group of $R^4$ is exemplified by a halogen atom, an alkoxy group or alkylamino group.

As the preferred compound of the present invention, a compound where $R^1$ is an optionally substituted alkyl group is mentioned.

The preferred substituent of the optionally substituted alkyl group is dialkylaminocarbonyl group, morpholinocarbonyl group, hydroxyl group, alkoxycarbonyl group or hydroxyalkylaminocarbonyloxy group.

As the preferred compound of the present invention, a compound where $R^1$ is an optionally substituted hydroxyl group is mentioned. Of these, preferred is a compound where $R^1$ is an optionally substituted alkoxy group. Additionally preferred is a compound where $R^1$ is an optionally substituted carbonyloxy group.

The preferred substituent of the optionally substituted alkoxy group is hydroxyl group, an alkylsulfonyloxy group, tetrahydropyranyloxy group, a triazolyl group, tetrazolyl group optionally substituted by alkyl group, or alkoxy group, and more preferred is hydroxyl group or tetrahydropyranyloxy group. The preferred substituent of the optionally substituted carbonyoxy group is morpholino group; imidazolyl group, an alkylamino group wherein the alkyl moiety thereof is optionally substituted by hydroxyl group, morpholinocarbonyl group, a dialkylaminocarbonyl group, an alkylaminocarbonyl group, alkanoylamino group, an alkylthio group, an alkoxy group, an alkylsulfonyl group, an alkanoyloxy group or carboxyl group; piperidino group substituted by hydroxyl group, an alkoxycarbonyl group, carboxyl group, a hydroxyalkylaminocarbonyl group, an alkoxyalkylaminocarbonyl group, an alkylthioalkylaminocarbonyl group, an alkylsulfinylalkylaminocarbonyl group, an alkylsulfonylalkylaminocarbonyl group or a hydroxyalkyl group; piperidinylamino group substituted by a hydroxyalkanoyl group or an alkoxyalkanoyl group; thiomorphorino group wherein the sulfur atom is optionally substituted by oxo group; oxopyrroridinyl group; oxotetrahydrothiazolinyl group; or dialkylaminosulfonylamino group, and more preferred is morpholino group; alkylamino group wherein the alkyl moiety thereof is optionally substituted by hydroxyl group; or thiomorpholino group wherein the sulfur atom is substituted by oxo group.

As the preferred compound of the present invention, a compound where $R^1$ is a substituted thiol group is mentioned.

The preferred substituent of the optionally substituted thiol group is an alkanoyl group; or an alkyl group optionally substituted by hydroxyl group, an alkylaminocarbonyl group, a dialkylaminocarbonyl group, an alkoxycarbonylamino group, a hydroxyalkanoylamino group, morpholinocarbonylamino group, a hydroxyalkylaminocarbonylamino group or an alkanoyloxy group.

As the preferred compound of the present invention, a compound where $R^1$ is a substituted carbonyl group is mentioned.

The preferred substituent of the optionally substituted carbonyl group is an alkoxy group; amino group optionally substituted by pyrimidyl group or an alkylpyrido group; an alkylamino group wherein the alkyl moiety thereof is optionally substituted by hydroxyl group or cyano group; a di(hydroxyalkyl)amino group; a pyridylamino group wherein the pyridyl moiety thereof is optionally substituted by hydroxyl group; piperidino group substituted by hydroxy group or oxo group; piperazino group substituted by oxo group, an alkyl group, an alkylsulfonyl group or alkanoyl group; morpholino group; thiomorpholino group; or pyrrolidino group substituted by an hydroxyalkyl group or hydroxyl group, and more preferred is pyrimidylamino group or hydroxypiperazino group.

As the preferred compound of the present invention, a compound where $R^1$ is a substituted sulfinyl group is mentioned.

The preferred substituent of the optionally substituted sulfinyl group is an alkyl group optionally substituted by hydroxyl group, or hydroxyl group, and more preferred is an alkyl group optionally substituted by hydroxyl group.

As the preferred compound of the present invention, a compound where $R^1$ is a substituted sulfonyl group is mentioned.

The preferred substituent of the optionally substituted sulfonyl group is an alkyl group optionally substituted by hydroxyl group or an alkanoyloxy group, and more preferred is an alkyl group optionally substituted by hydroxyl group.

As the preferred compound of the present invention, a compound where $R^1$ is the group of the formula:

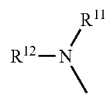

wherein $R^{11}$ and $R^{12}$ are the same or different and each is hydrogen atom, a substituted carbonyl group, a substituted sulfonyl group, an optionally substituted alkyl group or a heterocyclic group containing 1 to 4 atom(s) selected from nitrogen atom, oxygen atom and sulfur atom as a hetero atom, wherein the heterocyclic group is optionally substituted, and the nitrogen atom contained in the heterocyclic group is optionally oxidized, or $R^{11}$ and $R^{12}$ are taken together, with an adjacent nitrogen atom, to form a heterocyclic group selected from piperidino group, azacycloheptyl group, pyrrolidino group, imidazolidinyl group, hexahydropyrimidinyl group, thiazolidyl group, morpholino group, triazolyl group, tetrazolyl group and purinyl group, wherein the heterocyclic group is optionally substituted, and the nitrogen atom contained in the heterocyclic group is optionally oxidized, is mentioned.

Of these, preferred is a compound wherein $R^{11}$ is a substituted carbonyl group and $R^{12}$ is hydrogen atom or an alkyl group. Further, each of the compounds wherein $R^{11}$ is respectively, an optionally substituted alkanoyl group, an optionally substituted aminocarbonyl group, morpholinocarbonyl group, and piperidinylcarbonyl group substituted by an alkanoyl group is respectively preferred. Another preferred example is a compound wherein $R^{11}$ is a substituted sulfonyl group and $R^{12}$ is hydrogen atom or an alkyl group.

The preferred substituent of the optionally substituted alkanoyl group is an an alkanoyl group, an alkylaminocarbonyl group, a dialkylaminocarbonyl group, aminocarbonyl group, an alkoxycarbonylamino group, an alkanoylamino group, amino group substituted by an alkoxycarbonyl group and an alkyl group, amino group substituted by an alkanoyl group and alkyl group, an alkoxy group optionally substituted by phenyl group, furyl group, tetrazolyl group, hydroxyl group, an alkylthio group, an alkylsulfinyl group, an alkylsulfonyl group, 2-aminothiazolyl group, 2-oxopyrrolidino group, 2-thiol-4-alkylthiazolydinyl group or a cycloalkyl group, and more preferred is an alkoxy group, hydroxyl group or an cycloalkyl group. The preferred substituent of the optionally substituted aminocarbonyl group is halogen atom, hydroxyl group or an alkyl group optionally substituted by alkoxy group, and more preferred is an alkyl group. The preferred substituent of the optionally substituted sulfonyl group is an alkyl group optionally substituted by hydroxyl group or halogen group, an alkenyl group or a dialkylamino group, and more preferred is an alkyl group.

The compound of the present invention is exemplified by a compound of the formula [I] wherein Ring A is a benzene ring of the formula:

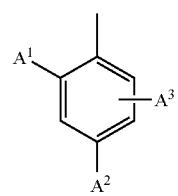

and Ring B is a benzene ring of the formula:

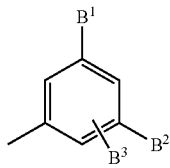

wherein $A^1$ is an alkyl group, hydrogen atom, a halogen atom or an alkoxy group, $A^2$ is hydrogen atom or a halogen atom, $A^3$ is hydrogen atom, $B^1$ is a trihalogenoalkyl group, a halogen atom or an alkyl group, $B^2$ is a trihalogenoalkyl group, a halogen atom or an alkyl group, $B^3$ is hydrogen atom, $R^1$ is hydroxyl group; an alkyl group substituted by a dialkylaminocarbonyl group, a morpholinocarbonyl group, hydroxyl group, an alkoxycarbonyl group, a morpholinoaminocarbonyl group, a hydroxyalkylaminocarbonyloxy group or an alkylpiperazinocarbonyl group; dihydroxyphenylthio group; alkanoylthio group; an alkylthio group optionally substituted by hydroxyl group, an alkylaminocarbonyl group, a dialkylaminocarbonyl group, an alkoxycarbonylamino group, hydroxyalkanoylamino group, a morpholinocarbonylamino group, a hydroxyalkylaminocarbonylamino group or an alkanoyloxy group; dialkylthionium group; an alkoxy group optionally substituted by hydroxyl group, an alkylsulfonyloxy group, a tetrahydropyranyloxy group, a dialkylamino group, pyridyl group, a triazolyl group, a tetrazolyl group optionally substituted by an alkyl group, piperidino group, morpholino group, pyrrolidino group or an alkoxy group; thienylsulfonyloxy group; morpholinocarbonyloxy group; alkyl piperazinocarbonyloxy group; imidazolylcarbonyloxy group; piperidinoalkylaminocarbonyloxy group; morpholinoalkylaminocarbonyloxy group; an alkylaminocarbonyloxy group wherein the alkyl moiety thereof is optionally substituted by hydroxyl group, a morpholinocarbonyl group, a dialkylaminocarbonyl group, an alkylaminocarbonyl group, an alkanoylamino group, an alkylthio group, an alkoxy group, an alkylsulfonyl group, an alkanoyloxy group or a carboxyl group; dialkylaminoalkylaminocarbonyloxy group; a piperidinocarbonyloxy group substituted by hydroxyl group, an alkoxycarbonyl group, a carboxyl group, a hydroxyalkylaminocarbonyl group, an alkoxyalkylaminocarbonyl group, an alkylthioalkylaminocarbonyl group, an alkylsulfinylalkylaminocarbonyl group, an alkylsulfonylalkylaminocarbonyl group or hydroxyalkyl group; dialkylaminocarbonyloxy group optionally substituted by hydroxyl group; a piperidinylaminocarbonyloxy group substituted by a hydroxyalkanoyl group or an alkoxyalkanoyl group; a thiomorpholinocarbonyloxy group wherein the sulfur atom is optionally substituted by an oxo group; oxopyrrolidinylcarbonyloxy group; oxotetrahydrothiazolinylcarbonyloxy group; dialkylaminosulfonylaminocarbonyloxy group; a carboxyl group; an alkoxycarbonyl group; an aminocarbonyl group optionally substituted by a pyrimidinyl group or a pyrazinyl group; an alkylaminocarbonyl group wherein the alkyl moiety is optionally substituted by hydroxyl group or a cyano group; a di(hydroxyalkyl)aminocarbonyl group; a pyridylaminocarbonyl group wherein the pyridyl group moiety is optionally substituted by hydroxyl group; an aminocarbonyl group substituted by an alkylpyrido group; a piperidinocarbonyl group substituted by hydroxyl group or an oxo group; a piperazinocarbonyl group substituted by an oxo group, an alkyl group, a pyrimidinyl group, a pyrazinyl group, an alkylsulfonyl group or an alkanoyl group; a morpholinocarbonyl group; thiomorpholinocarbonyl group; a pyrrolidinocarbonyl group substituted by a hydroxyalkyl group or hydroxyl group; an alkylsulfinyl group optionally substituted by hydroxyl group; a hydroxysulfinyl group; an alkylsulfonyl group optionally substituted by hydroxyl group or an alkanoyloxy group; or the group of the formula:

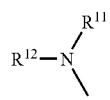

wherein $R^{11}$ is hydrogen atom; a pyridyl group; an alkanoyl group optionally substituted by a group selected from an alkanoyl group, an alkylaminocarbonyl group, a dialkylaminocarbonyl group, an aminocarbonyl group, an amino group, an alkoxycarbonylamino group, an alkanoylamino group, an amino group substituted by an alkoxycarbonyl group and an alkyl group, an amino group substituted by an alkanoyl group and an alkyl group, a halogen atom, a dialkylamino group, an alkoxy group optionally substituted by a phenyl group, a furyl group, a tetrazolyl group, hydroxyl group, an alkylthio group, an alkylsulfinyl group, an alkylsulfonyl group, 2-aminothiazolyl group, 2-oxopyrrolidino group, 2,2-dialkyl-1,3-dioxyranyl group, 2-thiol-4-alkylthiazolinyl group, a cycloalkyl group and a 5-alkyl-2,4(1H, 3H)pyrimidinedione group; a phenylcarbonyl group optionally substituted by an amino group or a nitro group; a pyridylcarbonyl group optionally substituted by an alkyl group or hydroxyl group; a furylcarbonyl group optionally substituted by a formyl group, a morpholinoalkyl group or hydroxyalkyl group; a thienylcarbonyl group; quinolylcarbonyl group; an indolylcarbonyl group substituted by an alkyl group; a pyrazinylcarbonyl group optionally substituted by an alkyl group or an alkanoyl group; a morpholinocarbonyl group; a pyrrolidinylcarbonyl group optionally substituted by a benzyloxy group, an alkoxycarbonyl group, an alkanoyl group, hydroxyl group or an oxo group; tetrahydrofurylcarbonyl group; a piperidinylcarbonyl group substituted by an alkoxycarbonyl group or an alkanoyl group; a thiomorpholinocarbonyl group wherein the sulfur atom is optionally substituted by an oxo group; 3-alkyl-2,4(1H,3H)pyrimidinedionecarbonyl group; an alkylaminocarbonyl group wherein the alkyl moiety thereof is optionally substituted by a halogen atom, hydroxyl group or an alkoxy group; a dialkylaminocarbonyl group; an alkoxycarbonyl group optionally substituted by an alkoxy group, hydroxyl group or a halogen atom; an alkylsulfonyl group optionally substituted by a group selected from hydroxyl group, morpholino group, an alkylpiperazino group, a dialkylamino group optionally substituted by hydroxyl group and a halogen atom; alkenylsulfonyl group; a dialkylamionsulfonyl group; or an alkyl group optionally substituted by morpholino group, a halogen atom, an alkoxy group, a cyano group, pyridyl group, a dialkylaminocarbonyl group or a dialkylamino group, and $R^{12}$ is hydrogen atom; pyridyl group; a pyrazinyl group; or an alkyl group, or —$N(R^{11})(R^{12})$ is triazolyl group, a tetrazolyl group, an aminopurinyl group, morpholino group, a morpholinio group wherein the nitrogen atom is substituted by an alkyl group, an N-oxomorpholino group, piperidino group optionally substituted by piperidino group, pyrrolidino group optionally substituted by hydroxyl group or an alkoxyalkyl group, an imidazolidinyl group substituted by a hydroxyalkyl group and oxo group, a hexahydropyrimidinyl group substituted by a hydroxyalkyl group and oxo group, a dioxopyrrolidino group, a thiazolidyl group or an azacycloheptyl group, $R^2$ is hydrogen atom, Z is an oxygen atom or a group represented by —N($R^3$)—, $R^3$ is an alkyl group optionally substituted by hydroxyl group or an alkanoyl group, $R^4$ is hydrogen atom or an alkyl group optionally substituted by hydroxyl group.

Of these, preferred is a compound wherein $R^1$ is substituted by hydroxyl group; an alkyl group substituted by a dialkylaminocarbonyl group, a morpholinocarbonyl group, a morpholinoaminocarbonyl group or an alkylpiperazinocarbonyl group; dihydroxyphenylthio group; alkanoylthio group; an alkylthio group optionally substituted by hydroxyl group; an alkoxy group optionally substituted by hydroxyl group, an alkylsulfonyloxy group, a tetrahydropyranyloxy group, a dialkylamino group, pyridyl group, a triazolyl group, a tetrazolyl group optionally substituted by an alkyl group, piperidino group, morpholino group, pyrrolidino group or an alkoxy group; a morpholinocarbonyloxy group; an alkylpiperazinocarbonyloxy group; an imidazolylcarbonyloxy group; a piperidinoalkylaminocarbonyloxy group; a morpholinoalkylaminocarbonyloxy group; an alkylaminocarbonyloxy group wherein the alkyl moiety thereof is optionally substituted by hydroxyl group, a morpholinocarbonyl group or a carboxyl group; dialkylaminoalkylaminocarbonyloxy group; a piperidino carbonyloxy group optionally substituted by hydroxyl group or hydroxyalkyl group; a dialkylaminocarbonyloxy group optionally substituted by hydroxyl group; a thiomorpholino carbonyloxy group wherein the sulfur atom is optionally substituted by an oxo group; an oxopyrrolidinylcarbonyloxy group; an oxo tetrahydrothiazolinylcarbonyloxy group; a dialkylaminosulfonylaminocarbonyloxy group; an alkoxycarbonyl group; an aminocarbonyl group optionally substituted by a hydroxyalkyl; an alkylsulfinyl group optionally substituted by hydroxyl group; an alkylsulfonyl group optionally substituted by hydroxyl group; or a group of the formula:

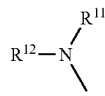

wherein $R^{11}$ is hydrogen atom ; an alkanoyl group optionally substituted by a group selected from an amino group, a halogen atom, a dialkylamino group, an alkoxy group, furyl group, a tetrazolyl group, hydroxyl group, an alkylthio group, an alkylsulfinyl group, an alkylsulfonyl group, 2-aminothiazolyl group, 2,2-dialkyl-1,3-dioxyranyl group, 2-thiol-4-alkylthiazolinyl group, a cycloalkyl group and 5-alkyl-2,4 (1H,3H)pyrimidinedione group; a phenylcarbonyl group optionally substituted by an amino group or nitro group; a pyridylcarbonyl group; a furylcarbonyl group optionally substituted by a formyl group, morpholinoalkyl group or hydroxyalkyl group; a thienylcarbonyl group; a quinolylcarbonyl group; a pyrazinylcarbonyl group optionally substituted by an alkyl group; a morpholinocarbonyl group; pyrrolidinocarbonyl group; tetrahydrofurylcarbonyl group; a piperidinylcarbonyl group substituted by an alkoxycarbonyl group; an alkylaminocarbonyl group optionally substituted by a halogen atom, hydroxyl group or an alkoxy group; a dialkylaminocarbonyl group; an alkoxycarbonyl group optionally substituted by an alkoxy group, hydroxyl group or a halogen atom; an alkylsulfonyl group optionally substituted by a group selected from hydroxyl group, morpholino group, an alkylpiperazino group, a dialkylamino group optionally substituted by hydroxyl group and a halogen atom; an alkenylsulfonyl group; a dialkylamionsulfonyl group; or an alkyl group optionally substituted by morpholino group, a halogen atom, an alkoxy group, cyano group, pyridyl group, dialkylaminocarbonyl group or a dialkylamino group, and $R^{12}$ is hydrogen atom; pyridyl group; or an alkyl group.

Further preferred is a compound wherein $R^1$ is hydroxyl group; an alkyl group substituted by a dialkylaminocarbonyl group a morpholinocarbonyl group, a morpholinoaminocarbonyl group or an alkylpiperazinocarbonyl group; a dihydroxyphenylthio group; an alkanoylthio group; an alkylthio group optionally substituted by hydroxyl group; an alkoxy group optionally substituted by hydroxyl group, an alkylsulfonyloxy group, a tetrahydropyranyloxy group, pyridyl group, a triazolyl group, a tetrazolyl group optionally substituted by an alkyl group or an alkoxy group; a morpholinocarbonyloxy group; an imidazolylcarbonyloxy group; a piperidinoalkylaminocarbonyloxy group; a morpholinoalkylaminocarbonyloxy group; an alkylaminocarbonyloxy group optionally substituted by hydroxyl group, a morpholinocarbonyl group or a carboxyl group; a dialkylaminoalkylaminocarbonyloxy group; a piperidinocarbonyloxy group optionally substituted by hydroxyl group or hydroxyalkyl group; a dialkylaminocarbonyloxy group optionally substituted by hydroxyl group; a thiomorpholinocarbonyloxy group wherein the sulfur atom is optionally substituted by an oxo group; an oxopyrrolidinylcarbonyloxy group; an oxotetrahydrothiazolinyl carbonyloxy group; a dialkylaminosulfonylaminocarbonyloxy group; an alkoxycarbonyl group; an aminocarbonyl group optionally substituted by a hydroxyalkyl group; an alkylsulfinyl group optionally substituted by hydroxyl group; an alkylsulfonyl group optionally substituted by hydroxyl group; or, a group of the formula:

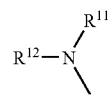

wherein $R^{11}$ is an alkanoyl group optionally substituted by a group selected from an amino group, a halogen atom, an alkoxy group, a furyl group, a tetrazolyl group, hydroxyl group, an alkylthio group, an alkylsulfinyl group, an alkylsulfonyl group, 2-aminothiazolyl group, 2,2-dialkyl-1,3-dioxyranyl group, 2-thiol-4-alkylthiazolinyl group, a cycloalkyl group and 5-alkyl-2,4(1H,3H) pyrimidinedione group; a phenylcarbonyl group optionally substituted by an amino group or a nitro group; a pyridylcarbonyl group; a furylcarbonyl group optionally substituted by a formyl group or a hydroxyalkyl group; a quinolylcarbonyl group; a morpholinocarbonyl group; a pyrrolidinocarbonyl group; a tetrahydrofurylcarbonyl group; a piperidinylcarbonyl group substituted by an alkoxycarbonyl group; an alkylaminocarbonyl group optionally substituted by a halogen atom, hydroxyl group or an alkoxy group; a dialkylaminocarbonyl group; an alkoxycarbonyl group optionally substituted by an alkoxy group, hydroxyl group or a halogen atom; an alkylsulfonyl group optionally substituted by hydroxyl group or a halogen atom; an alkenylsulfonyl group; or a thienylsulfonyl group, and $R^{12}$ is hydrogen atom; pyridyl group; or an alkyl group.

In the compound of the present invention, as a preferred compound there is mentioned a compound wherein Ring A is a benzene ring of the formula:

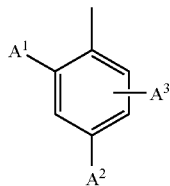

and Ring B is a benzene ring of the formula:

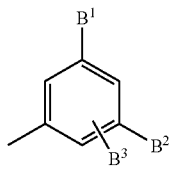

wherein $A^1$ is an alkyl group, hydrogen atom, a halogen atom or an alkoxy group, $A^2$ is hydrogen atom or a halogen atom, $A^3$ is hydrogen atom, $B^1$ is a trihalogenoalkyl group, hydrogen atom or an alkyl group, $B^2$ is a trihalogenoalkyl group, hydrogen atom or an alkyl group, $B^3$ is hydrogen atom, $R^1$ is hydroxyl group; an alkyl group substituted by a dialkylaminocarbonyl group, a morpholinocarbonyl group, hydroxyl group, an alkoxycarbonyl group or a hydroxyalkylaminocarbonyloxy group; dihydroxyphenylthionyl group; alkanoylthio group; an alkylthio group optionally substituted by hydroxyl group, an alkylaminocarbonyl group, a dialkylaminocarbonyl group, an alkoxycarbonylamino group, hydroxyalkanoylamino group, a morpholinocarbonylamino group, a hydroxyalkylaminocarbonylamino group or an alkanoyloxy group; dialkylthionium group; an alkoxy group optionally substituted by hydroxyl group, an alkylsulfonyloxy group, a tetrahydropyranyloxy group, a triazolyl group, a tetrazolyl group optionally substituted by an alkyl group, or an alkoxy group; thienylsulfonyloxy group; morpholinocarbonyloxy group; imidazolylcarbonyloxy group; an alkylaminocarbonyloxy group wherein the alkyl moiety thereof is optionally substituted by hydroxyl group, a morpholinocarbonyl group, a dialkylaminocarbonyl group, an alkylaminocarbonyl group, an alkanoylamino group, an alkylthio group, an alkoxy group, an alkylsulfonyl group, an alkanoyloxy group or a carboxyl group; a piperidinocarbonyloxy group substituted by hydroxyl group, an alkoxycarbonyl group, a carboxyl group, a hydroxyalkylaminocarbonyl group, an alkoxyalkylaminocarbonyl group, an alkylthioalkylaminocarbonyl group, an alkylsulfinylalkylaminocarbonyl group, an alkylsulfonylalkylaminocarbonyl group or hydroxyalkyl group; dialkylaminocarbonyloxy group optionally substituted by hydroxyl group; a piperidinylaminocarbonyloxy group substituted by a hydroxyalkanoyl group or an alkoxyalkanoyl group; a thiomorpholinocarbonyloxy group wherein the sulfur atom is optionally substituted by an oxo group; oxopyrrolidinylcarbonyloxy group; oxotetrahydrothiazolinylcarbonyloxy group; dialkylaminosulfonylaminocarbonyloxy group; a carboxyl group; an alkoxycarbonyl group; an aminocarbonyl group optionally substituted by a pyrimidinyl group; an alkylaminocarbonyl group wherein the alkyl moiety is optionally substituted by hydroxyl group or a cyano group; a di(hydroxyalkyl)aminocarbonyl group; a pyridylaminocarbonyl group wherein the pyridyl group moiety is optionally substituted by hydroxyl group; an aminocarbonyl group substituted by an alkylpyrido group; a piperidinocarbonyl group substituted by hydroxyl group or an oxo group; a piperazinocarbonyl group substituted by an oxo group, an alkyl group, an alkylsulfonyl group or an alkanoyl group; a morpholinocarbonyl group; thiomorpholinocarbonyl group; a pyrrolidinocarbonyl group substituted by a hydroxyalkyl group or hydroxyl group; an alkylsulfinyl group optionally substituted by hydroxyl group; a hydroxysulfinyl group; an alkylsulfonyl group optionally substituted by hydroxyl group or an alkanoyloxy group; or the group of the formula:

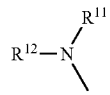

wherein $R^{11}$ is an alkanoyl group optionally substituted by (a) group(s) selected from an alkanoyl group, an alkylaminocarbonyl group, a dialkylaminocarbonyl group, an aminocarbonyl group, an alkoxycarbonylamino group, an alkanoylamino group, an amino group substituted by an alkoxycarbonyl group and an alkyl group, an amino group substituted by an alkanoyl group and an alkyl group, an alkoxy group optionally substituted by a phenyl group, a furyl group, a tetrazolyl group, hydroxyl group, an alkylthio group, an alkylsulfinyl group, an alkylsulfonyl group, 2-aminothiazolyl group, 2-oxopyrrolidino group, 2,2-dialkyl-1,3-dioxyranyl group, 2-thiol-4-alkylthiazolinyl group and a cycloalkyl group; a phenylcarbonyl group optionally substituted by an amino group or a nitro group; a pyridylcarbonyl group optionally substituted by hydroxyl group; a furylcarbonyl group optionally substituted by a formyl group, or hydroxyalkyl group; a thienylcarbonyl group; an indolylcarbonyl group substituted by an alkyl group; a morpholinocarbonyl group; a pyrrolidinylcarbonyl group optionally substituted by a benzyloxy group, an alkoxycarbonyl group, an alkanoyl group, hydroxyl group or an oxo group; tetrahydrofurylcarbonyl group; a piperidinylcarbonyl group substituted by an alkoxycarbonyl group or an alkanoyl group; a thiomorpholinocarbonyl group wherein the sulfur atom is optionally substituted by an oxo group; 3-alkyl-2,4(1H,3H)pyrimidinedionecarbonyl group; an alkylaminocarbonyl group wherein the alkyl moiety thereof is optionally substituted by a halogen atom, hydroxyl group or an alkoxy group; a dialkylaminocarbonyl group; an alkoxycarbonyl group optionally substituted by an alkoxy group, hydroxyl group or a halogen atom; an alkylsulfonyl group optionally substituted by a group selected from hydroxyl group, and a halogen atom; alkenylsulfonyl group; or a dialkylamionsulfonyl group; and $R^{12}$ is hydrogen atom; a pyrazinyl group; or an alkyl group, or —$N(R^{11})(R^{12})$ is triazolyl group, a tetrazolyl group, an aminopurinyl group, a morpholinio group wherein the nitrogen atom is substituted by an alkyl group, an N-oxomorpholino group, an imidazolidinyl group substituted by a hydroxyalkyl group and oxo group, a hexahydropyrimidinyl group substituted by a hydroxyalkyl group and oxo group, or a dioxopyrrolidino group, $R^2$ is hydrogen atom, Z is an oxygen atom or a group represented by —$N(R^3)$—, $R^3$ is an alkyl group optionally substituted by hydroxyl group, $R^4$ is hydrogen atom or an alkyl group optionally substituted by hydroxyl group.

Of these, preferred is a compound wherein Ring A is a benzene ring of the formula:

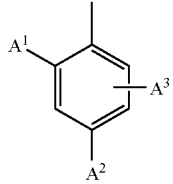

and Ring B is a benzene ring of the formula:

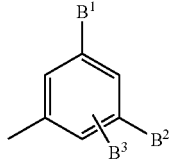

wherein $A^1$ is an alkyl group, $A^2$ is a halogen atom, $A^3$ is hydrogen atom, $B^1$ is a trihalogenoalkyl group, $B^2$ is a trihalogenoalkyl group, $B^3$ is hydrogen atom, $R^1$ is an alkoxy group substituted by hydroxyl group or tetrahydropyranyloxy; an alkylaminocarbonyloxy group wherein the alkyl moiety thereof is optionally substituted by hydroxyl group; a thiomorpholinocarbonyloxy group wherein the sulfur atom is substituted by an oxo group; an alkylthionyl group; an alkanoyl group substituted by hydroxyl group; aminocarbonyl group substituted by (a) group(s) selected from an alkyl group, pyrazinyl group and pyrimidinyl group; piperzinocarbonyl group substituted by an alkanoyl group; piperidinocarbonyl group substituted by hydroxyl group; an alkylsulfinyl group optionally substituted by hydroxyl group; an alkylsulfonyl group optionally substituted by hydroxyl group; or the group the formula:

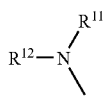

wherein $R^{11}$ is an alkanoyl group optionally substituted by (a) group(s) selected from an alkoxy group, hydroxyl group and a cycloalkyl group; an alkoxycarbonyl group; a pyridylcarbonyl group substituted by hydroxyl group; a morpholinocarbonyl group; an alkylaminocarbonyl group; or an alkylsulfonyl group; pyrazinyl group, and $R^{12}$ is hydrogen atom, or an alkyl group, —$N(R^{11})(R^{12})$ is triazolyl group, tetrazolyl group or an N-oxomorpholino group, $R^2$ is hydrogen atom, Z is a group represented by —$N(R^3)$—, $R^3$ is an alkyl group, $R^4$ is hydrogen atom or an alkyl group.

Further more preferred is a compound wherein $R^1$ is an alkylaminocarbonyloxy group wherein the alkyl moiety thereof is substituted by hydroxyl group; a thiomorpholinocarbonyloxy group wherein the sulfur atom is substituted by an oxo group; an alkanoyl group substituted by hydroxyl group; piperzinocarbonyl group substituted by an alkanoyl group; piperidinocarbonyl group substituted by hydroxyl group; an alkylsulfinyl group substituted by hydroxyl group; an alkylsulfonyl group optionally substituted by hydroxyl group; or the group the formula:

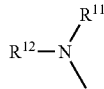

wherein $R^{11}$ is an alkanoyl group substituted by hydroxylgroup, and $R^{12}$ is hydrogen atom.

In the present invention, particularly preferred compound is a compound selected from the following (A) to (BK) or pharmaceutically acceptable salt thereof.

(A) (2R,4S)-1-[N-{1-(S)-(3,5-bistrifluoromethylphenyl)ethyl}-N-methyl]aminocarbonyl-2-(4-fluoro-2-methylphenyl)-4-(2-methylpropionylamino)piperidine, (B) (2R,4S)-1-{N-(3,5-bistrifluoromethylbenzyl)-N-methyl}-aminocarbonyl-2-(4-fluoro-2-methylphenyl)-4-morpholino-carbonylaminopiperidine, (C) (2R,4S)-1-{N-(3,5-bistrifluoromethylbenzyl)-N-methyl}-aminocarbonyl-2-(4-fluoro-2-methylphenyl)-4-(2-hydroxyethoxy)-piperidine, (D) (2R,4S)-1-[N-{1-(R)-(3,5-bistrifluoromethylphenyl)ethyl}-N-methyl]aminocarbonyl-2-(4-fluoro-2-methylphenyl)-4-{2-(2-tetrahydropyranyloxy) ethoxy}piperidine, (E) (2R,4S)-1-[N-{1-(S)-(3,5-bistrifluoromethylphenyl)ethyl}-N-methyl]aminocarbonyl-2-(4-fluoro-2-methylphenyl)-4-methoxy-acetylaminopiperidine, (F) (2R,4S)-1-[N-{1-(S)-(3,5-bistrifluoromethylphenyl)ethyl}-N-methyl]aminocarbonyl-2-(4-fluoro-2-methylphenyl)-4-methoxy-carbonylaminopiperidine, (G) (2R,4S)-1-[N-{1-(S)-(3,5-bistrifluoromethylphenyl)ethyl}-N-methyl]aminocarbonyl-4-ethoxycarbonylamino-2-(4-fluoro-2-methylphenyl)piperidine, (H) (2R,4S)-1-[N-{1-(S)-(3,5-bistrifluoromethylphenyl)ethyl}-N-methyl]aminocarbonyl-2-(4-fluoro-2-methylphenyl)-4-metansurfonylaminopiperidine, (I) (2R,4S)-1-[N-{1-(S)-(3,5-bistrifluoromethylphenyl)ethyl}-N-methyl]aminocarbonyl-2-(4-fluoro-2-methylphenyl)-4-(2-hydroxyethoxy)piperidine, (J) (2R,4S)-1-[N-{1-(R)-(3,5-bistrifluoromethylphenyl)ethyl}-N-methyl]aminocarbonyl-2-(4-fluoro-2-methylphenyl)-4-hydroxy-acetylaminopiperidine, (K) (2R,4S)-1-[N-{1-(R)-(3,5-bistrifluoromethylphenyl)ethyl}-N-methyl]aminocarbonyl-2-(4-fluoro-2-methylphenyl)-4-(3-hydroxypropoxy)piperidine, (L) (2R,4S)-1-[N-{1-(S)-(3,5-bistrifluoromethylphenyl)ethyl}-N-methyl]aminocarbonyl-4-(2-cyclopropyl-2-hydroxyacetylamino)-2-(4-fluoro-2-methylphenyl)piperidine, (M) (2R,4S)-1-[N-{1-(S)-(3,5-bistrifluoromethylphenyl)ethyl}-N-methyl]aminocarbonyl-2-(4-fluoro-2-methylphenyl)-4-(2-hydroxy-2-methylpropionylamino)piperidine, (N) (2R,4S)-1-[N-{1-(S)-(3,5-bistrifluoromethylphenyl)ethyl}-N-methyl]aminocarbonyl-2-(4-fluoro-2-methylphenyl)-4-((S)-3-hydroxybutyrylamino)piperidine, (O) (2R,4S)-1-{N-(3,5-bistrifluoromethylbenzyl)-N-methyl}-aminocarbonyl-2-(4-fluoro-2-methylphenyl)-4-(2-hydroxyethyl-aminocarbonyloxy)piperidine, (P) (2R,4S)-1-[N-{1-(R)-(3,5-bistrifluoromethylphenyl)ethyl}-N-methyl]aminocarbonyl-2-(4-fluoro-2-methylphenyl)-4-methanesulfinylpiperidine, (Q) (2R,4S)-1-[N-{1-(R)-(3,5-bistrifluoromethylphenyl)ethyl}-N-methyl]aminocarbonyl-2-(4-fluoro-2-methylphenyl)-4-methanesulfonylpiperidine, (R) (2R,4S)-1-{N-(3,5-bistrifluoromethylbenzyl)-N-methyl}-aminocarbonyl-4-ethylaminocarbonyloxy-2-(4-fluoro-2-methyl-phenyl)piperidine, (S) (2R,4S)-1-[N-{1-(S)-(3,5-bistrifluoromethylphenyl)ethyl}-N-methyl]aminocarbonyl-2-(4-fluoro-2-methylphenyl)-4-(2-methoxypropionylamino)piperidine, (T) (2R,4S)-1-[N-{1-(R)-(3,5-bistrifluoromethylphenyl)ethyl}-N-methyl]aminocarbonyl-2-(4-fluoro-2-methylphenyl)-4-(N-methanesulfonyl-N-methylamino)piperidine, (U) (2R,4S)-1-[N-{1-(R)-(3,5-bistrifluoromethylphenyl)ethyl}-N-methyl]aminocarbonyl-2-(4-fluoro-2-methylphenyl)-4-(2-hydroxyethylaminocarbonyloxy)piperidine, (V) (2R,4S)-1-[N-{1-(S)-(3,5-bistrifluoromethylphenyl)ethyl}-N-methyl]aminocarbonyl-2-(4-fluoro-2-methylphenyl)-4-(3-hydroxy-3-methylbutyrylamino)piperidine, (W) (2R,4S)-1-{N-(3,5-bistrifluoromethylbenzyl)-N-methyl}-aminocarbonyl-2-(4-fluoro-2-methylphenyl)-4-(2-hydroxyethane-sulfinyl)piperidine, (X) (2R,4S)-1-[N-{1-(S)-(3,5-bistrifluoromethylphenyl)ethyl}-N-methyl]aminocarbonyl-2-(4-fluoro-2-methylphenyl)-4-hydroxy-acetylaminopiperidine, (Y) (2R,4S)-1-[N-{1-(S)-(3,5-bistrifluoromethylphenyl)ethyl}-N-methyl]aminocarbonyl-2-(4-fluoro-2-methylphenyl)-4-((S)-2-hydroxypropionylamino)piperidine, (Z) (2R,4S)-1-[N-{1-(S)-(3,5-bistrifluoromethylphenyl)ethyl}-N-methyl]aminocarbonyl-2-(4-fluoro-2-methylphenyl)-4-((R)-3-hydroxybutyrylamino)piperidine, (AA) (2R,4S)-1-{N-(3,5-bistrifluoromethylbenzyl)-N-methyl}-aminocarbonyl-2-(4-fluoro-2-methylphenyl)-4-(2-hydroxy-2-methylpropanesulfonyl)piperidine, (AB) (2R,4S)-1-[N-{1-(R)-(3,5-bistrifluoromethylphenyl)ethyl}-N-methyl]aminocarbonyl-2-(4-fluoro-2-methylphenyl)-4-(2-hydroxyethanesulfinyl)piperidine, (AC) (2R,4S)-1-[N-{1-(R)-(3,5-bistrifluoromethylphenyl)ethyl}-N-methyl]aminocarbonyl-2-(4-fluoro-2-methylphenyl)-4-{(S)—((S)-2-hydroxypropane)sulfinyl}piperidine, (AD) (2R,4S)-1-[N-{1-(R)-(3,5-bistrifluoromethylphenyl)ethyl}-N-methyl]aminocarbonyl-2-(4-fluoro-2-methylphenyl)-4-{(R)—((S)-2-hydroxypropane)sulfinyl}piperidine, (AE) (2R,4S)-1-{N-(3,5-bistrifluoromethylbenzyl)-N-methyl}-aminocarbonyl-2-(4-fluoro-2-methylphenyl)-4-(2-hydroxy-2-methylpropanesulfinyl)piperidine, (AF) (2R,4S)-1-[N-{1-(R)-(3,5-bistrifluoromethylphenyl)ethyl}-N-methyl]aminocarbonyl-2-(4-fluoro-2-methylphenyl)-4-((S)-2-hydroxypropanesulfonyl)piperidine, (AG) (2R,4S)-1-[N-{1-(R)-(3,5-bistrifluoromethylphenyl)ethyl}-N-methyl]aminocarbonyl-2-(4-fluoro-2-methylphenyl)-4-(1-methylethanesulfonyl)piperidine, (AH) (2R,4S)-1-[N-{1-(R)-(3,5-bistrifluoromethylphenyl)ethyl}-N-methyl]aminocarbonyl-2-(4-fluoro-2-methylphenyl)-4-(2-hydroxy-2-methylpropanesulfinyl)piperidine, (AI) (2R,4S)-1-{N-(3,5-bistrifluoromethylbenzyl)-N-methyl}-aminocarbonyl-2-(4-fluoro-2-methylphenyl)-4-{(S)—((S)-2-hydroxypropane)sulfinyl}piperidine, (AJ) (2R,4S)-1-{N-(3,5-bistrifluoromethylbenzyl)-N-methyl}-aminocarbonyl-2-(4-fluoro-2-methylphenyl)-4-{(R)—((S)-2-hydroxypropane)sulfinyl}piperidine, (AK) (2R,4S)-1-{N-(3,5-bistrifluoromethylbenzyl)-N-methyl}-aminocarbonyl-2-(4-fluoro-2-methylphenyl)-4-{(R)—((R)-2-hydroxypropane)sulfinyl}piperidine, (AL) (2R,4S)-1-(N-(3,5-bistrifluoromethylbenzyl)-N-methyl)-aminocarbonyl-2-(4-fluoro-2-methylphenyl)-4-{(S)—((R)-2-hydroxypropane)sulfinyl}piperidine, (AM) (2R,4S)-1-{N-(3,5-bistrifluoromethylbenzyl)-N-methyl}-aminocarbonyl-2-(4-fluoro-2-methylphenyl)-4-((S)-2-hydroxy-propanesulfonyl)piperidine, (AN) (2R,4S)-1-{N-(3,5-bistrifluoromethylbenzyl)-N-methyl}-aminocarbonyl-2-(4-fluoro-2-methylphenyl)-4-((S)-3-hydroxy-butyrylamino)piperidine, (AO) (2R,4S)-1-{N-(3,5-bistrifluoromethylbenzyl)-N-methyl}-aminocarbonyl-2-(4-fluoro-2-methylphenyl)-4-((R)-3-hydroxy-butyrylamino)piperidine, (AP) (2R,4S)-4-(4-acetylpiperazinocarbonyl)-1-[N-{1-(R)-(3,5-bistrifluoromethylphenyl)ethyl}-N-methyl]aminocarbonyl-2-(4-fluoro-2-methylphenyl)piperidine, (AQ) (2R,4S)-1-{N-(3,5-bistrifluoromethylbenzyl)-N-methyl}-aminocarbonyl-2-(4-fluoro-2-methylphenyl)-4-(1-methyl-ethanesulfinyl)piperidine, (AR) (2R,4S)-1-{N-(3,5-bistrifluoromethylbenzyl)-N-methyl}-aminocarbonyl-2-(4-fluoro-2-methylphenyl)-4-(1-oxothio-morpholinocarbonyloxy)piperidine, (AS) (2R,4S)-1-{N-(3,5-bistrifluoromethylbenzyl)-N-methyl}-aminocarbonyl-2-(4-fluoro-2-methylphenyl)-4-(2-hydroxy-ethanesulfonyl)piperidine, (AT) (2R,4S)-1-{N-(3,5-bistrifluoromethylbenzyl)-N-methyl}-aminocarbonyl-2-(4-fluoro-2-methylphenyl)-4-(1-methyl-ethanesulfonyl)piperidine, (AU) (2R,4S)-1-[N-{1-(R)-(3,5-bistrifluoromethylphenyl)ethyl}-N-methyl]aminocarbonyl-2-(4-fluoro-2-methylphenyl)-4-(4-hydroxypiperidinocarbonyl)piperidine, (AV) (2R,4S)-1-{N-(3,5-bistrifluoromethylbenzyl)-N-methyl}-aminocarbonyl-2-(4-fluoro-2-methylphenyl)-4-methanesulfonyl-piperidine, (AW) (2R,4S)-1-{N-(3,5-bistrifluoromethylbenzyl)-N-methyl}-aminocarbonyl-2-(4-fluoro-2-methylphenyl)-4-((R)-2-hydroxy-propionyl)piperidine, (AX) (2R,4S)-1-{N-(3,5-bistrifluoromethylbenzyl)-N-methyl}-aminocarbonyl-2-(4-fluoro-2-methylphenyl)-4-(N-methyl-N-pyrazin-2-ylaminocarbonyl)piperidine, (AY) (2R,4S)-1-{N-(3,5-bistrifluoromethylbenzyl)-N-methyl}-aminocarbonyl-2-(4-fluoro-2-methylphenyl)-4-(pyrazin-2-yl-amino)piperidine, (AZ) (2R,4S)-1-{N-(3,5-bistrifluoromethylbenzyl)-N-methyl}-aminocarbonyl-2-(4-fluoro-2-methylphenyl)-4-(N-methyl-N-pyrazin-2-ylamino)piperidine, (BA) (2R,4S)-1-[N-{1-(R)-(3,5-bistrifluoromethylphenyl)ethyl}-N-methyl]aminocarbonyl-2-(4-fluoro-2-methylphenyl)-4-(1-methylethylthionyl)piperidine,
(BB) (2R,4S)-1-[N-{1-(R)-(3,5-bistrifluoromethylphenyl)ethyl}-N-methyl]aminocarbonyl-2-(4-fluoro-2-methylphenyl)-4-(1-triazoryl)piperidine,
(BC) (2R,4S)-1-[N-{1-(R)-(3,5-bistrifluoromethylphenyl)ethyl}-N-methyl]aminocarbonyl-2-(4-fluoro-2-methylphenyl)-4-(1-tetrazoryl)piperidine,
(BD) (2R,4S)-1-[N-{1-(S)-(3,5-bistrifluoromethylphenyl)ethyl}-N-methyl]aminocarbonyl-2-(4-fluoro-2-methylphenyl)-4-(N-oxo-morphorino)piperidine,
(BE) (2R,4S)-1-[N-{1-(R)-(3,5-bistrifluoromethylphenyl)ethyl}-N-methyl]aminocarbonyl-2-(4-fluoro-2-methylphenyl)-4-(N-oxo-morphorino)piperidine,
(BF) (2R,4S)-1-{N-(3,5-bistrifluoromethylbenzyl)-N-methyl}-aminocarbonyl-2-(4-fluoro-2-methylphenyl)-4-(N-oxomorphorino)-piperidine,
(BG) (2R,4S)-1-{N-(3,5-bistrifluoromethylbenzyl)-N-methyl}-aminocarbonyl-2-(4-fluoro-2-methylphenyl)-4-(2-hydroxypyridin-5-yl-carbonylamino)piperidine,
(BH) (2R,4S)-1-[N-{1-(R)-(3,5-bistrifluoromethylphenyl)ethyl}-N-methyl]aminocarbonyl-2-(4-fluoro-2-methylphenyl)-4-(N-pyrimidin-4-ylaminocarbonyl)piperidine,
(BI) (2R,4S)-1-[N-{1-(R)-(3,5-bistrifluoromethylphenyl)ethyl}-N-methyl]aminocarbonyl-2-(4-fluoro-2-methylphenyl)-4-(N-methyl-N-pyrimidin-4-ylaminocarbonyl)piperidine,
(BJ) (2R,4S)-1-[N-{1-(S)-(3,5-bistrifluoromethylphenyl)ethyl}-N-methyl]aminocarbonyl-2-(4-fluoro-2-methylphenyl)-4-(2-hydroxyacetylamino)piperidine, or
(BK) (2R,4S)-1-[N-{1-(R)-(3,5-bistrifluoromethylphenyl)ethyl}-N-methyl]aminocarbonyl-2-(4-fluoro-2-methylphenyl)-4-(1-methylethylthio)piperidine.

In the present invention, more particularly preferred compound is a compound selected from the following (a) to (s) or a pharmaceutically acceptable salt thereof.

(a) (2R,4S)-1-[N-{1-(S)-(3,5-bistrifluoromethylphenyl)ethyl}-N-methyl]aminocarbonyl-2-(4-fluoro-2-methylphenyl)-4-(2-hydroxy-2-methylpropionylamino)piperidine,
(b) (2R,4S)-1-[N-{1-(S)-(3,5-bistrifluoromethylphenyl)ethyl}-N-methyl]aminocarbonyl-2-(4-fluoro-2-methylphenyl)-4-((S)-3-hydroxybutyrylamino)piperidine,
(c) (2R,4S)-1-{N-(3,5-bistrifluoromethylbenzyl)-N-methyl}-aminocarbonyl-2-(4-fluoro-2-methylphenyl)-4-(2-hydroxyethyl-aminocarbonyloxy)piperidine,
(d) (2R,4S)-1-[N-{1-(S)-(3,5-bistrifluoromethylphenyl)ethyl}-N-methyl]aminocarbonyl-2-(4-fluoro-2-methylphenyl)-4-(3-hydroxy-3-methylbutyrylamino)piperidine,
(e) (2R,4S)-1-[N-{1-(S)-(3,5-bistrifluoromethylphenyl)ethyl}-N-methyl]aminocarbonyl-2-(4-fluoro-2-methylphenyl)-4-((R)-3-hydroxybutyrylamino)piperidine,
(f) (2R,4S)-1-{N-(3,5-bistrifluoromethylbenzyl)-N-methyl}-aminocarbonyl-2-(4-fluoro-2-methylphenyl)-4-(2-hydroxy-2-methylpropanesulfonyl)piperidine,
(g) (2R,4S)-1-{N-(3,5-bistrifluoromethylbenzyl)-N-methyl}-aminocarbonyl-2-(4-fluoro-2-methylphenyl)-4-(2-hydroxy-2-methylpropanesulfinyl)piperidine,
(h) (2R,4S)-1-{N-(3,5-bistrifluoromethylbenzyl)-N-methyl}-aminocarbonyl-2-(4-fluoro-2-methylphenyl)-4-((S)-2-hydroxy-propanesulfonyl)piperidine,
(i) (2R,4S)-1-{N-(3,5-bistrifluoromethylbenzyl)-N-methyl}-aminocarbonyl-2-(4-fluoro-2-methylphenyl)-4-((S)-3-hydroxy-butyrylamino)piperidine,
(j) (2R,4S)-1-{N-(3,5-bistrifluoromethylbenzyl)-N-methyl}-aminocarbonyl-2-(4-fluoro-2-methylphenyl)-4-((R)-3-hydroxy-butyrylamino)piperidine,
(k) (2R,4S)-4-(4-acetylpiperazinocarbonyl)-1-[N-{1-(R)-(3,5-bistrifluoromethylphenyl)ethyl}-N-methyl]aminocarbonyl-2-(4-fluoro-2-methylphenyl)piperidine,
(l) (2R,4S)-1-{N-(3,5-bistrifluoromethylbenzyl)-N-methyl}-aminocarbonyl-2-(4-fluoro-2-methylphenyl)-4-(1-oxothio-morpholinocarbonyloxy)piperidine,
(m) (2R,4S)-1-{N-(3,5-bistrifluoromethylbenzyl)-N-methyl}-aminocarbonyl-2-(4-fluoro-2-methylphenyl)-4-(2-hydroxy-ethanesulfonyl)piperidine,
(n) (2R,4S)-1-{N-(3,5-bistrifluoromethylbenzyl)-N-methyl}-amino-carbonyl-2-(4-fluoro-2-methylphenyl)-4-(1-methyl-ethanesulfonyl)piperidine,
(o) (2R,4S)-1-[N-{1-(R)-(3,5-bistrifluoromethylphenyl)ethyl}-N-methyl]aminocarbonyl-2-(4-fluoro-2-methylphenyl)-4-(4-hydroxypiperidinocarbonyl)piperidine,
(p) (2R,4S)-1-{N-(3,5-bistrifluoromethylbenzyl)-N-methyl}-aminocarbonyl-2-(4-fluoro-2-methylphenyl)-4-methanesulfonyl-piperidine,
(q) (2R,4S)-1-{N-(3,5-bistrifluoromethylbenzyl)-N-methyl}-aminocarbonyl-2-(4-fluoro-2-methylphenyl)-4-((R)-2-hydroxy-propionyl)piperidine,
(r) (2R,4S)-1-[N-{1-(S)-(3,5-bistrifluoromethylphenyl)ethyl}-N-methyl]aminocarbonyl-2-(4-fluoro-2-methylphenyl)-4-(2-hydroxyacetylamino)piperidine, or
(s) (2R,4S)-1-[N-{1-(R)-(3,5-bistrifluoromethylphenyl)ethyl}-N-methyl]aminocarbonyl-2-(4-fluoro-2-methylphenyl)-4-(1-methylethylthio)piperidine.

In the compound of the present invention, as a preferred compound there is mentioned a compound wherein Ring A is a benzene ring of the formula:

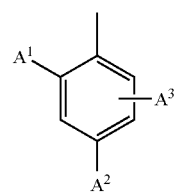

and Ring B is a benzene ring of the formula:

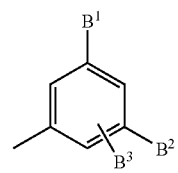

wherein $A^1$ is an alkyl group, $A^2$ is a halogen atom, $A^3$ is hydrogen atom, $B^1$ is a trihalogenoalkyl group or a halogen atom, $B^2$ is a trihalogenoalkyl group or a halogen atom, $B^3$ is hydrogen atom, $R^1$ is hydroxyl group; an alkyl group substituted by a dialkylaminocarbonyl group or a morpholinocarbonyl group, an alkoxy group optionally substituted by hydroxyl group, an alkylsulfonyloxy group, a triazolyl group, or a tetrazolyl group optionally substituted by an alkyl group; morpholino-carbonyloxy group; a hydroxyalkylaminocarbonyloxy group; an imidazolylcarbonyloxy group; an alkylsulfinyl group optionally substituted by hydroxyl group; an alkylsulfonyl group; an alkylaminocarbonyl group substituted by hydroxyl group; a piperidinocarbonyl group substituted by hydroxyl group; or a group of the formula:

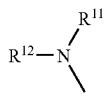

wherein $R^{11}$ is an alkanoyl group optionally substituted by hydroxyl group or a 5-alkyl-2,4(1H,3H)pyrimidine-dione group; a pyridylcarbonyl group; a furylcarbonyl group; a thienylcarbonyl group; a morpholinocarbonyl group; an alkoxycarbonyl group; or an alkylsulfonyl group;

$R^{12}$ is hydrogen atom; or an alkyl group, or

—N($R^{11}$)($R^{12}$) is triazolyl group, a morpholinio group wherein the nitrogen atom is substituted by an alkyl group, or an N-oxomorpholino group, $R^2$ is hydrogen atom, Z is a group represented by —N($R^3$)—, $R^3$ is an alkyl group, $R^4$ is hydrogen atom or an alkyl group.

Of these, preferred is a compound wherein $R^1$ is hydroxyl group; an alkyl group substituted by a dialkylaminocarbonyl group or a morpholinocarbonyl group; an alkoxy group optionally substituted by hydroxyl group, alkylsulfonyloxy group, a triazolyl group, or a tetrazolyl group optionally substituted by an alkyl group; a morpholinocarbonyloxy group; a hydroxyalkylaminocarbonyloxy group; an imidazolylcarbonyloxy group; an alkylsulfinyl group optionally substituted by hydroxyl group; an alkylsulfonyl group; an alkylaminocarbonyl group substituted by hydroxyl group; a piperidinocarbonyl group substituted by hydroxyl group; or a group of the formula:

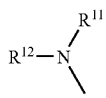

wherein $R^{11}$ is an alkanoyl group optionally substituted by hydroxyl group or 5-alkyl-2,4(1H,3H)pyrimidinedione group; a pyridylcarbonyl group; a furylcarbonyl group; a thienylcarbonyl group; a morpholinocarbonyl group; an alkoxycarbonyl group; an alkylsulfonyl group;

$R^{12}$ is hydrogen atom; or an alkyl group.

In the compounds of the present invention, more preferred is a compound wherein $R^1$ is hydroxyl group; an alkoxy group substituted by hydroxyl group, or a triazolyl group; a hydroxyalkylaminocarbonyloxy group; an alkylsulfinyl group optionally substituted by hydroxyl group; an alkylsulfonyl group; an alkylaminocarbonyl group substituted by hydroxyl group; a piperidinocarbonyl group substituted by hydroxyl group; or a group of the formula:

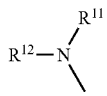

wherein $R^{11}$ is an alkanoyl group optionally substituted by hydroxyl group; and $R^{12}$ is hydrogen atom; or an alkyl group, or —N($R^{11}$)($R^{12}$) is a morpholinio group wherein the nitrogen atom is substituted by an alkyl group, a piperazino group substituted by an N-oxomorpholino group, an alkyl group or an alkanoyl group, $R^2$ is hydrogen atom, Z is a group represented by —N($R^3$)—, $R^3$ is an alkyl group, $R^4$ is hydrogen atom or an alkyl group.

The more preferred is the compound wherein $R^1$ is hydroxyl group; an alkoxy group substituted by hydroxyl group, or a triazolyl group; a hydroxyalkylaminocarbonyloxy group; an alkylsulfinyl group optionally substituted by hydroxyl group; an alkylsulfonyl group; an alkylaminocarbonyl group substituted by hydroxyl group; a piperidinocarbonyl group substituted by hydroxyl group; or a group of the formula:

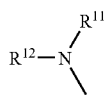

wherein $R^{11}$ is an alkanoyl group optionally substituted by hydroxyl group;

$R^{12}$ is hydrogen atom; or an alkyl group.

In the compound of the present invention, other preferred compound is a compound wherein $R^1$ is hydroxyl group; an alkoxy group optionally substituted by hydroxyl group, an alkylsulfonyloxy group or a tetrazolyl group; a hydroxyalkylaminocarbonyloxy group; an alkylsulfinyl group optionally substituted by hydroxyl group; an alkylsulfonyl group; an alkylaminocarbonyl group substituted by hydroxyl group; a piperidinocarbonyl group substituted by hydroxyl group; or a group of the formula:

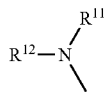

wherein $R^{11}$ is an alkanoyl group optionally substituted by hydroxyl group; a furylcarbonyl group; a morpholinocarbonyl group; an alkoxycarbonyl group; or an alkylsulfonyl group; and $R^{12}$ is hydrogen atom; or an alkyl group, or —N($R^{11}$)($R^{12}$) is a triazolyl group, or a tetrazolyl group, $R^2$ is hydrogen atom, Z is a group represented by —N($R^3$)—, $R^3$ is an alkyl group, $R^4$ is hydrogen atom or an alkyl group.

Another preferred compound is exemplified by the compound wherein Ring A is a benzene ring of the formula:

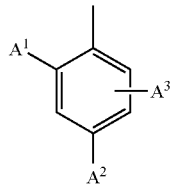

and Ring B is a benzene ring of the formula:

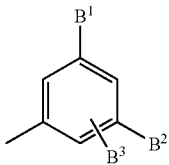

wherein $A^1$ is an alkyl group, $A^2$ is a halogen atom, $A^3$ is hydrogen atom, $B^1$ is a trihalogenoalkyl group, $B^2$ is a trihalogenoalkyl group, $B^3$ is hydrogen atom, $R^1$ is a hydroxyalkylaminocarbonyloxy group; an alkylsulfinyl group optionally substituted by hydroxyl group; an alkylsulfonyl group; an alkylaminocarbonyl group substituted by hydroxyl group; a piperidinocarbonyl group substituted by hydroxyl group; or a group of the formula:

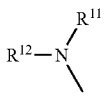

wherein $R^{11}$ is an alkanoyl group optionally substituted by hydroxyl group; or an alkoxycarbonyl group; and $R^{12}$ is hydrogen atom; or an alkyl group $R^2$ is hydrogen atom, Z is a group represented by $-N(R^3)-$, $R^3$ is an alkyl group, $R^4$ is hydrogen atom or an alkyl group.

Still another preferred compound is a compound wherein Ring A is a benzene ring of the formula:

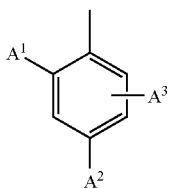

and Ring B is a benzene ring of the formula:

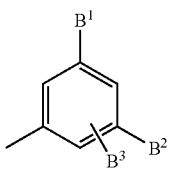

wherein $A^1$ is an alkyl group, $A^2$ is a halogen atom, $A^3$ is hydrogen atom, $B^1$ is a trihalogenoalkyl group, $B^2$ is a trihalogenoalkyl group, $B^3$ is hydrogen atom, $R^1$ is a hydroxyalkylaminocarbonyloxy group; an alkylsulfinyl group optionally substituted by hydroxyl group; an alkylsulfonyl group; an alkylaminocarbonyl group substituted by hydroxyl group; a piperidinocarbonyl group substituted by hydroxyl group; or a group of the formula:

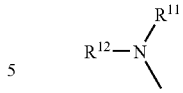

wherein $R^{11}$ is an alkanoyl group optionally substituted by hydroxyl group, and $R^{12}$ is hydrogen atom; or an alkyl group, or $-N(R^{11})(R^{12})$ is a morpholinio group wherein the nitrogen atom is substituted by an alkyl group, or an N-oxomorpholino group, $R^2$ is hydrogen atom, Z is a group represented by $-N(R^3)-$, $R^3$ is an alkyl group, $R^4$ is hydrogen atom or an alkyl group.

More preferred is a compound wherein $R^1$ is a hydroxyalkylaminocarbonyloxy group; an alkylsulfinyl group optionally substituted by hydroxyl group; an alkylsulfonyl group; an alkylaminocarbonyl group substituted by hydroxyl group; a piperidinocarbonyl group substituted by hydroxyl group; or a group of the formula:

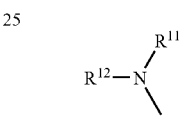

wherein $R^{11}$ is an alkanoyl group optionally substituted by hydroxyl group, and $R^{12}$ is hydrogen atom; or an alkyl group.

The compound [I] of the present invention can be used for a pharmaceuticl use either in a free form or in form of a pharmaceutically acceptable salt.

As the pharmaceutically acceptable salt of the compound [I] of the present invention, there may be mentioned, for example, an inorganic acid salt such as hydrochloride, sulfate, phosphate and hydrobromate; and an organic acid salt etc., such as acetate, fumarate, oxalate, citrate, methanesulfonate, benzenesulfonate, tosylate, maleate, succinate and tartarate.

Further, the compound [I] of the present invention or a pharmaceutically acceptable salt thereof includes any of its internal salts, solvate and hydrates, etc.

Although an optical isomer based on an asymmetric carbon can be present in the compound [I] of the present invention, the present invention includes any of these optical isomers and the mixture thereof. In the present invention, among these optical isomers, preferred is a compound having R configuration at 2-position of the piperidine ring (the connecting position of Ring A), and particularly preferred is a compound having R configuration at the second position of the piperidine ring (the connecting position of Ring A) and S configuration at 4-position (the connecting position of $R^1$).

The compound [I] or a pharmaceutically acceptable salt thereof of the present invention has an excellent tachykinin receptor antagonistic action, particularly an SP receptor antagonistic action, whereby it is useful as a safe medicament for prophylaxis and treatment for inflammation or allergic diseases (for example, atopic dermatitis, dermatitis, herpes, proriasis, asthma, bronchitis, expectoration, rhinitis, rheumatoid arthritis, osteoarthritis, osteoporosis, multiple sclerosis, conjunctivitis, ophthalmia, cystitis, etc.), pain, migraine, neuralgia, itchiness, cough, and further central nervous system diseases (for example, schizophrenia, Parkinson's disease, depression, uneasiness, psychosomatic disorder, morphine dependence, dementia (for example, Alzheimer's disease, etc.), etc.), digestive organs disease (for example, hypersensitive bowel disease, ulcerative colitis, Crohn's disease, disorder (for example, gastritis, gastric ulcer, etc.) related to urease-positive Spirillum (for example, helicobacter pylori, etc.), etc.), nausea, emesis, urinary disorder (for example, pollakiurea, urinary incontinence, etc.), circulatory disease (for example, angina pectoris, hypertension, cardiac failure, thrombosis, etc.) and immune disorder, etc. in mammals (for example, mouse, Mongolian gerbil, ferret, rat, hamster, rabbit, cat, dog, bovine, sheep, monkey, human, etc.). Particularly, since compound [I] or a pharmaceutically acceptable salt thereof which is an active ingredient of the present invention is highly transportable in the brain and at the same time has a low toxicity, showing almost no side effect, it is useful as a therapeutic or prophylactic agent for central nerve system disease such as emesis, depression and so forth, or urinary disorder such as pollakiuria, etc.

Measurements on the compound of the present invention or a pharmaceutically acceptable salt thereof can be carried out, according to the method described in European Journal of Pharmacology, vol. 254, pages 221-227 (1994) with respect to a neurokinin-1 receptor binding action, and according to the method described in European Journal of Pharmacology) vol. 265, pages 179-183 (1994) with respect to an action against the neurokinin-1 receptor induction, and according to the method described in British Journal of Pharmacology vol. 119, pages 931-936 (1996) with regard to the effect against emesis, further according to the method described in Journal of Urology, vol. 155, No. 1, pages 355-360 (1996) with regard to an inhibitory action on pollakiuria.

The compound [I] or a pharmaceutically acceptable salt thereof of the present invention can be administered orally or parenterally, and it can be formulated into a suitable preparation, using a conventionally used pharmaceutical carrier for an oral or parental administration. As such a pharmaceutical carrier, there may be mentioned, for example, a binder (syrup, Gum Arabic, gelatin, sorbitol, tragacanth, polyvinylpyrrolidone, etc.), an excipient (lactose, sugar, corn starch, potassium phosphate, sorbitol, glycine, etc.), a lubricant (magnesium stearate, talc, polyethylene glycol, silica, etc.), a disintegrator (potato starch, etc.) and a wetting agent (anhydrous lauryl sodium sulfate, etc.), and the like.

Also, when these pharmaceutical preparations are administered orally, they may be a solid preparation such as tablets, granules, capsules, powders, or a liquid preparation such as solution, suspension, and emulsion. On the other hand, when they are administered parentally, for example, they can be administered as an injection solution or an infusion solution, using distilled water for injection, physiological saline, aqueous glucose solution, etc., or they may be administered as a suppository, and the like.

A dose of the compound [I] or a pharmaceutically acceptable salt thereof of the present invention may vary depending on an administration method, an age, a body weight or a condition of a patient, etc., and, for example, in case of oral administration, it is usually administered in a dose of 0.1 to 20 mg/kg per day, and particularly preferably 0.1 to 10 mg/kg per day, and in case of parental administration, usually in a dose of 0.01 to 10 mg/kg per day, particularly preferably 0.01 to 1 mg/kg per day.

[Method A]

The target compound [I] of the present invention can be prepared, for example, by reacting the compound of the formula [II]:

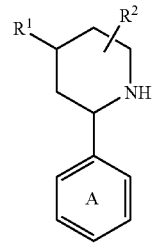

wherein Ring A represents an optionally substituted benzene ring, $R^1$ is an optionally substituted alkyl group, an optionally substituted hydroxyl group, a substituted thiol group, a substituted carbonyl group, a substituted sulfinyl group, a substituted sulfonyl group, or a group of the formula:

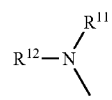

wherein $R^{11}$ and $R^{12}$ are the same or different and each is hydrogen atom, a substituted carbonyl group, a substituted sulfonyl group, an optionally substituted alkyl group or a heterocyclic group containing 1 to 4 atom(s) selected from nitrogen atom, oxygen atom and sulfur atom as a hetero atom, wherein the heterocyclic group is optionally substituted, and the nitrogen atom contained in the heterocyclic group is optionally oxidized, or $R^{11}$ and $R^{12}$ are taken together, with an adjacent nitrogen atom, to form a heterocyclic group selected from piperidino group, azacycloheptyl group, pyrrolidino group, thiazolidyl group, morpholino group, triazolyl group, tetrazolyl group and purinyl group, wherein the heterocyclic group is optionally substituted, and the nitrogen atom contained in the heterocyclic group is optionally oxidized, $R^2$ represents hydrogen atom, an optionally substituted hydroxyl group, an optionally substituted amino group, an optionally substituted alkyl group, a substituted carbonyl group or a halogen atom, with the compound of the formula [III]:

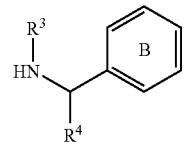

wherein Ring B represents an optionally substituted benzene ring, $R^3$ represents hydrogen atom or an optionally substituted alkyl group, and $R^4$ represents hydrogen atom or an optionally substituted alkyl group, in the presence of urea.

[Method B]

In the target compounds [I] of the present invention, the compound of the formula [I-a]:

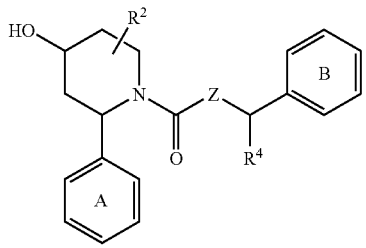

[I-a]

wherein Ring A, Ring B, $R^2$, Z, $R^3$ and $R^4$ have the same meanings as defined above, can be prepared, for example, by reducing the compound of the formula [IV]:

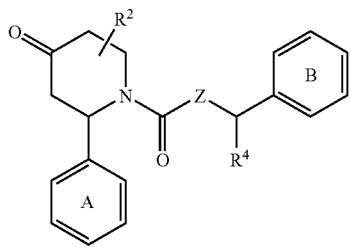

[IV]

wherein Ring A, Ring B, $R^2$, Z, $R^3$ and $R^4$ have the same meanings as defined above.

[Method C]

In the compounds of the present invention, the compound of formula [I-b]:

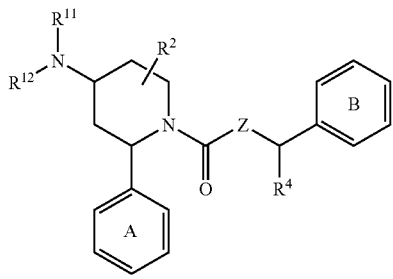

[I-b]

wherein Ring A, Ring B, $R^{11}$, $R^{12}$ $R^2$ Z, $R^3$ and $R^4$ have the same meanings as defined above, can be prepared by reacting the compound of the formula [IV]:

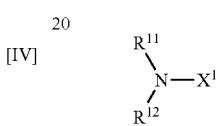

[IV]

wherein Ring A, Ring B, $R^2$, Z, $R^3$ and $R^4$ have the same meanings as defined above, with the compound of the formula [V]:

$$\begin{array}{c} R^{11} \\ \phantom{R}\diagdown \\ N\!-\!X^1 \\ \phantom{R}\diagup \\ R^{12} \end{array} \qquad [V]$$

wherein $X^1$ represents hydrogen atom, hydroxyl group, a silicon atom, lithium atom or magnesium atom, $R^{11}$ and $R^{12}$ have the same meaning as defined above.

[Method D]

In the compounds of the present invention, the compound of the formula [I-c]:

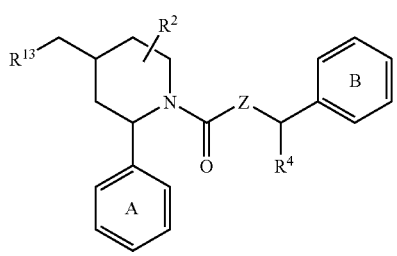

[I-c]

wherein Ring A, Ring B, $R^2$, Z, $R^3$ and $R^4$ have the same meanings as defined above, and $R^{13}$ represents an optionally substituted carboxyl group, can be prepared by reacting the compound of the formula [IV]:

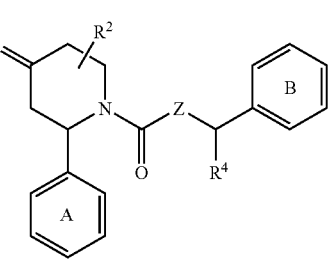

[IV]

wherein Ring A, Ring B, $R^2$, Z, $R^3$ and $R^4$ have the same meanings as defined above, with the compound of the formula [VI]:

X²CH₂R¹³     [VI]

wherein X² represents a leaving group, and R¹³ has the same meaning as defined above, and reducing the resulting compound of the formula[VII]:

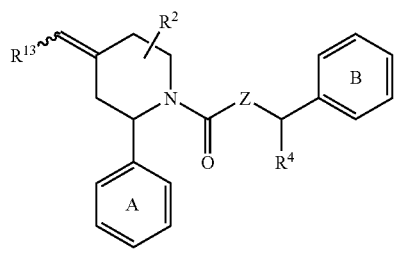

[VII]

wherein Ring A, Ring B, R¹³, Z, R², R³ and R⁴ have the same meanings as defined above.

[Method E]

In the compounds of the present invention, the compound of the formula [I″]:

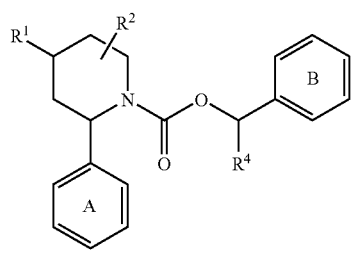

[I″]

wherein Ring A, Ring B, R¹, R² and R⁴ have the same meanings as defined above, can be prepared by reacting the compound of the formula [II]:

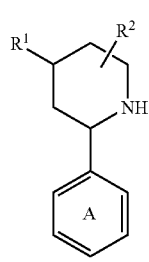

[II]

wherein Ring A, R¹ and R² have the same meanings as defined above, with the compound of the formula [III′]:

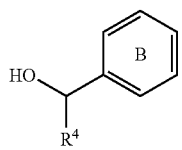

[III′]

wherein Ring B and R⁴ have the same meanings as defined above, in the presence of an urea bond forming agent.

These [Method A] to [Method E] can be carried out as described bellow.

[Method A]

The reaction of the compound [II] with the compound [III] can be carried out in a suitable solvent in the presence of an urea bond forming agent. The urea bond forming agent is exemplified by the compounds shown by the formula:

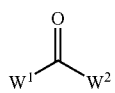

wherein W¹ and W² are the same or different, and each represents a leaving group, and the like.

W¹ and W² are the same or different and each is exemplified by an imidazolyl group, a halogen atom, phenoxy group and the like. Specifically preferred are 1,1'-carbonyldiimidazole, a phosgene and the like, and carbonyldihalides such as 1,1'-carbonyldiimidazole, a triphosgene or a phosgene etc. can be used. Further, any solvent can be used as long as it does not exert any bad effect on the reaction, for example, acetonitrile, dichloromethane, tetrahydrofuran etc. can be used appropriately. This reaction can proceed, for example, at 0° C. to 80° C., preferably at 0° C. to 50° C.

Further, in this reaction, the compound [I] can be prepared also by reacting the compound [II] with the urea bond forming agent of the formula:

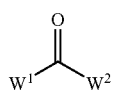

wherein W¹ and W² are the same or different and each represents a leaving group, to give the resulting compound of the formula [VIII-a]:

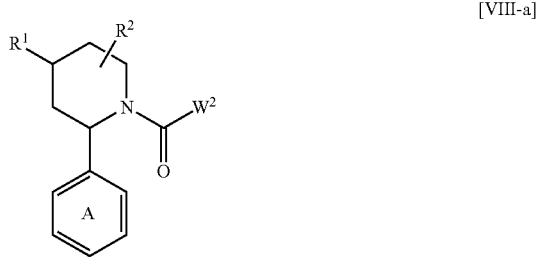

[VIII-a]

wherein Ring A, R¹, R² and W² have the same meanings as above, subsequently leading the compound [VIII-a] to a reactive derivative thereof, and reacting the same with the compound [III], or alternatively, the compound [I] can be prepared by reacting the compound [III] and the urea bond forming agent of the formula:

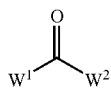

wherein $W^1$ and $W^2$ have the same meanings as defined above, to give the resulting compound of the formula [VIII-b]:

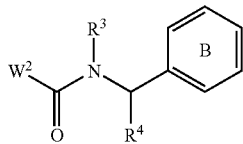

[VIII-b]

wherein Ring B, $R^3$, $R^4$ and $W^2$ have the same meanings as defined above, subsequently leading the compound [VIII-b] to a reactive derivative thereof, and reacting the same with the compound [II].

As the reactive derivative, there are mentioned a compound in which $W^2$ is lead to a group as shown by the formula:

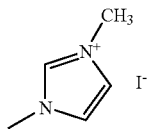

in the compound [VIII-a] or the compound [VIII-b], and the like.

The reaction of the compound [II] or the compound [III] with the urea linkage forming argent can proceed, for example, at 0° C. to 80° C., preferably at 0° C. to 50° C. Further, any solvent can be used as long as it does not exert any bad effect on the reaction, for example, acetonitrile, dichloromethane, tetrahydrofuran, etc. can be used appropriately.

The reaction to lead the compound [VIII-a] or the compound [VIII-b] to a reactive derivative thereof can be carried out using a derivative-leading agent such as methyl iodide, for example, 0° C. to 80° C., preferably at 0° C. to 50° C. Further, any solvent can be used as long as it does not exert any bad effect on the reaction, for example, acetonitrile, dichloromethane, tetrahydrofuran, etc. can be used appropriately.

The reaction of each reactive derivative with the compound [III] or the compound [II] can be carried out in the presence of a base, for example, at 0° C. to 80° C., preferably at 0° C. to 50° C. Further, triethylamine etc. can be used as a base, and any solvent can be used as long as it does not exert any bad effect on the reaction, for example, acetonitrile, dichloromethane, tetrahydrofuran, etc. can be used appropriately.

[Method B]

The reduction of the compound [IV] can be carried out in the presence of a reductive agent in suitable solvent. As a reductive agent, sodium borohydride and the like is preferred, for example, sodium borohydride, aluminum hydride such as diisobutyl aluminum hydride etc. can be used. Further, any solvent can be used as long as it does not exert any bad effect on the reaction, for example, ethanol, tetrahydrofuran, dichloromethane, etc. can be used appropriately. This reaction can be carried out, for example, at −70° C. to under reflux, preferably, at −70° C. to 20° C.

[Method C]

The reaction of the compound [IV] with the compound [V] can be carried out in a suitable solvent by subjecting the compounds to a reductive amination reaction. This reductive amination reaction can be carried out in acidic condition by hydrogenation in the presence of a reductive agent such as sodium borohydride, triacetoxysodium borohydride, sodium cyanoborohydride or a reduction catalyst such as palladium. As the group [$X^1$] in the compound [V], there are mentioned, for example, hydrogen atom, hydroxyl group, silicon atom, lithium atom or magnesium atom, and preferred are hydrogen atom and hydroxyl group. Any solvent can be used as long as it does not exert any bad effect on the reaction, for example, dichloromethane, acetic acid, ethanol, methanol, etc. can be used appropriately. As a salt of the compound [V], hydrochloride, acetate, etc. can be used appropriately. The present reaction can proceed, for example, at −10° C. to 80° C., preferably at 0° C. to 30° C.

[Method D]

The reaction of the compound [IV] with the compound [VI] can be carried out optionally in the presence of a base in a suitable solvent. As the leaving group [$X^2$] of the compound [VI], there are mentioned diethylphosphono group, triphenylphophinyl group, etc. As the base, there are mentioned, for example, potassium-tert-butoxide, triethylamine, sodium hydroxide, etc., and preferred are potassium-tert-butoxide, triethylamine, and the like. Further, any solvent can be used as long as it does not exert any bad effect on the reaction, for example, tetrahydrofuran, dichloromethane, etc. can be used appropriately. The present reaction can proceed, for example, at −30° C. to 80° C., preferably at −20° C. to 30° C.

Further, the reduction of the compound [VII] can be carried out by a conventional method, by hydrogenation in the presence of a reduction catalyst such as palladium, etc. As the solvent, methanol, ethanol, etc. can be used appropriately. The present reaction can proceed, for example, at 0° C. to 50° C.

[Method E]

The reaction of the compound [II] with the compound [III'] can be carried out in the presence of a urea bond forming agent in a suitable solvent. As the urea bond forming agent, those as shown by the formula:

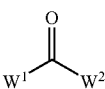

wherein $W^1$ and $W^2$ are the same or different, and each represents a leaving group.

As $W^1$ and $W^2$, being the same or different, there are mentioned imidazolyl group, a halogen atom or phenoxy group and the like. Specifically, 1,1'-carbonyldiimidazole, phosgene are preferred and for example, carbonyldihalide such as 1,1'-carbonyldiimidazole, triphosgene, phosgene, etc. may be used. Further, any solvent can be used as long as it does not exert any bad effect on the reaction, for example, acetonitrile, dichloromethane, tetrahydrofuran, etc. can be used appropriately. The present reaction can proceed, for example, at 0° C. to 80° C., preferably at 0° C. to 50° C.

Further, the compound [I"] can be prepared by reacting the compound [II] with the urea bond forming agent of the formula:

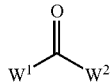

wherein W¹ and W² are the same or different, and each represents a leaving group, to give the compound of the formula [VIII-a]:

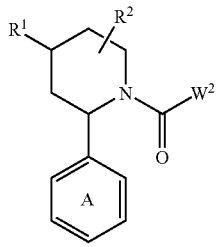

[VIII-a]

wherein Ring A, R¹, R² and W² have the same meanings as defined above, subsequently leading the compound [VIII-a] to a reactive derivative thereof, and reacting the same with the compound [III'], or alternatively, the compound [I"] can be prepared by reacting the compound [III'] with the urea bond forming agent of the formula:

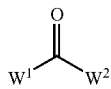

wherein W¹ and W² have the same meanings as defined above, to give the compound of the formula [VIII']:

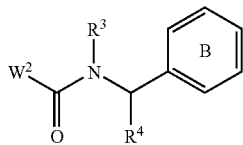

[VIII']

wherein Ring B, R⁴ and W² have the same meanings as defined above, subsequently leading the compound [VIII'] to a reactive derivative thereof, and reacting the same with the compound [II].

As the reactive derivative, for example, the compound in which W² is lead to the group as shown by the formula:

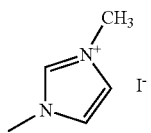

in the compound [VIII-a] or the compound [VIII'].

The reaction of the compound [II] or the compound [III'] with a urea bond forming agent can proceed, for example, at 0° C. to 80° C., preferably at 0° C. to 50° C. Further, any solvent can be used as long as it does not exert any bad effect on the reaction, for example, acetonitrile, dichloromethane, tetrahydrofuran, etc. can be used appropriately.

The reaction to lead the compound [VIII-a] or the compound [VIII'] to a reactive derivative thereof can be carried out using a derivative-leading agent such as methyl iodide, for example, 0° C. to 80° C., preferably at 0° C. to 50° C. Further, any solvent can be used as long as it does not exert any bad effect on the reaction, for example, acetonitrile, dichloromethane, tetrahydrofuran, etc. can be used appropriately.

The reaction of each reactive derivative with the compound [III] or the compound [II] can be carried out in the presence of a base, for example, at 0° C. to 80° C., preferably at 0° C. to 50° C. Further, triethylamine etc. can be used as a base, and any solvent can be used as long as it does not exert any bad effect on the reaction, for example, acetonitrile, dichloromethane, tetrahydrofuran, etc. can be used appropriately.

The compound [I] of the present invention can be also prepared by converting the group R¹ and group R³ of the compound obtained in the above described method, to a desired substituent. Method for conversion of the, substituents can be appropriately selected, depending on kinds of desired substituents, and the following (method a) to (method q) can be employed.

(Method a)

The compound [I] in which R¹ is a group comprising a substituted hydroxyl group (for example, an optionally substituted alkoxy group, a substituted carbonyloxy group or alkylsulfonyloxy group, etc.) in the formula [I] can be prepared by subjecting the corresponding compound having hydroxyl group as R¹ to alkylation, acylatoin or sulfonylation by a conventional method. For example, alkylation can proceed at −10° C. to 80° C., acylatoin can proceed at 5° C. to 80° C., and sulfonylation can proceed at 5° C. to 80° C.

(Method b)

The compound [I] in which R¹ is a group comprising a substituted amino group in the formula [I] can be prepared by substituting the corresponding compound having an amino group as R¹ with substituent(s) of the amino group by a conventional method (for example, an alkoxycarbonyl group such as tert-butoxycarbonyl, an arylalkoxycarbonyl group such as benzyloxycarbonyl group, etc., an alkanoyl group such as formyl group, acetyl group, propionyl group, etc., an alkyl group such as methyl group, ethyl group, propyl group, etc., an alkylsulfonyl group such as methanesulfonyl group, ethanesulfonyl group, etc., an alkenylsulfonyl group such as vinylsulfonyl group, etc., a heterocyclic group such as pyridyl group, etc., etc.). Alternatively, it can be prepared by using a carbamate synthesizing reagent such as N,N'-succinimidyl-carbonate, etc., by reacting with, for example, an alkoxyalkylalcohol, etc. Substitution can be suitably carried out by a conventional method, depending on the kinds of the substituent, by alkylation, acylation, sulfonylation, arylatoin, etc. Further, by substituting the hydrogen atom on the amino group, it can be made into a di-substituted compound. The present reaction can proceed at −20° C. to 50° C.

Further, in case that the compound [I] in which $R^1$ is a group comprising a substituted amino group has a urea bond, it can be prepared by reacting the corresponding amine compound and a urea bond forming agent, according to the same manner as in [method A] or, a method described in Japanese Provisional Patent Publication No. 10-195037.

Further, the compound [I] in which $R^1$ is a group comprising a substituted amino group in the formula [I] can be prepared by adding an amino group-containing compound to the corresponding compound having a carbon-carbon double bond at $R^1$. The present reaction can be carried out by refluxing a solvent under heating, or in the absence of a catalyst.

(Method c)

The compound [I] in which $R^1$ is a group comprising an amino group in the formula [I] can be prepared by removing a protective group from the corresponding compound having a protected amino group at $R^1$. Removal of the protecting group can be carried out by a conventional method (for example, acid treatment, base treatment, catalytic reduction, etc.). In the present reaction, a reaction by acid treatment can proceed at 5° C. to 120° C., a reaction by base treatment can proceed at 5° C. to 40° C., and a reaction by catalytic reduction can proceed at 10° C. to 40° C.

Further, the compound [I] in which $R^1$ is a group comprising an amino group in the formula [I] can be prepared by reducing the corresponding compound having a nitro group at $R^1$. Reduction can be carried out, in the presence of an acid, by reacting tin chloride, zinc, etc. For example, the present reaction can be carried out while refluxing the solvent under heating.

Further, the compound [I] in which $R^1$ is a group comprising an amino group in the formula [I] can be prepared by subjecting the corresponding compound having a carboxyl group at $R^1$ to Curtius rearrangement, etc. Curtius rearrangement can be carried out, for example, according to the method described in Advanced Organic Chemistry, vol.4, page 1054. That is, it can be carried out by converting a carboxyl group into an acid chloride by thionyl chloride, etc., and subsequently, subjecting the same to azidation by sodium azide, etc., followed by hydrolysis.

(Method d)

The compound [I] in which $R^1$ is a group comprising hydroxyl group in the formula [I] can be prepared by removing a protective group from the corresponding compound having a protected hydroxyl group at $R^1$ by a conventional method. Removal of the protecting group can be carried out by acid treatment, base treatment, catalytic reduction, etc. depending on the kinds of the protecting group. The present reaction can proceed, for example, at 0° C. to 80° C., particularly preferably at 5° C. to 50° C.

Further, the compound [I] in which $R^1$ is a group comprising hydroxyl group in the formula [I] can be prepared by reducing the corresponding compound having a formyl group at $R^1$. Reduction can be carried out by reacting the compound in the presence of a reductive agent such as sodium borohydride, etc. The present reaction can proceed, for example, at −80° C. to 80° C., particularly preferably at −70° C. to 20° C.

Further, the compound [I] in which $R^1$ is a group comprising hydroxyl group in the formula [I] can be prepared by reducing the corresponding compound having an ester or a carboxyl group at $R^1$. Reduction can be carried out by reacting the compound in the presence of a reductive agent such as lithium aluminum hydride, etc. The present reaction can proceed, for example, at −50° C. to 200° C., particularly preferably at −20° C. to 60° C.

(Method e)

In case that $R^1$ in the formula [I] is hydroxyl group and it has an asymmetric center at the bonding portion, the configuration of the compound can be converted to the opposite configuration, for example, according to a method of Mitsunobu, et al. as described in Synthesis, pages 1 to 28, 1981. Specifically, conversion can be carried out by reacting the compound in the presence of triphenylphosphine, benzoic acid and diethylazodicarboxylate, in a suitable solvent. The present reaction can proceed, for example, at 0° C. to 60° C., particularly preferably at 5° C. to 40° C.

(Method f)

The compound [I] in which $R^1$ is a group comprising an optionally substituted thiol group in the formula [I] can be prepared by reacting the corresponding compound having hydroxyl group at $R^1$ with the corresponding compound comprising a thiol group, for example, according to a method of Mitsunobu, et al. as described in Synthesis, pages 1 to 28, 1981. Specifically, reaction can be carried out by reacting the compound in the presence of triphenylphosphine, and diethylazodicarboxylate, in a suitable solvent. The present reaction can proceed, for example, while refluxing a solvent under heating.

The compound [I] in which $R^1$ is a group comprising an optionally substituted thiol group in the formula [I] can be prepared by reacting the corresponding compound [I] having a halogen atom at $R^1$ with the corresponding compound comprising a thiol group. The present reaction can proceed, for example, at −50° C. to 150° C., particularly preferably at 10° C. to 100° C.

Still further, the compound [I] in which $R^1$ is a group comprising an alkylthio group can be prepared by subjecting the corresponding compound [I] having a thiol group at $R^1$ or the corresponding compound having a protective thiol group (for example, an acetylated thiol group) to alkylation. The present reaction can proceed in the presence of a base, for example, at −10° C. to 80° C., particularly preferably at 5° C. to 50° C.

(Method g)

The compound [I] in which $R^1$ in the formula [I] is a group comprising a substituted amino group can be prepared by subjecting the corresponding compound [I] having hydroxyl group at $R^1$ to amination, for example, according to a method of Mitsunobu, et al. as described in Synthesis, pages 1 to 28, 1981.

(Method h)

The compound [I] in which $R^1$ in the formula [I] is a group comprising a free carboxyl group can be prepared by subjecting the corresponding compound [I] having an esterificated carboxyl group at $R^1$ to deesterification, according to the conventional method (for example, by hydrolysis with a base such as sodium hydroxide, etc., acid treatment with hydrogen chloride, hydrogen bromide, etc., reduction under hydrogen atmosphere using palladium (black), palladium carbon, etc., depending on the kinds of the ester residue). In the deesterification reaction, for example, hydrolysis with a base can proceed, at 5° C. to 70° C., acid treatment can proceed at 5° C. to 80° C., reduction can proceed at 10° C. to 40° C.

(Method i)

The compound [I] in which $R^1$ in the formula [I] is a group comprising an amido bond can be prepared by reacting the corresponding compound [I] having a free carboxyl group at $R^1$ with the corresponding amine compound, or by reacting the corresponding compound [I] having a free amino group at $R^1$ with the corresponding carboxylic acid compound, in the presence or in the absence of a condensing agent. As the condensing agent, there are used 1,1'-carbonyldiimidazole, 1,3-dicyclohexylcarbodiimide, 1-ethyl-3-(3-dimethylaminopropyl)carbodiimide hydrochloride, isobutyl chloroformate or N-methylmorpholine, etc., which are normally used in a reaction to form an amide bond from a carboxylic acid and an amine. The present reaction can proceed, for example, at $-20°$ C. to $50°$ C.

(Method j)

The compound [I] in which $R^1$ in the formula [I] is a group comprising a heterocyclic group whose nitrogen atom is substituted by an oxo group (a nitrogen atom is oxidized) (for example, N-oxomorpholino group, etc.) can be prepared by treating the corresponding compound [I] having a heterocyclic group at $R^1$ with an oxidizing agent (for example,3-chloroperbenzoic acid, hydrogen peroxide, peracetic acid, oxone, etc.). The present reaction can proceed, for example, at $5°$ C. to $50°$ C.

(Method k)

The compound [I] in which $R^1$ in the formula [I] is a group comprising a heterocyclic group whose nitrogen atom is oxidized, other than the compound of the above (method j) (for example, N-alkyl-4-morpholino group, etc.) can be prepared by reacting the corresponding compound [I] having a heterocyclic group at $R^1$ with an alkyl halide. The present reaction can proceed, for example, at $20°$ C. to $80°$ C.

(Method l)

The compound [I] in which $R^3$ in the formula (I) is an alkyl group can be prepared by subjecting the corresponding compound [I] in which $R^3$ is hydrogen atom to alkylation by a conventional method. The alkyl group may be substituted. The present reaction can proceed, for example, at $20°$ C. to $80°$ C.

(Method m)

The compound [I] in which $R^1$ in the formula [I] is a group comprising a group whose sulfur atom is mono-substituted by an oxo group (for example, a sulfinyl group, etc.) can be prepared by treating the corresponding compound [I] having a thio group at $R^1$ with an oxidizing agent (for example, 3-chloroperbenzoic acid, peracetic acid, sodium periodate, oxone, etc.). The present reaction can proceed, for example, at $-80°$ C. to $150°$ C., particularly preferably at $0°$ C. to $40°$ C.

(Method n)

The compound [I] in which $R^1$ in the formula [I] is a group comprising a group whose sulfur atom is di-substituted by oxo groups (for example, a sulfonyl group, etc.) can be prepared by treating the corresponding compound [I] having a thio group at $R^1$ with an oxidizing agent (for example, 3-chloroperbenzoic acid, peracetic acid, sodium periodate, oxone, etc.). The present reaction can proceed, for example, at $-80°$ C. to $150°$ C., particularly preferably at $0°$ C. to $40°$ C.

(Method o)

The compound [I] in which $R^1$ in the formula [I] is a group comprising an amino group can be prepared by subjecting the corresponding compound [I] having a carbonyl group at $R^1$ to reductive amination. The present reaction can be carried out in the same manner as in [Method C] mentioned above.

(Method p)

The compound [I] in which $R^1$ in the formula [I] is a group comprising a sulfinic acid can be prepared by reacting the corresponding compound [I] having an alkylsulfinyl group at $R^1$, for example, according to a method described in Synlett, April, pages 375 to 377, 1997.

(Method q)

The compound [I] in which $R^1$ in the formula [I] is a group comprising an imidazolidinyl group or a hexahydropyrimidinyl group can be prepared by subjecting the corresponding compound [I] having an aminoalkylamino group at $R^1$ to cyclization, for example, in the presence of a condensing agent such as a 1,1'-carbonyldiimidazole, etc. The present reaction can proceed, for example, at $-20°$ C. to $50°$ C.

As the solvents to be used in the reactions described in the above (method a) to (method q), any solvent can be used as long as it does not affect the reaction, for example, those can be used by appropriately selecting from dioxane, ethylene glycol dimethylether, dimethylacetamide, dimethylformamide, hexamethylphosphoramide, benzene, tetrahydrofuran, toluene, ethyl acetate, an alcohol, dichloromethane, carbon tetrachloride, 1,3-dimethyl-2-imidazolidine, acetic acid, diethyl ether, methoxyethane, dimethylsulfoxide, acetonitrile, water and the mixture thereof.

Incidentally, the compound [IV] as the starting material in the present invention is a novel compound, and it can be prepared, for example, as shown in the chemical formula below:

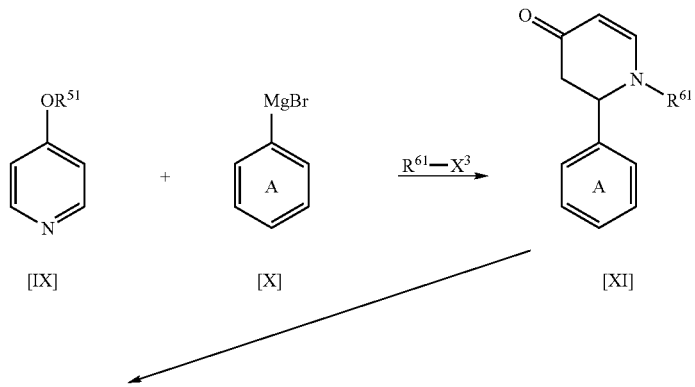

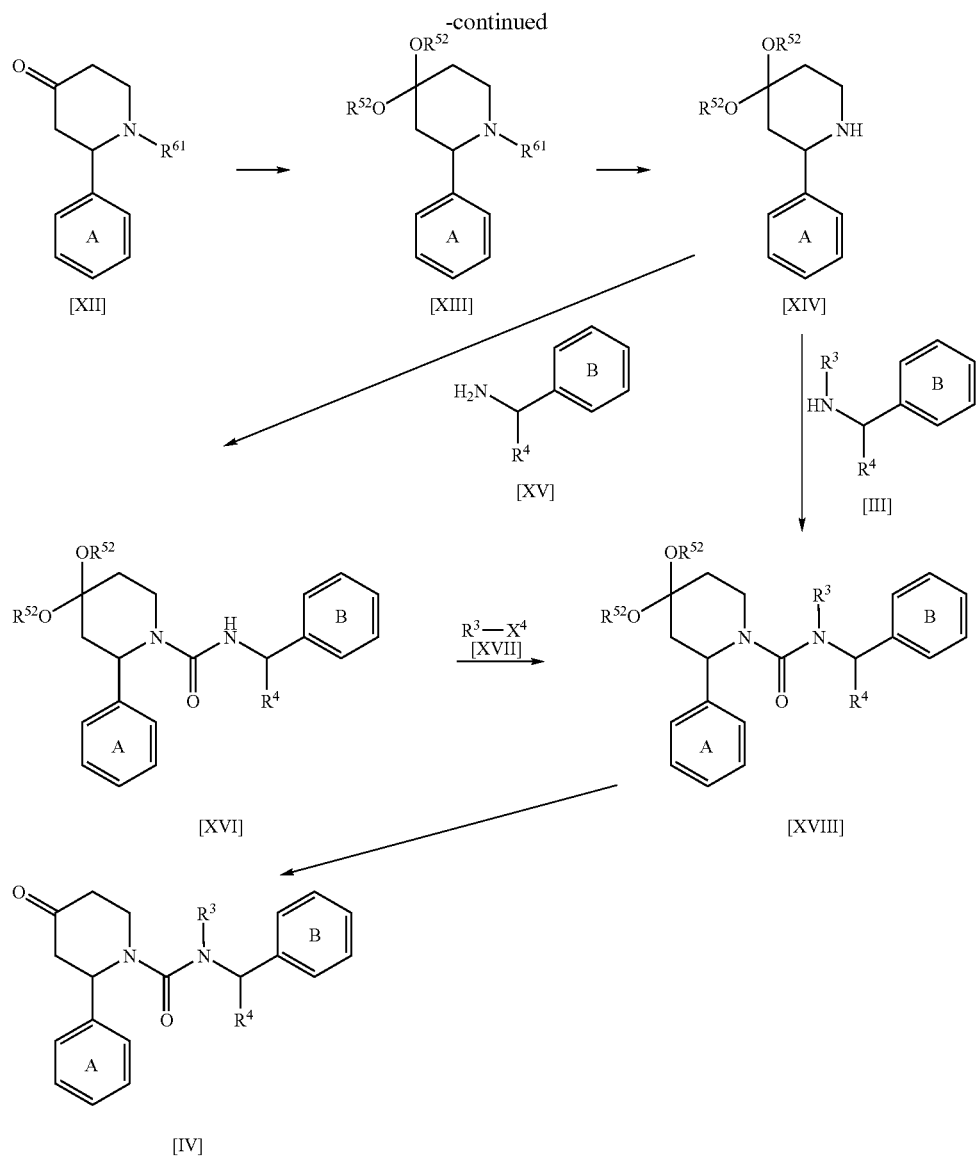

wherein $R^{51}$ represents an alkyl group, $R^{61}$ represents a protecting group for an amino group, $R^{52}$ represents an alkyl group which may form a bond at a terminal thereof, $X^3$ represents a leaving group, $X^4$ represents a leaving group, and Ring A, Ring B, $R^3$ and $R^4$ have the same meanings as defined above.

That is, pyridine compound [IX] and Grignard compound [X] are subjected to a condensation reaction, and further, an amino group is protected, to give a compound [XI]. Subsequently, it is subjected to a reduction reaction, to give a compound [XII]. Further, a carbonyl group of the compound [XII] is protected by a ketal, to prepare a compound [XIII], the protecting group for the amino group is removed, to give a compound [XIV]. Subsequently, the compound [XIV] and the compound [XV] are subjected to a condensation reaction, to give a compound [XVI], followed by reacting the same with a compound [XVII], or the compound [XIV] and the compound [III] are subjected to a condensation reaction, to give a compound [XVIII], and by removing the protecting group thereof, to give a compound [IV].

The compound [IV] has an asymmetric carbon, therefore, optical isomers are present based on the asymmetric carbon. By using an optical isomer of the above described compound [XIV], a desired optical isomer of the compound [IV] can be prepared.

The optical isomer of the compound [XIV] can be prepared by subjecting the racemic mixture of the compound [XIV] to an optical resolution by a conventional method. The optical resolution can be carried out, for example, by reacting the compound [XIV] with N-acyl-optically active amino acid or N-sulfonyl-optically active amino acid, to give two kinds of diastereomeric salts, and by separating and collecting one of the diastereomeric salts, using a difference in solubilities thereof.

The acyl group of N-acyl-optically active amino acid is exemplified by acetyl group, propionyl group, tosyl group or benzyloxycarbonyl group, and the optically active amino acid is exemplified by L-phenylalanine, L-leucine, L-glutamine, L-methionine, L-valine, L-threonine, D-phenylalanine or D-phenylglycine.

Further, the compound [II] as the starting material in the present invention is a novel compound, and it can be prepared, for example, as shown in the chemical formula below:

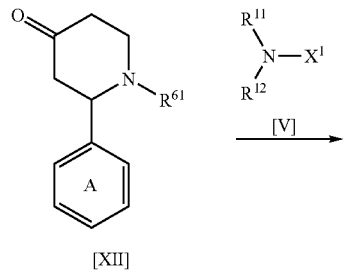

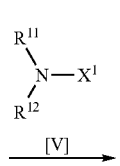

[XII]

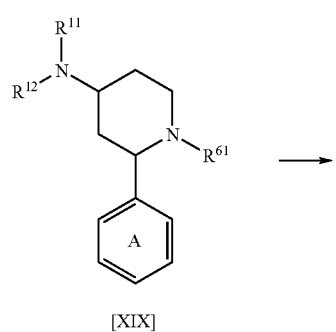

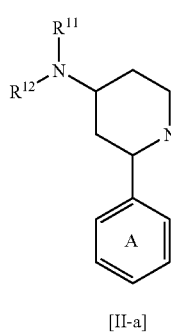

[XIX]   [II-a]

wherein Ring A, $R^{11}$, $R^{12}$, $R^{61}$ and $X^1$ have the same meanings as defined above.

That is, the compound [XII] and the compound [V] are subjected to a reductive amination, to give a compound [XIX], and by removing the protecting group of the amino group thereof, a compound [II-a] is prepared. Reductive amination can be carried out in the same manner as in [Method C].

In preparing the above compound [IV], each of the intermediate compounds are not limited to those as shown in the reaction formula, and a salt thereof or a reactive derivative thereof may be suitably used, as long as it does not affect the reaction.

Further, in the starting material [II] of the present invention, the compound [II-b] can be prepared, for example, as shown in the chemical formula below:

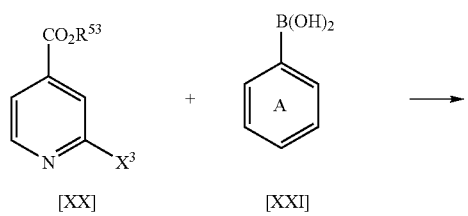

[XX]   [XXI]

-continued

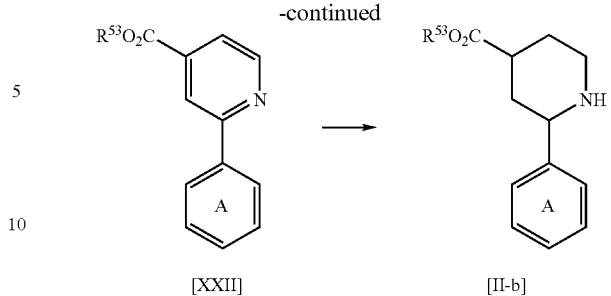

[XXII]   [II-b]

wherein $R^{53}$ represents an alkyl group, $X^3$ represents a halogen atom and Ring A has the same meaning as defined above.

That is, pyridine compound [XX] and the compound [XXI] are condensed, and the resulting compound [XXII] is reduced, to give a compound [II-b].

Further, in the starting materials of the present invention, the compound of the formula [II-c]:

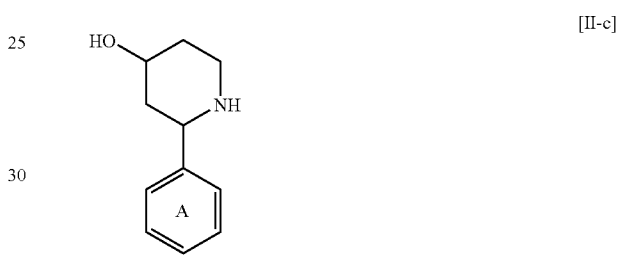

[II-c]

wherein a symbol has the same meaning as defined above, can be prepared as shown below.

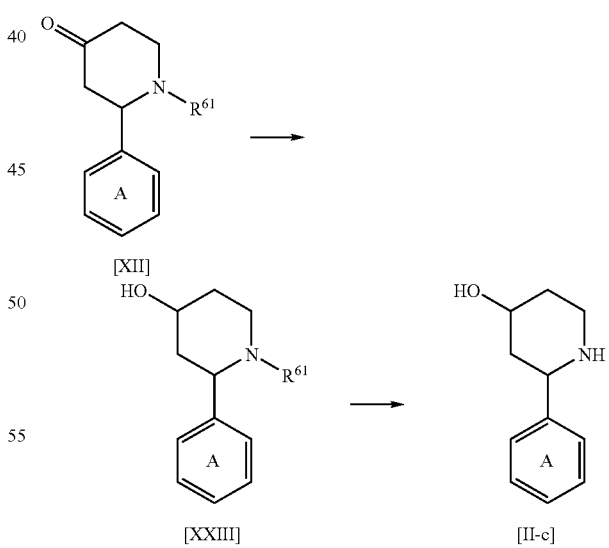

[XII]

[XXIII]   [II-c]

wherein symbols have the same meanings as defined above.

That is, the compound [XII] is reduced, to give a compound [XXIII], and deprotection of the amino group of the obtained compound [XXIII] is carried out to give the compound [II-c].

Although there are optical isomers of the compound [II-c], in the similar method as in the above mentioned optical resolution for the compound [XIV], it can be prepared by optical resolution from a racemic mixture.

Further, in preparation of the compound or the starting materials of the present invention, when the starting materials or the intermediates have a functional group, suitable protecting groups can be introduced to each of the functional group, by a conventional method, besides the above described method, and if they are not necessary, these protecting groups can be suitably removed.

In the present specification, the alkyl group means, for example, a straight or branched alkyl group having 1 to 6 carbon atoms such as methyl group, ethyl group, propyl group, butyl group, isobutyl group, tert-butyl group, isopentyl group, etc., preferably those having 1 to 4 carbon atoms. The alkenyl group means, for example, a straight or branched alkenyl group having 2 to 7 carbon atoms such as vinyl group, aryl group, propenyl group, isopropenyl group, etc., preferably those having 1 to 4 carbon atoms. The alkoxy group means a straight or branched alkoxy group having 1 to 6 carbon atoms such as methoxy group, ethoxy group, propoxy group, isopropoxy group, butoxy group, etc., preferably those having 1 to 4 carbon atoms. The alkanoyl group means a straight or branched alkanoyl group having 1 to 6 carbon atoms such as formyl group, acetyl group, propionyl group, butyryl group, valeryl group, tert-butylcarbonyl group, etc., preferably those having 1 to 4 carbon atoms. The cyclic lower alkyl group means a cycloalkyl group having 3 to 8 carbon atoms such as cyclopropyl group, cyclobutyl group, cyclopentyl group, cyclohexyl group, cycloheptyl group, cyclooctyl group, etc., preferably tose having 3 to 6 carbon atoms. Further, the halogen atom is exemplified by chlorine atom, bromine atom, fluorine atom and iodine atom.

EXAMPLES

In the following, the present invention will be explained in more detail by referring to Examples and Reference Examples, but the present invention is not limited by these Examples.

Example 1

(1) In 30 ml of methanol was dissolved 1.43 g of 1-{N-(3,5-bistrifluoromethylbenzyl)-N-methyl}aminocarbonyl-2-(4-fluoro-2-methylphenyl)-4-oxopiperidine, and 114 mg of sodium borohydride was added thereto. The mixture was stirred at room temperature for 3 hours. To the reaction mixture were added an aqueous ammonium chloride solution and ethyl acetate, and after stirring the mixture, layers were separated. The organic layer was washed with water and brine and dried, and then, the solvent was removed by distillation under reduced pressure. The residue was purified by silica gel column chromatography (chloroform:acetone=4:1), to give 0.99 g of 1-{N-(3,5-bistrifluoromethylbenzyl)-N-methyl}aminocarbonyl-2-(4-fluoro-2-methylphenyl)-4-hydroxypiperidine as shown in Table 1 below.

(2) 200 mg of the compound of the above (1) was further purified by silica gel column chromatography (hexane:ethyl acetate=4:1), to give 18 mg of (a) trans-1-{N-(3,5-bistrifluoromethylbenzyl)-N-methyl}aminocarbonyl-2-(4-fluoro-2-methylphenyl)-4-hydroxypiperidine and 125 mg of (b) cis-1-{N-(3,5-bistrifluoromethylbenzyl)-N-methyl}aminocarbonyl-2-(4-fluoro-2-methylphenyl)-4-hydroxypiperidine as shown in Table 1 below.

Example 2

In 10 ml of tetrahydrofuran was dissolved 200 mg of (2R)-1-[N-{1-(S)-(3,5-bistrifluoromethylphenyl)ethyl}-N-methyl]aminocarbonyl-2-(4-fluoro-2-methylphenyl)-4-oxopiperidine, and 60 mg of sodium borohydride was added thereto and the mixture was refluxed. While continuously refluxing the mixture, a mixed solvent of 1 ml of methanol and 5 ml of tetrahydrofuran was added thereto dropwise. After 5 hours, the reaction mixture was poured into water and layers were separated. The aqueous layer was extracted with ethyl acetate, and the combined organic layers were washed with water and saturated brine and dried, and then, the solvent was removed by distillation under reduced pressure. The residue was purified by silica gel column chromatography (hexane:ethyl acetate=1:1→1:2), to give 33 mg of (a) (2R,4R)-1-[N-{1-(S)-(3,5-bistrifluoromethylphenyl)ethyl}-N-methyl]aminocarbonyl-2-(4-fluoro-2-methylphenyl)-4-hydroxypiperidine and 160 mg of (b) (2R,4S)-1-[N-{1-(S)-(3,5-bistrifluoromethylphenyl)ethyl}-N-methyl]aminocarbonyl-2-(4-fluoro-2-methylphenyl)-4-hydroxypiperidine as shown in Table 2 below.

Example 3

(2R)-1-[N-(3,5-bistrifluoromethylbenzyl)-N-methyl]aminocarbonyl-2-(4-fluoro-2-methylphenyl)-4-oxopiperidine was used and treated in the same manner as in Example 2 to give (a) (2R,4R)-1-{N-(3,5-bistrifluoromethylbenzyl)-N-methyl}aminocarbonyl-2-(4-fluoro-2-methylphenyl)-4-hydroxypiperidine and (b) (2R,4S)-1-{N-(3,5-bistrifluoromethylbenzyl)-N-methyl}aminocarbonyl-2-(4-fluoro-2-methylphenyl)-4-hydroxypiperidine as shown in Table 2 below.

Example 4

In 5 ml of dimethylformamide was dissolved 150 mg of 1-{N-(3,5-bistrifluoromethylbenzyl)-N-methyl}aminocarbonyl-2-(4-fluoro-2-methylphenyl)-4-hydroxypiperidine, and 40 mg of sodium hydride (60%) was added thereto at 0° C. To this solution, 0.2 ml of methyl iodide was added at 0° C., and the mixture was stirred at room temperature for 16 hours. After water and ethyl acetate were added to this solution, and the mixture was stirred, layers were separated. The organic layer was washed with water, dried over magnesium sulfate, and concentrated under reduced pressure. The concentrated residue was purified by silica gel column chromatography (hexane:ethyl acetate=2:1), to give 72 mg of (a) cis-1-{N-(3,5-bistrifluoromethylbenzyl)-N-methyl}aminocarbonyl-2-(4-fluoro-2-methylphenyl)-4-methoxypiperidine and 36 mg of (b) trans-1-{N-(3,5-bistrifluoromethylbenzyl)-N-methyl}aminocarbonyl-2-(4-fluoro-2-methylphenyl)-4-methoxypiperidine as shown in Table 3 below.

Example 5

1-{N-(3,5-bistrifluoromethylbenzyl)-N-methyl}aminocarbonyl-2-(4-fluoro-2-methylphenyl)-4-hydroxypiperidine and 2-picolyl chloride hydrochloride were used and treated in the same manner as in Example 4 above, to give 1-{N-(3,5-bistrifluoromethylbenzyl)-N- methyl}aminocarbonyl-2-(4-fluoro-2-methylphenyl)-4-(2-pyridylmethoxy)piperidine as shown in Table 4 below.

Example 6

In 2 ml of a toluene solution containing 98 mg of 1-{N-(3,5-bistrifluoromethylbenzyl)-N-methyl}aminocarbonyl-2-(4-fluoro-2-methylphenyl)-4-hydroxypiperidine were added 57.6 mg of dimethylaminoethyl chloride hydrochloride, 12.5 mg of tetrabutylammonium bromide and 1 ml of 10M aqueous sodium hydroxide solution at room temperature. After stirring the mixture at room temperature for 2 hours, stirring was further carried out at 60° C. for 16 hours. After completion of the reaction, ethyl acetate and an aqueous sodium hydrogen carbonate solution were added to the reaction mixture and layers were separated. The organic layer was further washed with water, dried over magnesium sulfate, and concentrated under reduced pressure. The residue was purified by silica gel column chromatography (chloroform:methanol=19:1). The obtained oily substance was treated with 4M hydrochloric acid-ethyl acetate solution. The formed precipitates were collected by filtration and dried to give 53 mg of 1-{N-(3,5-bistrifluoromethylbenzyl)-N-methyl}aminocarbonyl-4-(1-dimethylaminoethoxy)-2-(4-fluoro-2-methylphenyl)piperidine hydrochloride as shown in Table 4 below.

Example 7

1-(2-chloroethyl)piperidine hydrochloride and 1-{N-(3,5-bistrifluoromethylbenzyl)-N-methyl}aminocarbonyl-2-(4-fluoro-2-methylphenyl)-4-hydroxypiperidine were treated in the same manner as in Example 6, to give 1-{N-(3,5-bistrifluoromethylbenzyl)-N-methyl}aminocarbonyl-2-(4-fluoro-2-methylphenyl)-4-(1-piperidylethoxy)piperidine hydrochloride as shown in Table 4 below.

Example 8

In 3 ml of dichloromethane was dissolved 100 mg of 1-{N-(3,5-bistrifluoromethylbenzyl)-N-methyl}aminocarbonyl-2-(4-fluoro-2-methylphenyl)-4-oxopiperidine, and added thereto were 0.03 ml of piperidine and 0.018 ml of acetic acid, and the mixture was stirred. 129.7 mg of sodium triacetoxy borohydride was added thereto and the mixture was stirred at room temperature for 12 hours. The reaction mixture was poured into a saturated aqueous sodium bicarbonate solution, layers were separated and the aqueous layer was extracted with dichloromethane. The combined organic layers were washed with water and brine, dried and the solvent was removed by distillation under reduced pressure. Subsequently, the residue was purified by NH silica gel column chromatography (hexane:ethyl acetate=4:1), to give trans-1-{N-(3,5-bistrifluoromethylbenzyl)-N-methyl}aminocarbonyl-2-(4-fluoro-2-methylphenyl)-4-piperidinopiperidine and cis-1-{N-(3,5-bistrifluoromethylbenzyl)-N-methyl}aminocarbonyl-2-(4-fluoro 2-methylphenyl)-4-piperidinopiperidine. Each of the obtained compounds was dissolved in 1 ml of chloroform, respectively, and 0.2 ml of 4M hydrochloric acid-ethyl acetate solution was added thereto. After stirring the mixture for a while, the mixture was concentrated under reduced pressure to give 58 mg of (a) trans-1-{N-(3,5-bistrifluoromethylbenzyl)-N-methyl}aminocarbonyl-2-(4-fluoro-2-methylphenyl)-4-piperidinopiperidine hydrochloride and 16 mg of (b) cis-1-{N-(3,5-bistrifluoromethylbenzyl)-N-methyl}aminocarbonyl-2-(4-fluoro-2-methylphenyl)-4-piperidinopiperidine hydrochloride as shown in Table 5 below.

Examples 9 to 44

The corresponding starting materials were used and treated in the same manner as in Example 8, to give compounds as shown in Tables 6 to 18 below.

Example 45

In 20 ml of acetic acid was dissolved 2.45 g of 1-{N-(3,5-bistrifluoromethylbenzyl)-N-methyl}aminocarbonyl-2-(4-fluoro-2-methylphenyl)-4-oxopiperidine, and 3.85 g of ammonium acetate and 5 g of sodium sulfate were added thereto. The mixture was stirred at room temperature for an hour. Subsequently, 1.18 g of sodium triacetoxy borohydride was added thereto and the mixture was stirred at room temperature for 24 hours. After the reaction was completed, a 2M aqueous sodium carbonate solution, chloroform and water were added thereto. The mixture was stirred for 0.5 hours, and layers were separated. The aqueous layer was extracted again by chloroform and combined organic layer was dried over sodium sulfate and concentrated under reduced pressure. The residue was purified by silica gel column chromatography (chloroform:methanol=10:1). The obtained oily substance was treated with 4M hydrochloric acid-ethyl acetate solution, and concentrated under reduced pressure. Subsequently, the concentrate was triturated by isopropyl ether, to give 1.16 g of 4-amino-1-{N-(3,5-bistrifluoromethylbenzyl)-N-methyl}aminocarbonyl-2-(4-fluoro-2-methylphenyl)piperidine hydrochloride as shown in Table 19 below.

Example 46

(2R)-1-{N-(3,5-bistrifluoromethylbenzyl)-N-methyl}aminocarbonyl-2-(4-fluoro-2-methylphenyl)-4-oxopiperidine was used and treated in the same manner as in Example 45, to give (2R)-4-amino-1-{N-(3,5-bistrifluoromethylbenzyl)-N-methyl}aminocarbonyl-2-(4-fluoro-2-methylphenyl)piperidine hydrochloride as shown in Table 19 below.

Example 47

In 20 ml of a dichloromethane solution containing 1.06 g of 4-amino-1-{N-(3,5-bistrifluoromethylbenzyl)-N-methyl}aminocarbonyl-2-(4-fluoro-2-methylphenyl)piperidine were added 0.42 ml of triethylamine and 660 mg of dibutyloxycarbonate, and the mixture was stirred at room temperature for 16 hours. The reaction mixture was concentrated under reduced pressure, and the residue was purified by silica gel column chromatography (hexane:ethyl acetate=4:1), to give 130 mg of (a) trans-1-{N-(3,5-bistrifluoromethylbenzyl)-N-methyl}aminocarbonyl-2-(4-fluoro-2-methylphenyl)-4-tert-butoxycarbonylaminopiperidine and 120 mg of (b) cis-1-{N-(3,5-bistrifluoromethylbenzyl)-N-methyl}aminocarbonyl-2-(4-fluoro-2-methylphenyl)-4-tert-butoxycarbonylaminopiperidine as shown in Table 20 below.

Example 48

100 mg of trans-1-{N-(3,5-bistrifluoromethylbenzyl)-N-methyl}aminocarbonyl-2-(4-fluoro-2-methylphenyl)-4-tert-butoxycarbonylaminopiperidine was treated with 4M hydrochloric acid-ethyl acetate solution. Ether and hexane were added thereto and formed precipitates were collected by filtration, washed with hexane and vacuum dried, to give 56 mg of trans-4-amino-1-{N-(3,5-bistrifluoromethylbenzyl)-N- methyl}aminocarbonyl-2-(4-fluoro-2-methylphenyl)piperidine hydrochloride as shown in Table 21 below.

Example 49 cis-1-{N-(3,5-bistrifluoromethylbenzyl)-N-methyl}aminocarbonyl-2-(4-fluoro-2-methylphenyl)-4-tert-butoxycarbonylaminopiperidine was used and treated in the same manner as in Example 48, to give cis-4-amino-1-{N-(3,5-bistrifluoromethylbenzyl)-N-methyl}aminocarbonyl-2-(4-fluoro-2-methylphenyl)piperidine hydrochloride as shown in Table 21 below.

Example 50

In 1.2 ml of dichloromethane was dissolved 60 mg of 4-amino-1-{N-(3,5-bistrifluoromethylbenzyl)-N-methyl}aminocarbonyl-2-(4-fluoro-2-methylphenyl)piperidine, and added thereto were 0.02 ml of triethylamine and 0.013 ml of propionyl chloride under ice-cooling, and the mixture was stirred under ice-cooling for 20 minutes. The reaction mixture was poured into saturated brine and layers were separated. The aqueous layer was extracted with dichloromethane and the combined organic layers were washed with brine, dried and the solvent was removed by distillation. The residue was purified by thin-layer silica gel chromatography (chloroform:methanol=9:1), to give 40 mg of (a) trans-1-{N-(3,5-bistrifluoromethylbenzyl)-N-methyl}aminocarbonyl-2-(4-fluoro-2-methylphenyl)-4-propionylaminopiperidine and 27 mg of (b) cis-1-{N-(3,5-bistrifluoromethylbenzyl)-N-methyl}aminocarbonyl-2-(4-fluoro-2-methylphenyl)-4-propionylaminopiperidine as shown in Table 22 below.

Examples 51 to 69

The corresponding starting materials were used and treated in the same manner as in Example 50 to give compounds as shown in Tables 23 to 33 below.

Example 70

In 4 ml of a dichloromethane solution containing 98 mg of 4-amino-1-{N-(3,5-bistrifluoromethylbenzyl)-N-methyl}aminocarbonyl-2-(4-fluoro-2-methylphenyl)piperidine were added 0.056 ml of triethylamine and 0.028 ml of acetyl chloride successively at 0° C., and the mixture was stirred at 0° C. for 0.5 hours. After the reaction was completed, an aqueous sodium hydrogen carbonate solution and chloroform were added thereto and the mixture was stirred and layers were separated. The aqueous layer was extracted again with chloroform, and the combined organic layers were dried over magnesium sulfate and concentrated under reduced pressure. The residue was purified by silica gel column chromatography (chloroform:ethyl acetate=4:1) and vacuum dried to give 86 mg of 4-acetylamino-1-{N-(3,5-bistrifluoromethylbenzyl)-N-methyl}aminocarbonyl-2-(4-fluoro-2-methylphenyl)piperidine in powder form as shown in Table 34 below.

Example 71

4-Amino-1-{N-(3,5-bistrifluoromethylbenzyl)-N-methyl}aminocarbonyl-2-(4-fluoro-2-methylphenyl)piperidine and nicotinic chloride hydrochloride were used and treated in the same manner as in Example 70, to give 1-{N-(3,5-bistrifluoromethylbenzyl)-N-methyl}aminocarbonyl-2-(4-fluoro-2-methylphenyl)-4-(3-pyridylcarbonylamino)piperidine as shown in Table 34 below.

Example 72

To 3 ml of a dimethylformamide solution containing 124 mg of 4-amino-1-{N-(3,5-bistrifluoromethylbenzyl)-N-methyl}aminocarbonyl-2-(4-fluoro-2-methylphenyl)piperidine were added 44 mg of N-tert-butoxycarbonyl glycine, 58 mg of 1-ethyl-3-(3-dimethylaminopropyl)carbodiimide hydrochloride and 13.5 mg of 1-hydroxy-1H-benzotriazol, and the mixture was stirred at room temperature for 16 hours. After the reaction was completed, an aqueous sodium hydrogen carbonate solution and chloroform were added thereto and the mixture was stirred and layers were separated. The aqueous layer was extracted again with chloroform, and the combined organic layers were dried over magnesium sulfate and concentrated under reduced pressure. The residue was purified by silica gel column chromatography (chloroform:methanol=19:1), and treated with 4M hydrochloric acid-ethyl acetate solution. The mixture was concentrated under reduced pressure. The formed precipitates were washed with isopropyl ether, collected by filtration and vacuum dried to give 83 mg of 4-aminoacetylamino-1-{N-(3,5-bistrifluoromethylbenzyl)-N-methyl}aminocarbonyl-2-(4-fluoro-2-methylphenyl)piperidine hydrochloride as shown in Table 35 below.

Example 73

4-Amino-1-{N-(3,5-bistrifluoromethylbenzyl)-N-methyl}aminocarbonyl-2-(4-fluoro-2-methylphenyl)piperidine and N,N-dimethyl glycine were used and treated in the same manner as in Example 72, to give 1-{N-(3,5-bistrifluoromethylbenzyl)-N-methyl}aminocarbonyl-4-dimethylaminoacetylamino-2-(4-fluoro-2-methylphenyl)piperidine hydrochloride as shown in Table 35 below.

Example 74

To 25 ml of an ethanol solution containing 320 mg of cis-1-{N-(3,5-bistrifluoromethylbenzyl)-N-methyl}aminocarbonyl-2-(4-fluoro-2-methylphenyl)-4-(4-nitrobenzoyl)aminopiperidine was added 480 mg of tin dichloride, and the mixture was refluxed for 4 hours. After the reaction was completed, ethanol was removed by distillation under reduced pressure. Added thereto were diethyl ether and an aqueous 2M sodium hydroxide solution and layers were separated. The organic layer was washed again with 2M aqueous sodium hydroxide solution and further washed with water. This organic layer was dried over magnesium sulfate and concentrated under reduced pressure. The residue was purified by silica gel column chromatography (chloroform:methanol=19:1), and the obtained oily substance was treated with 4M hydrochloric acid-ethyl acetate solution. The reaction mixture was concentrated under reduced pressure and triturated by isopropyl ether, to give 152 mg of cis-4-(4-aminobenzoyl)amino-1-{N-(3,5-bistrifluoromethylbenzyl)-N-methyl}aminocarbonyl-2-(4-fluoro-2-methylphenyl)piperidine hydrochloride as shown in Table 36 below.

Example 75

To 60 ml of a tetrahydrofuran solution containing 3.91 g of N-{1-(R)-(3,5-bistrifluoromethylphenyl)ethyl}-N-methylamine was added 2.34 g of 1,1'-carbonyldiimidazole, and the mixture was stirred at 40° C. overnight. After the solvent was removed by distillation, ethyl acetate was added. The whole organic layers were washed with water and saturated brine, and dried. The white crystals obtained by removing the solvent by distillation under reduced pressure were collected by diisopropyl ether. The obtained white crystals were dissolved in 60 ml of acetonitrile, and 3.5 ml of methyl iodide was added thereto. After the reaction proceeded at 60° C. for 2 hours, the solvent was removed by distillation under reduced pressure. 224 mg of the residue was dissolved in 2 ml of dichloromethane, and under ice-cooling, 100 mg of cis-2-(4-fluoro-2-methylphenyl)-4-(propanoylamino)piperidine and 0.11 ml of triethylamine were added thereto and the mixture was stirred at room temperature overnight. The reaction mixture was poured into water, and layers were separated. The aqueous layer was extracted with dichloromethane, and the combined organic layers were washed with water and saturated brine and dried, and the solvent was removed by distillation under reduced pressure. The residue was purified by silica gel column chromatography (hexane:ethyl acetate=1:3), to give 83.5 mg of (2R,4S)-1-[N-{1-(R)-(3,5-bistrifluoromethylphenyl)ethyl}-N-methyl]aminocarbonyl-2-(4-fluoro-2-methylphenyl)-4-propanoylaminopiperidine as shown in Table 37 below.

Examples 76 to 84

The corresponding starting materials were used and treated in the same manner as in Example 75 to give compounds as shown in Tables 37 to 39 below.

Example 85

To 1 ml of an ethyl acetate solution containing 212 mg of (2R,4S)-1-[N-{1-(R)-(3,5-bistrifluoromethylphenyl)ethyl}-N-methyl]aminocarbonyl-2-(4-fluoro-2-methylphenyl)-4-tert-butoxycarbonylaminopiperidine was added 2 ml of 4M hydrochloric acid-ethyl acetate solution under ice-cooling, and the mixture was stirred under ice-cooling for 30 minutes. After the solvent was removed by distillation under reduced pressure, chloroform and 2M aqueous sodium hydroxide solution were added to the residue. Layers were separated and the aqueous layer was extracted with chloroform and the combined organic layers were dried and the solvent was removed by distillation under reduced pressure, to give 177 mg of (2R,4S)-4-amino-1-[N-{1-(R)-(3,5-bistrifluoromethylphenyl)ethyl}-N-methyl]aminocarbonyl-2-(4-fluoro-2-methylphenyl)piperidine as shown in Table 40 below.

Example 86

(2R,4S)-1-[N-{1-(S)-(3,5-bistrifluoromethylphenyl)ethyl}-N-methyl]aminocarbonyl-2-(4-fluoro-2-methylphenyl)-4-tert-butoxycarbonylaminopiperidine was used and treated in the same manner as in Example 85, to give (2R,4S)-4-amino-1-[N-{1-(S)-(3,5-bistrifluoromethylphenyl)ethyl}-N-methyl]aminocarbonyl-2-(4-fluoro-2-methylphenyl)piperidine as shown in Table 40 below.

Example 87

To 2 ml of a dichloromethane solution containing 253 mg of (2R,4S)-4-amino-1-[N-{1-(R)-(3,5-bistrifluoromethylphenyl)ethyl}-N-methyl]aminocarbonyl-2-(4-fluoro-2-methylphenyl)piperidine and 0.139 ml of triethylamine was added 0.071 ml of methanesulfonyl chloride under ice-cooling, and the mixture was stirred for an hour. The reaction mixture was poured into water and layers were separated. The aqueous layer was extracted with chloroform, and the combined organic layers were washed and dried, and the solvent was removed by distillation under reduced pressure. The residue was purified by silica gel column chromatography (hexane:ethyl acetate=1:1), to give 243 mg of (2R,4S)-1-[N-{1-(R)-(3,5-bistrifluoromethylphenyl)ethyl}-N-methyl]aminocarbonyl-4-methanesulfonylamino-2-(4-fluoro-2-methylphenyl)piperidine as shown in Table 41 below.

Example 88

(2R,4S)-4-amino-1-[N-{1-(R)-(3,5-bistrifluoromethylphenyl)ethyl}-N-methyl]aminocarbonyl-2-(4-fluoro-2-methylphenyl)piperidine and ethanesulfonyl chloride were used and treated in the same manner as in Example 87, to give (2R,4S)-1-[N-{1-(R)-(3,5-bistrifluoromethylphenyl)ethyl}-N-methyl]aminocarbonyl-4-ethanesulfonylamino-2-(4-fluoro-2-methylphenyl)piperidine as shown in Table 41 below.

Example 89

To 1 ml of a dimethylformamide solution containing 58.4 mg of (2R,4S)-1-[N-{1-(R)-(3,5-bistrifluoromethylphenyl)ethyl}-N-methyl]aminocarbonyl-4-methanesulfonylamino-2-(4-fluoro-2-methylphenyl)piperidine was added 4.6 mg of sodium hydride under ice-cooling. The mixture was stirred for 30 minutes and 0.010 ml of methyl iodide was added thereto and the mixture was further stirred for an hour. The reaction mixture was poured into water, and the aqueous layer was extracted with ethyl acetate. The combined organic layers were washed with water and saturated brine and dried, and the solvent was removed by distillation under reduced pressure. Subsequently, the residue was purified with silica gel column chromatography (hexane:ethyl acetate=2:1), to give 36.7 mg of (2R,4S)-1-[N-{1-(R)-(3,5-bistrifluoromethylphenyl)ethyl}-N-methyl]aminocarbonyl-4 (N-methanesulfonyl-N-methyl)amino-2-(4-fluoro-2-methylphenyl)piperidine as shown in Table 41 below.

Example 90

(2R,4S)-1-[N-{1-(R)-(3,5-bistrifluoromethylphenyl)ethyl}-N-methyl]aminocarbonyl-2-(4-fluoro-2-methylphenyl)-4-ethanesulfonylaminopiperidine was used and treated in the same manner as in Example 89, to give (2R,4S)-1-[N-{1-(R)-(3,5-bistrifluoromethylphenyl)ethyl}-N-methyl]aminocarbonyl-2-(4-fluoro-2-methylphenyl)-4-(N-methyl N-ethanesulfonyl)aminopiperidine as shown in Table 41 below.

Example 91

To 20 ml of a toluene solution containing 985 mg of (2R,4S)-1-{N-(3,5-bistrifluoromethylbenzyl)-N-methyl}aminocarbonyl-2-(4-fluoro-2-methylphenyl)-4-hydroxypiperidine and 129 mg of tetrabutylammonium bromide and 10 ml of 10M aqueous sodium hydroxide solution was added 1.21 ml of 2-(2-bromoethoxy)tetrahydropyran at room temperature, and the temperature of the mixture was raised to 60° C. to 70° C. and the mixture was stirred overnight. Further added thereto was 2.42 ml of 2-(2-bromoethoxy)tetrahydropyran and the mixture was stirred overnight. The reaction mixture was poured into a saturated sodium bicarbonate solution, and extracted with ethyl acetate. The organic layer was washed with saturated brine and dried, and the solvent was removed by distillation under reduced pressure. The residue was purified by silica gel column chromatography (hexane:ethyl acetate=3:2), to give 1.12 g of (2R,4S)-1-{N-(3,5-bistrifluoromethylbenzyl)-N-methyl}aminocarbonyl-2-(4-fluoro-2-methylphenyl)-4-{2-(tetrahydropyran-2-yloxy)ethoxy}piperidine as shown in Table 42 below.

Example 92

To 30 ml of a methanol solution containing 1.04 g of (2R,4S)-1-{N-(3,5-bistrifluoromethylbenzyl)-N-methyl}aminocarbonyl-2-(4-fluoro-2-methylphenyl)-4-{2-(tetrahydropyran-2-yloxy)ethoxy}piperidine was added 64 mg of p-toluenesulfonic acid monohydrate, and the mixture was stirred for 20 minutes. The reaction mixture was concentrated under reduced pressure, and then, the residue was purified by silica gel column chromatography (chloroform:ethyl acetate=1:1), give 703 mg of (2R,4S)-1-{N-(3,5-bistrifluoromethylbenzyl)-N-methyl}aminocarbonyl-2-(4-fluoro-2-methylphenyl)-4-(2-hydroxyethoxy)piperidine as shown in Table 42 below.

Example 93

To 2 ml of a tetrahydrofuran solution containing 53.6 mg of (2R,4S)-1-{N-(3,5-bistrifluoromethylbenzyl)-N-methyl}aminocarbonyl-2-(4-fluoro-2-methylphenyl)-4-(2-hydroxyethoxy)piperidine, 13.8 mg of 4H-[1,2,4]-triazole and 24.4 mg of triphenylphosphine was added 0.092 ml of 40% diethylazodicarboxylate solution in toluene under ice-cooling. The temperature of the mixture was raised to room temperature and the mixture was stirred overnight. Further, the temperature was raised to 50° C., 24.4 mg of triphenylphosphine was added thereto, and the mixture was stirred for 30 minutes. The reaction mixture was poured into water and extracted with ethyl acetate, and the organic layer was washed with saturated brine, dried and the solvent was removed by distillation. The residue was purified by silica gel column chromatography (chloroform:ethyl acetate=1:1 and chloroform:methanol=19:1) to give 43.2 mg of (2R,4S)-1-{N-(3,5-bistrifluoromethylbenzyl)-N-methyl}aminocarbonyl-2-(4-fluoro-2-methylphenyl)-4-{2-(1,2,4)triazolylethoxy}piperidine as shown in Table 42 below.

Examples 94 and 95

The corresponding starting materials were treated in the same manner as in Example 93, to give compounds as shown in Table 42 below.

Example 96

To 2 ml of a dichloromethane solution containing 215 mg of (2R,4S)-1-{N-(3,5-bistrifluoromethylbenzyl)-N-methyl}aminocarbonyl-2-(4-fluoro-2-methylphenyl)-4-(2-hydroxyethoxy)piperidine and 0.084 ml of triethylamine was added 0.037 ml of methanesulfonyl chloride under ice-cooling, and the mixture was stirred for 30 minutes. The reaction mixture was poured into water and extracted with chloroform. The organic layer was washed with brine and dried, and the solvent was removed by distillation under reduced pressure. The residue was purified by silica gel column chromatography (chloroform:ethyl acetate=2:1), to give 189 mg of (2R,4S)-1-{N-(3,5-bistrifluoromethylbenzyl)-N-methyl}aminocarbonyl-2-(4-fluoro-2-methylphenyl)-4-(2-methanesulfonyloxyethoxy)piperidine as shown in Table 42 below.

Example 97

(1) To 1 ml of a dichloromethane solution containing 61.5 mg of (2R,4S)-1-{N-(3,5-bistrifluoromethylbenzyl)-N-methyl}aminocarbonyl-2-(4-fluoro-2-methylphenyl)-4-(2-methane sulfonyloxyethoxy)piperidine and 0.028 ml of triethylamine was added 0.013 ml of morpholine under ice-cooling, and the mixture was refluxed under heating overnight. Further added thereto was 1 ml of morpholine and the mixture was stirred for 8 hours. The reaction mixture was poured into water and extracted with ethyl acetate. The organic layer was washed with saturated brine and dried, and the solvent was removed by distillation. The residue was purified by silica gel column chromatography (chloroform:methanol=19:1) and NH silica gel column chromatography (hexane:ethyl acetate=2:1), to give 36.3 mg of (2R,4S)-1-{N-(3,5-bistrifluoromethylbenzyl)-N-methyl}aminocarbonyl-2-(4-fluoro-2-methylphenyl)-4-(2-morpholinoethoxy)piperidine.

(2) In 1.0 ml of chloroform was dissolved 30.7 mg of the compound of the above (1), and 0.02 ml of 4M hydrochloric acid-ethyl acetate solution was added thereto. The mixture was stirred for a while and concentrated under reduced pressure, to give 35.3 mg of (2R,4S)-1-{N-(3,5-bistrifluoromethylbenzyl)-N-methyl}aminocarbonyl-2-(4-fluoro-2-methylphenyl)-4-(2-morpholinoethoxy)piperidine hydrochloride as shown in Table 42 below.

Example 98

(2R,4S)-1-{N-(3,5-bistrifluoromethylbenzyl)-N-methyl}aminocarbonyl-2-(4-fluoro-2-methylphenyl)-4-(2-methane sulfonyloxyethoxy)piperidine and diethylamine were used and treated in the same manner as in Example 97(1), to give (2R,4S)-1-{N-(3,5-bistrifluoromethylbenzyl)-N-methyl}aminocarbonyl-4-(2-diethylaminoethoxy)-2-(4-fluoro-2-methylphenyl)piperidine as shown in Table 42.

Example 99

In 2 ml of a dichloromethane was dissolved 200 mg of (2R,4S)-1-{N-(3,5-bistrifluoromethylbenzyl)-N-methyl}aminocarbonyl-2-(4-fluoro-2-methylphenyl)-4-hydroxypiperidine, and subsequently, 0.1 ml of ethyl isocyanate and 0.1 ml of triethylamine were added thereto and the mixture was stirred under heating at 60° C. for 3 days. The reaction mixture was cooled down to room temperature, water and chloroform were added thereto, and layers were separated. The aqueous layer was extracted again with chloroform, and the combined organic layers were dried over sodium sulfate. The solvent was removed by distillation under reduced pressure, and the residue was purified by silica gel column chromatography (hexane:ethyl acetate=1:1), to give 78 mg of (2R,4S)-1-{N-(3,5-bistrifluoromethylbenzyl)-N-methyl}aminocarbonyl-4-ethylaminocarbonyloxy-2-(4-fluoro 2-methylphenyl)piperidine as shown in Table 42 below.

Example 100

In 2 ml of a dichloromethane was dissolved 200 mg of (2R,4S)-1-{N-(3,5-bistrifluoromethylbenzyl)-N-methyl}aminocarbonyl-2-(4-fluoro-2-methylphenyl)-4-hydroxypiperidine, and subsequently, 0.1 ml of morpholin-4-carboxylic chloride and 0.1 ml of triethylamine were added thereto and the mixture was stirred under heating at 60° C. for 3 days. After the reaction mixture was cooled down to room temperature, water and chloroform were added thereto, and layers were separated: The aqueous layer was extracted again with chloroform, and the combined organic layers were dried over sodium sulfate. After the solvent was removed by distillation under reduced pressure, the residue was purified by silica gel column chromatography (hexane:ethyl acetate=1:1), to give 68 mg of (2R,4S)-1-{N-(3,5-bistrifluoromethylbenzyl)-N-methyl}aminocarbonyl-2-(4-fluoro-2-methylphenyl)-4-morpholinocarbonyloxypiperidine as shown in Table 42 below.

Example 101

In 5 ml of tetrahydrofuran was dissolved 248 mg of (2R,4S)-1-{N-(3,5-bistrifluoromethylbenzyl)-N-methyl}aminocarbonyl-2-(4-fluoro-2-methylphenyl)-4-hydroxypiperidine, and subsequently, 81 mg of 1,1'-carbonyldiimidazole was added thereto and the mixture was stirred under heating at 60° C. for 16 hours. The reaction mixture was cooled down to room temperature, water and chloroform were added and layers were separated. The aqueous layer was extracted again with chloroform, and the combined organic layers were further washed with water. The organic layer was dried over sodium sulfate, and the solvent was removed by distillation under reduced pressure. The obtained concentrated residue was purified by NH silica gel column chromatography (hexane:ethyl acetate=1:1), to give 135 mg of (2R,4S)-1-{N-(3,5-bistrifluoromethylbenzyl)-N-methyl}aminocarbonyl-2-(4-fluoro-2-methylphenyl)-4-(1-imidazolyl)carbonyloxypiperidine as shown in Table 42 below.

Example 102

(1) In 3 ml of acetonitrile was dissolved 298 mg of (2R,4S)-1-{N-(3,5-bistrifluoromethylbenzyl)-N-methyl}aminocarbonyl-2-(4-fluoro-2-methylphenyl)-4-(1-imidazolyl)carbonyloxypiperidine, and subsequently, 0.06 ml of methyl iodide was added thereto and the mixture was stirred under heating for an hour. The solution was cooled down to room temperature and the solvent was removed by distillation under reduced pressure. To the residue were added 2.5 ml of methylene chloride, 0.11 ml of 4-methylpiperazine and 0.14 ml of triethylamine and the mixture was stirred at room temperature for 16 hours. To the reaction mixture was added an aqueous sodium hydrogen carbonate solution and chloroform and the mixture was stirred for 30 minutes. The layers were separated and the obtained organic layer was washed further with water, and dried over magnesium sulfate. The solvent was removed by distillation under reduced pressure, and resultant residue was purified by NH silica gel column chromatography (hexane:ethyl acetate=2:1), to give (2R,4S)-1-{N-(3,5-bistrifluoromethylbenzyl)-N-methyl}aminocarbonyl-2-(4-fluoro-2-methylphenyl)-4-(4-methyl piperazino)carbonyloxypiperidine.

(2) The compound of the above (1) was treated with 4M hydrochloric acid-ethyl acetate solution, to give 78 mg of (2R,4S)-1-{N-(3,5-bistrifluoromethylbenzyl)-N-methyl}aminocarbonyl-4-(4-methylpiperazino)carbonyloxy-2-(4-fluoro-2-methylphenyl)piperidine hydrochloride as shown in Table 43 below.

Examples 103 to 105

The corresponding starting materials were used and treated in the same manner as in Example 102 (1) and (2), to give the compounds as shown in Table 43 below.

Example 106

(1) In 100 ml of tetrahydrofuran were dissolved 5 g of cis-1-{N-(3,5-bistrifluoromethylbenzyl)-N-methyl}aminocarbonyl-2-(4-fluoro-2-methylphenyl)-4-hydroxypiperidine, 10.5 g of triphenylphosphine and 4.88 g of benzoic acid, and subsequently, added thereto was 18.3 ml of a 40% diethylazodicarboxylate-toluene solution under ice-cooling and the mixture was stirred at room temperature for 3 hours. To the reaction mixture were added water and ethyl acetate and the mixture was stirred for 30 minutes. The solution was separated by layers, and the obtained organic layer was dried over magnesium sulfate and concentrated under reduced pressure. The residue was purified by silica gel column chromatography (hexane:ethyl acetate=4:1), to give 4.36 g of trans-1-{N-(3,5-bistrifluoromethylbenzyl)-N-methyl}aminocarbonyl-4-benzoyloxy-2-(4-fluoro-2-methylphenyl)piperidine.

(2) In 10 ml of methanol was dissolved 1.4 g of the compound of the above (1), and subsequently, added thereto was 325 mg of potassium carbonate and the mixture was stirred at room temperature for 16 hours. After the solution was concentrated under reduced pressure for the solvent to be removed by distillation, water and ethyl acetate were added thereto and layers were separated. The organic layer was dried over magnesium sulfate and concentrated under reduced pressure. The residue was purified by silica gel column chromatography (hexane:ethyl acetate=4:1), to give 0.68 g of trans-1-{N-(3,5-bistrifluoromethylbenzyl)-N-methyl}aminocarbonyl-2-(4-fluoro-2-methylphenyl)-4-hydroxypiperidine as shown in Table 44 below.

Example 107

In 10 ml of tetrahydrofuran were added 98 mg of trans-1-{N-(3,5-bistrifluoromethylbenzyl)-N-methyl}aminocarbonyl-2-(4-fluoro-2-methylphenyl)-4-hydroxypiperidine, 70 mg of [1, 2,4]triazole and 262 mg of triphenylphosphine, and subsequently added thereto was 0.48 ml of a 40% diethylazodicarboxylate-toluene solution, and the mixture was stirred under reflux for 16 hours. After reaction is completed, an aqueous sodium bicarbonate solution and ethyl acetate were added thereto and the mixture was stirred for 30 minutes. The reaction mixture was separated by layers, and the obtained organic layer was dried over magnesium sulfate and concentrated under reduced pressure. The residue was purified by silica gel column chromatography (chloroform:methanol=9:1), to give 46 mg of cis-1-{N-(3,5-bistrifluoromethylbenzyl)-N-methyl}aminocarbonyl-2-(4-fluoro-2-methylphenyl)-4-(1,2,4-triazolyl)piperidine as show in Table 44 below.

Example 108

Cis-1-{N-(3,5-bistrifluoromethylbenzyl)-N-methyl}aminocarbonyl-2-(4-fluoro-2-methylphenyl)-4-hydroxypiperidine and 4,6-dihydroxy-2-mercaptopyrimidine were used and treated in the same manner as in Example 107, to give a compound as shown in Table 45 below.

Example 109

(2R,4S)-1-[N-{1-(R)-(3,5-bistrifluoromethylphenyl)ethyl}-N-methyl]aminocarbonyl-2-(4-fluoro-2-methylphenyl)-4-hydroxypiperidine was used and treated in the same manner as in Example 106 (1) and (2), to give (2R,4R)-1-[N-{1-(R)-(3,5-bistrifluoromethylphenyl)ethyl}-N-methyl]

aminocarbonyl-2-(4-fluoro-2-methylphenyl)-4-hydroxypiperidine as shown in Table 46 below.

Examples 110 to 112

The corresponding starting materials were used and treated in the same manner as in Example 107, to give compounds as shown in Table 46 below.

Example 113

(1) 30 ml of tetrahytdrofuran solution containing 1.2 ml of triethylphosphonoacetate was ice cooled and slowly added thereto was sodium hydride. While keeping the same temperature, the mixture was stirred for 30 minutes and added dropwise thereto was 30 ml of a tetrahydrofuran solution containing 3.02 g of (2R)-1-[N-{1-(R)-(3,5-bistrifluoromethylphenyl)ethyl}-N-methyl]aminocarbonyl-2-(4-fluoro-2-methylphenyl)-4-oxopiperidine. The mixture was stirred at room temperature overnight. The reaction mixture was poured into water and extracted with ethyl acetate. The combined organic layers were washed with water and saturated brine and dried, and the solvent was removed by distillation under reduced pressure. The residue was purified by silica gel column chromatography (hexane:ethyl acetate=4:1), to give (2R)-1-[N-{1-(R)-(3,5-bistrifluoromethylphenyl)ethyl}-N-methyl]aminocarbonyl-4-ethoxycarbonylmethylidene-2-(4-fluoro-2-methylphenyl)piperidine as a colorless liquid.

(2) The compound of the above (1) was dissolved in 50 ml of methanol, and added thereto was 500 mg of palladium-carbon, and the mixture was stirred under hydrogen atmosphere at room temperature overnight. The catalyst was removed and methanol was removed by distillation under reduced pressure, and the residue was purified by silica gel column chromatography (hexane:ethyl acetate=4:1), to give 3.23 g of (2R)-1-[N-{1-(R)-(3,5-bistrifluoromethylphenyl)ethyl}-N-methyl]aminocarbonyl-4-ethoxycarbonylmethyl-2-(4-fluoro-2-methylphenyl)piperidine as shown in Table 46 below.

Example 114

(1) In 20 ml of methanol was dissolved 3.23 g of (2R)-1-[N-{1-(R)-(3,5-bistrifluoromethylphenyl)ethyl}-N-methyl]aminocarbonyl-4-ethoxycarbonylmethyl-2-(4-fluoro-2-methylphenyl)piperidine, and added thereto was 5.73 ml of a 2M aqueous sodium hydroxide solution. The mixture was stirred at room temperature overnight. After neutralizing the mixture by 2M hydrochloric acid, methanol was removed by distillation under reduced pressure, and an aqueous layer was extracted with ethyl acetate. The organic layer was washed with water and saturated brine and dried and the solvent was removed by distillation under reduced pressure, to give 2.97 g of (2R)-1-[N-{1-(R)-(3,5-bistrifluoromethylphenyl)ethyl}-N-methyl]aminocarbonyl-4-carboxymethyl-2-(4-fluoro-2-methylphenyl)piperidine as yellow powder.

(2) 200 mg of the compound of the above (1) was dissolved in 2 ml of dimethylformamide, and added thereto were 84 mg of 1-ethyl 3-(3-dimethylaminopropyl)carbodiimide hydrochloride, 65 mg of 1-hydroxy-1H-benzotriazole and 0.037 ml of morpholine and the mixture was stirred at room temperature overnight. The reaction mixture was diluted with ethyl acetate, and washed with a saturated aqueous citric acid solution, a saturated aqueous sodium bicarbonate solution and saturated brine. The organic layer was dried, and the solvent was removed by distillation to obtain the residue, and the residue was purified by NH silica gel column chromatography (hexane:ethyl acetate=2:1), to give 138 mg of (2R)-1-[N-{1-(R)-(3,5-bistrifluoromethylphenyl)ethyl}-N-methyl]aminocarbonyl-2-(4-fluoro-2-methylphenyl)-4-morpholinocarbonylmethylpiperidine as shown in Table 46 below.

Examples 115 to 117

The corresponding starting materials were used and treated in the same manner as in Example 114 (2), to give compound as shown in Table 46 below.

Example 118

(1) In 10 ml of ethanol was dissolved 1.49 g of (2R)-1-[N-{1-(S)-(3,5-bistrifluoromethylphenyl)ethyl}-N-methyl]aminocarbonyl-2-(4-fluoro-2-methylphenyl)-4-oxopiperidine, and added thereto was 226 mg of hydroxylamine hydrochloride, 267 mg of sodium acetate. The mixture was stirred overnight. Ethanol was removed by distillation under reduced pressure and water was added to the residue and extracted with ethyl acetate. The organic layer was washed with saturated brine and dried. The solvent was removed by distillation under reduced pressure to give a compound in a resin state.

(2) The compound of the above (1) was dissolved in 50 ml of methanol, and added thereto was 844 mg of nickel chloride. The mixture was ice cooled and slowly added thereto was 224 mg of sodium borohydride. After stirring the mixture overnight, it was concentrated under reduced pressure, and water and ethyl acetate were added thereto and the layers were separated. The organic layer was washed with saturated brine and dried. The solvent was removed by distillation under reduced pressure, to give 1.44 g of (2R)-4-amino-1-[N-{1-(S)-(3,5-bistrifluoromethylphenyl)ethyl}-N-methyl]aminocarbonyl-2-(4-fluoro-2-methylphenyl)piperidine as shown in Table 47 below.

Example 119

(2R)-1-{N-(3,5-bistrifluoromethylphenyl)methyl N-methyl}aminocarbonyl-2-(4-fluoro-2-methylphenyl)-4-oxopiperidine was used and treated in the same manner as in Example 119 (1) and (2), to give (2R)-4-amino-1-{N-(3,5-bistrifluoromethylphenyl)methyl-N-methyl}aminocarbonyl-2-(4-fluoro-2-methylphenyl)piperidine as shown in Table47 below.

Example 120

(2R)-4-amino-1-[N-{1-(S)-(3,5-bistrifluoromethylphenyl)ethyl}-N-methyl]aminocarbonyl-2-(4-fluoro-2-methylphenyl)piperidine was used and treated in the same manner as in Example 50, to give (a) (2R,4S)-1-[N-{1-(S)-(3,5-bistrifluoromethylphenyl)ethyl}-N-methyl]aminocarbonyl-2-(4-fluoro-2-methylphenyl)-4-(2-pyrazinylcarbonylamino)piperidine and (b) (2R,4R)-1-[N-{1-(S)-(3,5-bistrifluoromethylphenyl)ethyl}-N-methyl]aminocarbonyl-2-(4-fluoro-2-methylphenyl)-4-(2-pyrazinylcarbonylamino)piperidine as shown in Table 47 below.

Example 121

In 2 ml of an acetonitrile solution containing 80 mg of (2R,4S)-1-[N-{1-(S)-(3,5-bistrifluoromethylphenyl)ethyl}-N-methyl]aminocarbonyl-2-(4-fluoro-2-methylphenyl)-4-morpholinopiperidine was added 0.034 ml of methyl iodide and the mixture was stirred at 60° C. overnight. The solvent was removed by distillation, and precipitated yellow powder was dried, to give 98 mg of (2R,4S)-1-[N-{1-(S)-(3,5-bistrifluoromethylphenyl)ethyl}-N-methyl]aminocarbonyl-2-(4-fluoro-2-methylphenyl)-4-(N-methyl-4-morpholinio)piperidine iodide as shown in Table 48 below.

Example 122

(2R,4S)-1-[N-{1-(R)-(3,5-bistrifluoromethylphenyl)ethyl}-N-methyl]aminocarbonyl-2-(4-fluoro-2-methylphenyl)-4-morpholinopiperidine was used and treated in the same manner as in Example 121, to give(2R,4S)-1-[N-{1-(R)-(3,5-bistrifluoromethylphenyl)ethyl}-N-methyl]aminocarbonyl-2-(4-fluoro-2-methylphenyl)-4-(N-methyl-4-morpholinio)piperidine iodide as show in Table 48 below.

Example 123

In 2 ml of a dichloromethane solution containing 80 mg of (2R,4S)-1-[N-{1-(S)-(3,5-bistrifluoromethylphenyl)ethyl}-N-methyl]aminocarbonyl-2-(4-fluoro-2-methylphenyl)-4-morpholinopiperidine was added 34 mg of 3-chloroperbenzoic acid, and the mixture was stirred at room temperature overnight. The reaction mixture was poured into a saturated aqueous sodium bicarbonate solution, and the aqueous layer was extracted with dichloromethane. The combined organic layers were washed with water and saturated brine and dried, and the solvent was removed by distillation under reduced pressure. The precipitated white powder was dried, to give 79 mg of (2R,4S)-1-[N-{1-(S)-(3,5-bistrifluoromethylphenyl)ethyl}-N-methyl]aminocarbonyl-2-(4-fluoro-2-methylphenyl)-4-(N-oxo morpholino)piperidine as shown in Table 48 below.

Example 124

(2R,4S)-1-[N-{1-(R)-(3,5-bistrifluoromethylphenyl)ethyl}-N-methyl]aminocarbonyl-2-(4-fluoro-2-methylphenyl)-4-morpholinopiperidine was used and treated in the same manner as in Example 123, to give (2R,4S)-1-[N-{1-(R)-(3,5-bistrifluoromethylphenyl)ethyl}-N-methyl]aminocarbonyl-2-(4-fluoro-2-methylphenyl)-4-(N-oxo morpholino)piperidine as shown in Table 48 below.

Examples 125 to 127

The corresponding starting materials were used and treated in the same manner as in Example 8, to give compounds as shown in Table 49 below.

Examples 128 to 136

The corresponding starting materials were used and treated in the same manner as in Example 50, to give compounds as shown in Tables 49 to 51 below.

Example 137

In 2 ml of dichloromethane was dissolved 263 mg of (2R)-4-amino-1-[N-(3,5-bistrifluoromethylbenzyl)-N-methyl]aminocarbonyl-2-(4-fluoro-2-methylphenyl)piperidine, and at room temperature, were added thereto 52 µl of 2-chloro ethylisocyanate and 167 µl of triethylamine, and the mixture was stirred for 2 hours. To the solution was added a saturated sodium hydrogen carbonate solution, the dichloromethane layer was separated, and the aqueous layer was further extracted with chloroform. The combined organic layers were washed with saturated brine, dried and concentrated. The residue was purified by silica gel column chromatography (chloroform:methanol=9:1), to give 109 mg of (2R)-4-(2-chloroethyl)ureido-1-[N-(3,5-bistrifluoromethylbenzyl)-N-methyl]aminocarbonyl-2-(4-fluoro-2-methylphenyl)piperidine as shown in Table 51.

Example 138

In 20 ml of dimethylformamide were dissolved 2.65 g of (2R)-4-amino-1-[N-(3,5-bistrifluoromethylbenzyl)-N-methyl]aminocarbonyl-2-(4-fluoro-2-methylphenyl)piperidine hydrochloride and 1 g of 5-formylfuran-2-carboxylic acid, and added thereto were 1.92 g of 1-ethyl-3-(3-dimethylaminopropyl)carbodiimide hydrochloride, 0.6 g of 1-hydroxy-1H-benzotriazole and 1.4 ml of triethylamine. The mixture was stirred at room temperature for 3 hours. After the reaction was completed, an aqueous citric acid solution and ethyl acetate were added thereto and layers were separated. The organic layer was further washed with saturated brine, and the combined organic layers were dried over magnesium sulfate, and concentrated under reduced pressure. The residue was purified by NH silica gel column chromatography (hexane:ethyl acetate=2:1), to give 289 mg of (a) (2R,4S)-1-[N-(3,5-bistrifluoromethylbenzyl)-N-methyl]aminocarbonyl-4-(5-formylfuran-2-yl)carbamoyl-2-(4-fluoro-2-methylphenyl)piperidine and 185 mg of (b) (2R,4S)-1-[N-(3,5-bistrifluoromethylbenzyl)-N-methyl]aminocarbonyl-4-(5-formylfuran-2-yl)carbamoyl-2-(4-fluoro-2-methylphenyl)piperidine as shown in Table 52 below.

Examples 140 to 168

The corresponding starting materials were used and treated in the same manner as in Example 138, to give compounds as shown in Tables 53 to 57 below.

Example 169

In 1 ml of tetrahydrofuran was dissolved 80 mg of (2R,4S)-4-amino-1-[N-{1-(S)-(3,5-bistrifluoromethylphenyl)ethyl}-N-methyl]aminocarbonyl-2-(4-fluoro-2-methylphenyl)piperidine, and under ice-cooling, 25.7 mg of 1,1-carbonyldiimidazole was added thereto and the mixture was stirred under ice-cooling for 30 minutes. To the solution, 19 µl of 2-aminoethanol, 44 µl of triethylamine were added under ice-cooling, and the mixture was stirred at room temperature for 22 hours. The solvent was removed by distillation and to the residue, and added thereto were water and dichloromethane and layers were separated. The organic layer was washed with saturated brine, dried and concentrated. To the residue was added isopropyl ether, and precipitated white crystals were collected by filtration, to give 74 mg of (2R,4S)-1-[N-{1-(S)-(3,5-bistrifluoromethylphenyl)ethyl}-N-methyl]aminocarbonyl-2-(4-fluoro-2-methylphenyl)-4-(2-hydroxyethyl)ureidopiperidine as shown in Table 57 below.

Examples 170 to 173

The corresponding starting materials were used and treated in the same manner as in Example 169, to give compounds as shown in Table 57 below.

Examples 174 to 177

The corresponding starting materials were used and treated in the same manner as in Example 87, to give compounds as shown in Table 58 below.

Example 178

In 10 ml of dichloromethane was dissolved 1.01 g of (2R,4S)-4-amino-1-[N-{1-(R)-(3,5-bistrifluoromethylphenyl)ethyl}-N-methyl]aminocarbonyl-2-(4-fluoro-2-methylphenyl)piperidine and 0.558 ml of triethylamine, and under ice-cooling, added thereto was 0.314 ml of 2-chloroethanesulfonylchloride, and the mixture was stirred for 4 hours. The solution was poured into water, layers were separated, and the aqueous layer was further extracted with dichloromethane. The combined organic layers were washed with saturated brine, dried and concentrated. The residue was purified by silica gel column chromatography (hexane:ethyl acetate=2:1), to give 725 mg of (2R,4S)-1-[N-{1-(R)-(3,5-bistrifluoromethylphenyl)ethyl}-N-methyl]aminocarbonyl-4-ethylenesulfonylamino-2-(4-fluoro-2-methylphenyl)piperidine as shown in Table 58 below.

Example 179

(2R,4S)-1-[N-{1-(R)-(3,5-bistrifluoromethylphenyl)ethyl}-N-methyl]aminocarbonyl-2-(4-fluoro-2-methylphenyl)-4-methylaminopiperidine was used and treated in the same manner as in Example 178, to give (2R,4S)-1-[N-{1-(R)-(3,5-bistrifluoromethylphenyl)ethyl}-N-methyl]aminocarbonyl-4-(1-ethylenesulfonyl-1-methylamino)-2-(4-fluoro-2-methylphenyl)piperidine as shown in Table 58.

Examples 180 to 181

The corresponding starting materials were used and treated in the same manner as in Example 87, to give compounds as shown in Table 59 below.

Examples 183 to 184

The corresponding starting materials were used and treated in the same manner as in Example 89, to give compounds as shown in Table 59 below.

Example 185

(2R,4S)-1-[N-{1-(S)-(3,5-bistrifluoromethylphenyl)ethyl}-N-methyl]aminocarbonyl-2-(4-fluoro-2-methylphenyl)-4-hydroxypiperidine and 2-methoxyethyl chloride were used and treated in the same manner as in Example 91, to give (2R,4S)-1-[N-{1-(S)-(3,5-bistrifluoromethylphenyl)ethyl}-N-methyl]aminocarbonyl-2-(4-fluoro-2-methylphenyl)-4-(2-methoxyethoxy)piperidine as shown in Table 59 below.

Examples 186 to 189

The corresponding starting materials were used and treated in the same manner as in Example 91 and Example 92, to give compounds as shown in Tables 59 to 60 below.

Example 190

(2R,4S)-1-[N-{1-(R)-(3,5-bistrifluoromethylphenyl)ethyl}-N-methyl]aminocarbonyl-2-(4-fluoro-2-methylphenyl)-4-(2-hydroxyethoxy)piperidine and methanesulfonyl chloride were used and treated in the same manner as in Example 96, to give (2R,4S)-1-[N-{1-(R)-(3,5-bistrifluoromethylphenyl)ethyl}-N-methyl]aminocarbonyl-2-(4-fluoro-2-methylphenyl)-4-(2-methanesulfonyloxyethoxy)piperidine as shown in Table 60 below.

Examples 191 to 196

The corresponding starting materials were used and treated in the same manner as in Example 97, to give compounds as shown in Tables 60 to 61 below.

Examples 197 to 198

The corresponding starting materials were used and treated in the same manner as in Example 101, to give compounds as shown in Table 62 below.

Examples 199 to 205

The corresponding starting materials were used and treated in the same manner as in Example 102 (1) or in Example 102 (1) and (2), to give compounds as shown in Table 63 below.

Example 206

(2R,4S)-1-[N-(3,5-bistrifluoromethylbenzyl)-N-methyl]aminocarbonyl-2-(4-fluoro-2-methylphenyl)-4-piperidinopiperidine were used and treated in the same manner as in Example 123, to give (2R,4S)-1-[N-(3,5-bistrifluoromethylbenzyl)-N-methyl]aminocarbonyl-2-(4-fluoro-2-methylphenyl)-4-(N-oxopiperidino)piperidine as shown in Table 65 below.

Example 207

In 4 ml of ethanol was dissolved 124 mg of (2R,4S)-1-[N-(3,5-bistrifluoromethylbenzyl)-N-methyl]aminocarbonyl-4-(5-formylfuran-2-yl)carbamoyl-2-(4-fluoro-2-methylphenyl)piperidine, and added thereto was 3.8 mg of sodium borohydride, and the mixture was stirred at room temperature for 2 hours. To the solution was added an aqueous sodium hydrogen carbonate solution, and the mixture was stirred for 10 minutes and concentrated, and ethanol was removed by distillation. To the residue was added ethyl acetate and water, and layers were separated. The organic layer was dried and concentrated. The residue was purified by silica gel column chromatography (chloroform:methanol=19:1), to give 68 mg of (2R,4S)-1-[N-(3,5-bistrifluoromethylbenzyl)-N-methyl]aminocarbonyl-2-(4-fluoro-2-methylphenyl)-4-(5-hydroxymethylfuran-2-yl)carbamoylpiperidine as shown in Table 65 below.

Example 208

In 4 ml of dichloroethane were dissolved 124 mg of (2R,4S)-1-[N-(3,5-bistrifluoromethylbenzyl)-N-methyl]aminocarbonyl-4-(5-formylfuran-2-yl)carbamoyl-2-(4-fluoro-2-methylphenyl)piperidine, 44 μl of morpholine and 2.9 μl of acetic acid, and added thereto 106 mg of sodium triacetoxyborohydride, and the mixture was stirred at room temperature for 3 hours. To the solution was added an aqueous sodium carbonate solution and chloroform, and the mixture was stirred for 10 minutes and layers were separated. The organic layer was dried over magnesium sulfate and concentrated. The residue was purified by NH silica gel column chromatography (n-hexane:ethyl acetate=1:1). The obtained oily substance was treated with 4M hydrochloric acid-ethyl acetate solution, to give 78 mg of (2R,4S)-1-[N-(3,5-bistrifluoromethylbenzyl)-N-methyl]aminocarbonyl-2-(4-fluoro-2-methylphenyl)-4-(5-morpholinomethylfuran-2-yl)carbamoylpiperidine hydrochloride as shown in Table 65 below.

Example 209

In mixture of 3.3 ml of toluene and 0.4 ml of dichloromethane was dissolved 197 mg of (2R,4S)-1-[N-(3,5-bistrifluoromethylbenzyl)-N-methyl]aminocarbonyl-2-(4-fluoro-2-methylphenyl)-4-hydroxypiperidine, and added thereto was 78 mg of 1,1'-carbonyldiimidazole. The mixture was stirred at 60° C. for 4 hours. Distilled water was added thereto and the mixture was extracted with chloroform, dried over magnesium sulfate and concentrated under reduced pressure. The residue was dissolved in 3.7 ml of acetonitrile, and added thereto was 100 µl of methyl iodide, and the mixture was stirred at 50° C. for 3 hours. The solution was concentrated under reduced pressure, and to the residue were added 3.6 ml of toluene and 156 µl of thiomorpholine, and the mixture was stirred at 70° C. for 16 hours. Distilled water was added thereto and the mixture was extracted with chloroform, dried over magnesium sulfate and concentrated under reduced pressure. The residue was purified by silica gel column chromatography (hexane: ethyl acetate=2:1→1:2), to give 197 mg of (2R,4S)-1-[N-(3,5-bistrifluoromethylbenzyl)-N-methyl]aminocarbonyl-2-(4-fluoro-2-methylphenyl)-4-thiomorpholinocarbonyloxypiperidine as shown in Table 65 below.

Examples 210 to 212

The corresponding starting materials were used and treated in the same manner as in Example 209, to give compounds as shown in Table 65 below.

Example 213

In 1.9 ml of dichloromethane was dissolved 62 mg of (2R,4S)-1-[N-(3,5-bistrifluoromethylbenzyl)-N-methyl]aminocarbonyl-2-(4-fluoro-2-methylphenyl)-4-thiomorpholinocarbonyloxypiperidine, and under ice-cooling, 22 mg of 3-chloroperbenzoic acid was added thereto and the mixture was stirred at 0° C. for 30 minutes. The solution was extracted by adding a 0.1M aqueous sodium hydroxide solution and ethyl acetate. The organic layer was dried over magnesium sulfate and concentrated. The residue was purified by thin-layer silica gel chromatography (chloroform:acetone=4:1), to give 63 mg of (2R,4S)-1-[N-(3,5-bistrifluoromethylbenzyl)-N-methyl]aminocarbonyl-2-(4-fluoro-2-methylphenyl)-4-(1-oxothiomorpholino)carbonyloxypiperidine as shown in Table 65 below.

Example 214

In 2.4 ml of dichloromethane was dissolved 79 mg of (2R,4S)-1-[N-(3,5-bistrifluoromethylbenzyl)-N-methyl]aminocarbonyl-2-(4-fluoro-2-methylphenyl)-4-thiomorpholinocarbonyloxypiperidine, and added thereto was 68 mg of 3-chloroperbenzoic acid, and the mixture was stirred at room temperature for 4 hours. The solution was extracted by adding a 01.M aqueous sodium hydroxide solution and ethyl acetate. The organic layer was dried over magnesium sulfate and concentrated. The residue was purified by thin-layer silica gel chromatography (chloroform:acetone=4:1), to give 76 mg of (2R,4S)-1-[N-(3,5-bistrifluoromethylbenzyl)-N-methyl]aminocarbonyl-4-(1,1-dioxothiomorpholino)carbonyloxy-2-(4-fluoro-2-methylphenyl)piperidine as shown in Table 65 below.

Example 215

In 1 ml of tetrahydrofuran was dissolved 78 mg of (2R,4S)-1-[N-{1-(R)-(3,5-bistrifluoromethylphenyl)ethyl}-N-methyl]aminocarbonyl-2-(4-fluoro-2-methylphenyl)-4-(2,2,5-trimethyl[1,3]dioxolan-5-yl)carbamoylpiperidine, and under ice-cooling, 0.5 ml of a 2M aqueous hydrochloric acid solution was added thereto. After 15 minutes, the temperature was raised to room temperature and the mixture was further stirred for 30 minutes. The mixture was poured into a saturated aqueous sodium hydrogen carbonate solution, and extracted with ethyl acetate. The organic layer was washed with saturated brine, dried and concentrated. The residue was purified by silica gel column chromatography (chloroform:ethyl acetate=2:1), to give 64 mg of (2R,4S)-1-[N-{1-(R)-(3,5-bistrifluoromethylphenyl)ethyl}-N-methyl]aminocarbonyl-2-(4-fluoro-2-methylphenyl)-4-{1,1-di(hydroxymethyl)ethyl}carbamoylpiperidine as shown in Table 66 below.

Example 216

In 1 ml of dichloromethane was dissolved 50.5 mg of (2R,4S)-4-amino-1-[N-{1-(R)-(3,5-bistrifluoromethylphenyl)ethyl}-N-methyl]aminocarbonyl-2-(4-fluoro-2-methylphenyl)piperidine, and under ice-cooling, 25.3 mg of methylisocyanate was added thereto. After the temperature of the mixture was raised to room temperature, the mixture was stirred for 30 minutes. The solution was poured into water, the dichloromethane layer was separated and the aqueous layer was further extracted with chloroform. The combined organic layers were washed with saturated brine, dried and concentrated. The residue was purified by silica gel column chromatography (chloroform:methanol=19:1), to give 47.9 mg of (2R,4S)-1-[N-{1-(R)-(3,5-bistrifluoromethylphenyl)ethyl}-N-methyl]aminocarbonyl-2-(4-fluoro-2-methylphenyl)-4-methylureidopiperidine as shown in Table 66 below.

Example 217

(2R,4S)-4-amino-1-[N-{1-(R)-(3,5-bistrifluoromethylphenyl)ethyl}-N-methyl]aminocarbonyl-2-(4-fluoro-2-methylphenyl)piperidine and tert-butyl isocyanate were used and treated in the same manner as in Example 216, to give (2R,4S)-1-[N-{1-(R)-(3,5-bistrifluoromethylphenyl)ethyl}-N-methyl]aminocarbonyl-4-tert-butylureido-2-(4-fluoro-2-methylphenyl)piperidine as shown in Table 66.

Example 218

In 1 ml of dichloromethane was dissolved 50.5 mg of (2R,4S)-4-amino-1-[N-{1-(R)-(3,5-bistrifluoromethylphenyl)ethyl}-N-methyl]aminocarbonyl-2-(4-fluoro-2-methylphenyl)piperidine, and under ice-cooling, 42 µl of triethylamine and 18 µl of dimethylcarbamoyl chloride were added thereto. After the temperature of the mixture was raised to room temperature, the mixture was stirred overnight. The solvent was poured into water, and the dichloromethane layer was separated, and the aqueous layer was further extracted with chloroform. The combined organic layers were washed with saturated brine, dried and concentrated. The residue was purified by silica gel column chromatography (chloroform:methanol=39:1), to give 41.8 mg of (2R,4S)-1-[N-{1-(R)-(3,5-bistrifluoromethylphenyl)ethyl}-N-methyl]aminocarbonyl-4-(3,3-dimethylureido)-2-(4-fluoro-2-methylphenyl)piperidine as shown in Table 66 below.

Examples 219 to 224

The corresponding starting materials were used and treated in the same manner as in Example 216, to give compounds as shown in Table 67 below.

Example 225

(1) 80 mg of (2R,4S)-4-amino-1-[N-{1-(S)-(3,5-bistrifluoromethylphenyl)ethyl}-N-methyl]aminocarbonyl-2-(4-fluoro -2-methylphenyl)piperidine was used and treated in the same manner as in Example 216, to give (2R,4S)-1-[N-{1-(S)-(3,5-bistrifluoromethylphenyl)ethyl}-N-methyl]aminocarbonyl-2-(4-fluoro-2-methylphenyl)-4-(4-methylpiperazinocarbamoyl)piperidine.

(2) The compound of the above (1) was dissolved in 1 ml of ethyl acetate, and under ice-cooling, 0.5 ml of 4M hydrochloric acid-ethyl acetate solution was added thereto and the mixture was stirred for 30 minutes under ice-cooling. The solvent was removed by distillation under reduced pressure and added thereto was diethyl ether. Precipitated white crystals were collected by filtration, to give 80 mg of (2R,4S)-1-[N-{1-(S)-(3,5-bistrifluoromethylphenyl)ethyl}-N-methyl]aminocarbonyl-2-(4-fluoro-2-methylphenyl)-4-(4-methylpiperazinocarbamoyl)piperidine hydrochloride as shown in Table 67 below.

Example 226

In 2 ml of dichloromethane was dissolved 100 mg of (2R,4S)-4-amino-1-[N-{1-(S)-(3,5-bistrifluoromethylphenyl)ethyl}-N-methyl]aminocarbonyl-2-(4-fluoro-2-methylphenyl)piperidine, and under ice-cooling, 33 μl of triethylamine and 19 μl of methylchloroformate were added thereto and the mixture was stirred under ice-cooling for 30 minutes. The solution was poured into water and the dichloromethane layer was separated, and the aqueous layer was further extracted with dichloromethane. The combined organic layers were washed with saturated brine, dried and concentrated. The residue was purified by silica gel column chromatography (chloroform:methanol=19:1), to give 80 mg of (2R,4S)-1-[N-{1-(S)-(3,5-bistrifluoromethylphenyl)ethyl}-N-methyl]aminocarbonyl-2-(4-fluoro-2-methylphenyl)-4-methoxycarbamoylpiperidine as shown in Table 66 below.

Examples 227 to 229

The corresponding starting materials were used and treated in the same manner as in Example 226, to give compounds as shown in Table 68 below.

Example 230

In 1.2 ml of acetonitrile was dissolved 22 mg of 2-ethoxyethanol, and 94 mg of N,N'-disuccinimidylcarbonate and 0.1 ml of triethylamine were added thereto, and the mixture was stirred at room temperature for 1.5 hours. The solvent was removed by distillation, and to the residue were added a saturated aqueous sodium hydrogen carbonate solution and ethyl acetate, and extracted. The organic layer was washed with saturated brine, dried, and concentrated. The residue was dissolved in 0.8 ml of dichloromethane, and added thereto were 80 mg of (2R,4S)-4-amino-1-[N-{1-(S)-(3,5-bistrifluoromethylphenyl)ethyl}-N-methyl]aminocarbonyl-2-(4-fluoro-2-methylphenyl)piperidine and 33 μl of triethylamine, and the mixture was stirred at room temperature for 30 minutes. To the solution were added a saturated aqueous sodium hydrogen carbonate solution and dichloromethane and extracted. The combined organic layers were washed with saturated brine, dried and concentrated. The residue was purified by thin-layer silica gel chromatography (chloroform:methanol=19:1), to give 85 mg of (2R,4S)-1-[N-{1-(S)-(3,5-bistrifluoromethylphenyl)ethyl}-N-methyl]aminocarbonyl-4-(2-ethoxyethoxy)carbamoyl-2-(4-fluoro-2-methylphenyl)piperidine as shown in Table 68 below.

Example 231

3-hydroxy-3-methylbutanol and (2R,4S)-4-amino-1-[N-{1-(S)-(3,5-bistrifluoromethylphenyl)ethyl}-N-methyl]aminocarbonyl-2-(4-fluoro-2-methylphenyl)piperidine were used and treated in the same manner as in Example 230, to give (2R,4S)-1-[N-{1-(S)-(3,5-bistrifluoromethylphenyl)ethyl}-N-methyl]aminocarbonyl-2-(4-fluoro-2-methylphenyl)-4-(3-hydroxy-3-methylbutoxy)carbamoylpiperidine as shown in Table 68 below.

Example 232

(1) In 1 ml of tetrahydrofuran was dissolved 119 mg of (2R,4S)-1-[N-{1-(R)-(3,5-bistrifluoromethylphenyl)ethyl}-N-methyl]aminocarbonyl-2-(4-fluoro-2-methylphenyl)-4-vinylsulfonylaminopiperidine. Added thereto was 26 μl of morpholine at room temperature, and the mixture was refluxed under heating. Five hours later, 26 μl of morpholine was added and the mixture was further refluxed under heating for 2.5 hours. The solution was concentrated and the residue was purified by silica gel column chromatography (chloroform:methanol=19:1), to give 129 mg of (2R,4S)-1-[N-{1-(R)-(3,5-bistrifluoromethylphenyl)ethyl}-N-methyl]aminocarbonyl-2-(4-fluoro-2-methylphenyl)-4-(2-morpholinoethyl)sulfonylaminopiperidine.

(2) In 1 ml of chloroform was dissolved 34.1 mg of the compound of the above (1), and added thereto 25 μl of 4M hydrochloric acid-ethyl acetate solution. The mixture was concentrated, to give 33.1 mg of (2R,4S)-1-[N-{1-(R)-(3,5-bistrifluoromethylphenyl)ethyl}-N-methyl]aminocarbonyl-2-(4-fluoro-2-methylphenyl)-4-(2-morpholinoethyl)sulfonylaminopiperidine hydrochloride as shown in Table 69 below.

Examples 233 to 238

The corresponding starting materials were used and treated in the same manner as in Example 232 (1) and (2), to give compounds as shown in Table 69 below.

Example 239

In mixture of 1.6 ml of dimethylformamide and 0.2 ml of dichloromethane was dissolved 101 mg of (2R,4S)-1-[N-{1-(S)-(3,5-bistrifluoromethylphenyl)ethyl}-N-methyl]aminocarbonyl-2-(4-fluoro-2-methylphenyl)-4-hydroxypiperidine, and added thereto were 39 mg of (S)-(−)-2-pyrrolidone-5-carboxilic acid, 58 mg of 1-ethyl-3-(3-dimethylaminopropyl)carbodiimide hydrochloride and 12 mg of 4-(dimethylamino)pyridine, and the mixture was stirred at room temperature for 6 hours, followed by stirring at 60° C. for 4 days. To the solution was added a 5% aqueous citric acid solution, and the mixture was extracted with chloroform. The organic layer was washed with a saturated aqueous sodium hydrogen carbonate solution and saturated brine, and dried over magnesium sulfate and concentrated. The residue was purified by silica gel column chromatography (chloroform:acetone=4:1→2:1), to give 64 mg of (2R,4S)-1-[N-{1-(S)-(3,5-bistrifluoromethylphenyl)ethyl}-N-methyl]aminocarbonyl-4-{(2S)-5-oxopyrrolidin-2-yl}carbonyloxy-2-(4-fluoro-2-methylphenyl)piperidine as shown in Table 70 below.

Example 240

(1) In a mixture of 3.2 ml of toluene and 0.4 ml of dichloromethane was dissolved 179 mg of (2R,4S)-1-[N-{1-(S)-(3,5-bistrifluoromethylphenyl)ethyl}-N-methyl]aminocarbonyl-2-(4-fluoro-2-methylphenyl)-4-hydroxypiperidine, and added thereto was 69 mg of 1,1'-carbonyldiimidazole, and the mixture was stirred at 60° C. for 3 hours. Distilled water was added thereto and the mixture was extracted with chloroform. The organic layer was dried over magnesium sulfate, and concentrated under reduced pressure. The residue was dissolved in 3.2 ml of acetonitrile, 88 μl of methyl iodide was added thereto, and the mixture was stirred at 50° C. for 3 hours. After the solution was concentrated, 3.2 ml of toluene and 114 μl of thiazolidine were added and the mixture was stirred at 70° C. for 16 hours. Distilled water was added thereto and the mixture was extracted with chloroform. The organic layer was dried over magnesium sulfate and concentrated under reduced pressure. The residue was purified by silica gel column chromatography (hexane:ethyl acetate=:1:1→1:2), to give 141 mg of (2R,4S)-1-[N-{1-(S)-(3,5-bistrifluoromethylphenyl)ethyl}-N-methyl]aminocarbonyl-2-(4-fluoro-2-methylphenyl)-4-(1,3-tetrahydrothiazol-3-yl)carbonyloxypiperidine.

(2) In 2 ml of dichloroethane was dissolved 62 mg of the compound of the above (1), and under ice-cooling, 22 mg of 3-chloroperbenzoic acid was added thereto and the mixture was stirred at 0° C. for an hour. To the mixture was added a saturated aqueous sodium hydrogen carbonate solution and extracted. The organic layer was dried over magnesium sulfate and concentrated under reduced pressure. The residue was purified by thin-layer silica gel chromatography (chloroform:acetone=4:1), to give 42 mg of (2R,4S)-1-[N-{1-(S)-(3,5-bistrifluoromethylphenyl)ethyl}-N-methyl]aminocarbonyl-2-(4-fluoro-2-methylphenyl)-4-(1-oxo-1,3-tetrahydrothiazol-3-yl)carbonyloxypiperidine as shown in Table 70 below.

Example 241

(1) In 1.9 ml of toluene was dissolved 101 mg of (2R,4S)-1-[N-{1-(S)-(3,5-bistrifluoromethylphenyl)ethyl}-N-methyl]aminocarbonyl-2-(4-fluoro-2-methylphenyl)-4-hydroxypiperidine, and added thereto were 46 μl of isocyanate acetic acid ethyl ester and one drop of acetic acid, and the mixture was stirred at 70° C. for 16 hours. The solution was concentrated and the residue was purified by silica gel column chromatography (hexane:ethyl acetate=2:1→1:1), to give 124 mg of (2R,4S)-1-[N-{1-(S)-(3,5-bistrifluoromethylphenyl)ethyl}-N-methyl]aminocarbonyl-4-ethoxycarbonylmethylaminocarbonyloxy-2-(4-fluoro-2-methylphenyl)piperidine.

(2) In a mixture of 1.35 ml of tetrahydrofuran and 0.15 ml of methanol was dissolved 106 mg of the compound of the above (1), and added thereto was 92 μl of a 2M aqueous sodium hydroxide solution, and the mixture was stirred at room temperature for 1 hour. After the solution was concentrated, a 10% aqueous citric acid solution was added thereto, and the precipitates were collected by filtration and washed with water, to give 92 mg of (2R,4S)-1-[N-{1-(S)-(3,5-bistrifluoromethylphenyl)ethyl}-N-methyl]aminocarbonyl-4-carboxymethylaminocarbonyloxy-2-(4-fluoro-2-methylphenyl)piperidine as shown in Table 70 below.

Example 242

In 0.9 ml of dimethylformamide was dissolved 61 mg of (2R,4S)-1-[N-{1-(S)-(3,5-bistrifluoromethylphenyl)ethyl}-N-methyl]aminocarbonyl-4-carboxymethylaminocarbonyloxy-2-(4-fluoro-2-methylphenyl)piperidine, and added thereto were 9 μl of morpholine, 15 mg of 1-hydroxybenzotriazole monohydrate and 19 mg of 1-ethyl-3-(3-dimethylaminopropyl)carbodiimide hydrochloride, and the mixture was stirred at room temperature for a day. To the solution was added distilled water and the mixture was extracted with chloroform, and the organic layer was dried over magnesium sulfate and concentrated. The residue was purified by silica gel column chromatography (chloroform:methanol=19:1), to give 50 mg of (2R,4S)-1-[N-{1-(S)-(3,5-bistrifluoromethylphenyl)ethyl}-N-methyl]aminocarbonyl-2-(4-fluoro-2-methylphenyl)-4-morpholinocarbonylmethylaminocarbonyloxypiperidine as shown in Table 70 below.

Example 243

In 1.9 ml of toluene was dissolved 101 mg of (2R,4S)-1-[N-{1-(S)-(3,5-bistrifluoromethylphenyl)ethyl}-N-methyl]aminocarbonyl-2-(4-fluoro-2-methylphenyl)-4-hydroxypiperidine, and added thereto was 37 μl of chlorosulfonylisocyanate, and the mixture was stirred at room temperature for 10 minutes. Added thereto was 207 μl of diethylamine, and the mixture was stirred at room temperature for an hour. To the solution was added distilled water, and the mixture was extracted with chloroform. The organic layer was dried over magnesium sulfate and concentrated. The residue was purified by silica gel column chromatography (chloroform:methanol=19:1), to give 116 mg of (2R,4S)-1-[N-{1-(S)-(3,5-bistrifluoromethylphenyl)ethyl}-N-methyl]aminocarbonyl-4-diethylaminosulfonylaminocarbonyloxy-2-(4-fluoro-2-methylphenyl)piperidine as shown in Table 70 below.

Example 244

(2R,4S)-1-[N-(3,5-bistrifluoromethylbenzyl)-N-methyl]aminocarbonyl-2-(4-fluoro-2-methylphenyl)-4-hydroxypiperidine and (S)-(−)-2-pyrrolidone-5-carboxylic acid were used and treated in the same manner as in Example 239, to give (2R,4S)-1-[N-(3,5-bistrifluoromethylbenzyl)-N-methyl]aminocarbonyl-4-{(2S)-5-oxopyrrolidin-2-yl}carbonyloxy-2-(4-fluoro-2-methylphenyl)piperidine as shown in Table 70 below.

Example 245

In 2 ml of toluene were dissolved 264 mg of (2R)-4-amino-1-[N-(3,5-bistrifluoromethylbenzyl)-N-methyl]aminocarbonyl-2-(4-fluoro-2-methylphenyl)piperidine hydrochloride, 80 mg of 2-bromopyridine, 12 mg of palladium acetate, 32 mg of 2,2'-bis(diphenylphosphino)-1,1'-bisnaphtyl and 48 mg of sodium tert-butoxide, and the mixture was stirred at 80° C. for 16 hours. The solution was cooled down to room temperature, and added thereto were ethyl acetate and an aqueous sodium hydrogen carbonate solution and the mixture was extracted. The organic layer was dried over magnesium sulfate and concentrated. The residue was purified by NH silica gel column chromatography (hexane:ethyl acetate=2:1), to give 68 mg of (a) (2R,4S)-1-[N-(3,5-bistrifluoromethylbenzyl)-N-methyl]aminocarbonyl-2-(4-fluoro-2-methylphenyl)-4-(2-pyridylamino)piperidine and 56 mg of (b) (2R,4R)-1-[N-(3,5-bistrifluoromethylbenzyl)-N-methyl]

aminocarbonyl-2-(4-fluoro-2-methylphenyl)-4-(2-pyridylamino)piperidine as shown in Table 71 below.

Examples 246 to 247

The corresponding starting materials were used and treated in the same manner as in Example 245, to give compounds as shown in Tables 71 to 72 below.

Examples 248 to 249

The corresponding starting materials were used and treated in the same manner as in Example 75, to give compounds as shown in Table 72 below.

Example 250

(1) In 5 ml of tetrahydrofuran was dissolved 800 mg of (2R,4S)-1-[N-{1-(S)-(3,5-bistrifluoromethylphenyl)ethyl}-N-methyl]aminocarbonyl-4-ethoxycarbonyl-2-(4-fluoro-2-methylphenyl)piperidine, and 5 ml of a 2M aqueous sodium hydroxide solution was added thereto and the mixture was stirred at room temperature for 3 days. To the reaction mixture was added an aqueous citric acid solution to make it acidic, and the mixture was extracted with ethyl acetate. The organic layer was washed with saturated brine and dried. This solution was concentrated, to give 700 mg of (2R,4S)-1-[N-{1-(S)-(3,5-bistrifluoromethylphenyl)ethyl}-N-methyl]aminocarbonyl-4-carboxy-2-(4-fluoro-2-methylphenyl)piperidine.

(2) In dimethylformamide was dissolved 110 mg of the compound of the above (1), and added thereto were 96 mg of 1-[3-(dimethylamino)propyl]-3-ethylcarbodiimide hydrochloride, 30 mg of 1-hydroxybenzotriazole, 0.1 ml of a 40% aqueous ammonium solution, and the mixture was stirred at room temperature for 3 hours. To the solution were added an aqueous citric acid solution and ethyl acetate, and the layers were separated. The organic layer was washed with saturated brine, dried and concentrated. The residue was purified by silica gel column chromatography (chloroform:methanol=9:1), to give 87 mg of (2R,4S)-4-aminocarbonyl-1-[N-{1-(S)-(3,5-bistrifluoromethylphenyl)ethyl}-N-methyl]aminocarbonyl-2-(4-fluoro-2-methylphenyl)piperidine as shown in Table 73 below.

Examples 251 to 253

The corresponding starting materials were used and treated in the same manner as in Example 250 (1) and (2) or Example 250 (2), to give compounds as shown in Table 73 below.

Example 254

(1) In 40 ml of tetrahydrofuran was dissolved 2 g of (2R,4S)-1-[N-{1-(R)-(3,5-bistrifluoromethylphenyl)ethyl}-N-methyl]aminocarbonyl-2-(4-fluoro-2-methylphenyl)-4-hydroxypiperidine, and added thereto were 1.59 g of carbon tetrabromide and 1.26 g of triphenylphosphine, and the mixture was stirred at room temperature for 2 hours. To the solution was added 80 ml of diethyl ether, and after stirring the mixture, precipitated insoluble matters were removed by filtration. The organic layer was concentrated and the residue was purified by silica gel column chromatography (n-hexane:ethyl acetate=10:1), to give 1.26 g of (2R,4R)-1-[N-{1-(S)-(3,5-bistrifluoromethylphenyl)ethyl}-N-methyl]aminocarbonyl-4-bromo-2-(4-fluoro-2-methylphenyl)piperidine.

(2) In 20 ml of dimethylformamide was dissolved 1.14 g of the compound of the above (1), and added thereto was 1.14 g of potassium thioacetate and the mixture was stirred at 80° C. for 2 hours. After the solution was cooled down to room temperature, an aqueous citric acid solution and ethyl acetate were added thereto and layers were separated. The organic layer was washed with saturated brine, dried and concentrated. The residue was purified by silica gel column chromatography (n-hexane:ethyl acetate=6:1), to give 920 mg of (2R,4S)-4-acetylthio-1-[N-{1-(S)-(3,5-bistrifluoromethylphenyl)ethyl}-N-methyl]aminocarbonyl-2-(4-fluoro-2-methylphenyl)piperidine as shown in Table 74 below.

Examples 255 to 256

The corresponding starting materials were used and treated in the same manner as in Example 254 (1) and (2), to give compounds as shown in Table 74 below.

Example 257

In 10 ml of methanol was dissolved 880 mg of (2R,4S)-4-acetylthio-1-[N-{1-(S)-(3,5-bistrifluoromethylphenyl)ethyl}-N-methyl]aminocarbonyl-2-(4-fluoro-2-methylphenyl)piperidine, and added thereto were methyl iodide and 5 ml of a 1M aqueous sodium hydroxide solution, and the mixture was stirred at room temperature for 2 hours. To the solution was added an aqueous citric acid solution to neutralize the same, and methanol was removed by distillation. To the residue were added ethyl acetate and saturated brine and layers were separated. The organic layer was dried and concentrated. The residue was purified by silica gel column chromatography ( n-hexane:ethyl acetate=6:1), to give 560 mg of (2R,4S)-1-[N-{1-(S)-(3,5-bistrifluoromethylphenyl)ethyl}-N-methyl]aminocarbonyl-2-(4-fluoro-2-methylphenyl)-4-methylthiopiperidine as shown in Table 74 below.

Examples 258 to 263

The corresponding starting materials were used and treated in the same manner as in Example 257, to give compounds as shown in Tables 74 to 75 below.

Examples 264 to 270

The corresponding starting materials were used and treated in the same manner as in Example 213, to give compounds as shown in Tables 76 to 77 below.

Examples 271 to 278

The corresponding starting materials were used and treated in the same manner as in Example 214, to give compounds as shown in Tables 78 to 79 below.

Examples 279 to 312

The corresponding starting materials were used and treated in the same manner as in Example 138, to give compounds as shown in Tables 80 to 87 below.

Example 313

To 4.2 ml of 4M hydrochloric acid in ethyl acetate was added 361 mg of (2R,4S)-1-{N-(3,5-bistrifluoromethylbenzyl)-N-methyl}amino-carbonyl-4-[{(2S,4R)-4-benzyloxy-1-tert-butyloxycarbonyl-pyrrolidin-2-ylcarbonyl}amino]-2-

(4-fluoro-2-methylphenyl)-piperidine and the mixture was stirred for 1 hour at room temperature. After the evaporation in vacuo the residue was triturated with hexane and the solvent was removed by decantation. The residue was dissolved in 4 ml of methylenechloride and 158 ml of triethylamine and 36 ml of acetylchloride were added to the mixture under ice-cooling. After stirring for 1 hour under ice-cooling water was added to the mixture and the mixture was extracted with chloroform. The organic layer was dried over magnesium sulfate and evaporated in vacuo. The residue was purified by silica gel column chromatography (chroloform:methanol=49:1→19:1), to give 304 mg of (2R,4S)-1-{N-(3,5-bistrifluoromethylbenzyl)-N-methyl}-aminocarbonyl-4-{[(2S, 4R)-4-benzyloxy-1-acetylpyrrolidin-2-ylcarbonyl]amino}-2-(4-fluoro-2-methylphenyl)piperidine as shown in Table 86.

Examples 314 to 316

The corresponding starting materials were used and treated the same manner of Examples 313, to give the compounds as shown in Tables 86 and 87.

Examples 317 to 318

The corresponding starting materials were used and treated the same manner of Examples 113(2), to give the compounds as shown in Table 87.

Example 319

In 1.8 ml of toluene was dissolved 98 mg of (2R,4S)-4-amino-1-{N-(3,5-bistrifluoromethylbenzyl)-N-methyl}amino-carbonyl-2-(4-fluoro-2-methylphenyl)piperidine, and added thereto was 24 mg of succinic anhydride and 0.033 ml of triethylamine, and the mixture was refluxed for 18 hours. The mixture was cooled down at room temperature, and then was added water. The mixture was extracted with ethyl acetate, the organic layer was dried and concentrated. The residue was purified by thin layer silica gel column chromatography (chloroform:methanol=19:1), to give 79 mg of (2R,4S)-1-{N-(3,5-bistrifluoromethylbenzyl)-N-methyl}aminocarbonyl-4-(2,5-dioxopyrrolino)-2-(4-fluoro-2-methylphenyl)piperidine as shown in Table 87 below.

Examples 320 to 330

The corresponding starting materials were used and treated in the same manner as in Example 209, to give compounds as shown in Tables 88 to 90 below.

Example 331

The corresponding starting materials were used and treated in the same manner as in Example 113, to give (2R,4S)-1-{N-(3,5-bistrifluoromethylbenzyl)-N-methyl}aminocarbonyl-2-(4-fluoro-2-methylphenyl)-4-(ethoxycarbonylmethyl)-piperidine as shown in Table 91 below.

Example 332

In 20 ml of tetrahydrofuran was dissolved 2.03 g of (2R, 4S)-1-{N-(3,5-bistrifluoromethylbenzyl)-N-methyl}aminocarbonyl-2-(4-fluoro-2-methylphenyl)-4-ethoxycarbonylmethylpiperidine, and added thereto was 450 mg of aluminum lithium hydride under ice-cooling, and the mixture was stirred for an hour. Slowly added thereto was 2 ml of water and after stirring the mixture for 10 minutes, 5 ml of a 1M aqueous sodium hydroxide solution was added and the mixture was further stirred for 10 minutes. Formed white precipitates were removed, and diethyl ether and water were added to the filtrate, and layers were separated. The organic layer was further washed with water, dried, and concentrated under reduced pressure. The residue was purified by silica gel column chromatography (hexane:ethyl acetate=4:1→3:2), to give 830 mg of (2R,4S)-1-{N-(3,5-bistrifluoromethylbenzyl)-N-methyl}aminocarbonyl-2-(4-fluoro-2-methylphenyl)-4-(2-hydroxyethyl)piperidine as shown in Table 91 below.

Example 333

The corresponding starting material was used and treated in the same manner as in Example 245, to give (2R,4S)-1-{N-(3,5-bistrifluoromethylbenzyl)-N-methyl}aminocarbonyl-2-(4-fluoro-2-methylphenyl)-4-(N-pirazine-2-ylamino)piperidine as shown in Table 91 below.

Example 334

In 2 ml of N,N-dimethylformamide was dissolved 114 mg of (2R,4S)-1-{N-(3,5-bistrifluoromethylbenzyl)-N-methyl}aminocarbonyl-2-(4-fluoro-2-methylphenyl)-4-(N-pyrazin-2-ylamino)piperidine, and 10 mg of sodium hydride (40% oil mixture) was added thereto under ice-cooling, and after stirring the mixture for 5 minutes, 0.013 ml of methyl iodide was added and the mixture was stirred at room temperature for 2 hours. To the solution were added water and ethyl acetate, and after stirring the mixture for 10 minutes, layers were separated. The organic layer was washed with brine, dried and concentrated under reduced pressure. The residue was purified by NH silica gel column chromatography(hexane:ethyl acetate=85:15→1:1), to give 98 mg of (2R, 4S)-1-{N-(3,5-bistrifluoromethylbenzyl)-N-methyl}aminocarbonyl-2-(4-fluoro-2-methylphenyl)-4-(N-pyrazine-2-yl-N-methylamino)piperidine as shown in Table 91 below.

Example 335

In 40 ml of dichloromethane was dissolved 8.0 g of (2R)-1-{N-(3, 5-bistrifluoromethylbenzyl)-N-methyl}aminocarbonyl-2-(4-fluoro-2-methylphenyl)-4-oxopiperidine, and added thereto were 10 ml of an ethanol solution of methylamine (35%, about 8M), 2 ml of acetic acid and 4.24 g of sodium triacetoxy borohydride, and the mixture was stirred at room temperature for 16 hours. To the solution were added a 2M aqueous sodium carbonate solution and chloroform, and after stirring the mixture for 30 minutes, layers were separated. The aqueous layer was further extracted with chloroform, and the combined organic layers were dried and concentrated under reduced pressure. The residue was purified by NH silica gel column chromatography(hexane:ethyl acetate=2:1), to give a mixture of (a) (2R, 4S)-1-{N-(3,5-bistrifluoromethylbenzyl)-N-methyl}aminocarbonyl-2-(4-fluoro-2-methylphenyl)-4-methylaminopiperidine and (b) (2R,4R)-1-{N-(3,5-bistrifluoromethylbenzyl)-N-methyl}aminocarbonyl-2-(4-fluoro-2-methylphenyl)-4-methylaminopiperidine.

(2) The mixture obtained in the above (1) was dissolved in 40 ml of dichloromethane, and added thereto was 4.4 g of di-tert-butyldicarbonate, and the mixture was stirred at room temperature for 16 hours. The solution was concentrated under reduced pressure, and the residue was purified by silica gel column chromatography(hexane:ethyl acetate=10:1), to give 4.2 g of (2R,4S)-1-{N-(3,5-bistrifluoromethylbenzyl)-N-methyl}aminocarbonyl-2-(4-fluoro-2-methylphenyl)-4-(tert-butoxycarbonyl-N-methylamino)piperidine.

(3) The compound of the above (2) was treated with 4M hydrochloric acid-ethyl acetate solution, and concentrated under reduced pressure. The residue was recrystallized by a mixed solution of hexane and ethyl acetate, to give 3.6 g of (2R,4S)-1-{N-(3,5-bistrifluoromethylbenzyl)-N-methyl}aminocarbonyl-2-(4-fluoro-2-methylphenyl)-4-methylaminopiperidine hydrochloride as shown in Table 91 below.

Example 336

(1) 2.12 g of (2R,4S)-4-ethoxycarbonyl-2-(4-fluoro-2-methylphenyl)-4-piperidine was used and treated in the same manner as in Example 248, to give 3.8 g of (2R,4S)-1-{N-(3, 5-bistrifluoromethylbenzyl)-N-methyl}aminocarbonyl-4-ethoxycarbonyl-2-(4-fluoro-2-methylphenyl)piperidine.

(2) The compound of the above (1) was treated in the same manner as in Example 250(1), to give 2.3 g of (2R,4S)-1-{N-(3,5-bistrifluoromethylbenzyl)-N-methyl}amino-4-carboxy-2-(4-fluoro-2-methylphenyl)piperidine as shown in Table 91 below.

Examples 337 to 340

The corresponding starting materials were used and treated in the same manner as in Example 250 (2), to give compounds as shown in Table 91 below.

Example 341

(1) 4-ethoxycarbonyl-2-(4-fluoro-2-methylphenyl)piperidine and the corresponding starting material were used and treated in the same manner as in Example 248, and purified by silica gel column chromatography (hexane:ethyl acetate=4:1), to give (2R,4S)-1-[N-{1-(S)-(3,5-bistrifluoromethylphenyl)ethyl}-N-methyl]aminocarbonyl-2-(4-fluoro-2-methylphenyl)-4-ethoxycarbonylpiperidine.

(2) The compound of the above (1) was used and treated in the same manner as in Example 250 (1), to give (2R,4S)-1-[N-{1-(S)-(3,5-bistrifluoromethylphenyl)ethyl}-N-methyl]aminocarbonyl-4-carboxy-2-(4-fluoro-2-methylphenyl)piperidine as shown in Table 92 below.

Examples 342 to 349

(2R,4S)-1-[N-{1-(S)-(3,5-bistrifluoromethylphenyl)ethyl}-N-methyl]aminocarbonyl-4-carboxy-2-(4-fluoro-2-methylphenyl)piperidine and the corresponding starting materials were used and treated in the same manner as in Example 250 (2), to give compounds as shown in Table 92 below.

Example 350

In 12 ml of tetrahydrofuran was dissolved 1.62 g of (2R, 4S)-1-[N-{1-(S)-(3,5-bistrifluoromethylphenyl)ethyl}-N-methyl]aminocarbonyl-4-carboxy-2-(4-fluoro-2-methylphenyl)piperidine, and added dropwise thereto was 2 ml of dimethylsulfide complex of borane (about 10M), and the mixture was stirred at room temperature for 16 hours. To the reaction mixture was added 10 ml of methanol and the mixture was stirred for 0.5 hours. After the reaction was completed, the mixture was concentrated under reduced pressure, and the residue was purified by silica gel column chromatography (chloroform:methanol=9:1), to give 1.32 g of (2R,4S)-1-[N-{1-(S)-(3,5-bistrifluoromethylphenyl)ethyl}-N-methyl]aminocarbonyl-2-(4-fluoro-2-methylphenyl)-4-hydroxymethylpiperidine as shown in Table 93 below.

Examples 351 to 352

(2R,4S)-1-[N-{1-(S)-(3,5-bistrifluoromethylphenyl)ethyl}-N-methyl]aminocarbonyl-2-(4-fluoro-2-methylphenyl)-4-hydroxymethylpiperidine and the corresponding starting materials were used and treated in the same manner as in Example 209, to give compounds as shown in Table 93 below.

Example 353

4-ethoxycarbonyl-2-(4-fluoro-2-methylphenyl)piperidine and the corresponding starting material were used and treated in the same manner as in Example 341, to give compound (2R,4S)-1-[N-{1-(R)-(3,5-bistrifluoromethylphenyl)ethyl}-N-methyl]aminocarbonyl-4-carboxy-2-(4-fluoro-2-methylphenyl)piperidine as shown in Table 94 below.

Examples 354 to 365

(2R,4S)-1-[N-{1-(R)-(3,5-bistrifluoromethylphenyl)ethyl}-N-methyl]aminocarbonyl-4-carboxy-2-(4-fluoro-2-methylphenyl)piperidine and the corresponding starting materials were used and treated in the same manner as in Example 250 (2), to give compounds as shown in Tables 94 and 95 below.

Example 366

In 2 ml of dichloromethane was dissolved 132 mg of (2R, 4S)-1-[N-{1-(R)-(3,5-bistrifluoromethylphenyl)ethyl}-N-methyl]aminocarbonyl-4-carboxy-2-(4-fluoro-2-methylphenyl)piperidine, and added thereto were 0.027 ml of oxalic dichloride and one drop of N,N-dimethylformamide, and the mixture was stirred at room temperature for 2 hours. The reaction mixture was concentrated under reduced pressure. To the residue were added 2.5 ml of tetrahydrofuran and 0.12 ml of 2-aminopyrazine and the mixture was stirred at room temperature for 16 hours. The reaction mixture was concentrated under reduced pressure, and the residue was purified by NH silica gel column chromatography (hexane:ethyl acetate=1:1), to give 63 mg of (2R,4S)-1-[N-{1-(R)-(3,5-bistrifluoromethylphenyl)ethyl}-N-methyl]aminocarbonyl-2-(4-fluoro-2-methylphenyl)-4-(2-pyrazylaminocarbonyl)piperidine as shown in Table 96 below.

Example 367

(2R,4S)-1-[N-{1-(R)-(3,5-bistrifluoromethylphenyl)ethyl}-N-methyl]aminocarbonyl-4-carboxy-2-(4-fluoro-2-methylphenyl)piperidine was used and treated in the same manner as in Example 350, to give (2R,4S)-1-[N-{1-(R)-(3,5-bistrifluoromethylphenyl)ethyl}-N-methyl]aminocarbonyl-2-(4-fluoro-2-methylphenyl)-4-hydroxymethylpiperidine as shown in Table 96 below.

Example 368

In a mixture of 20 ml of toluene and 20 ml of acetic acid anhydride was dissolved 1.07 g of the compound of Example 268, and added thereto 165 mg of sodium acetate and the mixture was stirred while being refluxed under heating for 16 hours. After the reaction mixture was cooled down to room temperature, an aqueous sodium hydrogen carbonate solution was slowly added thereto until no foam was generated. To the mixture were added water and ethyl acetate, and layers were separated. The aqueous layer was further extracted with ethyl acetate, and the combined organic layers were dried and concentrated under reduced pressure. The residue was purified by silica gel column chromatography (hexane:ethyl acetate=1:1), to give 980 mg of (2R,4S)-1-{N-(3,5-bistrifluoromethylbenzyl)-N-methyl}aminocarbonyl-2-(4-fluoro-2-methylphenyl)-4-acetoxymethylthiopiperidine as shown in Table 97 below.

Example 369

(2R,4S)-4-acetoxymethylthio-1-{N-(3,5-bistrifluoromethylbenzyl)-N-methyl}aminocarbonyl-2-(4-fluoro-2-methylphenyl)piperidine was used and treated in the same manner as in Example 214, to give (2R,4S)-4-acetoxymethylsulfonyl-1-{N-(3,5-bistrifluoromethylbenzyl)-N-methyl}aminocarbonyl-2-(4-fluoro-2-methylphenyl)piperidine as shown in Table 97 below.

Example 370

In 10 ml of tetrahydrofuran and 5 ml of a 2M aqueous sodium hydroxide solution was dissolved 200 mg of (2R,4S)-4-acetoxymethylsulfonyl-1-{N-(3,5-bistrifluoromethylbenzyl)-N-methyl}aminocarbonyl-2-(4-fluoro-2-methylphenyl) piperidine, and the mixture was stirred at room temperature for 3 hours. The reaction mixture was neutralized by 2M hydrochloric acid, and the mixture was extracted with ethyl acetate twice. The combined organic layers were dried and concentrated under reduced pressure, to give 80 mg of (2R,4S)-1-{N-(3,5-bistrifluoromethylbenzyl)-N-methyl}aminocarbonyl-2-(4-fluoro-2-methylphenyl)-4-hydroxysulfinylpiperidine as shown in Table 97 below.

Example 371

In 2.5 ml of acetonitrile was dissolved 130 mg of the compound of Example 261, and added thereto was 0.5 ml of methyl iodide, and the mixture was stirred at 50° C. for 2 hours. The reaction mixture was concentrated and the residue was washed with diethyl ether, to give 117 mg of (2R,4S)-[1-{N-(3,5-bistrifluoromethylbenzyl)-N-methyl}aminocarbonyl-2-(4-fluoro-2-methylphenyl)piperidine-4-yl]dimethylsulfonium iodide as shown in Table 97 below.

Example 372

In 100 ml of tetrahydrofuran was dissolved 10.7 g of (2R)-1-{N-(3,5-bistrifluoromethylbenzyl)-N-hydroxypropyl}aminocarbonyl-2-(4-fluoro-2-methylphenyl)-4-oxopiperidine, and added thereto were 20 ml of pyridine and 20 ml of acetic acid anhydride, and the mixture was stirred at room temperature for S hours. To the reaction mixture were added an aqueous sodium hydrogen carbonate solution and diethyl ether, and the mixture was stirred for an hour. Layers were separated and after the organic layer was washed with water twice, it was dried and concentrated under reduced pressure. The residue was dissolved in 100 ml of ethanol, and added thereto was 1.5 g of sodium borohydride under ice-cooling and the mixture was stirred for 0.5 hours. To the reaction mixture was added an aqueous ammonium chloride solution and after stirring the mixture for 30 minutes, the solvent was removed by distillation under reduced pressure. To the residue was added water and the solution was extracted with chloroform twice. The combined organic layers were dried and concentrated under reduced pressure. The residue was purified by silica gel column chromatography (chloroform:methanol=9:1), to give 9.6 g of (2R,4S)-1-{N-(3-acetoxypropyl)-N-(3,5-bistrifluoromethylbenzyl)}aminocarbonyl-2-(4-fluoro-2-methylphenyl)-4-hydroxypiperidine as shown in Table 98 below.

Examples 373 to 376

(2R,4S)-1-{N-(3-acetoxypropyl)-N-(3,5-bistrifluoromethylbenzyl)}aminocarbonyl-2-(4-fluoro-2-methylphenyl)-4-hydroxypiperidine and the corresponding starting materials were used and treated in the same manner as in Example 209, to give compounds as shown in Table 98 below.

Example 377

In 5 ml of methanol was dissolved 600 mg of (2R,4S)-1-{N-(3-acetoxypropyl)-N-(3,5-bistrifluoromethylbenzyl)}aminocarbonyl-4-ethylaminocarbonyloxy-2-(4-fluoro-2-methylphenyl)piperidine, and added thereto was 5 ml of a 2M aqueous sodium hydroxide solution, and the mixture was stirred at room temperature for 16 hours. To the reaction mixture was added a 2M aqueous hydrochloric acid solution to neutralize, and the mixture was extracted with chloroform twice. The combined organic layers were dried, concentrated under reduced pressure and purified by silica gel column chromatography (chloroform:methanol=9:1), to give 550 mg of (2R,4S)-1-{N-(3,5-bistrifluoromethylbenzyl)-N-(3-hydroxypropyl)}aminocarbonyl-4-ethylaminocarbonyloxy-2-(4-fluoro-2-methylphenyl)piperidine as shown in Table 99 below.

Examples 378 to 381

The corresponding starting materials were used and treated in the same manner as in Example 377 to give compounds as shown in Table 99 below.

Example 382

(2R,4S)-1-{N-(3,5-bistrifluoromethylbenzyl)-N-(3-hydroxypropyl)}aminocarbonyl-4-thiomorpholinocarbonyloxy-2-(4-fluoro-2-methylphenyl)piperidine was used and treated in the same manner as in Example 213, to give (2R,4S)-1-{N-(3,5-bistrifluoromethylbenzyl)-N-(3-hydroxypropyl)}aminocarbonyl-4-(1-oxothiomorpholino)carbonyloxy-2-(4-fluoro-2-methylphenyl)piperidine as shown in Table 99 below.

Example 383

(1) (2R,4S)-1-{N-acetoxypropyl-N-(3,5-bistrifluoromethylbenzyl)}aminocarbonyl-2-(4-fluoro-2-methylphenyl)-4-hydroxypiperidine was used and treated in the same manner as in Example 254 (1) and (2), to give (2R,4S)-1-{N-acetoxypropyl-N-(3,5-bistrifluoromethylbenzyl)}aminocarbonyl-2-(4-fluoro-2-methylphenyl)-4-acetylthiopiperidine.

(2) The compound of the above (1) was used and treated in the same manner as in Example 257, to give (2R,4S)-1-{N-(3,5-bistrifluoromethylbenzyl)-N-hydroxypropyl}aminocarbonyl-2-(4-fluoro-2-methylphenyl)-4-(2-propylthio)piperidine.

(3) The compound of the above (2) was used and treated in the same manner as in Example 213, to give (2R,4S)-1-{N-

(3,5-bistrifluoromethylbenzyl)-N-hydroxypropyl}aminocarbonyl-2-(4-fluoro-2-methylphenyl)-4-(propane-2-sulfinyl)piperidine as shown in Table 99 below.

Example 384

(2R,4S)-1-{N-(3,5-bistrifluoromethylbenzyl)-N-hydroxypropyl}aminocarbonyl-2-(4-fluoro-2-methylphenyl)-4-(2-propylthio)piperidine was used and treated in the same manner as in Example 214, to give (2R,4S)-1-{N-(3,5-bistrifluoromethylbenzyl)-N-hydroxypropyl}aminocarbonyl-2-(4-fluoro-2-methylphenyl)-4-(propane-2-sulfonyl)piperidine as shown in Table 99 below.

Example 385

148 mg of (2R,4S)-2-(4-fluoro-2-methylphenyl)-4-(2-hydroxyethylaminocarbonyloxy)piperidine and the corresponding starting material were used and treated in the same manner as in Reference Example 6, to give 36 mg of (2R,4S)-1-{N-(3,5-dimethylbenzyl)-N-methyl}aminocarbonyl-2-(4-fluoro-2-methylphenyl)-4-(2-hydroxyethylaminocarbonyloxy)piperidine as shown in Table 100 below.

Example 386

The corresponding starting materials were used and treated in the same manner as in Example 385, to give (2R,4S)-1-{N-(3,5-dichlorobenzyl)-N-methyl}aminocarbonyl-2-(4-fluoro-2-methylphenyl)-4-(2-hydroxyethylaminocarbonyloxy)piperidine as shown in Table 100 below.

Example 387

In 10 ml of tetrahydrofuran was dissolved 676 mg of (2R,4S)-2-(4-fluoro-2-methylphenyl)-4-(2-acetoxyethylaminocarbonyloxy)piperidine hydrochloride, and added thereto was 0.28 ml of triethylamine and the mixture was stirred for 30 minutes. To the reaction mixture was added 330 mg of 1,1'-carbonyldiimidazole, and the mixture was stirred at 65° C. for 2 hours. The solvent was removed by distillation under reduced pressure, and the residue was dissolved in 5 ml of dichloromethane. The mixture was washed with water and saturated brine and dried. The mixture was evaporated in vacuo, and the residue was dissolved in 5 ml of acetonitrile. To the solution was added 1 ml of methyl iodide, and the mixture was stirred at 60° C. for 2 hours. The solvent was removed by distillation under reduced pressure. The residue was dissolved in 20 ml of tetrahydrofuran, and added thereto were 600 mg of N-{1-(3,5-bistrifluoromethylphenyl)-2-hydroxyethyl}-N-methylamine and 0.5 ml of triethylamine, and the mixture was stirred at 70° C. for 3 hours. To the reaction mixture were added ethyl acetate and water, and layers were separated. The organic layer was dried and concentrated under reduced pressure. The residue was purified by silica gel column chromatography (chloroform:methanol=19:1), to give 780 mg of a mixture of the compounds (a) (2R,4S)-4-(2-acetoxyethylaminocarbonyloxy)-1-[N-{1-(S)-(3,5-bistrifluoromethylphenyl)-2-hydroxyethyl}-N-methyl]aminocarbonyl-2-(4-fluoro-2-methylphenyl)piperidine and (b) (2R,4S)-4-(2-acetoxyethylaminocarbonyloxy)-1-[N-{1-(R)-(3,5-bistrifluoromethylphenyl)-2-hydroxyethyl}-N-methyl]aminocarbonyl-2-(4-fluoro-2-methylphenyl)piperidine, as shown in Table 101 below.

Example 388

In 2 ml of methanol was dissolved 122 mg of the compound of Example 387, and added thereto was 1 ml of a 2M aqueous sodium hydroxide solution, and the mixture was stirred at room temperature for 16 hours. The reaction mixture was neutralized with a 6M aqueous hydrochloric acid solution, and the solvent was removed by distillation under reduced pressure. To the residue were added chloroform and water and layers were separated. The aqueous layer was further extracted with chloroform, and the combined organic layers were dried and concentrated under reduced pressure. The residue was vacuum dried, to give 88 mg of a mixture of the compounds (a) (2R,4S)-1-[N-{1-(S)-(3,5-bistrifluoromethylphenyl)-2-hydroxyethyl}-N-methyl]aminocarbonyl-2-(4-fluoro-2-methylphenyl)-4-(2-hydroxyethylaminocarbonyloxy)piperidine and (b) (2R,4S)-1-[N-{1-(S)-(3,5-bistrifluoromethylphenyl)-2-hydroxyethyl}-N-methyl]aminocarbonyl-2-(4-fluoro-2-methylphenyl)-4-(2-hydroxyethylaminocarbonyloxy)piperidine as shown in Table 101 below.

Example 389

(1) In 50 ml of dichloromethane was dissolved 4.92 g of (2R,4S)-1-{N-(3,5-bistrifluoromethylbenzyl)-N-methyl}aminocarbonyl-2-(4-fluoro-2-methylphenyl)-4-hydroxypiperidine, and 2.43 g of carbodiimidazole was added to the solution at room temperature, and the mixture was stirred for 1.5 hours. To the reaction mixture was added water and layers were separated with dichloromethane. The organic layer was washed with saturated brine, dried and the solvent was removed by distillation under reduced pressure, to give 5.99 g of (2R,4S)-1-{N-(3,5-bistrifluoromethylbenzyl)-N-methyl}aminocarbonyl-2-(4-fluoro-2-methylphenyl)-4-(1-imidazolylcarbonyloxy)piperidine.

(2) In a toluene solution (12 ml) of N,N-dimethylformamide (5 ml) was dissolved 1.17 g of the compound of the above (1), and added thereto was 0.925 ml of ethyl nipecotate at room temperature, and the mixture was stirred overnight. To the reaction mixture was added ethyl acetate, and the mixture was washed with water and saturated brine and dried. The solvent was removed by distillation under reduced pressure and the residue was purified by silica gel column chromatography (chloroform:methanol=39:1), to give 1.24 g of (2R,4S)-1-{N-(3,5-bistrifluoromethylbenzyl)-N-methyl}aminocarbonyl-4-(4-ethoxycarbonylpiperidinocarbonyloxy)-2-(4-fluoro-2-methylphenyl)piperidine as shown in Table 102.

Example 390

In 15 ml of ethanol was dissolved 1.08 g of the compound of Example 389, and added thereto 4.8 ml of 1M potassium hydroxide-ethanol solution at room temperature. After the temperature of the mixture was raised to 50° C., the mixture was stirred for 3 hours. To the reaction mixture was added a 2M aqueous hydrochloric acid solution and ethanol was removed by distillation under reduced pressure. Water and chloroform were added thereto and layers were separated with chloroform. The organic layer was washed with saturated brine and dried, and the solvent was removed by distillation under reduced pressure. The residue was purified by silica gel column chromatography (chloroform:methanol=9:1), to give 1.05 g of (2R,4S)-1-{N-(3,5-bistrifluoromethylbenzyl)-N-methyl}aminocarbonyl-4-(4-carboxypiperidinocarbonyloxy)-2-(4-fluoro-2-methylphenyl)piperidine as shown in Table 102 below.

Example 391

In 1 ml of dichloromethane were dissolved 64.8 mg of the compound of Example 390 and 18.6 mg of ethanolamine, and added thereto at room temperature was 48.6 mg of carbodiimidazole, and the mixture was stirred at room temperature overnight. A saturated aqueous ammonium chloride solution was added thereto and the mixture was extracted with dichloromethane. The organic layer was dried and the solvent was removed by distillation under reduced pressure. The residue was purified by silica gel column chromatography (chloroform:methanol=19:1), to give 17.8 mg of (2R,4S)-1-{N-(3,5-bistrifluoromethylbenzyl)-N-methyl}aminocarbonyl-2-(4-fluoro-2-methylphenyl)-4-{4-(2-hydroxyethylaminocarbonyl)piperidinocarbonyloxy}piperidine as shown in Table 102.

Examples 392 to 398

The compound of Example 390 and the corresponding starting materials were used and treated in the same manner as in Example 391, to give compounds as shown in Tables 102 to 103 below.

Example 399

(1) In 12 ml of toluene was dissolved 1.17 g of (2R,4S)-1-{N-(3,5-bistrifluoromethylbenzyl)-N-methyl}aminocarbonyl-2-(4-fluoro-2-methylphenyl)-4-(1-imidazolylcarbonyloxy)piperidine, and added thereto at room temperature was 1.14 g of 4-amino-1-benzylpiperidine, and the mixture was stirred for 3 days. To the reaction mixture was added ethyl acetate, and the mixture was washed with water and saturated brine and dried. The solvent was removed by distillation under reduced pressure. The residue was purified by silica gel column chromatography (chloroform:methanol=19:1), to give 0.89 g of (2R,4S)-1-{N-(3,5-bistrifluoromethylbenzyl)-N-methyl}aminocarbonyl-4-(1-benzylpiperidine-4-yl)aminocarbonyloxy-2-(4-fluoro-2-methylphenyl)piperidine.

(2) In 10 ml of methanol was dissolved 890 mg of the compound of the above (1), and added thereto were 400 mg of palladium carbon and one drop of concentrated hydrochloric acid, and the mixture was stirred in hydrogen atmosphere for 4.5 hours. After the reaction mixture was filtered and the filtrate was evaporated in vacuo, the residue was crystallized (ethyl acetate-hexane), to give 802 mg of (2R,4S)-1-{N-(3,5-bistrifluoromethylbenzyl)-N-methyl}aminocarbonyl-2-(4-fluoro-2-methylphenyl)-4-(4-piperidinyl)aminocarbonyloxypiperidine.

(3) In 2 ml of dichloromethane was dissolved 14.2 mg of 3-hydroxy-3-methylbutanoic acid, and added thereto at room temperature was 21.1 mg of carbodiimidazole, and the mixture was stirred at room temperature overnight. To the reaction mixture was added 61.9 mg of the compound of the above (2), and the mixture was further stirred overnight. To the reaction mixture was added water, and the mixture was extracted with chloroform. The organic layer was dried and the solvent was removed by distillation under reduced pressure. The residue was purified by silica gel column chromatography (chloroform:methanol=19:1), to give 57.5 mg of (2R,4S)-1-{N-(3,5-bistrifluoromethylbenzyl)-N-methyl}aminocarbonyl-2-(4-fluoro-2-methylphenyl)-4-{1-(3-hydroxy-3-methylbutyryl)piperidine-4-yl}aminocarbonyloxypiperidine as shown in Table 104 below.

Examples 400 to 402

The compound of Example 399 (2) and the corresponding starting materials were treated in the same manner as in Example 399 (3), to give compounds as shown in Table 104 below.

Example 403

(2R,4S)-1-{N-(3,5-bistrifluoromethylbenzyl)-N-ethyl}aminocarbonyl-2-(4-fluoro-2-methylphenyl)-4-hydroxypiperidine obtained by treating the compound of Reference Example 11 (2) in the same manner as in Example 2 was treated in the same manner as in Example 209, to give a compound as shown in Table 105 below.

Example 404

The corresponding starting material was treated in the same manner as in Example 209, to give a compound as shown in Table 105 below.

Example 405

The compound of Example 404 was treated in the same manner as in Example 213, to give a compound as shown in Table 105 below.

Example 406

The compound of Example 404 was treated in the same manner as in Example 214, to give a compound as shown in Table 105 below.

Examples 407 to 413

The corresponding starting materials were treated in the same manner as in Example 257, to give compounds as shown in Tables 106 to 107 below.

Example 414

In 50 ml of methanol was dissolved 1.17 g of (2R,4S)-4-acetylthio-1-{N-(3,5-bistrifluoromethylbenzyl)-N-methyl}aminocarbonyl-2-(4-fluoro-2-methylphenyl)piperidine, and added thereto at room temperature was 1.17 g of tert-butyl 2-bromoethylcarbamate. Subsequently, 25 ml of a 1M aqueous sodium hydroxide solution was added dropwise thereto. The reaction mixture was stirred for 5 minutes, and the solvent was removed by distillation under reduced pressure, and the mixture was extracted with dichloromethane, washed with saturated brine and dried. The solvent was removed by distillation under reduced pressure. The residue was purified by silica gel column chromatography (hexane:ethyl acetate=2:1), to give 710 mg of (2R,4S)-1-{N-(3,5-bistrifluoromethylbenzyl)-N-methyl}aminocarbonyl-4-(2-tert-butoxycarbonylaminoethylthio)-2-(4-fluoro-2-methylphenyl)piperidine as shown in Table 107 below.

Example 415

(1) To 681 mg of the compound of Example 414 was added 2 ml of 4M hydrochloric acid-ethyl acetate solution under ice-cooling, and the mixture was stirred at room temperature for an hour. The solvent was removed by distillation, and a saturated aqueous sodium bicarbonate solution was added and the mixture was extracted with chloroform. The organic layer was dried and the solvent was removed by distillation under reduced pressure, to give 612 mg of (2R,4S)-4-(2-aminoethylthio)-1-{N-(3,5-bistrifluoromethylbenzyl)-N-methyl}aminocarbonyl-2-(4-fluoro-2-methylphenyl)piperidine hydrochloride as shown in Table 107 below.

(2) In 1 ml of N,N-dimethylformamide were dissolved 55.2 mg of the compound of the above (1) and 9.1 mg of glycolic acid, and added thereto were 24.9 mg of 1-(3-dimethylaminopropyl)-3-ethylcarbodiimide hydrochloride and 19.9 ml of N-hydroxybenzotriazole monohydrate, and the mixture was stirred at room temperature overnight. Ethyl acetate was added thereto and the mixture was washed with water and saturated brine, dried and the solvent was removed by distillation under reduced pressure. The residue was purified by silica gel column chromatography (chloroform:methanol=19:1), to give 28.8 mg of (2R,4S)-1-{N-(3,5-bistrifluoromethylbenzyl)-N-methyl}aminocarbonyl-2-(4-fluoro-2-methylphenyl)-4-{2-(1-hydroxyacetylamino)ethylthio}piperidine as shown in Table 107 below.

Examples 416 to 419

The compound of Example 415 (1) and the corresponding starting materials were treated in the same manner as in Example 415 (2), to give compounds as shown in Table 108 below.

Example 420

In 1 ml of N,N-dimethylformamide was dissolved 55.2 mg of the compound of Example 415 (1), and 9.1 mg of carbodiimidazole was added thereto, and the mixture was stirred at room temperature for 3 hours. To the reaction mixture was added ethyl acetate, and the mixture was washed with water and brine and dried. The solvent was removed by distillation, and the residue was dissolved in 1 ml of acetonitrile, and 0.025 ml of methyl iodide was added thereto. The mixture was stirred at 50° C. overnight. Subsequently, 0.025 ml of methyl iodide was further added and the mixture was stirred at the same temperature overnight. After removing N,N-dimethylformamide and methyl iodide by distillation under reduced pressure, 1 ml of toluene and 0.040 ml of morpholine were added, and the mixture was stirred at room temperature for 5 days. To the reaction mixture was added water, and the mixture was extracted with ethyl acetate. The organic layer was dried and the solvent was removed by distillation under reduced pressure. The residue was purified by silica gel column chromatography (chloroform:methanol=19:1), to give 38.0 mg of (2R,4S)-1-{N-(3,5-bistrifluoromethylbenzyl)-N-methyl}aminocarbonyl-2-(4-fluoro-2-methylphenyl)-4-(2-morpholinocarbonylaminoethylthio)piperidine as shown in Table 108 below.

Example 421

The compound of Example 415 (1) and the corresponding starting material were treated in the same manner as in Example 420, to give (2R,4S)-1-{N-(3,5-bistrifluoromethylbenzyl)-N-methyl}aminocarbonyl-2-(4-fluoro-2-methylphenyl)-4-{2-(2-hydroxymethylamino)carbonylaminoethylthio}piperidine as shown in Table 108 below.

Example 422

The corresponding starting materials were used and treated in the same manner as in Example 213, to give (2R,4S)-1-{N-(3,5-bistrifluoromethylbenzyl)-N-methyl}aminocarbonyl-2-(4-fluoro-2-methylphenyl)-4-{4-(2-methylsulfinylethylaminocarbonyl)piperidinocarbonyloxy}-piperidine as shown in Table 108 below.

Example 423

The corresponding starting materials were used and treated in the same manner as in Example 214, to give (2R,4S)-1-{N-(3,5-bistrifluoromethylbenzyl)-N-methyl}aminocarbonyl-2-(4-fluoro-2-methylphenyl)-4-{4-(3-methylsulfonylpropylaminocarbonyl)piperidinocarbonyloxy}-piperidine as shown in Table 108 below.

Examples 424 to 425

The corresponding starting materials were used and treated in the same manner as in Example 209, to give compounds as shown in Table 109 below.

Example 426

In 1.5 ml of dichloromethane was dissolved 82.0 mg of (2R,4S)-1-{N-(3,5-bistrifluoromethylbenzyl)-N-methyl}aminocarbonyl-2-(4-fluoro-2-methylphenyl)-4-(2-methylthioethylaminocarbonyloxy)piperidine, and added thereto at room temperature 99.5 mg of m-chloroperbenzoic acid and the mixture was stirred for an hour. To the reaction mixture was added a saturated aqueous sodium hydrogen carbonate solution, and layers were separated with ethyl acetate. The organic layer was washed with saturated brine and dried, and the solvent was removed by distillation under reduced pressure. The residue was purified by silica gel column chromatography (chloroform:methanol=19:1), to give 48.6 mg of (2R,4S)-1-{N-(3,5-bistrifluoromethylbenzyl)-N-methyl}aminocarbonyl-2-(4-fluoro-2-methylphenyl)-4-(2-methylsulfonylethylaminocarbonyloxy)piperidine as shown in Table 109 below.

Example 427

(2R,4S)-1-{N-(3,5-bistrifluoromethylbenzyl)-N-methyl}aminocarbonyl-2-(4-fluoro-2-methylphenyl)-4-(3-methylthiopropylaminocarbonyloxy)piperidine was treated in the same manner as in Example 426, to give (2R,4S)-1-{N-(3,5-bistrifluoromethylbenzyl)-N-methyl}aminocarbonyl-2-(4-fluoro-2-methylphenyl)-4-(3-methylsulfonylpropylaminocarbonyloxy)piperidine as shown in Table 109 below.

Examples 428 to 431

The corresponding starting materials were treated in the same manner as in Example 169, to give compounds as shown in Table 110 below.

Examples 432 to 433

The corresponding starting materials were treated in the same manner as in Example 213, to give compounds as shown in Table 111 below.

Examples 434 to 435

The corresponding starting materials were treated in the same manner as in Example 214, to give compounds as shown in Table 111 below.

Example 436

In 2.8 ml of acetonitrile was dissolved 130 mg of imidazole-1-carboxylic acid N-(3,5-bistrifluoromethylbenzyl)-N-

(2-methoxyethyl)amide, and added thereto was 411 μl of methyl iodide, and the mixture was stirred at 50° C. for 3 hours. The reaction mixture was concentrated under reduced pressure. The residue was suspended in 2.7 ml of dichloromethane, and added thereto were 89 mg of (2R,4S)-2-(4-fluoro-2-methylphenyl)-4-(2-hydroxyethylaminocarbonyloxy)piperidine and 50 μl of triethylamine, and the mixture was stirred at room temperature for 20 hours. To the reaction mixture was added a 5% aqueous citric acid solution, and the mixture was extracted with chloroform. The organic layer was dried over magnesium sulfate, and concentrated under reduced pressure. The residue was purified by thin-layer silica gel chromatography (chloroform:methanol=19:1), to give 63 mg of (2R,4S)-1-{N-(3,5-bistrifluoromethylbenzyl)-N-(2-methoxyethyl)}aminocarbonyl-2-(4-fluoro-2-methylphenyl)-4-(2-hydroxyethylaminocarbonyloxy)piperidine as shown in Table 112 below.

Example 437

In 2.7 ml of dichloromethane was dissolved 94 mg of 2-(4-fluoro-2-methoxyphenyl)-4-(2-hydroxyethylaminocarbonyloxy)piperidine, and added thereto were 163 mg of 3-[(3,5-bistrifluoromethylbenzyl)-methylcarbamoyl]-1-methyl-3H-imidazol-1-ium iodide and 50 μl of triethylamine, and the mixture was stirred at room temperature for 18 hours. To the reaction mixture was added distilled water and the mixture was extracted with chloroform. The organic layer was dried over magnesium sulfate and concentrated under reduced pressure. The residue was purified by thin-layer silica gel chromatography (chloroform:methanol=19:1), to give 84 mg of 1-{N-(3,5-bistrifluoromethylbenzyl)-N-methyl}aminocarbonyl-2-(4-fluoro 2-methoxyphenyl)-4-(2-hydroxyethylaminocarbonyloxy)piperidine as shown in Table 112 below.

Example 438

In 5.2 ml of acetonitrile was dissolved 201 mg of imidazole-1-carboxylic acid N-[(1S)-1-(3,5-bistrifluoromethylphenyl)ethyl]-N-methylamide, and added thereto was 137 μl of methyl iodide. After the mixture was stirred at 50° C. for 3 hours, the reaction mixture was concentrated under reduced pressure. The residue was dissolved in 4.5 ml of dichloromethane, and added thereto was 132 mg of 4-(2-hydroxyethylcarbamoyloxy)-2-phenylpiperidine and 84 μl of triethylamine, and the mixture was stirred at room temperature for 18 hours. To the reaction mixture was added a 5% aqueous citric acid solution, and the mixture was extracted with chloroform, and the organic layer was dried and concentrated under reduced pressure. The residue was purified by thin-layer silica gel chromatography (chloroform:acetone=4:1), to give 75 mg of (2R,4R)-1-[N-{(S)-1-(3,5-bistrifluoromethylphenyl)ethyl}-N-methyl]aminocarbonyl-4-(2-hydroxyethylaminocarbonyloxy)-2-phenylpiperidine as shown in Table 112 below.

Example 439

(1) In 3 ml of acetonitrile was dissolved 127 mg of 1-(3,5-bistrifluoromethylphenyl)ethyl imidazole-1-carboxylate, and added thereto was 448 μl of methyl iodide. The mixture was stirred at 50° C. for 3 hours, and the reaction mixture was concentrated. The residue was suspended in 2.7 ml of dichloromethane, and added thereto were 102 mg of 2-[(2R,4S)-2-(4-fluoro-2-methylphenyl)piperidine-4-yloxycarbonylamino]ethyl acetate and 50 μl of triethylamine, and the mixture was stirred at room temperature for 18 hours. To the reaction mixture was added distilled water and the mixture was extracted with chloroform. The organic layer was dried and concentrated. The residue was purified by thin-layer silica gel chromatography (hexane:ethyl acetate=1:1), to give 43 mg of (2R,4S)-4-(2-acetoxyethylaminocarbonyloxy)-1-{(S)-1-(3,5-bistrifluoromethylphenyl)ethyl}oxycarbonyl-2-(4-fluoro-2-methylphenyl)piperidine.

MS(m/z):623[M++1]

(2)In a mixture of 0.9 ml of tetrahydrofuran and 0.1 ml of methanol was dissolved 43 mg of the compound of the above (1), and added thereto was 103 μl of a 1M aqueous sodium hydroxide solution, and the mixture was stirred at room temperature for an hour. To the reaction mixture was added distilled water and the mixture was extracted with ethyl acetate. The organic layer was dried and concentrated. The residue was purified by thin-layer silica gel chromatography (chloroform:methanol=19:1), to give 37 mg of (2R,4S)-1-{(S)-1-(3,5-bistrifluoromethylphenyl)ethyl}oxycarbonyl-2-(4-fluoro-2-methylphenyl)-4-(2-hydroxyethylaminocarbonyloxy)piperidine as shown in Table 112 below.

Example 440

In 2.4 ml of N,N-dimethylformamide was dissolved 50 mg of (2R,4S)-2-(4-fluoro-2-methyl)phenyl-4-hydroxypiperidine, and added thereto under nitrogen atmosphere at room temperature were 0.044 ml of triethylamine and 99.3 mg of N-(3,5-bistrifluoromethylbenzyl)-N-methylaminocarbonylchloride. The reaction mixture was stirred at room temperature for 21 hours. The reaction mixture was poured into water, and the mixture was extracted with ethyl acetate twice. The organic layers were combined and washed with saturated brine, dried and concentrated. The residue was purified by silica gel column chromatography (hexane:ethyl acetate=2:1→1:2), to give 128 mg of (2R,4S)-1-{N-(3,5-bistrifluoromethylbenzyl)-N-methyl}aminocarbonyl-2-(4-fluoro-2-methylphenyl)-4-hydroxypiperidine as shown in Table 113 below.

Example 441

In 2.0 ml of dichloromethane was dissolved 560 mg of (2R,4S)-1-{N-(3,5-bistrifluoromethylbenzyl)-N-methyl}aminocarbonyl-2-(4-fluoro-2-methylphenyl)-4-hydroxypiperidine, and added thereto under nitrogen atmosphere under ice-cooling, 1.5 ml of dichloromethane solution containing 0.22 ml of pyridine and 0.314 ml of phenyl chloroformate. The reaction mixture was stirred at a temperature of 0° C. to 5° C. for 3.5 hours, and further stirred at room temperature for 16 hours. The reaction mixture was poured into water and extracted by adding dichloromethane twice. The organic layers were combined and washed with a 1M aqueous hydrochloric acid solution twice, and was further washed with saturated brine. The organic layer was dried and concentrated. The residue was dissolved in 11 ml of N,N-dimethylformamide, and added thereto under nitrogen atmosphere and at room temperature was 0.274 ml of ethanolamine, and the mixture was stirred at 60° C. for 26 hours. The reaction mixture was poured into water and extracted by adding ethyl acetate twice. The organic layers were combined and washed with saturated brine, dried and concentrated. The residue was purified by silica gel column chromatography (chloroform:methanol=39:1), to give 493 mg of (2R,4S)-1-{N-(3,5-bistrifluoromethylbenzyl)-N-methyl}aminocarbonyl-2-(4-fluoro-2-methylphenyl)-4-(2-hydroxyethylaminocarbonyloxy)piperidine as shown in Table 113 below.

Example 442

In 8 ml of dichloromethane was dissolved 1.0 g of (2R)-4-amino-1-{N-(3,5-bistrifluoromethylbenzyl)-N-methyl}aminocarbonyl-2-(4-fluoro-2-methylphenyl)piperidine, and added thereto were 0.31 ml of triethylamine and 466 mg of di-tert-butyloxycarbonate, and the mixture was stirred at room temperature for 16 hours. To the reaction mixture was added water and the mixture was extracted with dichloromethane twice. The organic layers were combined and washed with saturated brine, dried and concentrated. The residue was purified by silica gel column chromatography (hexane:ethyl acetate=4:1), to give 481 mg of (a) (2R,4R)-1-{N-(3,5-bistrifluoromethylbenzyl)-N-methyl}aminocarbonyl-2-(4-fluoro-2-methylphenyl)-4-tert-butoxycarbonylaminopiperidine and 516 mg of (b) (2R,4S)-1-{N-(3,5-bistrifluoromethylbenzyl)-N-methyl}aminocarbonyl-2-(4-fluoro-2-methylphenyl)-4-tert-butoxycarbonylaminopiperidine as shown in Table 113 below.

Example 443

In 3.5 ml of ethyl acetate was dissolved 700 mg of (2R,4S)-1-{N-(3,5-bistrifluoromethylbenzyl)-N-methyl}aminocarbonyl-2-(4-fluoro-2-methylphenyl)-4-tert-butoxycarbonylaminopiperidine, and added thereto under ice-cooling was 3.5 ml of 4M hydrochloric acid-ethyl acetate solution, and the mixture was stirred under ice-cooling for 30 minutes. The solvent was removed by distillation, and added to the residue was ethyl acetate and subjected to filtration. To the collected materials were added chloroform and a 2M aqueous sodium hydroxide solution and layers were separated. The aqueous layer was extracted with chloroform. The combined organic layers were dried and concentrated, to give 489 mg of (2R,4S)-4-amino-1-{N-(3,5-bistrifluoromethylbenzyl)-N-methyl}aminocarbonyl-2-(4-fluoro-2-methylphenyl)piperidine as shown in Table 113 below.

Examples 444 to 449

The corresponding starting materials were used and treated in the same manner as in Example 138, to give compounds as shown in Table 114 below.

Examples 450 to 451

The corresponding starting materials were used and treated in the same manner as in Example 102 (1), to give compounds as shown in Table 114 below.

Examples 452 to 469

The corresponding starting materials were used and treated in the same manner as in Example 250 (2), to give compounds as shown in Tables 115 to 117 below.

Example 470

In 1 ml of dichloromethane was dissolved 52.8 mg of (2R,4S)-4-amino-1-{N-(3,5-bistrifluoromethylbenzyl)-N-methyl}amino-carbonyl-2-(4-fluoro-2-methylphenyl)piperidine hydrochloride, and added thereto at room temperature was 0.017 ml of triethylamine and 24.3 mg of 1,1-carbodiimidazole, and the mixture was stirred for 30 minutes. The reaction mixture was added water and the mixture was extracted with dichloromethane. The organic layers were washed with saturated brine, dried and concentrated. In 1 ml of acetonitrile was dissolved the residue, and added 0.025 ml of methyl iodide, and the mixture was stirred at 60° C. overnight. The reaction mixture was concentrated, and in 1 ml of toluene-acetonitrile (7:3) solution was dissolved the residue, and added 24.4 mg of ethanolamine, and the mixture was stirred at room temperature for 30 minutes. To the reaction mixture was added water, and the mixture was extracted with ethyl acetate. The organic layer was dried and concentrated. The residue was purified by silica gel column chromatography (chloroform:methanol=9:1), to give 53.1 mg of (2R,4S)-1-{N-(3,5-bistrifluoromethylbenzyl)-N-methyl}aminocarbonyl-2-(4-fluoro-2-methylphenyl)-4-(2-hydroxyethylamino)piperidine as shown in Table 118 below.

Examples 471 to 480

The corresponding starting materials were used and treated in the same manner as in Example 470, to give compounds as shown in Tables 118 to 119 below.

Example 481

In 10 ml of dichloromethane was dissolved 490 mg of (2R)-1-{N-(3,5-bistrifluoromethylbenzyl)-N-methyl}amino-carbonyl-2-(4-fluoro-2-methylphenyl)-4-oxopiperidine and 312 mg of 2-(2-aminoethylamino)ethanol, and added thereto at room temperature were 0.086 ml of acetic acid and 669 mg of sodium triacetoxyborohydride, and the mixture was stirred overnight. To the reaction mixture was added water, and extracted with chloroform. The organic layer was washed with saturated brine, dried and concentrated, to give 581 mg of (2R,4RS)-1-{N-(3,5-bistrifluoromethylbenzyl)-N-methyl}aminocarbonyl-2-(4-fluoro-2-methyl-phenyl)-4-{2-(2-hydroxyethylamino)ethylamino}piperidine [(2R,4S):(2R,4R)=74:26]. In 2 ml of dichloromethane was dissolved 116 mg of (2R,4RS)-1-{N-(3,5-bistrifluoromethylbenzyl)-N-methyl}aminocarbonyl-2-(4-fluoro-2-methylphenyl)-4-{2-(2-hydroxyethylamino)ethylamino}piperidine, and added thereto at room temperature was 39 mg of 1,1-carbodiimidazole, and the mixture was stirred for 40 minutes. To the reaction mixture was added water, and the mixture was extracted with chloroform. The organic layers were washed with saturated brine, dried and concentrated. The residue was purified by silica gel column chromatography (chloroform:methanol=9:1), to give (a) 75.5 mg of (2R,4S)-1-{N-(3,5-bistrifluoromethylbenzyl)-N-methyl}aminocarbonyl-2-(4-fluoro-2-methylphenyl)-4-[3-(2-hydroxyethyl)-2-oxoimidazolidine-1-yl]piperidine and give (b) 22.6 mg of (2R,4R)-1-{N-(3,5-bistrifluoromethylbenzyl)-N-methyl}aminocarbonyl-2-(4-fluoro-2-methylphenyl)-4-[3-(2-hydroxyethyl)-2-oxoimidazolidine-1-yl]piperidine as shown in Table 120 below.

Examples 482 to 486

The corresponding starting materials were used and treated in the same manner as in Example 481, to give compounds as shown in Tables 120 to 122 below.

Example 487

In 1 ml of dichloromethane was dissolved 12.4 ml of ethylene glycol, and added thereto at room temperature was 32.4 mg of 1,1-carbodiimidazole. The mixture was stirred at room temperature for 7.5 hours, and to the mixture were added 52.8 mg of (2R,4S)-4-amino-1-{N-(3,5-bistrifluoromethylbenzyl)-N-methyl}-aminocarbonyl-2-(4-fluoro-2-methylphenyl)piperidine hydrochloride and 0.021 ml of triethylamine. The mixture was stirred for 4 days, and the reaction mixture was concentrated. The residue was purified by silica gel column chromatography (chloroform:methanol=9:1), to give 16.4 mg of (2R,4S)-1-{N-(3,5-bistrifluoromethylbenzyl)-N-methyl}-amino-carbonyl-2-(4-fluoro-2-methylphenyl)-4-(2-hydroxyethyloxycarbonylamino)-piperidine as shown in Table 123 below.

Example 488

(1) In 3 ml of dichloromethane was dissolved 58 mg of triphosgene, and added dropwise thereto under −60° C. was 2 ml dichloromethane solution containing 138 mg of N-{2-methoxy-5-(5-trifluoromethyltetrazole-1-yl)benzyl}-N-methylamine and 0.201 ml of triethylamine, and then the mixture was warmed up at 0° C. The mixture was concentrated, and in 2 ml dichloromethane was dissolved the residue. To the mixture was added dropwise 2 ml of dichloromethane solution containing 135 mg of (2R,4S)-4-(2-acetyloxyethylaminocarbonyloxy)-2-(4-fluoro-2-methylphenyl)-piperidine and 0.084 ml of triethylamine, and the mixture was stirred at room temperature for one day. To the reaction mixture was added water, and the mixture was extracted with chloroform. The organic layer was dried over magnesium sulfate and concentrated. The residue was purified by thin layer silica gel column chromatography (chloroform:acetone=10:1), to give 44 mg of (2R,4S)-4-(2-acetyloxyethylaminocarbonyloxy)-1-[N-{2-methoxy-5-(5-trifluoromethyltetrazole-1-yl)benzyl}-N-methyl]aminocarbonyl-2-(4-fluoro-2-methylphenyl)piperidine.

MS(m/z):652[M$^+$+1]

(2) In 0.9 ml of the mixture solution (tetrahydro-furan:methanol=8:1) was dissolved 44 mg of (2R,4S)-4-(2-acetyloxyethylaminocarbonyloxy)-1-[N-{2-methoxy-5-(5-trifluoromethyltetrazole-1-yl)benzyl}-N-methyl]aminocarbonyl-2-(4-fluoro-2-methylphenyl)piperidine, and added thereto was 0.101 ml of a 1 M aqueous sodium hydroxide solution, and the mixture was stirred at room temperature for 6 hours. To the reaction mixture was added water, and the mixture was extracted with ethyl acetate. The organic layers were dried over magnesium sulfate and concentrated. The residue was purified by thin layer silica gel column chromatography (chloroform:methanol=19:1), to give 36 mg of (2R,4S)-1-[N-{2-methoxy-5-(5-trifluoromethyltetrazole-1-yl)benzyl}-N-methyl]aminocarbonyl-2-(4-fluoro-2-methylphenyl)-4-(2-hydroxyethylaminocarbonyloxy)piperidine as shown in Table 124 below.

Reference Example 1

To Grignard reagent prepared from 14.2 g of magnesium, 93.1 g of 2-bromo-5-fluorotoluene and 500 ml of tetrahydrofuran was added dropwise 50 ml of 4-methoxypyridine at −20° C. under nitrogen atmosphere. After completion of dripwise addition, the mixture was stirred at the same temperature for 20 minutes. Further, the reaction mixture was cooled down to −50° C., and 85 ml of benzylchlorocarbonate was added dropwise, while keeping the temperature at −40° C. or below. After completion of dropwise addition, the temperature of the reaction mixture was slowly raised, 200 g of ice was added thereto at −15C, and the mixture was stirred for 30 minutes. Further, 200 ml of a 5M aqueous citric acid solution was added thereto and the mixture was stirred at room temperature for an hour. From the reaction mixture tetrahydrofuran was removed by distillation under reduced pressure. To the residue was added 200 ml of ethyl acetate and the mixture was extracted twice. The organic layers were combined and washed with an aqueous sodium hydrogen carbonate solution and saturated brine, dried over magnesium sulfate, and the solvent was removed by distillation under reduced pressure. The residue was collected by filtration and washed with isopropyl ether, to give 146.5 g of 1-benzyloxycarbonyl-2-(4-fluoro-2-methylphenyl)-4-oxo-3,4-dihydro-2H-pyridine as shown in Table 125 below.

Reference Example 2

In 4600 ml of acetic acid was dissolved 190 g of 1-benzyloxycarbonyl-2-(4-fluoro-2-methylphenyl)-4-oxo-3,4-dihydro-2H-pyridine, and added thereto was 91 g of zinc powder and the mixture was stirred at room temperature for 24 hours. From the reaction mixture was removed insoluble matters by filtration, and the solvent was removed by distillation under reduced pressure. To the residue was added 400 ml of ethyl acetate, and the mixture was washed with an aqueous sodium hydrogen carbonate solution and saturated brine, and dried over magnesium sulfate. The solvent was removed by distillation under reduced pressure, and the residue was purified by silica gel column chromatography (ethyl acetate:hexane=2:1), to give 166 g of 1-benzyloxycarbonyl-2-(4-fluoro-2-methylphenyl)-4-oxopiperidine as shown in Table 125 below.

Reference Example 3

To 132 g of 1-benzyloxycarbonyl-2-(4-fluoro-2-methylphenyl)-4-oxopiperidine were added 650 ml of methanol, 84 ml of trimethoxymethane and 2 g of strongly acidic resin IR-120 (manufactured by Japan Organo Co., Ltd.), and the mixture was stirred at room temperature for 3 days. From the reaction mixture was removed insoluble matters by filtration, and the solvent was removed by distillation under reduced pressure, to give 146 g of 1-benzyloxycarbonyl-2-(4-fluoro-2-methylphenyl)-4,4-dimethoxypiperidine as shown in Table 125 below.

Reference Example 4

In 300 ml of ethanol were added 30 g of 1-benzyloxycarbonyl-2-(4-fluoro-2-methylphenyl)-4,4-dimethoxypiperidine and 3.0 g of 10% palladium-carbon, and the mixture was stirred under hydrogen atmosphere at room temperature for 3 hours. From the reaction mixture was removed insoluble matters by filtration, and the solvent was removed by distillation under reduced pressure. To the residue was added 300 ml of ethyl acetate. Under ice-cooling 20 ml of 4M hydrochloric acid-ethyl acetate solution was slowly added dropwise. The crystals were collected by filtration and washed with ethyl acetate. After drying, the crystals were added to a mixture of dichloromethane—an aqueous sodium carbonate solution, and the mixture was stirred. After the organic layer was separated, the aqueous layer was further extracted with dichloromethane. The organic layers were combined and dried over sodium sulfate, the solvent was removed by distillation under reduced pressure, to give 16.7 g of 2-(4-fluoro-2-methylphenyl)-4,4-dimethoxypiperidine as shown in Table 125 below.

Reference Example 5

To 130 ml of ethyl acetate suspension of 10.1 g of 2-(4-fluoro-2-methylphenyl)-4,4-dimethoxypiperidine and 3.18 g of L-N-acetylvaline was added 35 ml of methanol, and the mixture was heated to dissolve, and then, cooled down at room temperature. After 3.5 hours, precipitated crystals were collected by filtration, and washed with 20 ml of ethyl acetate. The obtained crystals were dried under reduced pressure. Subsequently, 50 ml of chloroform was added thereto, and the mixture was washed with 30 ml of a 2M aqueous sodium hydroxide solution and 30 ml of saturated brine, dried over magnesium sulfate and concentrated under reduced pressure. To the obtained residue was added ether, and precipitated crystals were further concentrated under reduced pressure, to give 2.94 g of (2R)-2-(4-fluoro-2-methylphenyl)-4,4-dimethoxypiperidine (optical purity:97.0% ee) as shown in Table 125 below.

Reference Example 6

In 36 ml of tetrahydrofuran solution of 5.0 g of N-(3,5-bistrifluoromethylbenzyl)-N-methylamine was added 3.47 g of 1,1'-carbonyldiimidazole, and the mixture was stirred at 65° C. for 20 minutes. The solvent was removed by distillation under reduced pressure and added thereto was dichloromethane. The whole organic layer was washed with saturated brine and dried, and the solvent was removed by distillation. The residue was dissolved in 26 ml of acetonitrile, and 4.84 ml of methyl iodide was added thereto and the mixture was stirred at 60° C. for 2 hours. The solvent was removed by distillation under reduced pressure, and the residue was dissolved in 80 ml of dichloromethane. Under ice-cooling, 5.17 g of 2-(4-fluoro-2-methylphenyl)-4,4-dimethoxypiperidine and 3 ml of triethylamine were added thereto, and the mixture was stirred at room temperature for 2 hours. The reaction mixture was poured into water and layers were separated. The aqueous layer was extracted with dichloromethane. The combined organic layers were washed with saturated brine and dried, and the solvent was removed by distillation. The residue was purified by silica gel column chromatography (hexane:ethyl acetate=4:3), to give 9.7 g of 1-{N-(3,5-bistrifluoromethylbenzyl)-N-methyl}aminocarbonyl-2-(4-fluoro-2-methylphenyl)-4,4-dimethoxypiperidine as shown in Table 126 below.

Reference Example 7

In 180 ml of tetrahydrofuran was dissolved 9.7 g of 1-{N-(3,5-bistrifluoromethylbenzyl)-N-methyl}aminocarbonyl-2-(4-fluoro-2-methylphenyl)-4,4-dimethoxypiperidine, and under ice-cooling, 70 ml of a 1M aqueous sulfuric acid solution was added thereto, and the mixture was stirred at room temperature for an hour. After adjusting pH of the mixture to 8 to 9 by a 1M aqueous sodium hydroxide solution, tetrahydrofuran was removed by distillation. To the residue were added water and ethyl acetate, and layers were separated. The aqueous layer was extracted with ethyl acetate. The combined organic layers were washed with saturated brine and dried. The solvent was removed by distillation. To the obtained residue was added diisopropyl ether, and white crystals were collected by filtration, to give 7.86 g of 1-{N-(3,5-bistrifluoromethylbenzyl)-N-methyl}aminocarbonyl-2-(4-fluoro-2-methylphenyl)-4-oxopiperidine as shown in Table 126 below.

Reference Example 8

In 60 ml of tetrahydrofuran solution of 3.91 g of N-{1-(S)-(3,5-bistrifluoromethylphenyl)ethyl}-N-methylamine was added 2.34 g of 1,1'-carbonyldiimidazole, and the mixture was stirred at 40° C. overnight. From the reaction mixture the solvent was removed by distillation, ethyl acetate was added thereto and the whole organic layer was washed with water and saturated brine, and dried. The solvent was removed by distillation, and the obtained white crystals were collected by filtration with diisopropyl ether. The obtained white crystals were dissolved in 60 ml of acetonitrile and 3.4 ml of methyl iodide was added and the mixture was stirred at 60° C. for 2 hours. The solvent was removed by distillation under reduced pressure, and the residue was dissolved in 40 ml of dichloromethane. Under ice-cooling, added thereto were 3.47 g of 2-(4-fluoro-2-methylphenyl)-4,4-dimethoxypiperidine and 3.82 ml of triethylamine and the mixture was stirred at room temperature overnight. The reaction mixture was poured into water and layers were separated. The aqueous layer was extracted with dichloromethane. The combined organic layers were washed with water and saturated brine and dried, and the solvent was removed by distillation under reduced pressure. The residue was dissolved in 90 ml of tetrahydrofuran, and under ice-cooling, 30 ml of 1M aqueous sulfuric acid solution was added thereto, and the mixture was stirred at room temperature for 5 hours. After adjusting pH of the mixture to 8 to 9 by a 1M aqueous sodium hydroxide solution, tetrahydrofuran was removed by distillation. To the residue were added water and ethyl acetate, and layers were separated. The aqueous layer was extracted with ethyl acetate. The combined organic layers were washed with water and saturated brine and dried, and the solvent was removed by distillation under reduced pressure. The residue was purified by silica gel column chromatography (hexane:ethyl acetate=2:1), to give 2.12 g of (2R)-1-[N-{1-(S)-(3,5-bistrifluoromethylphenyl)ethyl}-N-methyl]aminocarbonyl-2-(4-fluoro-2-methylphenyl)-4-oxopiperidine as shown in Table 126 below.

Reference Examples 9 to 11

The corresponding starting materials were used and treated in the same manner as in Reference Example 8, to give compounds as shown in Tables 126 to 127 below.

Reference Example 12

In 140 ml of ethanol was dissolved 16.7 g of 1-benzyloxycarbonyl-2-(4-fluoro-2-methylphenyl)-4-oxopiperidine, and added thereto were 3.74 g of hydroxylamine hydrochloride and 4.41 g of sodium acetate, and the mixture was stirred at room temperature for 2 hours. Ethanol was removed under reduced pressure. To the residue were added water and ethyl acetate, and layers were separated. The aqueous layer was extracted with ethyl acetate. The combined organic layers were washed with saturated brine and dried, and the solvent was removed under reduced pressure. The residue was dissolved in 500 ml of methanol, and 23.2 g of nickel chloride hexahydrate was added thereto and after stirring the mixture, 3.7 g of sodium borohydride was slowly added under ice-cooling, and the mixture was stirred under ice-cooling for 4 hours. Methanol was removed by distillation under reduced pressure, and to the residue were added an aqueous ammonia and dichloromethane, and the mixture was stirred at room temperature for an hour. The reaction mixture was separated by layers, and the aqueous layer was extracted with dichloromethane. The combined organic layers were washed with saturated brine and dried, and the solvent was removed by distillation. The residue was dissolved in 480 ml of dichloromethane, and under ice-cooling added thereto were 8.2 ml of triethylamine and 5.1 ml of propionyl chloride, and the mixture was stirred under ice-cooling for an hour. The reaction mixture was poured into saturated brine and layers were separated. The aqueous layer was extracted with dichloromethane. The combined organic layers were washed with saturated brine and dried, and the solvent was removed by distillation under reduced pressure. The residue was purified by silica gel column chromatography (hexane:ethyl acetate=1:1), to give 6.43 g of (a) trans-1-benzyloxycarbonyl-2-(4-fluoro-2-methylphenyl)-4-propanoylaminopiperidine and 5.65 g of (b) cis-1-benzyloxycarbonyl-2-(4-fluoro-2-methylphenyl)-4-propanoylaminopiperidine as shown in Table 127 below.

Reference Example 13

1-Benzyloxycarbonyl-2-(4-fluoro-2-methylphenyl)-4-oxopiperidine and isobutyroyl chloride were used and treated in the same manner as in Reference Example 12, to give (a) trans-1-benzyloxycarbonyl-2-(4-fluoro-2-methylphenyl)-4-isobutanoylaminopiperidine and (b) cis-1-benzyloxycarbonyl-2-(4-fluoro-2-methylphenyl)-4-isobutanoylaminopiperidine as shown in Table 128 below.

Reference Example 14

In 17 ml of ethanol was dissolved 1.73 g of trans-1-benzyloxycarbonyl-2-(4-fluoro-2-methylphenyl)-4-propanoylaminopiperidine, and added thereto was 280 mg of palladium-carbon (moisture content of 50.9%), and the mixture was stirred under hydrogen atmosphere at room temperature for 3 hours. The reaction mixture was filtered through Celite, and ethanol was removed by distillation. The residue was purified by NH silica gel column chromatography (chloroform:hexane:ethyl acetate=5:5:2), to give 772 mg of trans-2-(4-fluoro-2-methylphenyl)-4-propanoylaminopiperidine as shown in Table 129 below.

Reference Examples 15 to 17

The corresponding starting materials were used and treated in the same manner as in Reference Example 14, to give compounds as shown in Tables 129 to 130 below.

Reference Example 18

In 900 ml of ethanol was dissolved 110 g of 1-benzyloxycarbonyl-2-(4-fluoro-2-methylphenyl)-4-oxopiperidine, and added thereto were 24.8 g of hydroxylamine hydrochloride and 29.3 g of sodium acetate, and the mixture was stirred at room temperature for 5 hours. Ethanol was removed by distillation, and to the residue were added water and ethyl acetate. Layers were separated and the aqueous layer was extracted with ethyl acetate. The combined organic layers were washed with saturated brine and dried, and the solvent was removed by distillation under reduced pressure. The residue was dissolved in 2.4 l of methanol, and 92.5 g of nickel chloride hexahydrate was added thereto. After stirring the mixture, 18.4 g of sodium borohydride was slowly added under ice-cooling, and the mixture was stirred under ice-cooling for 4 hours. Methanol was removed by distillation, and to the residue were added aqueous ammonia and dichloromethane, and the mixture was stirred at room temperature for an hour. The reaction mixture was separated by layers, and the aqueous layer was extracted with dichloromethane. The combined organic layers were washed with saturated brine and dried, and the solvent was removed by distillation. The residue was dissolved in 1.2 l of dichloromethane, and under ice-cooling added thereto were 45.2 ml of triethylamine, 74.5 ml of di-tert-butyldicarbonate, and the mixture was stirred at room temperature for an hour. The reaction mixture was poured into saturated brine, and the aqueous layer was extracted with dichloromethane. The combined organic layers were washed with saturated brine and dried, and the solvent was removed by distillation under reduced pressure. The residue was purified by silica gel column chromatography (hexane:ethyl acetate=4:1), to give 36.7 g of (a) trans-1-benzyloxycarbonyl-2-(4-fluoro-2-methylphenyl)-4-tert-butoxycarbonylaminopiperidine and 37.9 g of (b) cis-1-benzyloxycarbonyl-2-(4-fluoro-2-methylphenyl)-4-tert-butoxycarbonylaminopiperidine as shown in Table 131 below.

Reference Example 19

In 350 ml of ethanol was dissolved 37.0 g of cis-1-benzyloxycarbonyl-2-(4-fluoro-2-methylphenyl)-4-tert-butoxycarbonylaminopiperidine, and 5.5 g of palladium-carbon (moisture content of 50.9%) was added thereto, and the mixture was stirred under hydrogen atmosphere at room temperature for 2 hours. The reaction mixture was filtered through Celite, and ethanol was removed by distillation, to give 25.8 g of cis-2-(4-fluoro-2-methylphenyl)-4-tert-butoxycarbonylaminopiperidine as shown in Table 132 below.

Reference Example 20

To 1.34 g of 3-hydroxyl-2-hydroxymethyl-2-methylpropionic acid and 13 ml of acetonedimethylacetal was added 95 mg of p-toluenesulfonic acid monohydrate at room temperature, and the mixture was stirred for 6 hours. Further added thereto was 95 mg of p-toluenesulfonic acid monohydrate, and the mixture was stirred overnight. The solution was concentrated and poured into water and extracted. The aqueous layer was extracted with chloroform. The combined organic layers were washed with saturated brine, dried, and concentrated. The residue was purified by silica gel column chromatography (chloroform:methanol=19:1), to give 333 mg of 2,2,5-trimethyl-[1,3]dioxolane-5-carboxylic acid as shown in Table 132 below.

Reference Example 21

In 400 ml of tetrahydrofuran was dissolved 31.5 g of 2-chloroisonicotinic acid, and 32.5 g of 1,1'-carbonyldiimidazole was added thereto. The mixture was stirred under ice-cooling for an hour. To the solution was added 50 ml of ethanol, and the mixture was stirred at room temperature for 2 hours. The solution was concentrated, and extracted by adding ethyl acetate and water. The organic layer was dried over magnesium sulfate, and the residue was vacuum dried, to give 35.6 g of ethyl 2-chloroisonicotinate as shown in Table 132 below.

Reference Example 22

In a mixed solvent of 250 ml of toluene and 50 ml of ethanol were dissolved 20 g of ethyl 2-chloroisonicotinate and 20 g of 2-methyl-4-fluorophenylboronic acid, and 5.8 g of palladium tetrakistriphenylphosphine and 250 ml of a 2M aqueous sodium carbonate solution, and the mixture was stirred at 50 to 70° C. for 2 hours. The solution was cooled down to room temperature and extracted by adding ethyl acetate and water. The organic layer was further washed with water, and dried over magnesium sulfate and concentrated. The residue was purified by silica gel column chromatography (hexane:ethyl acetate=6:1), to give 24.8 g of 4-ethoxycarbonyl-2-(4-fluoro-2-methylphenyl)pyridine as shown in Table 132 below.

Reference Example 23

In 200 ml of ethanol were dissolved 5.2 g of 4-ethoxycarbonyl-2-(4-fluoro-2-methylphenyl)pyridine and 1.5 g of platinum oxide, and 15 ml of concentrated hydrochloric acid was added to the solution. The mixture was stirred under hydrogen atmosphere at room temperature for 5 hours. Added thereto was 200 ml of water and the mixture was stirred for 30 minutes, and then, insoluble matters were removed by filtration through Celite. The insoluble matters were washed with ethanol and the filtrate and the liquid used for washing were combined and concentrated. To the residue were added ethyl acetate and a saturated aqueous sodium hydrogen carbonate solution. After confirming that the aqueous solution was sufficiently alkaline, then extraction was carried out. The aqueous layer was extracted with ethyl acetate for 3 times, and the combined organic layers were dried over sodium sulfate and concentrated, to give 3.6 g of 2,4-cis-4-ethoxycarbonyl-2-(4-fluoro-2-methylphenyl)piperidine as shown in Table 132 below.

Reference Example 24

(1) In a mixture of 50 ml of ethyl acetate and 50 ml of diethylether were dissolved under heating 7.4 g of 2,4-cis-4-ethoxycarbonyl-2-(4-fluoro-2-methylphenyl)piperidine and 4.0 g of N-p-toluenesulfonyl-D-phenylalanine. The solvent was concentrated by heating, 30 ml of diisopropyl ether was added thereto and the mixture was stirred. Precipitated crystals were removed and mother liquor was washed with a concentrated aqueous ammonia solution, dried and concentrated under reduced pressure. To the residue was added 4.0 g of N-p-toluenesulfonyl-L-phenylalanine, and 50 ml of ethyl acetate and 30 ml of diisopropyl ether were added thereto and dissolved by heating, the mixture was stirred at room temperature for 16 hours. Precipitated crystals were collected by filtration, washed with diisopropyl ether, and dried, to give 4.0 g of N-p-toluenesulfonyl-L-phenylalanine salt of (2R,4S)-4-ethoxycarbonyl-2-(4-fluoro-2-methylphenyl)-4-piperidine.

(2) The compound of the above (1) was dissolved in an aqueous ammonia solution, and after confirming that the solution was sufficiently basic, it was extracted with chloroform twice. The combined organic layers were dried and concentrated under reduced pressure, to give 2.6 g of (2R,4S)-4-ethoxycarbonyl-2-(4-fluoro-2-methylphenyl)-4-piperidine (optical purity: 96% ee) as shown in Table 133 below.

Reference Example 25

(1) In 50 ml of N,N-dimethylformamide was dissolved 7.5 g of 3-aminopropanol, and 16 g of tert-butyldimethylsilyl chloride and 6.8 g of imidazole were added thereto, and the mixture was stirred at room temperature for 16 hours. To the reaction mixture was added 11 g of citric acid and after stirring the mixture at room temperature for an hour, the mixture was concentrated under reduced pressure. To the residue were added a 2M aqueous sodium hydroxide solution and diethyl ether and layers were separated. The organic layer was dried and concentrated under reduced pressure. The residue and 12.1 g of 3,5-bistrifluoromethylbenzaldehyde were dissolved in 300 ml of dichloromethane and 21.2 g of sodium triacetoxy borohydride and 2.9 ml of acetic acid were added and the mixture was stirred at room temperature for 3 hours. To the reaction mixture was added a 2M aqueous sodium carbonate solution. The mixture was stirred for 30 minutes, and extracted with chloroform twice. The combined organic layers were dried, concentrated under reduced pressure, and purified by silica gel column chromatography(hexane:ethyl acetate=4:1), to give 20 g of 3-tert-butyldimethylsiloxypropyl-3,5-bistrifluoromethylbenzylamine.

(2) 12.5 g of the compound of the above (1) and the compound of Reference Example 5 were used and treated in the same manner as in Reference Example 6, to give 19 g of (2R)-1-{N-(3,5-bistrifluoromethylbenzyl)-N-(3-tert-butyldimethylsiloxypropyl)}aminocarbonyl-2-(4-fluoro-2-methylphenyl)-4,4-dimethoxypiperidine.

(3) 19.0 g of the compound of the above (2) was used and treated in the same manner as in Reference Example 7, to give 19 g of (2R)-1-{N-(3,5-bistrifluoromethylbenzyl)-N-(3-hydroxypropyl)}aminocarbonyl-2-(4-fluoro-2-methylphenyl)-4-oxopiperidine as shown in Table 133 below.

Reference Example 26

(1) In 40 ml of dichloromethane was dissolved 4.8 g of the compound of Reference Example 5, and 4.4 g of di-tert-butyldicarbonate was added thereto and the mixture was stirred at room temperature for 16 hours. The reaction mixture was concentrated under reduced pressure. The residue was dissolved in 100 ml of acetone, and 200 mg of an acidic resin (IR-120) was added thereto and the mixture was stirred at room temperature for 3 days. After removing the resine from the reaction mixture, the mixture was concentrated under reduced pressure. The residue was purified by silica gel column chromatography (hexane:ethyl acetate=4:1), to give 3.9 g of (R)-1-tert-butoxycarbonyl-2-(4-fluoro-2-methylphenyl)-4-oxopiperidine.

(2) In 20 ml of ethanol was dissolved 3.9 g of the compound of the above (1), added thereto was 400 mg of sodium borohydride at −20° C., and the mixture was stirred for an hour. To the reaction mixture was added an aqueous ammonium chloride solution, and ethanol was removed by distillation. To the residue were added ethyl acetate and water and layers were separated, and further washed with water. The organic layer was dried and concentrated under reduced pressure. The residue was purified by silica gel column chromatography (hexane:ethyl acetate=4:1), to give 3.1 g of (2R,4S)-1-tert-butoxycarbonyl-2-(4-fluoro-2-methylphenyl)-4-hydroxypiperidine.

(3) 3.1 g of the compound of the above (2) and the corresponding starting material were used and treated in the same manner as in Example 209, to give 2.3 g of (2R,4S)-1-tert-butoxycarbonyl-2-(4-fluoro-2-methylphenyl)-4-(2-hydroxyethylaminocarbonyloxy)piperidine.

(4) In 20 ml of a 4M hydrochloric acid-ethyl acetate solution was dissolved 2.3 g of the compound of the above (3), and the solution was stirred at room temperature for an hour. The reaction mixture was concentrated under reduced pressure. The residue was dried, to give 1.5 g of (2R,4S)-2-(4-fluoro-2-methylphenyl)-4-(2-acetoxyethylaminocarbonyloxy)piperidine hydrochloride.

(5) In 25 ml of a 1M aqueous sodium hydroxide solution was dissolved 1.5 g of the compound of the above (4), and the solution was extracted with chloroform twice. The combined organic layers were dried and concentrated under reduced pressure. The residue was dried, to give 1.5 g of (2R,4S)-2-(4-fluoro-2-methylphenyl)-4-(2-hydroxyethylaminocarbonyloxy)piperidine as shown in Table 133 below.

Reference Example 27

In 250 ml of acetonitrile was dissolved 4.8 g of 3,5-bistrifluoromethylbenzaldehyde, added thereto were 6.6 g of trimethylsulfonium iodide, 3.2 g of ground potassium hydroxide and 0.5 ml of water, and the mixture was stirred at a temperature of 65° C. to 70° C. for 16 hours, in the presence of an alumina ball. After the reaction was completed, insoluble matters were removed, and ethyl acetate and water were added to the filtrate and layers were separated. The organic layer was washed, dried and concentrated under reduced pressure. To the residue was added 50 ml of a 40% methylamine-methanol solution, and the mixture was stirred at room temperature for 16 hours. The reaction mixture was concentrated under reduced pressure. The residue was purified by NH silica gel column chromatography (hexane:ethyl acetate=1:2), to give 1.23 g of 1-(3,5-bistrifluoromethylphenyl)-2-hydroxyethylamine as shown in Table 133 below.

Reference Example 28

(1) In 43 ml of dichloromethane were dissolved 2.45 g of 3,5-bistrifluoromethylbenzaldehyde, 835 mg of 2-methoxyethylamine and 687 µl of acetic acid, added thereto was 3.12 g of sodium triacetoxy borohydride, and the mixture was stirred at room temperature for an hour under nitrogen atmosphere. The reaction mixture was washed with a 0.5M aqueous sodium hydroxide solution, dried over magnesium sulfate, and concentrated under reduced pressure. The residue was purified by NH silica gel column chromatography (hexane:ethyl acetate=19:1→9:1), to give 2.76 g of 3,5-bistrifluoromethylbenzyl-2-methoxyethylamine.

MS(m/z): 302 [M$^+$+1]$^+$ (2) In a mixed solution of 37 ml of toluene and 4 ml of methylene chloride was dissolved 2.76 g of 3,5-bistrifluoromethylbenzyl-2-methoxyethylamine, added thereto was 1.78 g of 1,1'-carbonyldiimidazole, and the mixture was stirred at 60° C. for 3 hours. To the reaction mixture was added distilled water, and extracted with chloroform. The organic layer was dried over magnesium sulfate, dried and concentrated under reduced pressure. The residue was purified by silica gel column chromatography (chloroform:acetone=9:1→2:1), to give 3.45 g of imidazole-1-carboxylic acid 3,5-bistrifluoromethylbenzyl-2-methoxyethylamide as shown in Table 133 below.

Reference Example 29

(1) In 15 ml of N,N-dimethylformamide were dissolved 3.94 g of 2-bromo-5-fluorophenol and 1.62 ml of methyl iodide, slowly added thereto was 5.08 g of potassium carbonate under ice-cooling. The mixture was stirred at room temperature for 3 hours. After insoluble matters were removed by filtration, distilled water was added to the filtrate, and the mixture was extracted with diethyl ether and washed with saturated brine. The organic layer was dried over magnesium sulfate and concentrated under reduced pressure. The residue was purified by silica gel column chromatography-(hexane:ethyl acetate=19:1→9:1), to give 4.10 g of 1-bromo4-fluoro-2-methoxybenzene.

MS(m/z): 204/206 (M$^+$+1).

(2) To 7 ml of tetrahydrofuran were added 486 mg of magnesium and trace of iodine, and dropped thereto was a solution of 4.10 g of the compound of the above (1) in 16 ml of tetrahydrofuran, to prepare Grignard reagent. To the solution, a solution of 1.96 g of 4-methoxypyridine in 7 ml of tetrahydrofuran was added dropwise under nitrogen atmosphere at −60° C. or below. Subsequently, a solution of 3.75 g of benzyl chloroformate in 18 ml of tetrahydrofuran was added dropwise, and the mixture was stirred for 3 hours. The temperature of the mixture was raised to room temperature, and 40 ml of a 5% aqueous citric acid solution was added thereto. The mixture was extracted with ethyl acetate and washed with saturated brine. The organic layer was dried and concentrated. The residue was purified by silica gel column chromatography (hexane:ethyl acetate=2:1→1:2), to give 3.15 g of 1-benzyloxycarbonyl-2-(4-fluoro-2-methoxyphenyl)-4-oxo-3,4-dihydro-2H-pyridine.

MS(m/z): 356 [M$^+$+1]

(3) In a mixed solution of 79 ml of ethanol and 6 ml of tetrahydrofuran was dissolved 3.15 g of the compound of the above (2), and added thereto was 706 mg of sodium borohydride and the mixture was stirred at room temperature for 6 hours. The reaction mixture was concentrated and distilled water was added to the residue. The mixture was extracted with chloroform, and the organic layer was dried and concentrated under reduced pressure. The residue was purified by silica gel column chromatography (chloroform:acetone=19:1→9:1), to give 1.62 g of 1-benzyloxycarbonyl-2-(4-fluoro-2-methoxyphenyl)-4-hydroxypiperidine.

MS(m/z): 360 [M$^+$+1]

(4) In 20 ml of toluene was dissolved 1.62 g of the compound of the above (3), added thereto was 876 mg of 1,1'-carbonyldiimidazole and the mixture was stirred at 60° C. for an hour. Added thereto was 1.09 ml of ethanolamine, and the mixture was stirred at 60° C. for 6 hours. To the reaction mixture was added distilled water and the mixture was extracted with chloroform. The organic layer was dried and concentrated. The residue was purified by silica gel column chromatography (chloroform:acetone=4:1→1:1), to give 1.81 g of 1-benzyloxycarbonyl-2-(4-fluoro-2-methoxyphenyl)-4-(2-hydroxyethylaminocarbonyloxy)piperidine.

MS(m/z): 447 [M$^+$+1]

(5) In 20 ml of methanol was dissolved 1.81 g of the compound of the above (4), and added thereto was 90 mg of 10% palladium-carbon, and the mixture was stirred at room temperature for an hour under hydrogen atmosphere. After insoluble matters were removed by filtration, the filtrate was concentrated. To the residue was added diethyl ether and precipitates were collected by filtration, to give 1.30 g of 2-(4-fluoro 2-methoxyphenyl)-4-(2-hydroxyethylaminocarbonyloxy)piperidine as shown in Table 134 below.

Reference Example 30

(1) In 40 ml of tetrahydrofuran was dissolved 5.46 g of 4-methoxypyridine, and added dropwise thereto was 55 ml of a 1M phenylmagnesiumbromide-tetrahydrofuran solution under nitrogen atmosphere at −60° C. of below. Subsequently, added dropwise thereto was a solution of 10.24 g of benzyl chloroformate in 50 ml of tetrahydrofuran, and the mixture was stirred for 3 hours. The temperature of the mixture was raised to room temperature, and 120 ml of a 5% aqueous citric acid solution was added thereto. The mixture was extracted with ethyl acetate and washed with saturated brine. The organic layer was dried and concentrated. To the residue was added diisopropyl ether and the precipitates were collected by filtration, to give 8.51 g of 1-benzyloxycarbonyl-4-oxo-2-phenyl-3,4-dihydro-2H-pyridine.

MS(m/z): 308 [M$^+$+1]

(2) In 260 ml of acetic acid was dissolved 8.48 g of the compound of the above (1), added thereto was 3.61 g of zinc powder, and the mixture was stirred at room temperature for 18 hours. Subsequently, 1.8 g of zinc powder was added and after stirring the mixture at room temperature for 6 hours, 1.8 g of zinc powder was further added thereto and the mixture was stirred at 50° C. for 3 days. After insoluble matters were removed by filtration, the filtrate was concentrated under reduced pressure. The residue was extracted with ethyl acetate, and washed with a saturated aqueous sodium hydrogen carbonate solution and saturated brine. The organic layer was dried and concentrated, to give 8.54 g of 1-benzyloxycarbonyl-4-oxo-2-phenylpiperidine.

MS(m/z): 310 [M$^+$+1]

(3) In 15 ml of tetrahydrofuran was dissolved 619 mg of the compound of the above (2), and added dropwise thereto was 4 ml of a 1M diisobutylalminiun hydride solution in toluene under nitrogen atmosphere at −60° C. or below. The mixture was stirred for 10 minutes. To the reaction mixture was added 667 μl of a 6M aqueous hydrochloric acid solution, and the mixture was concentrated. To the residue was added distilled water and the mixture was extracted with ethyl acetate. The organic layer was washed with saturated brine, dried and concentrated under reduced pressure. The residue was purified by silica gel column chromatography (hexane:ethyl acetate=2:1→1:1), to give 553 mg of 1-benzyloxycarbonyl-4-hydroxy-2-phenylpiperidine.

MS(m/z): 312 [M$^+$+1]

(4) In a mixed solution of 14 ml of toluene and 1.6 ml of dichloromethane was added 511 mg of the compound of the above (3), and added thereto was 319 mg of 1,1'-carbonyldiimidazole, and the mixture was stirred at 60° C. for 2 hours. Added thereto was 396 μl of ethanolamine, and the mixture was stirred at 60° C. for 3 hours. To the reaction mixture was added distilled water and the mixture was extracted with chloroform. The organic layer was dried and concentrated. The residue was purified by silica gel column chromatography(chloroform:acetone=9:1→2:1), to give 462 mg of 1-benzyloxycarbonyl-4-(2-hydroxyethylaminocarbonyloxy)-2-phenylpiperidine.

MS(m/z): 399 [M$^+$+1]

(5) In 10 ml of methanol was dissolved 430 mg of the compound of the above (4), and added thereto was 30 mg of 10% palladium-carbon, and the mixture was stirred at room temperature for 5 days under hydrogen atmosphere. Insoluble matters were removed by filtration and the filtrate was concentrated, to give 348 mg of 4-(2-hydroxyethylaminocarboxyoxy)-2-phenylpiperidine as shown in Table 134 below.

Reference Example 31

(1) In 47 ml of ethanol was dissolved 2.61 g of 3,5-bistrifluoromethylacetophenone, added thereto was 478 mg of sodium borohydride, and the mixture was stirred at room temperature for 30 minutes. To the reaction mixture was added a saturated aqueous ammonium chloride solution and the mixture was concentrated. The residue was extracted with ethyl acetate and washed with saturated brine. The organic layer was dried and concentrated under reduced pressure. The residue was purified by silica gel column chromatography (hexane:ethyl acetate=9:1→4:1), to give 2.51 g of 1-(3,5-bistrifluoromethylphenyl)-ethanol.

MS(m/z): 258 [M$^+$+1]

(2) In a mixed solution of 40 ml of toluene and 4 ml of acetonitrile was dissolved 2.49 g of the compound of the above (1), added thereto was 1.72 g of 1,1'-carbonyldiimidazole, and the mixture was stirred at room temperature for 3 hours. To the reaction mixture was added water and the mixture was extracted with ethyl acetate and washed with saturated brine. The organic layer was dried and concentrated under reduced pressure, to give 3.40 g of 1-(3,5-bistrifluoromethylphenyl)ethyl imidazole-1-carboxylate as shown in Table 134 below.

Reference Example 32

To 1.74 g of magnesium and 40 ml of tetrahydrofuran was added trace of iodine, and under nitrogen atmosphere and at room temperature, 10.4 g of 2-bromo-5-fluorotoluene was added dropwise spending 40 minutes. The reaction mixture was refluxed under heating for an hour, to prepare Grignard reagent solution. To the prepared Grignard reagent solution was added dropwise 5.46 g of 4-methoxypyridine spending 20 minutes, at −40° C. under nitrogen atmosphere. After completion of dropwise addition, the mixture was stirred at a temperature from −40° C. to −30° C. for 30 minutes. Subsequently, the reaction mixture was cooled down to −40° C., and while keeping the temperature at −40° C. or below, added dropwise thereto was a solution of 12 g of di-tert-butyldicarbonate in 20 ml of tetrahydrofuran. After completion of dropwise addition, the temperature of the reaction mixture was slowly raised. At −15° C., ice was added thereto and the mixture was stirred for 20 minutes. Further added thereto was an aqueous citric acid solution and the mixture was stirred at room temperature for 40 minutes. Tetrahydrofuran was removed by distillation and to the resultant residue was added ethyl acetate, and extracted twice. The combined organic layers were washed with saturated brine, dried and concentrated under reduced pressure. To the residue was added diisopropyl ether, and the obtained crystals were collected by filtration with diisopropyl ether, to give 11.9 g of 1-tert-butoxycarbonyl-2-(4-fluoro-2-methylphenyl)-4-oxo-3,4-dihydro-2H-pyridine as shown in Table 134 below.

Reference Example 33

To 6.0 ml of ethanol were added 916 mg of 1-tert-butoxycarbonyl-2-(4-fluoro-2-methylphenyl)-4-oxo-3,4-dihydro-2H-pyridine and 110 mg of 10% palladium-carbon (moisture content of 50.5%), and the mixture was stirred at room temperature for 12 hours under hydrogen atmosphere. After insoluble matters were removed by filtration, the solvent was removed by distillation. The residue was dissolved in 15 ml of toluene and the solution was cooled down to −78° C. To the solution was slowly added dropwise 1.8 ml of butyl lithium aluminum hydride (a 65% by weight toluene solution) under nitrogen atmosphere. After completion of dropwise addition, the mixture was stirred at a temperature from −78° C. to −60° C. for an hour. To the reaction mixture was added a 1M aqueous sodium hydroxide solution, and the mixture was stirred for 10 minutes. Formed precipitates were separated by filtration through Celite, and extracted with ethyl acetate twice. The organic layers were combined and washed with saturated aqueous ammonia and saturated brine. The organic layer was dried and concentrated under reduced pressure. After adding 7.5 ml of ethyl acetate to the residue, slowly added dropwise thereto was 7.5 ml of 4M hydrochloric acid-ethyl acetate solution under ice-cooling. Crystals were collected by filtration and washed with ethyl acetate. After drying, the crystals were added to a mixture of ethyl acetate-a 1M aqueous sodium hydroxide solution, and stirred. The organic layer was separated and the aqueous layer was extracted with ethyl acetate for 3 times. The organic layers were combined and dried over sodium sulfate. The solvent was removed by distillation under reduced pressure, to give 471 mg of 2-(4-fluoro-2-methyl)phenyl-4-hydroxypiperidine as shown in Table 134 below.

Reference Example 34

In 3.0 ml of dichloromethane was dissolved 831 ml of triphosgene, and added dropwise thereto were a solution of 1.08 g of N-(3,5-bistrifluoromethylbenzyl)-N-methylamine and 1.76 ml of triethylamine in 5.0 ml of dichloromethane, spending 10 minutes, under nitrogen atmosphere under ice-cooling. The reaction mixture was stirred at 0° C. to 5° C. for 30 minutes. The solvent was removed by distillation, and the residue was dried. To the residue were added water and dichloromethane and the mixture was extracted twice with dichloromethane. The organic layers were combined and washed with saturated brine, and dried. Then, the solvent was removed by distillation. The residue was purified by silica gel column chromatography (hexane→hexane:ethyl acetate=10:1), to give 760 mg of N-(3,5-bistrifluoromethylbenzyl)-N-methylaminocarbonyl chloride as shown in Table 134 below.

Reference Example 35

In 20 ml of methanol was dissolved 24.5 g of 3,5-bistrifluoromethylbenzaldehyde, and under ice-cooling, added thereto was 60 ml of ethylamine (a 2M tetrahydrofuran solution). Subsequently, 4.38 g of sodium borohydride was slowly added thereto, and the mixture was stirred at room temperature for 3 hours. To the reaction mixture was added distilled water and concentrated under reduced pressure. The residue was extracted with dichloromethane, and the organic layer was dried and concentrated under reduced pressure. The residue was purified by silica gel column chromatography (hexane:ethyl acetate=4:1→chloroform:methanol=9:1), to give 6.35 g of N-(3,5-bistrifluoromethylbenzyl)-N-ethylamine as shown in Table 135 below.

Reference Example 36

(1) To 20 ml of tetrahydrofuran were added 1.34 g of magnesium and trace of iodine, and added dropwise thereto was a solution of 9.50 g of 2-bromotoluene in 45 ml of tetrahydrofuran, to prepare Grignard reagent. To the Grignard reagent was added dropwise a solution of 5.46 g of 4-methoxypyridine in 20 ml of tetrahydrofuran under nitrogen atmosphere at −60° C. or below. Subsequently, a solution of 10.24 g of chlorobenzyl formate in 50 ml of tetrahydrofuran was added dropwise thereto at −40° C. and the mixture was stirred for 3 hours. The temperature of the mixture was raised to room temperature and added thereto was 120 ml of a 5% aqueous citric acid solution. The mixture was extracted with ethyl acetate and washed with saturated brine. The organic layer was dried and concentrated under reduced pressure. The residue was crystallized with diisopropyl ether, and the crystals were collected by filtration, to give 11.15 g of 1-benzyloxycarbonyl-2-(2-methylphenyl)-4-oxo-3,4-dihydro-2H-pyridine.

MS(m/z): 322 [M$^+$+1]

(2) In a mixed solution of 125 ml of ethanol and 35 ml of tetrahydrofuran was dissolved 11.15 g of 1-benzyloxycarbonyl-2-(2-methylphenyl)-4-oxo-3,4-dihydro-2H-pyridine, added thereto was 2.76 g of sodium borohydride, and the mixture was stirred at room temperature for a day. Further added thereto was 1.38 g of sodium borohydride, and the mixture was stirred at room temperature for a day. The reaction mixture was concentrated under reduced pressure and to the residue was added distilled water. The mixture was extracted with chloroform, and the organic layer was dried and concentrated under reduced pressure. The residue was purified by silica gel column chromatography (chloroform:acetone=49:1→9:1), to give 6.18 g of 1-benzyloxycarbonyl-4-hydroxy-2-(2-methylphenyl piperidine.

MS(m/z): 326 [M$^+$+1]

(3) In 21 ml of toluene was dissolved 1.63 g of 1-benzyloxycarbonyl-4-hydroxy-2-(2-methylphenyl)piperidine, added thereto was 973 mg of 1,1'-carbonyldiimidazole, and the mixture was stirred at 60° C. for an hour. To the solution was added 1.21 ml of ethanolamine, and the mixture was stirred at 60° C. for 6 hours. To the reaction mixture was added distilled water, and extracted with chloroform. The organic layer was dried and concentrated under reduced pressure. The residue was purified by silica gel column chromatography (chloroform:acetone=9:1→chloroform:methanol=19:1), to give 1.34 g of 1-benzyloxycarbonyl-4-(2-hydroxyethylaminocarbonyloxy)-2-(2-methylphenyl)piperidine.

MS(m/z): 413 [M$^+$+1]

(4) In 30 ml of methanol was dissolved 1.33 g of 1-benzyloxycarbonyl-4-(2-hydroxyethylaminocarbonyloxy)-2-(2-methylphenyl)piperidine, and added thereto was 70 mg of 10% palladium-carbon, and the mixture was stirred at room temperature for 14 hours under hydrogen atmosphere. After insoluble matters were removed by filtration, the filtrate was concentrated, to give 880 mg of 4-(2-hydroxyethylaminocarbonyloxy)-2-(2-methylphenyl)piperidine as shown in Table 135 below.

Reference Example 37

(1) 25 g of 4-fluoro-1-bromobenzene was used and treated in the same manner as in Reference Example 1, to give 22.3 g of 1-benzyloxycarbonyl-2-(4-fluorophenyl)-4-oxo-3,4-dihydro-2H-pyridine.

(2) In 400 ml of ethanol was dissolved 20 g of the compound of the above (1), and added thereto was 7.6 g of sodium borohydride, and the mixture was stirred at −20° C. for 2 hours. After reaction was completed, slowly added thereto was an aqueous citric acid solution until no foam was generated. The solvent was removed by distillation under reduced pressure, and layers were separated with addition of water and chloroform. The aqueous layer was further extracted with chloroform, and the combined organic layers were dried and concentrated under reduced pressure. The residue was purified by silica gel column chromatography (chloroform:ethyl acetate=10:1), to give 6.3 g of a mixture of (a) (2R,4S)-1-benzyloxycarbonyl-2-(4-fluorophenyl)-4-hydroxypiperidine and (b) (2S,4R)-1-benzyloxycarbonyl-2-(4-fluorophenyl)-4-hydroxypiperidine.

(3) 6.2 g of the compound of the above (2) was used and treated in the same manner as in Example 209, to give 7.3 g of a mixture of (a) (2R,4S)-1-benzyloxycarbonyl-2-(4-fluorophenyl)-4-(2-hydroxyethylaminocarbonyloxy)piperidine and (b) (2S,4R)-1-benzyloxycarbonyl-2-(4-fluorophenyl)-4-(2-hydroxyethylaminocarbonyloxy)piperidine.

(4) 6.3 g of the compound of the above (3) was used and treated in the same manner as in Reference Example 4, to give 2.6 g of a mixture of (a) (2R,4S)-2-(4-fluorophenyl)-4-(2-hydroxyethylaminocarbonyloxy)piperidine and (b) (2S,4R)-2-(4-fluorophenyl)-4-(2-hydroxyethylaminocarbonyloxy)piperidine as shown in Table 135 below.

Reference Example 38

In 5 ml of methanol was dissolved 0.639 g of N-tosyl-D-phenylalanine, and the solution was warmed up to 59° C. and then added dropwise thereto was 1.3 ml of methanol solution containing 0.418 g of 2-(4-fluro-2-methyl)phenyl-4-hydroxypiperidine. After the crystals were formed in 20 minutes from the beginning of the crystallization, the other methanol solution in 2-(4-fluro-2-methyl)phenyl-4-hydroxypiperidine was added dropwise to the mixture in the period of 5 minutes. The mixture was cooled down from 59° C. to 30° C. in one hour, and then the crystals were formed for 1.5 hours. The obtained crystal was removed by filtration and washed by cooled-methanol, and dried by air at 60° C. for one night to give 0.325 g of (2R,4S)-2-(4-fluro-2-methyl)phenyl-4-hydroxypiperidine N-tosyl-D-phenylalanine salt. The obtained salt was added 0.62 ml of a 2 M aqueous hydrogen chloride solution, the mixture was extracted with ethyl acetate. The water layer was added 0.3 ml of a 5 M aqueous sodium hydroxide and then extracted with ethyl acetate for four times. The organic layer was dried, concentrated under reduced pressure, to give 0.129 g of (2R,4S)-2-(4-fluro-2-methyl)phenyl-4-hydroxypiperidine as shown in Table 136 below.

Reference Example 39

In 40 ml of dichloromethane was dissolved 2.72 g of 2-methoxy-5-(5-trifluoromethyltetrazole-1-yl)benzaldehyde, and added thereto was 2.5 ml of 8 M methylamine in ethanol solution, 0.572 ml of acetic acid and 3.12 g of triacetoxy sodium borohydride, the mixture was stirred at room temperature for 6 hours. The reaction mixture was washed with saturated aqueous sodium hydrocarbonate solution, and the organic layers were dried and concentrate. The residue was purified by silica gel column chromatography (chloroform:methanol=49:1 to 4:1), to give 2.2 g of N-{2-methoxy-5-(5-trifluromethyltetrazole-1-yl)benzyl}-N-methylamine as shown in Table 136 below.

TABLE 1

| Example No. | Structural Formula | MS |
|---|---|---|
| 1 (1) | | 493 (M+ + 1) |
| 1 (2) (a) | | 493 (M+ + 1) and |
| 1 (2) (b) | | 493 (M+ + 1) and |

TABLE 2

| Example No. | Structural Formula | MS |
|---|---|---|
| 2 (a) | | 507 (M⁺ + 1) |
| 2 (b) | | 507 (M⁺ + 1) |
| 3 (a) | | 493 (M⁺ + 1) |
| 3 (b) | | 493 (M⁺ + 1) |

TABLE 3

| Example No. | Structural Formula | MS |
|---|---|---|
| 4 (a) | (two structures) and | 507 (M⁺ + 1) |
| 4 (b) | (two structures) and | 507 (M⁺ + 1) |

TABLE 4
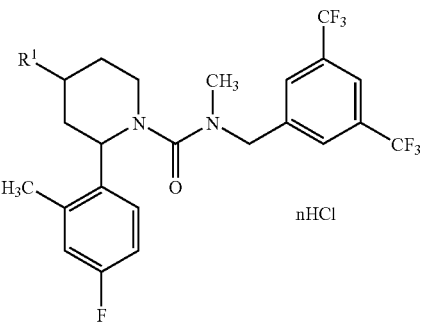
nHCl
| Example No. | R¹ | n | MS |
|---|---|---|---|
| 5 | 2-pyridyl-CH₂-O-CH₃ group | 0 | 584 (M⁺ + 1) |
| 6 | (CH₃)₂N-CH₂CH₂-O-CH₃ | 1 | 564 (M⁺ + 1) |
| 7 | piperidinyl-CH₂CH₂-O-CH₃ | 1 | 604 (M⁺ + 1) |
TABLE 5
| Example No. | Structural Formula | MS |
|---|---|---|
| 8 (a) | 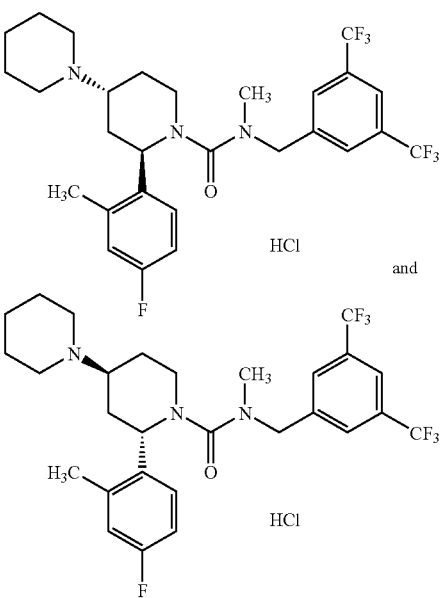 HCl and HCl | 560 (M⁺ + 1) |
TABLE 5-continued
| Example No. | Structural Formula | MS |
|---|---|---|
| 8 (b) | HCl and HCl | 560 (M⁺ + 1) |
TABLE 6
| Example No. | Structural Formula | MS |
|---|---|---|
| 9 (a) | 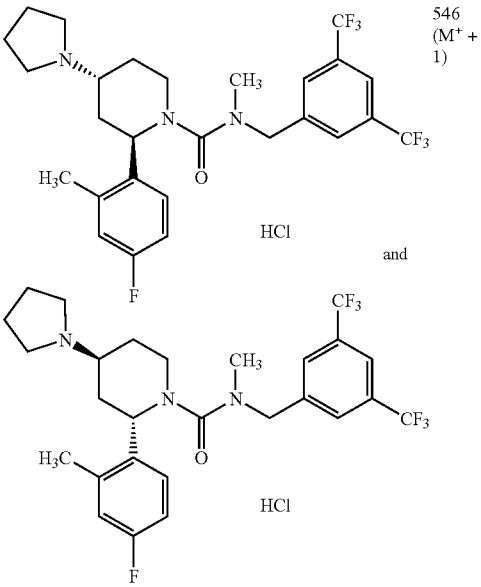 HCl and HCl | 546 (M⁺ + 1) |

TABLE 6-continued
| Example No. | Structural Formula | MS |
|---|---|---|
| 9 (b) | 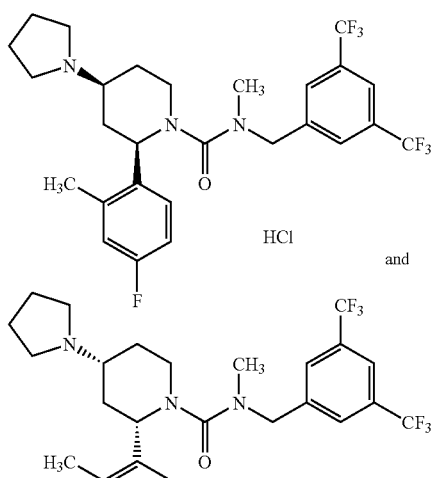 | 546 (M⁺ + 1) |
TABLE 7
| Example No. | Structural Formula | MS |
|---|---|---|
| 10 (a) | | 520 (M$^+$+1) |
TABLE 7-continued
| Example No. | Structural Formula | MS |
|---|---|---|
| 10 (b) | | 520 (M$^+$+1) |
TABLE 8
| Example No. | Structural Formula | MS |
|---|---|---|
| 11 (a) | | 548 (M$^+$+1) |

TABLE 8-continued
| Example No. | Structural Formula | MS |
|---|---|---|
| 11 (b) | 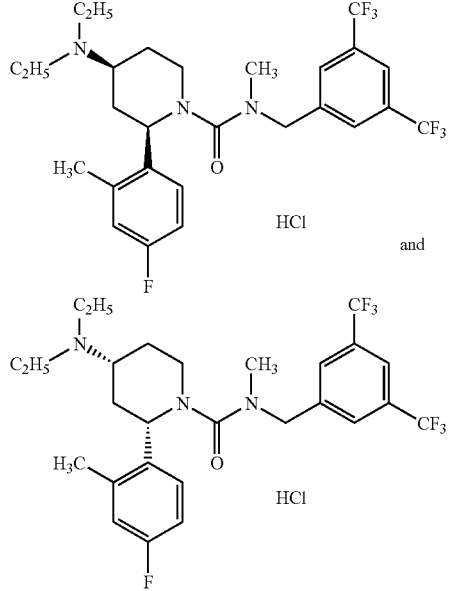 | 548 (M+ + 1) |
TABLE 9
| Example No. | Structural Formula | MS |
|---|---|---|
| 12 (a) | 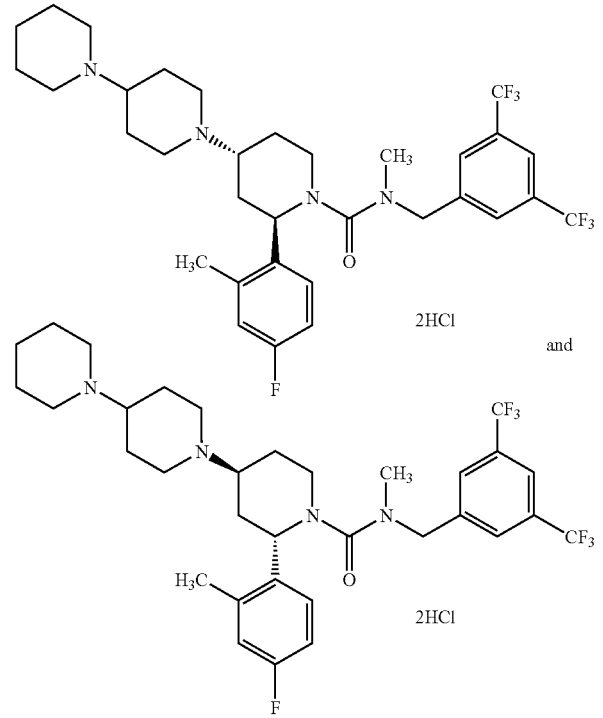 | 643 (M+ + 1) |

TABLE 9-continued
| Example No. | Structural Formula | MS |
|---|---|---|
| 12 (b) | 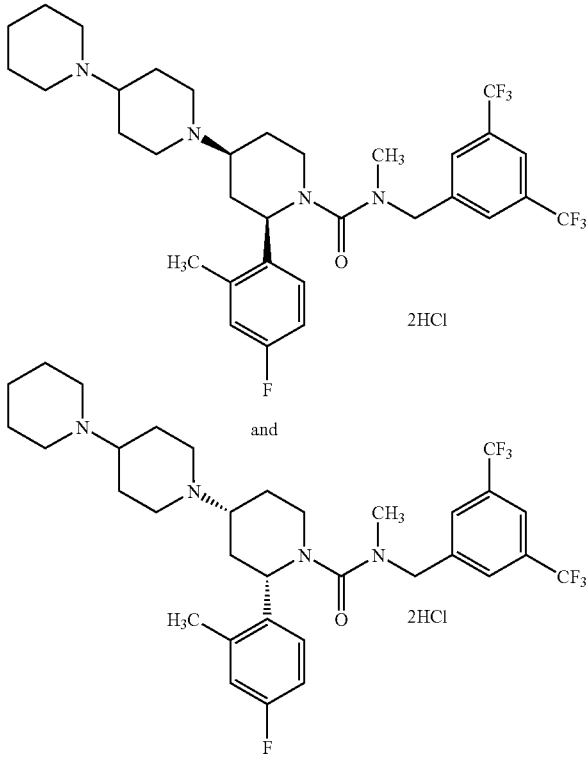 | 643 (M+ + 1) |
TABLE 10
| Example No. | Structural Formula | MS |
|---|---|---|
| 13 (a) | 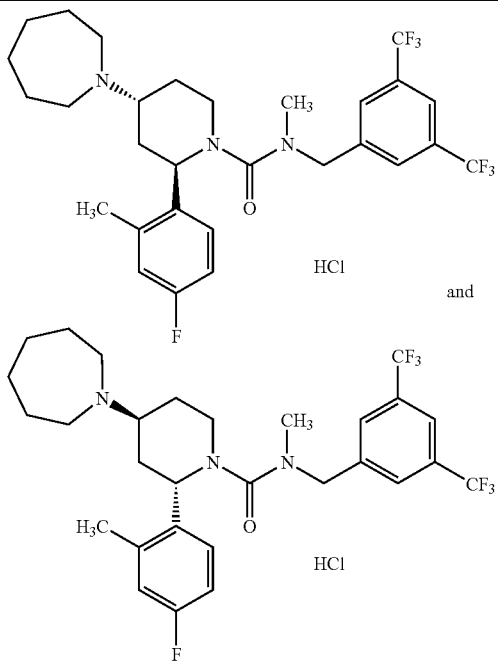 | 574 (M+ + 1) |

TABLE 10-continued
| Example No. | Structural Formula | MS |
|---|---|---|
| 13 (b) | 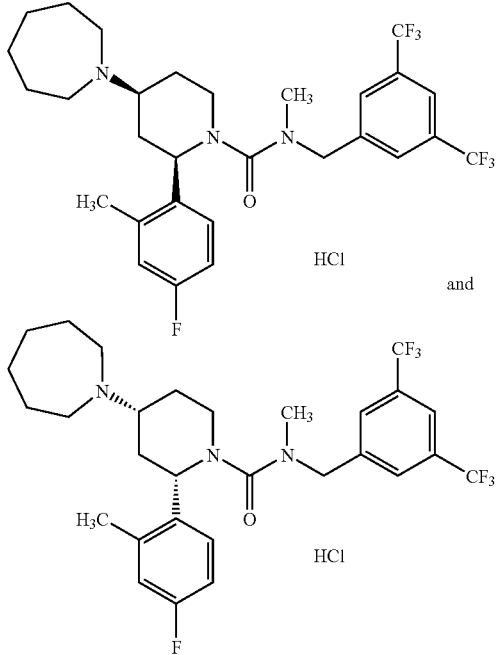 HCl and HCl | 574 (M+ + 1) |
TABLE 11
| Example No. | Structural Formula | MS |
|---|---|---|
| 14 (a) | 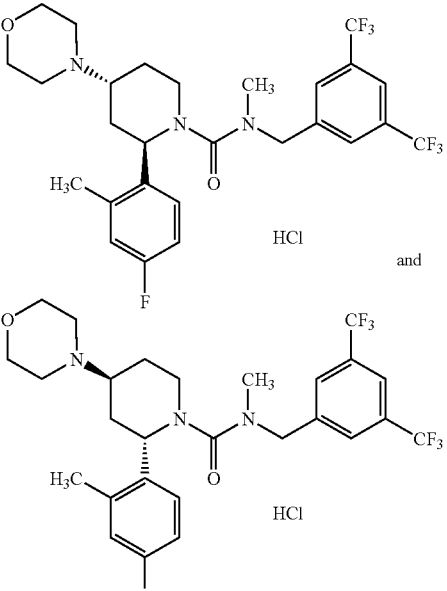 HCl and HCl | 562 (M+ + 1) |
TABLE 11-continued
| Example No. | Structural Formula | MS |
|---|---|---|
| 14 (b) | 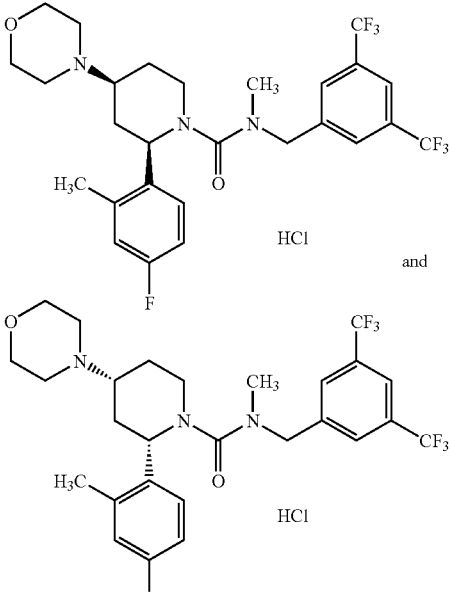 HCl and HCl | 562 (M+ + 1) |

TABLE 12
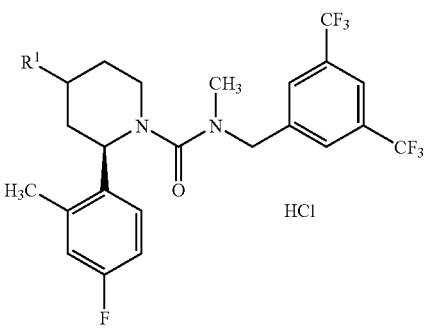
| Example No. | R¹ | MS |
|---|---|---|
| 15 (a) | piperidinyl | 560 (M⁺ + 1) |
| 15 (b) | piperidinyl | 560 (M⁺ + 1) |
| 16 (a) | pyrrolidinyl | 546 (M⁺ + 1) |
| 16 (b) | pyrrolidinyl | 546 (M⁺ + 1) |
| 17 (a) | morpholinyl | 562 (M⁺ + 1) |
| 17 (b) | morpholinyl | 562 (M⁺ + 1) |
| 18 (a) | N(CH₃)₂ | 520 (M⁺ + 1) |
| 18 (b) | N(CH₃)₂ | 520 (M⁺ + 1) |
| 19 (a) | N(C₂H₅)₂ | 548 (M⁺ + 1) |
| 19 (b) | N(C₂H₅)₂ | 548 (M⁺ + 1) |
TABLE 13
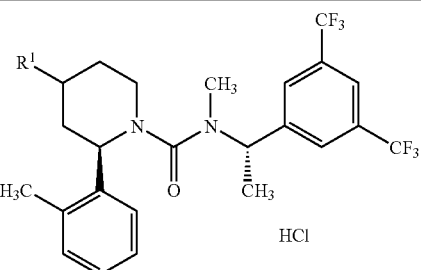
| Example No. | R¹ | MS |
|---|---|---|
| 20 (a) | piperidinyl | 574 (M⁺ + 1) |
| 20 (b) | piperidinyl | 574 (M⁺ + 1) |
| 21 (a) | pyrrolidinyl | 560 (M⁺ + 1) |
| 21 (b) | pyrrolidinyl | 560 (M⁺ + 1) |
| 22 (a) | morpholinyl | 576 (M⁺ + 1) |
| 22 (b) | morpholinyl | 576 (M⁺ + 1) |
TABLE 14
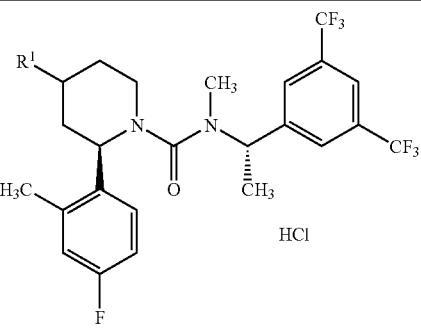
| Example No. | R¹ | MS |
|---|---|---|
| 23 (a) | N(CH₃)₂ | 534 (M⁺ + 1) |

TABLE 14-continued

[Structure: piperidine with R¹ at 4-position, 2-(2-methyl-4-fluorophenyl), N-methyl-N-[(1S)-1-(3,5-bis(trifluoromethyl)phenyl)ethyl]carboxamide, HCl salt]

| Example No. | R¹ | MS |
|---|---|---|
| 23 (b) | (CH₃)(H₃C)N— (dimethylamino) | 534 (M⁺ + 1) |
| 24 (a) | (C₂H₅)(C₂H₅)N— (diethylamino) | 562 (M⁺ + 1) |
| 24 (b) | (C₂H₅)(C₂H₅)N— (diethylamino) | 562 (M⁺ + 1) |
| 25 (a) | F₃C-CH₂-NH— | 588 (M⁺ + 1) |
| 25 (b) | F₃C-CH₂-NH— | 588 (M⁺ + 1) |

TABLE 15

[Structure: same piperidine core as above, HCl salt]

| Example No. | R¹ | MS |
|---|---|---|
| 26 (a) | piperidin-1-yl | 574 (M⁺ + 1) |
| 26 (b) | piperidin-1-yl | 574 (M⁺ + 1) |
| 27 (a) | pyrrolidin-1-yl | 560 (M⁺ + 1) |

TABLE 15-continued

| Example No. | R¹ | MS |
|---|---|---|
| 27 (b) | pyrrolidin-1-yl | 560 (M⁺ + 1) |
| 28 (a) | morpholin-4-yl | 576 (M⁺ + 1) |
| 28 (b) | morpholin-4-yl | 476 (M⁺ + 1) |
| 29 (a) | (CH₃)(H₃C)N— (dimethylamino) | 534 (M⁺ + 1) |
| 29 (b) | (CH₃)(H₃C)N— (dimethylamino) | 534 (M⁺ + 1) |
| 30 (a) | 3-hydroxypyrrolidin-1-yl | 576 (M⁺ + 1) |
| 30 (b) | 3-hydroxypyrrolidin-1-yl | 576 (M⁺ + 1) |

TABLE 16

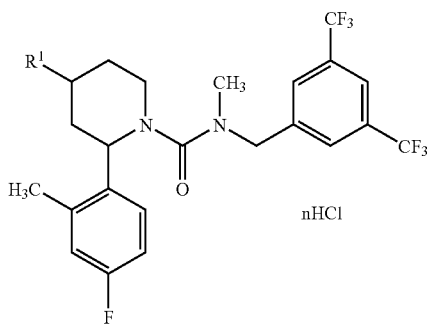

nHCl

| Example No. | R¹ | n | MS |
|---|---|---|---|
| 31 | H₃C-NH-CH₃ (isopropyl-N-methylamine) | 1 | 534 (M⁺ + 1) |
| 32 | morpholine-N-CH₂CH₂-NH-CH₃ | 2 | 605 (M⁺ + 1) |
| 33 | H₃CO-CH₂CH₂-N(CH₃)₂ | 1 | 564 (M⁺ + 1) |
| 34 | NC-CH₂CH₂-N(CH₃)₂ | 1 | 559 (M⁺ + 1) |
| 35 | (CH₃)₂N-CH₂CH₂-N(CH₃)₂ | 2 | 577 (M⁺ + 1) |
| 36 | H₃C-NH-CH₃ | 1 | 506 (M⁺ + 1) |
| 37 | 4-methylmorpholine | 1 | 562 (M⁺ + 1) |
| 38 | 2-(pyridin-2-yl)ethyl-N,N-dimethylamine | 2 | 611 (M⁺ + 1) |

TABLE 17

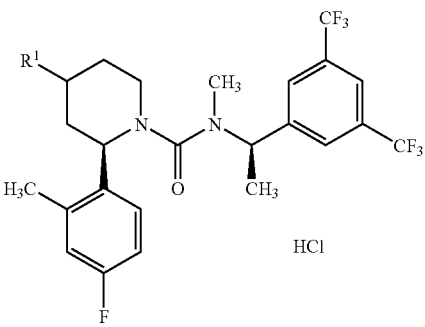

HCl

| Example No. | R¹ | MS |
|---|---|---|
| 39 | 3-methylthiazolidine | 578 (M⁺ + 1) |
| 40 | (S)-2-(methoxymethyl)-1-methylpyrrolidine | 604 (M⁺ + 1) |
| 41 | CH₃O-CH₂CH₂-N(CH₃)₂ | 578 (M⁺ + 1) |
| 42 | (CH₃)₂N-CH₂-C(O)-N(CH₃)₂ | 605 (M⁺ + 1) |

TABLE 18
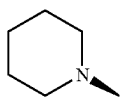
| Example No. | R¹ | MS |
|---|---|---|
| 43 (a) | piperidinyl | 574 (M⁺ + 1) |
| 43 (b) | piperidinyl | 574 (M⁺ + 1) |
| 44 (a) | pyrrolidinyl | 560 (M⁺ + 1) |
| 44 (b) | pyrrolidinyl | 560 (M⁺ + 1) |
TABLE 19
| Example No. | Structural Formula | MS |
|---|---|---|
| 45 | | 492 (M⁺ + 1) |
| 46 | | 492 (M⁺ + 1) |

TABLE 20

| Example No. | Structural Formula | MS |
|---|---|---|
| 47 (a) | (structures) | 592 (M⁺ + 1) |
| 47 (b) | (structures) | 592 (M⁺ + 1) |

TABLE 21

| Example No. | Structural Formula | MS |
|---|---|---|
| 48 | (structure) HCl and (structure) HCl | 492 (M⁺ + 1) |

TABLE 21-continued

| Example No. | Structural Formula | MS |
|---|---|---|
| 49 | (structure) HCl and (structure) HCl | 492 (M⁺ + 1) |

TABLE 22

| Example No. | Structural Formula | MS |
|---|---|---|
| 50 (a) | (structure) and (structure) | 548 (M⁺ + 1) |

TABLE 22-continued
| Example No. | Structural Formula | MS |
|---|---|---|
| 50 (b) | 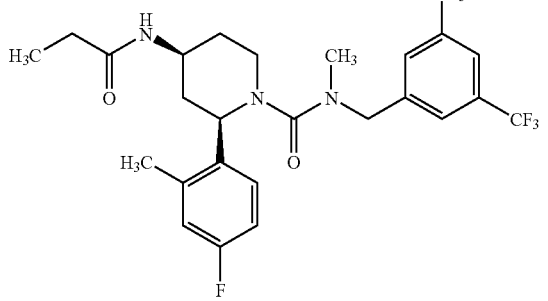 and 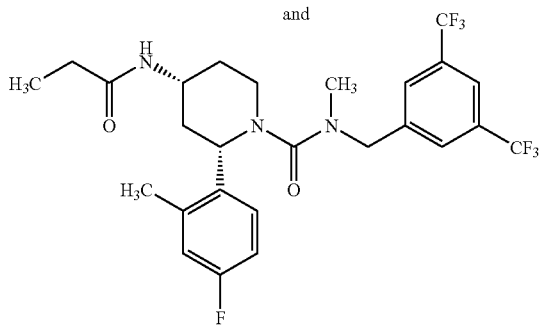 | 548 (M⁺ + 1) |
TABLE 23
| Example No. | Structural Formula | MS |
|---|---|---|
| 51 (a) | 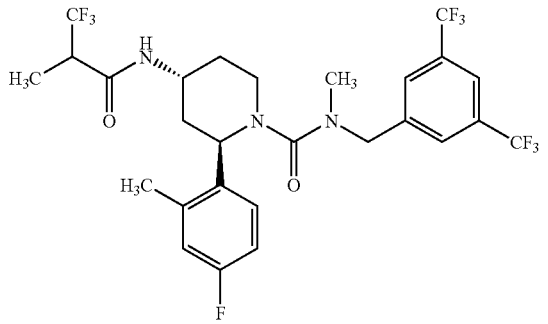 and 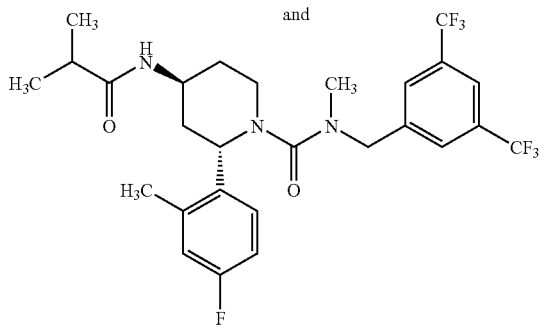 | 562 (M⁺ + 1) |

TABLE 23-continued
| Example No. | Structural Formula | MS |
|---|---|---|
| 51 (b) | 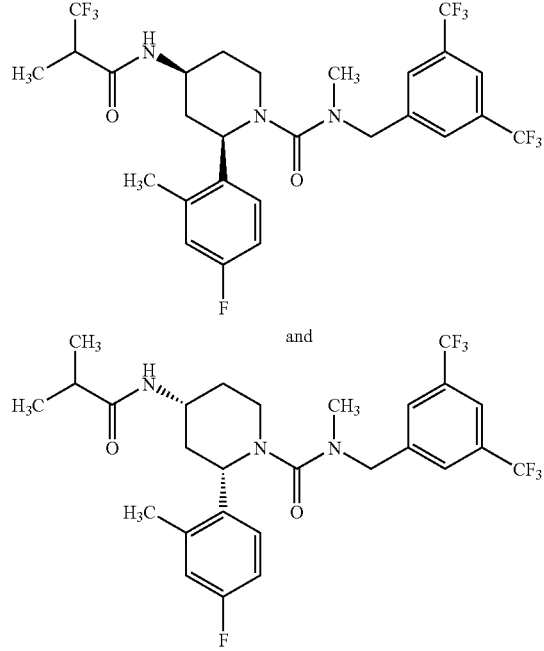 and | 562 (M⁺ + 1) |
TABLE 24
| Example No. | Structural Formula | MS |
|---|---|---|
| 52 (a) | 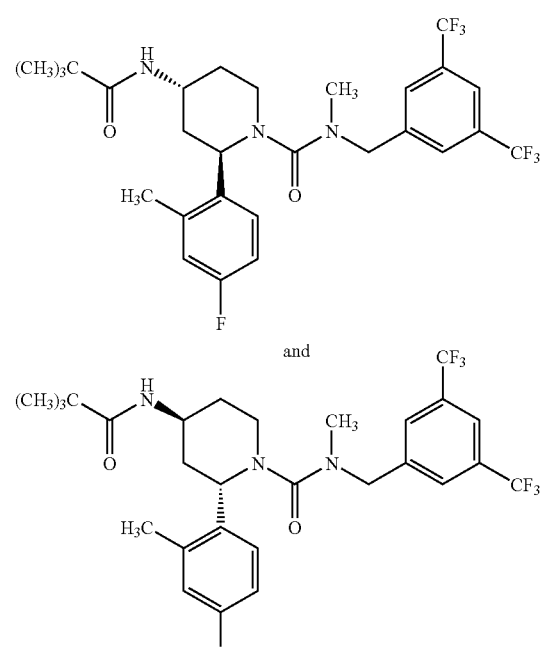 and | 576 (M⁺ + 1) |

TABLE 24-continued
| Example No. | Structural Formula | MS |
|---|---|---|
| 52 (b) | 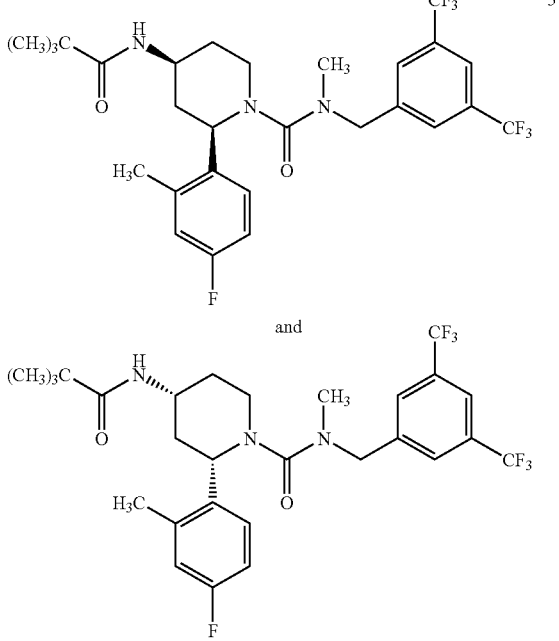 and | 576 (M⁺ + 1) |
TABLE 25
| Example No. | Structural Formula | MS |
|---|---|---|
| 53 (a) | 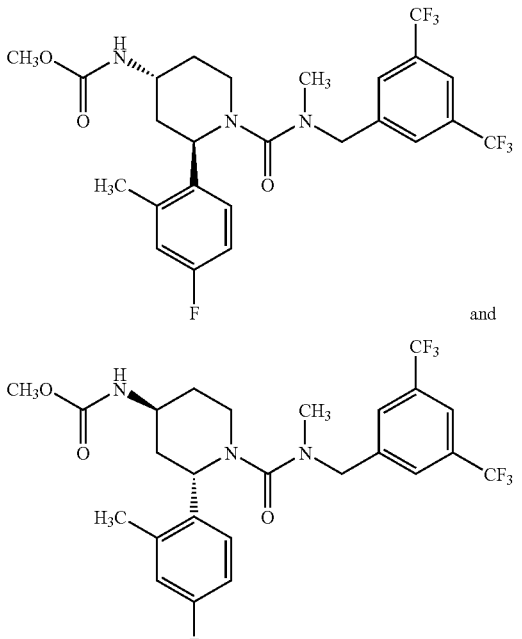 and | 550 (M⁺ + 1) |

TABLE 25-continued
| Example No. | Structural Formula | MS |
|---|---|---|
| 53 (b) | 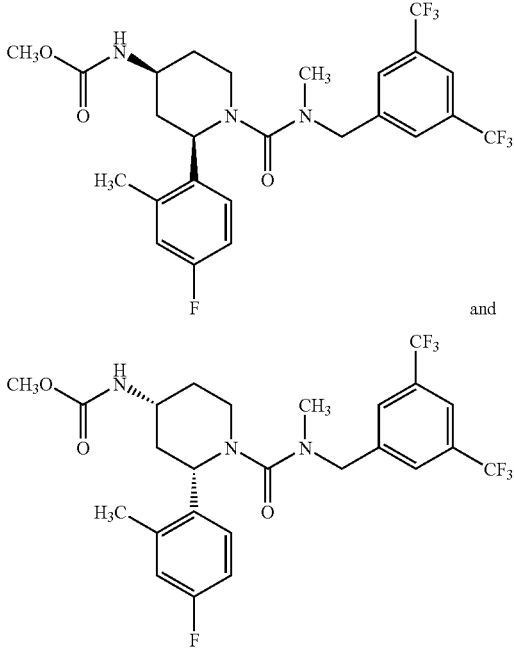 and | 550 (M⁺ + 1) |
TABLE 26
| Example No. | Structural Formula | MS |
|---|---|---|
| 54 (a) | 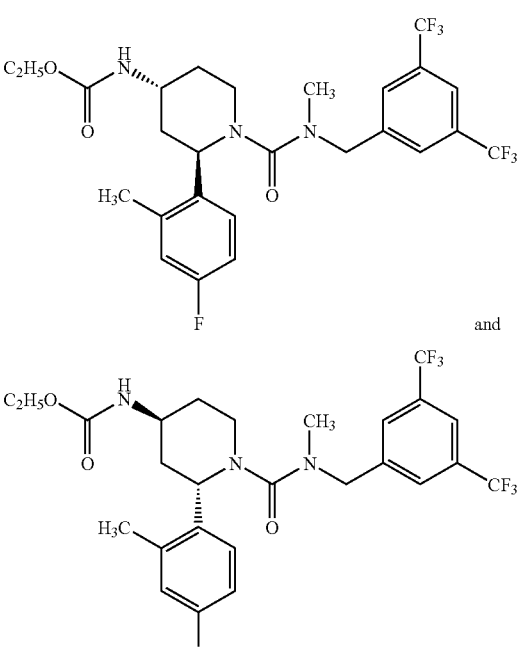 and | 564 (M⁺ + 1) |

TABLE 26-continued
| Example No. | Structural Formula | MS |
|---|---|---|
| 54 (b) | 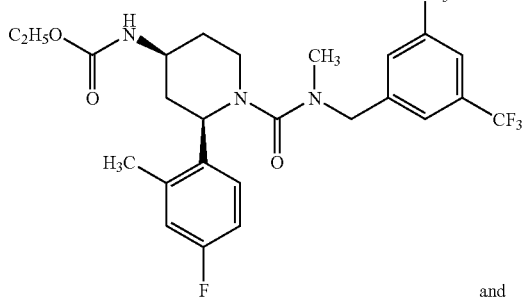 and 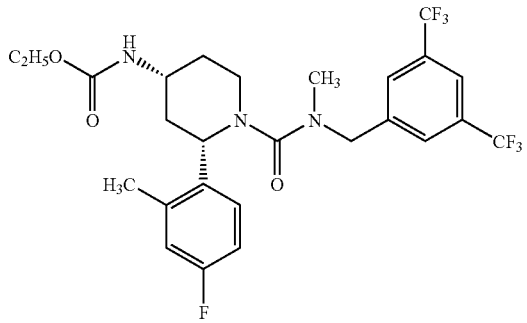 | 564 (M⁺ + 1) |
TABLE 27
| Example No. | Structural Formula | MS |
|---|---|---|
| 55 (a) | 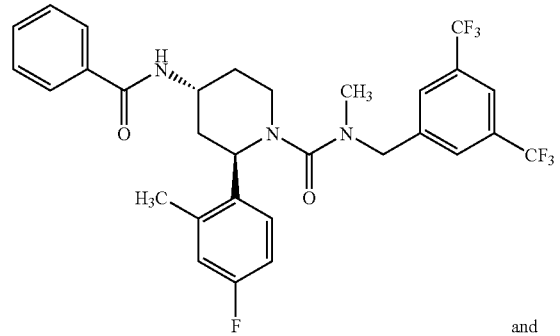 and 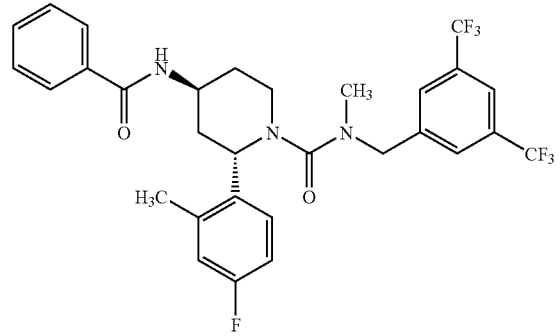 | 596 (M⁺ + 1) |

TABLE 27-continued
| Example No. | Structural Formula | MS |
| --- | --- | --- |
| 55 (b) | 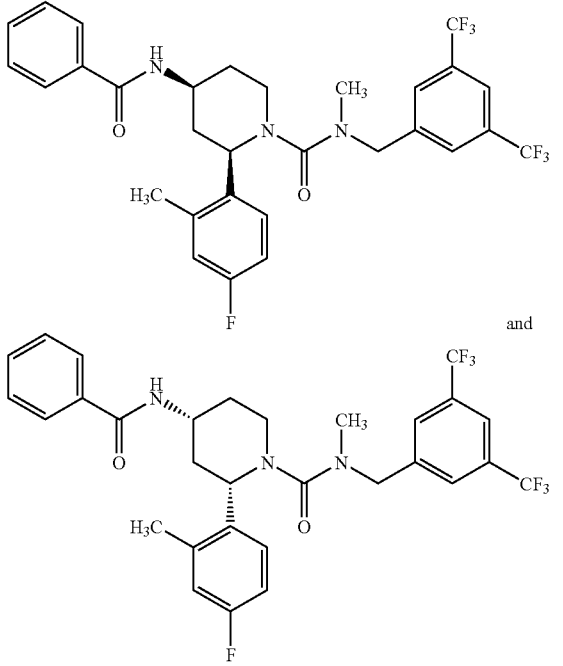 | 596 (M⁺ + 1) |
and
TABLE 28
| Example No. | Structural Formula | MS |
| --- | --- | --- |
| 56 (a) | 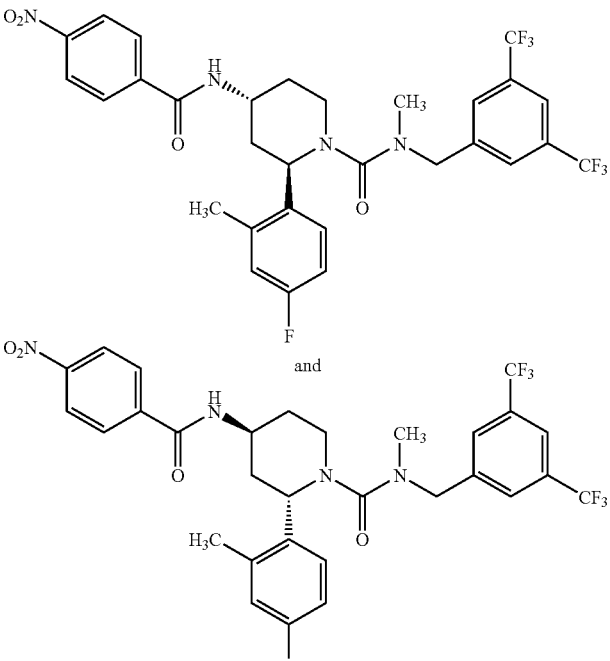 | 641 (M⁺ + 1) |
and TABLE 28-continued
| Example No. | Structural Formula | MS |
|---|---|---|
| 56 (b) | (structure shown) and (structure shown) | 641 (M⁺ + 1) |
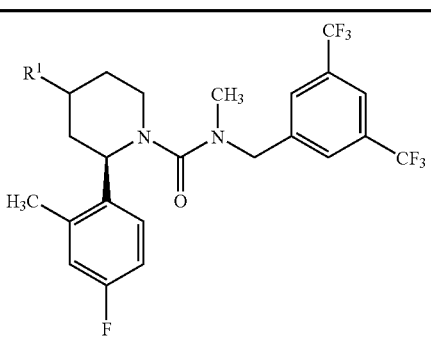
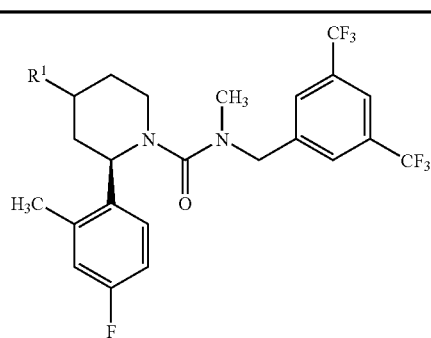
TABLE 29 / TABLE 29-continued
| Example No. | R¹ | MS |
|---|---|---|
| 57 (a) | (isobutyramide, H₃C, H₃C, NH, =O) | 562 (M⁺ + 1) |
| 57 (b) | (isobutyramide, H₃C, H₃C, NH...., =O) | 562 (M⁺ + 1) |
| 58 (a) | (morpholine carboxamide) | 604 (M⁺ + 1) |
| 58 (b) | (morpholine carboxamide) | 604 (M⁺ + 1) |
| 59 (a) | (C₂H₅SO₂NH) | 584 (M⁺ + 1) |
| 59 (b) | (C₂H₅SO₂NH) | 584 (M⁺ + 1) |

TABLE 29-continued
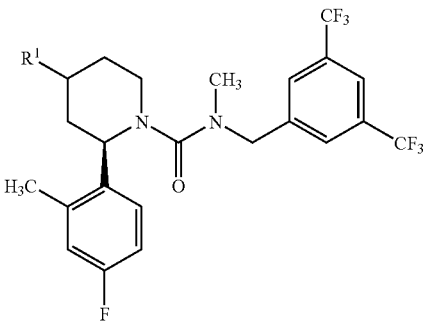
| Example No. | R¹ | MS |
|---|---|---|
| 60 (a) | furan-2-yl-C(O)NH- | 586 (M⁺ + 1) |
| 60 (b) | furan-2-yl-C(O)NH- | 586 (M⁺ + 1) |
TABLE 30
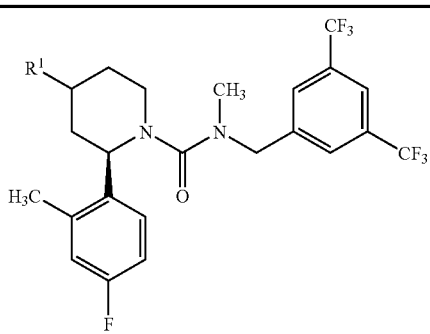
| Example No. | R¹ | MS |
|---|---|---|
| 61 (a) | thiophen-2-yl-C(O)NH- | 602 (M⁺ + 1) |
| 61 (b) | thiophen-2-yl-C(O)NH- | 602 (M⁺ + 1) |
| 62 (a) | CH₃S(O)₂N(CH₃)- | 584 (M⁺ + 1) |
TABLE 30-continued
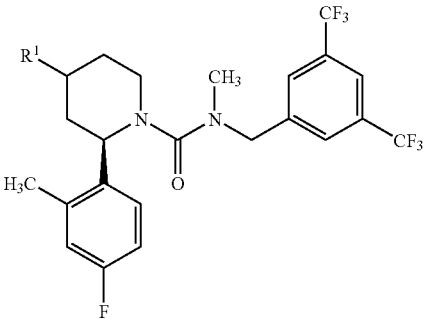
| Example No. | R¹ | MS |
|---|---|---|
| 62 (b) | CH₃S(O)₂N(CH₃)- | 584 (M⁺ + 1) |
| 63 | F₃C-C(O)NH- | 588 (M⁺ + 1) |
| 64 (a) | thiophen-3-yl-C(O)NH- | 602 (M⁺ + 1) |
| 64 (b) | thiophen-3-yl-C(O)NH- | 602 (M⁺ + 1) |
TABLE 31
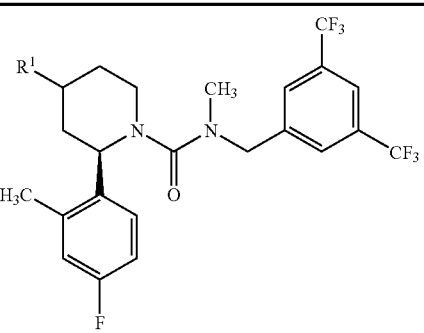
| Example No. | R¹ | MS |
|---|---|---|
| 65 (a) | 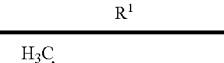 | 649 (M⁺ + 1) |

TABLE 31-continued
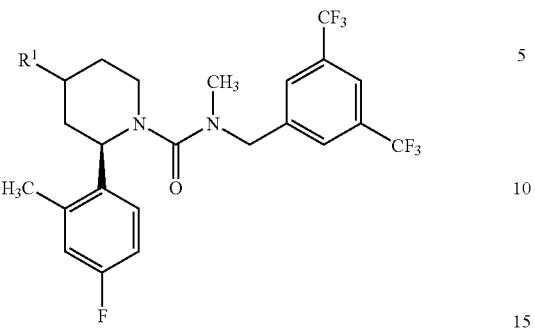
| Example No. | R[1] | MS |
|---|---|---|
| 65 (b) | 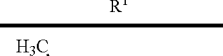 | 649 (M[+] + 1) |
TABLE 32
| Example No. | Structural Formula | MS |
|---|---|---|
| 66 | | 646 (M[+] + 1) |
and TABLE 32-continued
| Example No. | Structural Formula | MS |
|---|---|---|
| 67 | 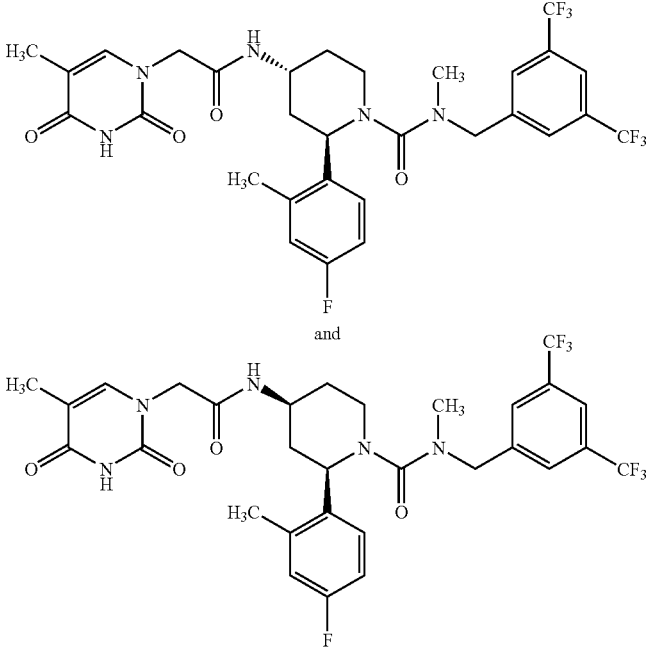 and | 657 (M⁺ + 1) |
TABLE 33
| Example No. | Structural Formula | MS |
|---|---|---|
| 68 | 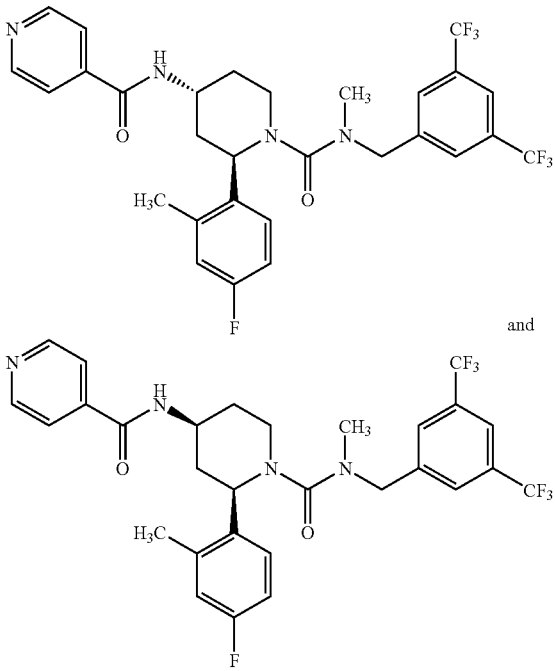 and | 597 (M⁺ + 1) |

TABLE 33-continued
| Example No. | Structural Formula | MS |
|---|---|---|
| 69 | 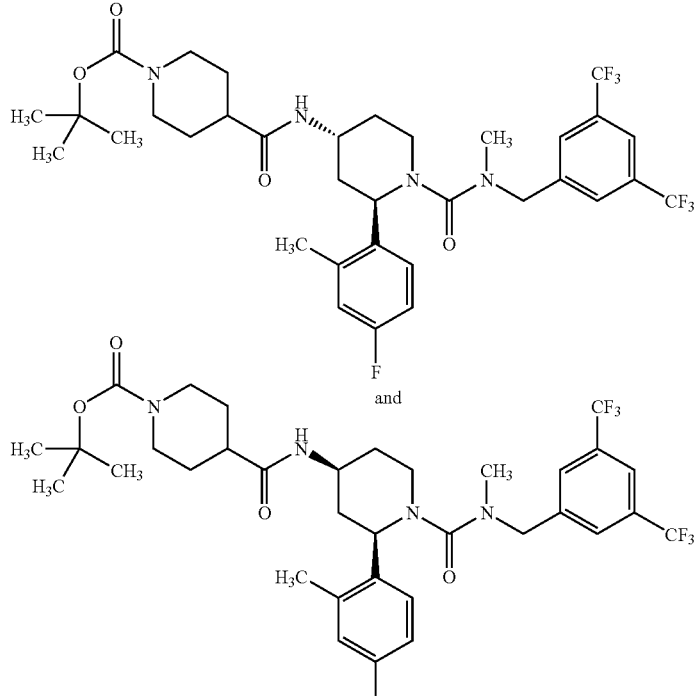 and | 703 (M⁺ + 1) |
| TABLE 34 | | |
|---|---|---|
| Example No. | R¹ | MS |
| 70 | H₃C−C(=O)−NH−CH₃ | 534 (M⁺ + 1) |
| 71 | pyridin-3-yl−C(=O)−NH−CH₃ | 597 (M⁺ + 1) |
| TABLE 35 | | |
|---|---|---|
| Example No. | R¹ | MS |
| 72 | H₂N−CH₂−C(=O)−NH−CH₃ | 549 (M⁺ + 1) |
| 73 | (H₃C)₂N−CH₂−C(=O)−NH−CH₃ | 577 (M⁺ + 1) |

TABLE 36
| Example No. | Structural Formula | MS |
|---|---|---|
| 74 | 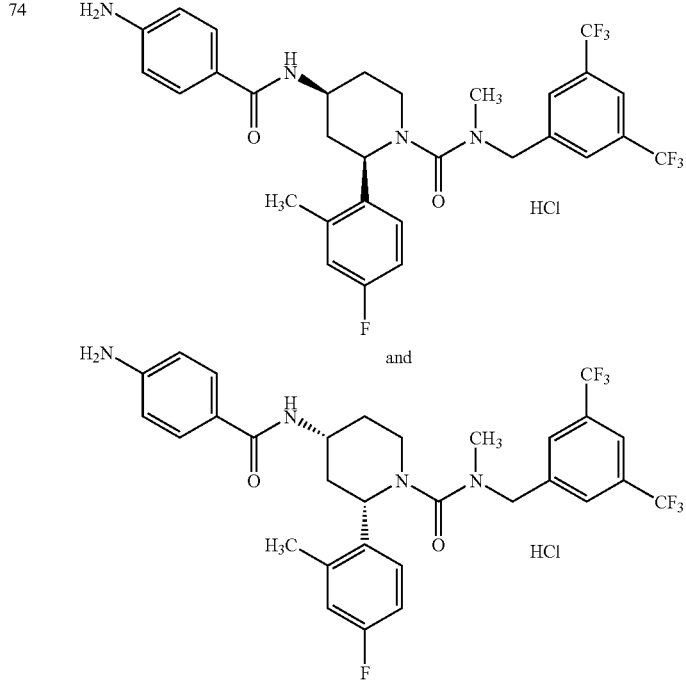 and (HCl salts shown) | 611 (M⁺ + 1) |
TABLE 37
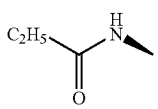
| Example No. | R¹ | MS |
|---|---|---|
| 75 | 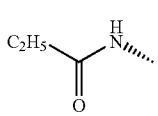 C₂H₅-C(=O)-NH- | 562 (M⁺ + 1) |
| 76 | 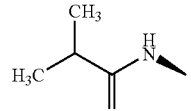 C₂H₅-C(=O)-NH•••• | 562 (M⁺ + 1) |
TABLE 37-continued
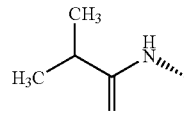
| Example No. | R¹ | MS |
|---|---|---|
| 77 | 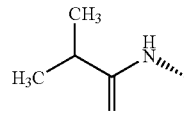 (CH₃)₂CH-C(=O)-NH- | 576 (M⁺ + 1) |
| 78 | (CH₃)₂CH-C(=O)-NH•••• | 576 (M⁺ + 1) |

TABLE 38
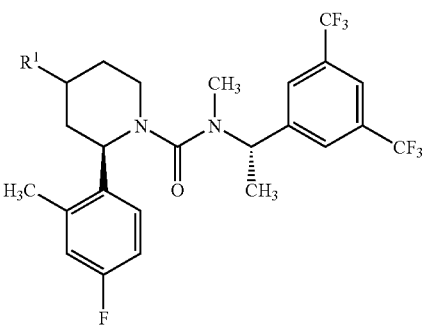
| Example No. | R¹ | MS |
|---|---|---|
| 79 (a) | C₂H₅-C(=O)-NH- | 562 (M⁺ + 1) |
| 79 (b) | C₂H₅-C(=O)-NH⋯ | 562 (M⁺ + 1) |
TABLE 38-continued
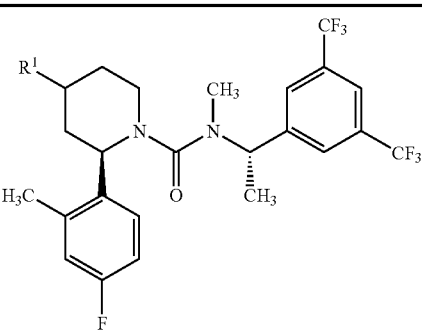
| Example No. | R¹ | MS |
|---|---|---|
| 80 (a) | (CH₃)₂CH-C(=O)-NH- | 576 (M⁺ + 1) |
| 80 (b) | (CH₃)₂CH-C(=O)-NH⋯ | 576 (M⁺ + 1) |
TABLE 39
| Example No. | Structural Formula | MS |
|---|---|---|
| 81 | 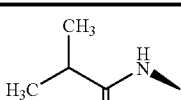 | 606 (M⁺ + 1) |
| 82 | 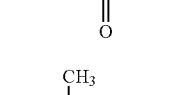 | 606 (M⁺ + 1) |

TABLE 39-continued

| Example No. | Structural Formula | MS |
| --- | --- | --- |
| 83 | | 606 (M⁺ + 1) |
| 84 | | 606 (M⁺ + 1) |

TABLE 40

| Example No. | Structural Formula | MS |
| --- | --- | --- |
| 85 | | 506 (M⁺ + 1) |
| 86 | | 506 (M⁺ + 1) |

TABLE 41

| Example No. | R¹ | MS |
| --- | --- | --- |
| 87 | $H_3C-SO_2-NH-$ | 584 (M⁺ + 1) |
| 88 | $C_2H_5-SO_2-NH-$ | 598 (M⁺ + 1) |
| 89 | $H_3C-SO_2-N(CH_3)-$ | 598 (M⁺ + 1) |
| 90 | $C_2H_5-SO_2-N(CH_3)-$ | 612 (M⁺ + 1) |

TABLE 42

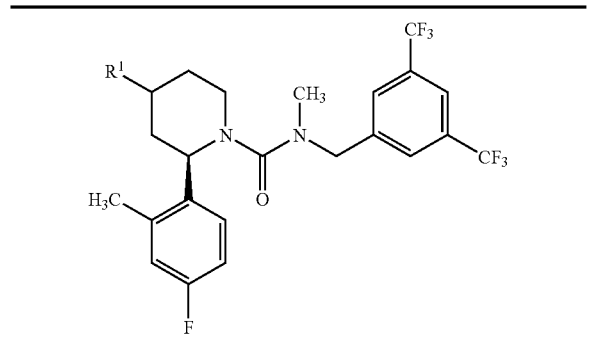

| Example No. | R¹ | MS |
|---|---|---|
| 91 | tetrahydropyran-2-yl-O-CH₂CH₂-O- | 621 (M⁺ + 1) |
| 92 | HO-CH₂CH₂-O- | 537 (M⁺ + 1) |
| 93 | 1,2,4-triazol-1-yl-CH₂CH₂-O- | 588 (M⁺ + 1) |
| 94 | tetrazol-2-yl-CH₂CH₂-O- | 589 (M⁺ + 1) |
| 95 | 5-methyl-tetrazol-2-yl-CH₂CH₂-O- | 603 (M⁺ + 1) |
| 96 | H₃C-SO₂-O-CH₂CH₂-O- | 615 (M⁺ + 1) |
| 97 (2) | morpholino-CH₂CH₂-N(CH₃)-, HCl | 606 (M⁺ + 1) |
| 98 | (C₂H₅)₂N-CH₂CH₂-O- | 592 (M⁺ + 1) |
| 99 | C₂H₅-NH-C(O)-O- | 564 (M⁺ + 1) |
| 100 | morpholino-C(O)-O- | 606 (M⁺ + 1) |

TABLE 42-continued

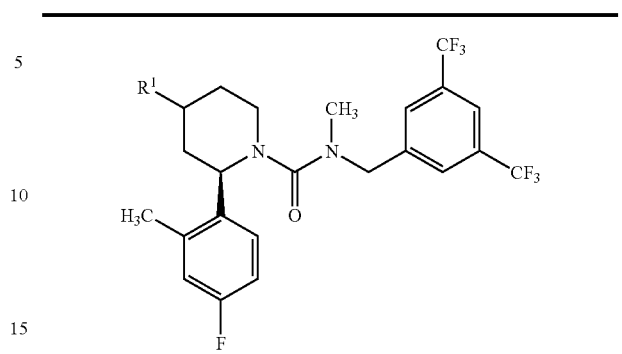

| Example No. | R¹ | MS |
|---|---|---|
| 101 | imidazol-1-yl-C(O)-O- | 588 (M⁺ + 1) |

TABLE 43

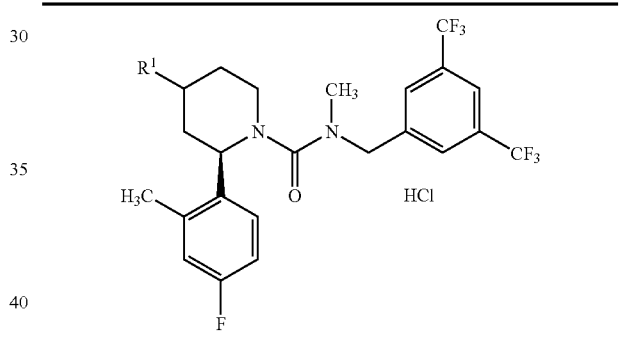

| Example No. | R¹ | MS |
|---|---|---|
| 102 (2) | 4-methyl-piperazin-1-yl-C(O)-O- | 619 (M⁺ + 1) |
| 103 | (CH₃)₂N-CH₂CH₂-NH-C(O)-O- | 607 (M⁺ + 1) |
| 104 | piperidin-1-yl-CH₂CH₂-NH-C(O)-O- | 647 (M⁺ + 1) |
| 105 | morpholino-CH₂CH₂-NH-C(O)-O- | 649 (M⁺ + 1) |

TABLE 44
| Example No. | Structural Formula | MS |
|---|---|---|
| 106 (2) | 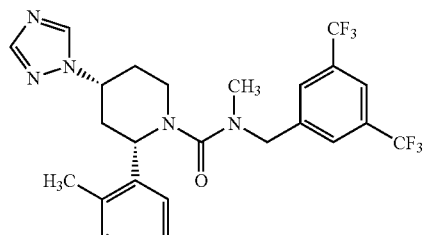 and | 493 (M⁺ + 1) |
TABLE 44-continued
| Example No. | Structural Formula | MS |
|---|---|---|
| 107 | 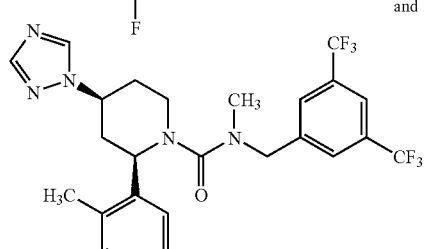 and | 544 (M⁺ + 1) |
TABLE 45
| Example No. | Structural Formula | MS |
|---|---|---|
| 108 | 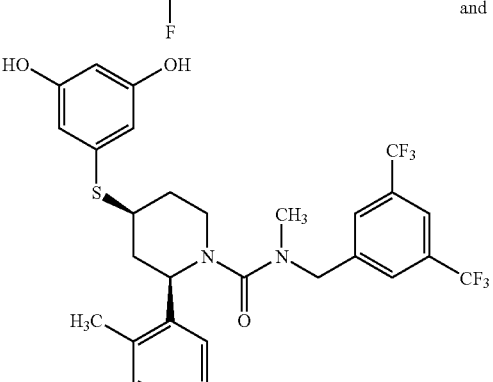 and | 619 (M⁺ + 1) |

TABLE 46
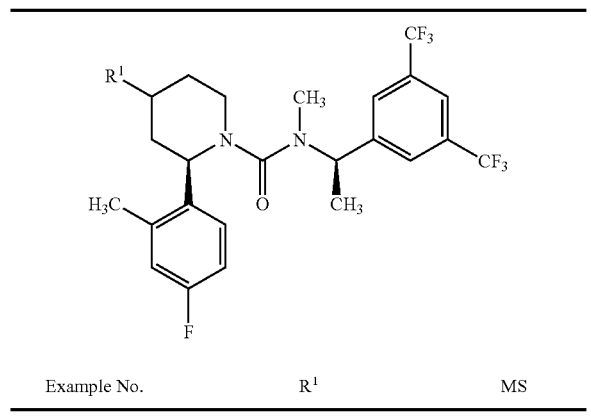
| Example No. | R¹ | MS |
|---|---|---|
| 109 | HO⫲⫲⫲⫲ | 507 (M⁺ + 1) |
| 110 | (1,2,4-triazol-1-ylmethyl) | 558 (M⁺ + 1) |
| 111 | (2H-tetrazol-2-ylmethyl) | 559 (M⁺ + 1) |
| 112 | (6-amino-9H-purin-9-ylmethyl) | 624 (M⁺ + 1) |
| 113 (2) | EtO-C(O)-CH₂CH₂- | 577 (M⁺ + 1) |
TABLE 46-continued
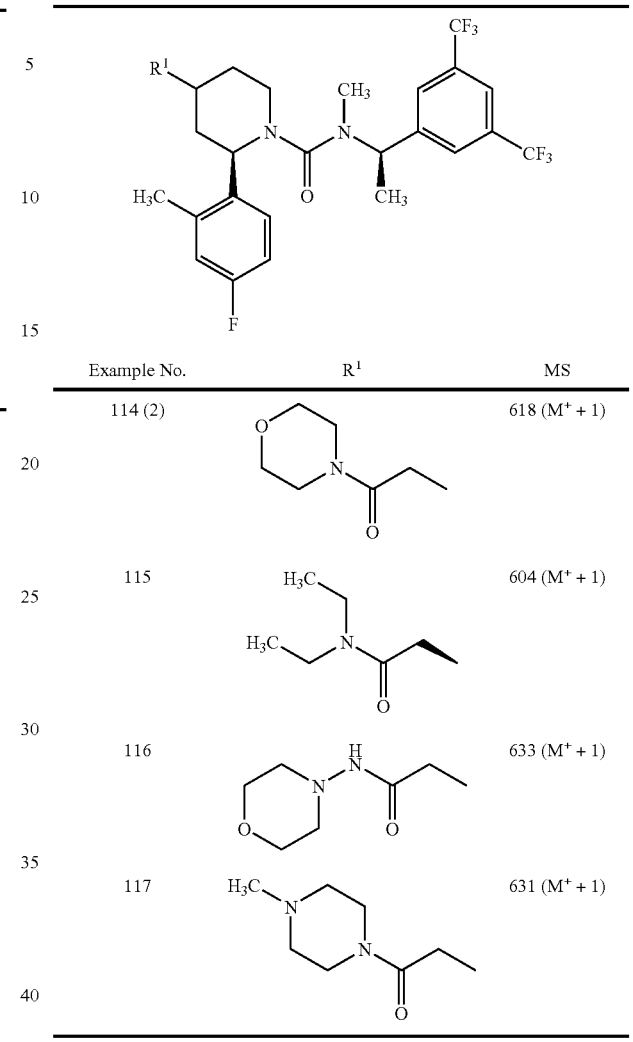
| Example No. | R¹ | MS |
|---|---|---|
| 114 (2) | (morpholin-4-yl)-C(O)-CH₂CH₂- | 618 (M⁺ + 1) |
| 115 | (Et)₂N-C(O)-CH₂CH₂- | 604 (M⁺ + 1) |
| 116 | (morpholin-4-yl)-NH-C(O)-CH₂CH₂- | 633 (M⁺ + 1) |
| 117 | (4-methylpiperazin-1-yl)-C(O)-CH₂CH₂- | 631 (M⁺ + 1) |
TABLE 47
| Example No. | Structural Formula | MS |
|---|---|---|
| 118 (2) | 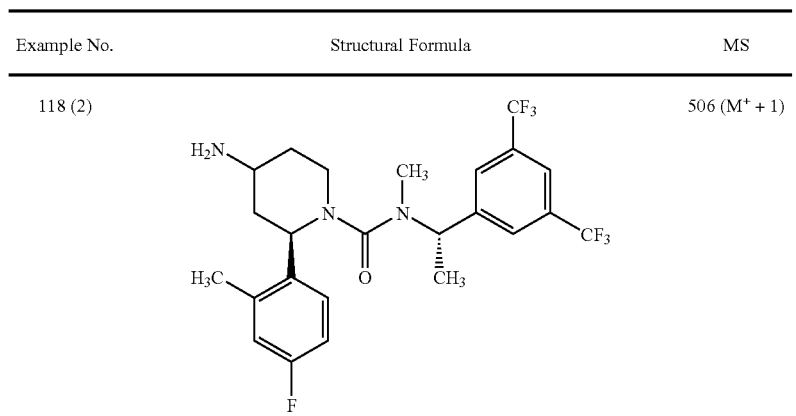 | 506 (M⁺ + 1) |

TABLE 47-continued

| Example No. | Structural Formula | MS |
|---|---|---|
| 119 | | 492 (M⁺ + 1) |
| 120 (a) | | 612 (M⁺ + 1) |
| 120 (b) | | 612 (M⁺ + 1) |

TABLE 48

| Example No. | Structural Formula | MS |
|---|---|---|
| 121 | | 590 (M⁺ + 1) |
| 122 | | 590 (M⁺ + 1) |

TABLE 48-continued

| Example No. | Structural Formula | MS |
|---|---|---|
| 123 | | 592 (M⁺ + 1) |
| 124 | | 592 (M⁺ + 1) |

TABLE 49

| Example No. | Structural Formula | MS |
|---|---|---|
| 125 | | 506 (M⁺ + 1) |
| 126 | | 520 (M⁺ + 1) |
| 127 | | 520 (M⁺ + 1) |

TABLE 49-continued

| Example No. | Structural Formula | MS |
|---|---|---|
| 128 | | 604 (M+ + 1) |

TABLE 50

| Example No. | Structural Formula | MS |
|---|---|---|
| 129 | | 548 (M+ + 1) |
| 130 | | 576 (M+ + 1) |
| 131 | | 614 (M+ + 1) |

TABLE 50-continued

| Example No. | Structural Formula | MS |
|---|---|---|
| 132 | | 548 (M⁺ + 1) |
| 133 | | 590 (M⁺ + 1) |

TABLE 51

| Example No. | Structural Formula | MS |
|---|---|---|
| 134 | | 578 (M⁺ + 1) |
| 135 | | 576 (M⁺ + 1) |

TABLE 51-continued
| Example No. | Structural Formula | MS |
|---|---|---|
| 136 | 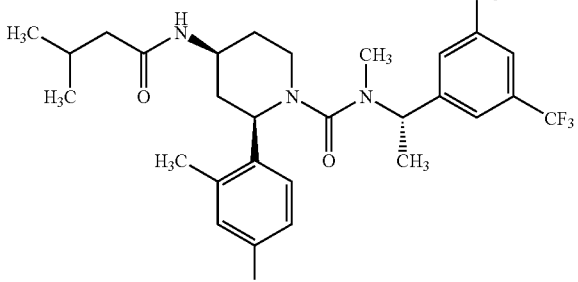 | 590 (M+ + 1) |
| 137 | 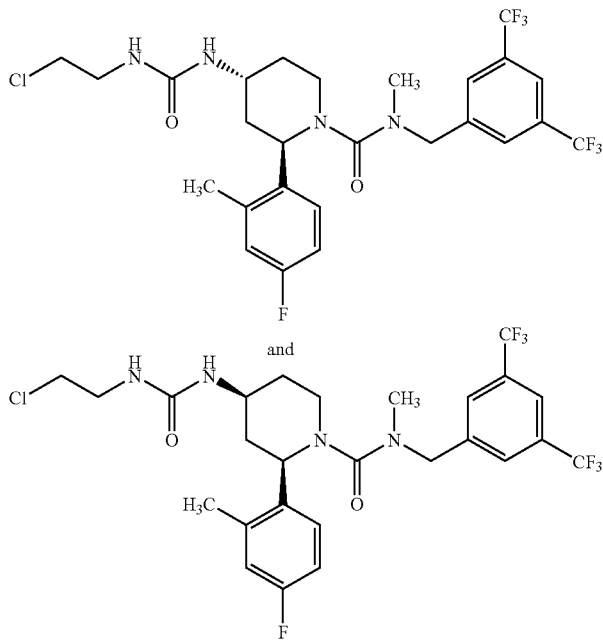 | 597 (M+ + 1) |

TABLE 52
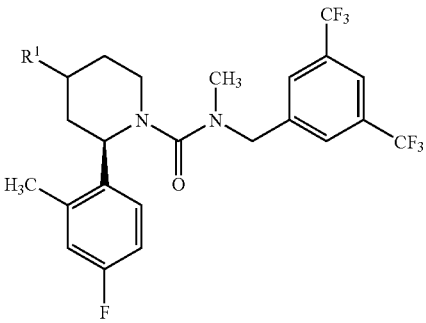
| Example No. | R[1] | MS |
|---|---|---|
| 138 (a) | OHC-furan-C(O)NH- | 614 (M+ + 1) |
| 138 (b) | OHC-furan-C(O)NH- (stereo) | 614 (M+ + 1) |
TABLE 53
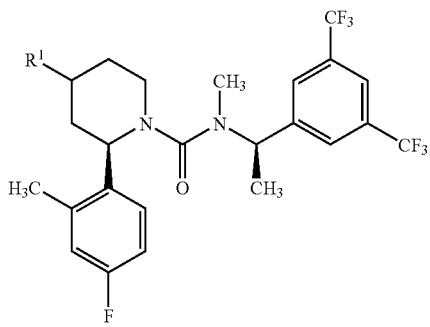
| Example No. | R[1] | MS |
|---|---|---|
| 140 | furan-CH2CH2-C(O)NH- | 628 (M+ + 1) |
| 141 | furan-3-C(O)NH- | 600 (M+ + 1) |
| 142 | tetrazole-CH2-C(O)NH- | 616 (M+ + 1) |
TABLE 53-continued
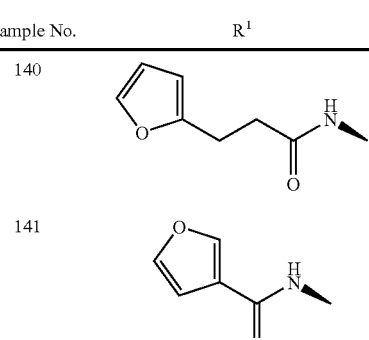
| Example No. | R[1] | MS |
|---|---|---|
| 143 | HO-CH2-C(O)NH- | 564 (M+ + 1) |
| 144 | H3CO-CH2CH2-C(O)NH- | 592 (M+ + 1) |
| 145 | H3CS-CH2-C(O)NH- | 594 (M+ + 1) |
| 146 | H2N-thiazole-CH2-C(O)NH- | 646 (M+ + 1) |
| 147 | pyridine-C(O)NH- | 611 (M+ + 1) |
TABLE 54
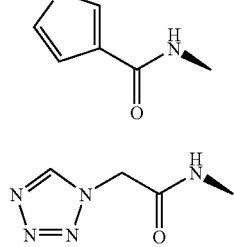
| Example No. | R[1] | MS |
|---|---|---|
| 148 | 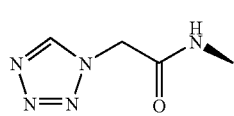 | 576 (M+ + 1) |

TABLE 54-continued

[Structure: R¹-substituted piperidine with N-methyl carboxamide linked to (1S)-1-(3,5-bis(trifluoromethyl)phenyl)ethyl group; 2-position of piperidine bears 4-fluoro-2-methylphenyl]

| Example No. | R¹ | MS |
|---|---|---|
| 149 | CH₃-N(CH₃)-C(=O)-CH₂-(1H-tetrazol-1-yl) | 630 (M⁺ + 1) |

TABLE 55

[Structure: R¹-substituted piperidine with N-methyl carboxamide linked to (1S)-1-(3,5-bis(trifluoromethyl)phenyl)ethyl group; 2-position of piperidine bears 4-fluoro-2-methylphenyl]

| Example No. | R¹ | MS |
|---|---|---|
| 150 | 2-amino-thiazol-4-yl-CH₂-C(=O)-NH-CH₃ | 646 (M⁺ + 1) |
| 151 | H₃CS-CH₂-C(=O)-NH-CH₃ | 594 (M⁺ + 1) |
| 152 | H₃CO-CH₂CH₂-C(=O)-NH-CH₃ | 592 (M⁺ + 1) |
| 153 | HO-CH₂-C(=O)-NH-CH₃ | 564 (M⁺ + 1) |
| 154 | CH₃-CH(OH)-C(=O)-NH-CH₃ | 578 (M⁺ + 1) |

TABLE 55-continued

| Example No. | R¹ | MS |
|---|---|---|
| 155 | H₃C-CH(OH)-C(=O)-NH-CH₃ | 578 (M⁺ + 1) |
| 156 | 1-hydroxy-cyclopropane-C(=O)-NH-CH₃ | 590 (M⁺ + 1) |
| 157 | (CH₃)₂C(OH)-C(=O)-NH-CH₃ | 592 (M⁺ + 1) |

TABLE 56

[Structure: R¹-substituted piperidine with N-methyl carboxamide linked to (1S)-1-(3,5-bis(trifluoromethyl)phenyl)ethyl group; 2-position of piperidine bears 4-fluoro-2-methylphenyl]

| Example No. | R¹ | MS |
|---|---|---|
| 158 | HO-CH₂CH₂-C(=O)-NH-CH₃ | 578 (M⁺ + 1) |
| 159 | C₂H₅O-CH₂CH₂-C(=O)-NH-CH₃ | 606 (M⁺ + 1) |
| 160 | HO-CH(CH₃)-CH₂-C(=O)-NH-CH₃ | 592 (M⁺ + 1) |

TABLE 56-continued

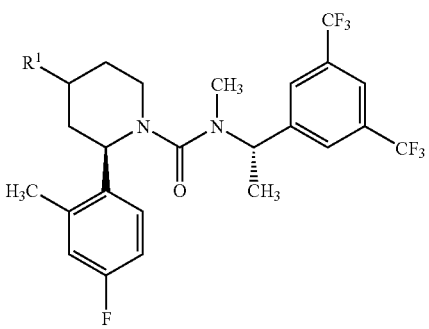

| Example No. | R¹ | MS |
|---|---|---|
| 161 | HO–CH(CH₃)–CH₂–C(=O)–NH– | 592 (M⁺ + 1) |
| 162 | HOCH₂–C(CH₃)₂–C(=O)–NH– | 606 (M⁺ + 1) |
| 163 | (CH₃)₂C(OH)–CH₂–C(=O)–NH– | 606 (M⁺ + 1) |
| 164 | tetrazol-1-yl–CH₂–C(=O)–NH– | 616 (M⁺ + 1) |
| 165 | pyridin-4-yl–C(=O)–NH– | 590 (M⁺ + 1) |

TABLE 57

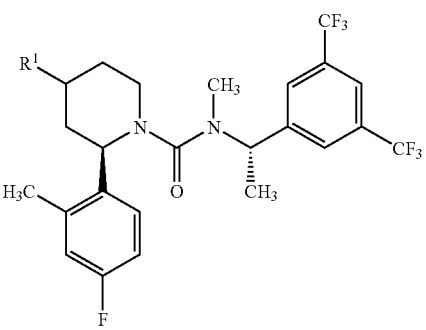

| Example No. | R¹ | MS |
|---|---|---|
| 166 | tetrahydrofuran-2-yl–C(=O)–NH– | 592 (M⁺ + 1) |
| 167 | tetrahydrofuran-2-yl–C(=O)–NH– | 578 (M⁺ + 1) |
| 168 | 2-mercapto-4-methylthiazol-5-yl–CH₂–C(=O)–NH– | 677 (M⁺ + 1) |
| 169 | HO–CH₂CH₂–NH–C(=O)–NH– | 593 (M⁺ + 1) |
| 170 | C₂H₅O–CH₂CH₂–NH–C(=O)–NH– | 621 (M⁺ + 1) |
| 171 | H₃CO–CH₂CH₂–NH–C(=O)–NH– | 607 (M⁺ + 1) |
| 172 | (S)-CH₃–CH(OH)–CH₂–NH–C(=O)–NH– | 607 (M⁺ + 1) |
| 173 | (R)-CH₃–CH(OH)–CH₂–NH–C(=O)–NH– | 607 (M⁺ + 1) |

TABLE 58
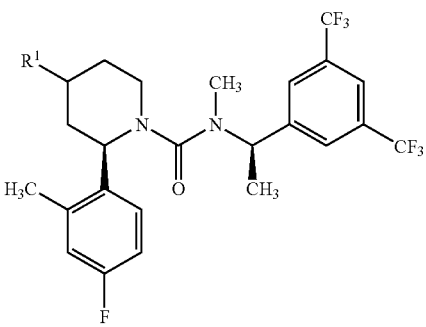
| Example No. | R¹ | MS |
|---|---|---|
| 174 | ClCH₂S(O)₂NH-CH₃ | 618 (M⁺ + 1) |
| 175 | HOCH₂CH₂S(O)₂NH-CH₃ | 614 (M⁺ + 1) |
| 176 | HOCH₂CH₂S(O)₂N(CH₃)-CH₃ | 628 (M⁺ + 1) |
| 177 | (CH₃)₂NS(O)₂NH-CH₃ | 613 (M⁺ + 1) |
| 178 | CH₂=CHS(O)₂NH-CH₃ | 596 (M⁺ + 1) |
| 179 | CH₂=CHS(O)₂N(CH₃)-CH₃ | 610 (M⁺ + 1) |
TABLE 59
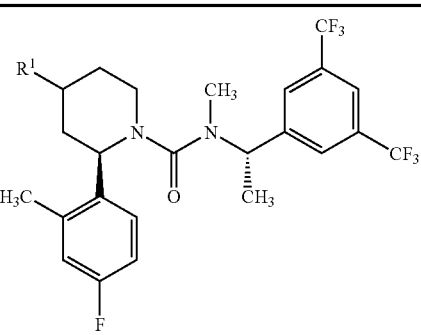
| Example No. | R¹ | MS |
|---|---|---|
| 180 | H₃CS(O)₂NH-CH₃ | 584 (M⁺ + 1) |
| 181 | H₃CCH₂S(O)₂NH-CH₃ | 598 (M⁺ + 1) |
| 183 | H₃CS(O)₂N(CH₃)-CH₃ | 584 (M⁺ + 1) |
| 184 | H₃CCH₂S(O)₂N(CH₃)-CH₃ | 598 (M⁺ + 1) |
| 185 | H₃COCH₂CH₂O- | 565 (M⁺ + 1) |
| 186 | HOCH₂CH₂O- | 551 (M⁺ + 1) |
| 187 | HOCH₂CH₂CH₂O- | 565 (M⁺ + 1) |
TABLE 60
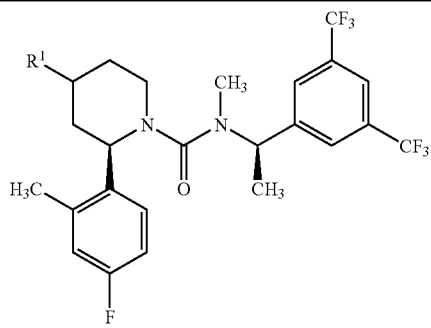
| Example No. | R¹ | MS |
|---|---|---|
| 188 | HOCH₂CH₂O- | 551 (M⁺ + 1) |

TABLE 60-continued
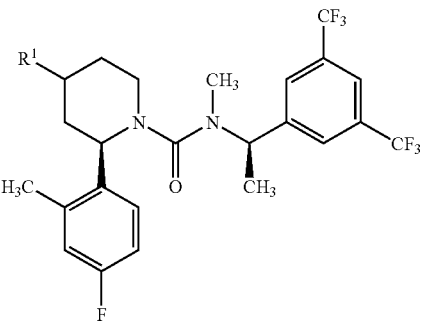
| Example No. | R¹ | MS |
|---|---|---|
| 189 | HO~~~O~ | 565 (M⁺ + 1) |
| 190 | H₃C-S(O)₂-O~~O~ | 629 (M⁺ + 1) |
| 191 | morpholine-N-CH₂CH₂-O~ HCl | 620 (M⁺ + 1) |
| 192 | (H₃C-CH₂)₂N-CH₂CH₂-O~ HCl | 606 (M⁺ + 1) |
TABLE 61
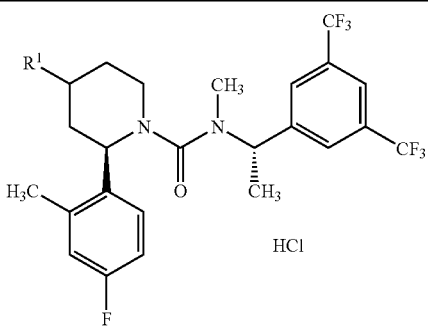
| Example No. | R¹ | MS |
|---|---|---|
| 193 | morpholine-N-CH₂CH₂-O~ | 620 (M⁺ + 1) |
| 194 | (H₃C-CH₂)₂N-CH₂CH₂-O~ | 606 (M⁺ + 1) |
| 195 | (H₃C)₂N-CH₂CH₂-O~ | 578 (M⁺ + 1) |
TABLE 61-continued
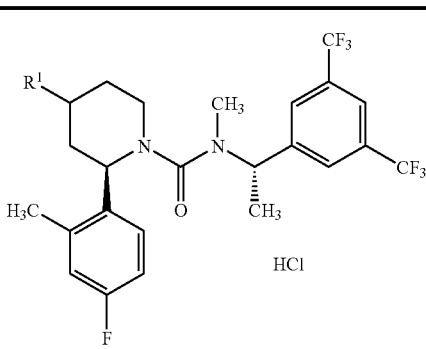
| Example No. | R¹ | MS |
|---|---|---|
| 196 | pyrrolidine-N-CH₂CH₂-O~ | 604 (M⁺ + 1) |
TABLE 62
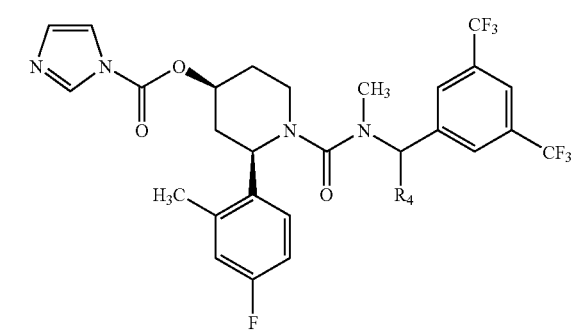
| Example No. | R⁴ | MS |
|---|---|---|
| 197 | CH₃ (wedge) | 601 (M⁺ + 1) |
| 198 | CH₃ (dashed) | 601 (M⁺ + 1) |

TABLE 63

| Example No. | R¹ | MS |
|---|---|---|
| 199 | HO-[4-hydroxypiperidine-1-carboxylate methyl ester] | 634 (M⁺ + 1) |
| 200 | H₃C-[4-methylpiperazine-1-carboxylate methyl ester]·HCl | 633 (M⁺ + 1) |
| 201 | HO-CH₂-CH₂-N(CH₃)-C(O)-O-CH₃ | 608 (M⁺ + 1) |
| 202 | HO-CH₂-CH₂-NH-C(O)-O-CH₃ | 594 (M⁺ + 1) |

TABLE 64

| Example No. | R¹ | MS |
|---|---|---|
| 203 | HO-CH₂-CH₂-NH-C(O)-O-CH₃ | 594 (M⁺ + 1) |

TABLE 64-continued

| Example No. | R¹ | MS |
|---|---|---|
| 204 | HO-CH₂-CH₂-[piperidine-1-carboxylate methyl ester] | 662 (M⁺ + 1) |
| 205 | H₃C-[4-methylpiperazine-1-carboxylate methyl ester]·HCl | 633 (M⁺ + 1) |

TABLE 65

| Example No. | R¹ | MS |
|---|---|---|
| 206 | piperidine N-oxide | 578 (M⁺ + 1) |
| 207 | HO-CH₂-[furan-2-carboxamide N-methyl] | 616 (M⁺ + 1) |
| 208 | morpholine-CH₂-[furan-2-carboxamide N-methyl]·HCl | 685 (M⁺ + 1) |

TABLE 65-continued

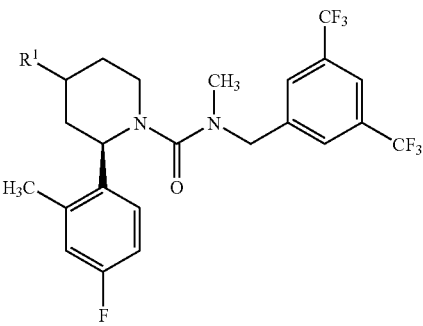

| Example No. | R¹ | MS |
|---|---|---|
| 209 | methyl thiomorpholine-4-carboxylate | 622 (M⁺ + 1) |
| 210 | HOCH₂CH₂NHC(O)OCH₃ | 580 (M⁺ + 1) |
| 211 | (S)-HOCH(CH₃)CH₂NHC(O)OCH₃ | 594 (M⁺ + 1) |
| 212 | (R)-HOCH(CH₃)CH₂NHC(O)OCH₃ | 594 (M⁺ + 1) |
| 213 | methyl 1-oxo-thiomorpholine-4-carboxylate | 638 (M⁺ + 1) |
| 214 | methyl 1,1-dioxo-thiomorpholine-4-carboxylate | 654 (M⁺ + 1) |

TABLE 66

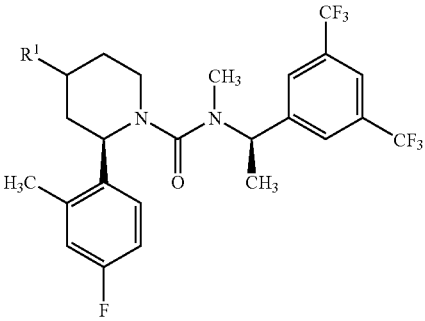

| Example No. | R¹ | MS |
|---|---|---|
| 215 | HOCH₂C(CH₃)(CH₂OH)C(O)NHCH₃ | 622 (M⁺ + 1) |
| 216 | CH₃NHC(O)NHCH₃ | 563 (M⁺ + 1) |
| 217 | (CH₃)₃CNHC(O)NHCH₃ | 605 (M⁺ + 1) |
| 218 | (CH₃)₂NC(O)NHCH₃ | 577 (M⁺ + 1) |

TABLE 67

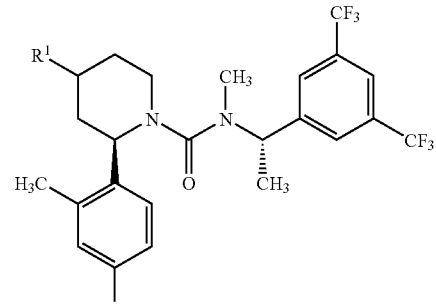

| Example No. | R¹ | MS |
|---|---|---|
| 219 | C₂H₅NHC(O)NHCH₃ | 577 (M⁺ + 1) |
| 220 | (CH₃)₂CHNHC(O)NHCH₃ | 591 (M⁺ + 1) |

TABLE 67-continued
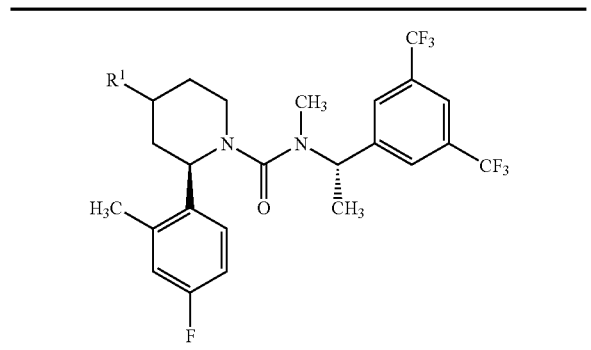
| Example No. | R¹ | MS |
|---|---|---|
| 221 | 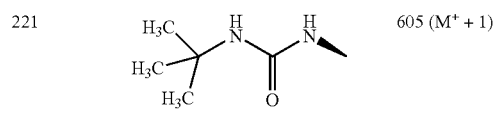 | 605 (M⁺ + 1) |
| 222 | 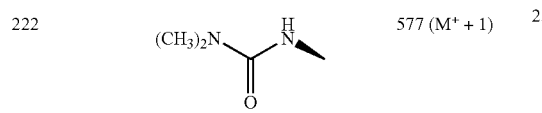 | 577 (M⁺ + 1) |
| 223 | 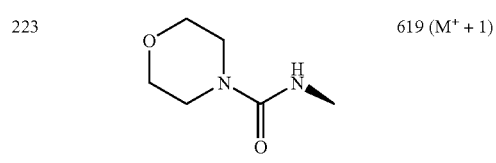 | 619 (M⁺ + 1) |
| 224 | 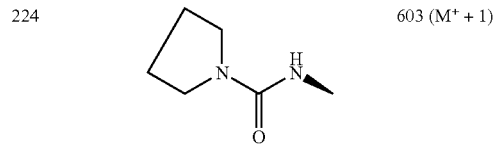 | 603 (M⁺ + 1) |
| 225 | 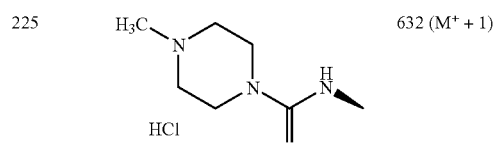 | 632 (M⁺ + 1) |
| 226 | 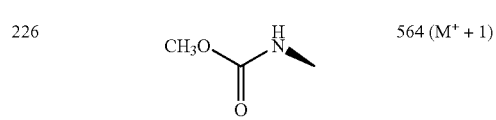 | 564 (M⁺ + 1) |
TABLE 68
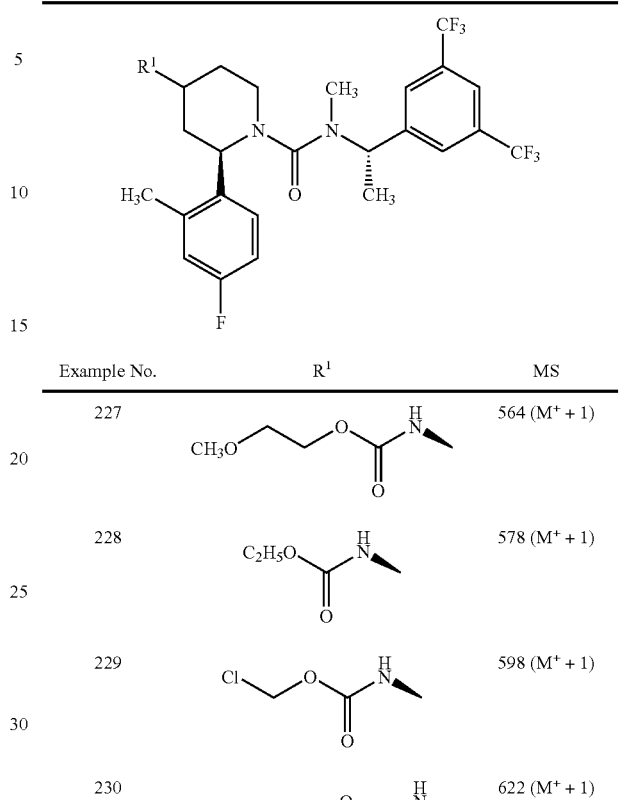
| Example No. | R¹ | MS |
|---|---|---|
| 227 | 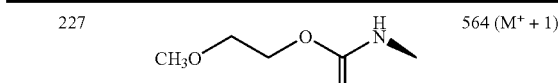 | 564 (M⁺ + 1) |
| 228 | 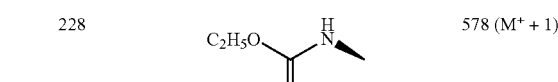 | 578 (M⁺ + 1) |
| 229 | 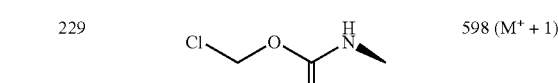 | 598 (M⁺ + 1) |
| 230 | 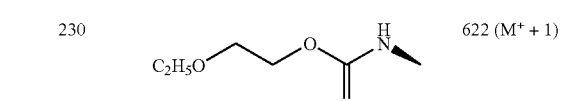 | 622 (M⁺ + 1) |
| 231 | 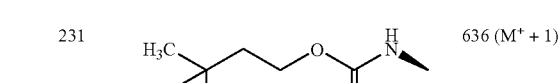 | 636 (M⁺ + 1) |
TABLE 69
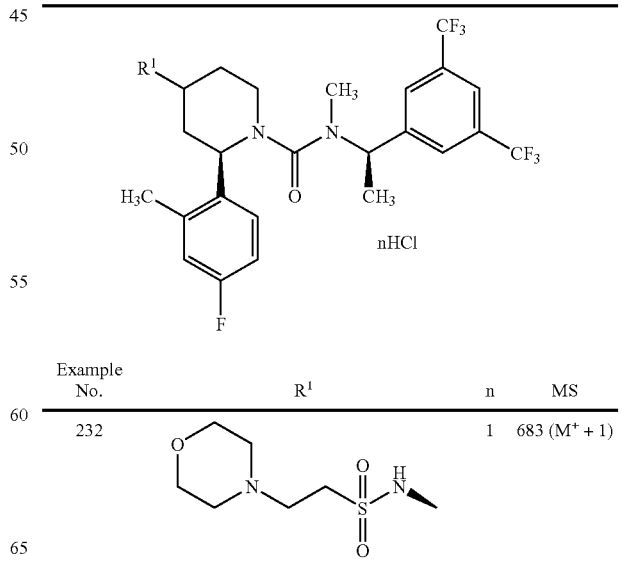
| Example No. | R¹ | n | MS |
|---|---|---|---|
| 232 | 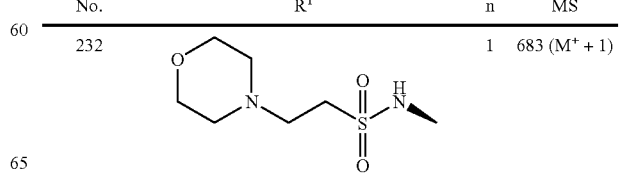 | 1 | 683 (M⁺ + 1) |

TABLE 69-continued
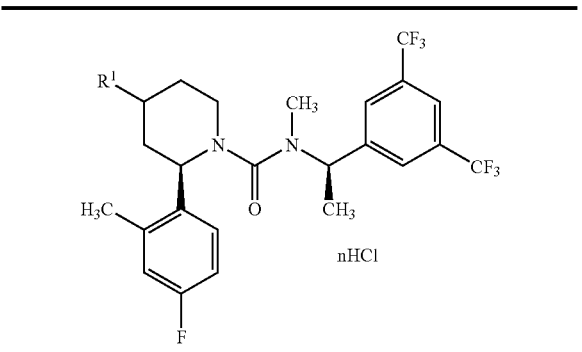
nHCl
| Example No. | R¹ | n | MS |
|---|---|---|---|
| 233 | 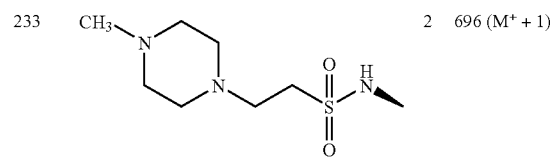 | 2 | 696 (M⁺ + 1) |
| 234 | 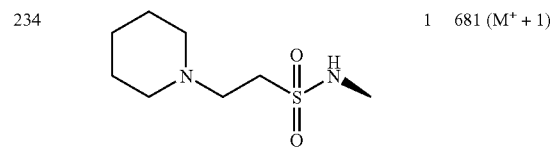 | 1 | 681 (M⁺ + 1) |
| 235 | 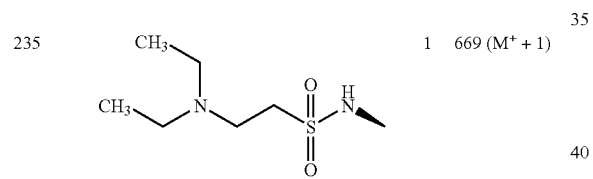 | 1 | 669 (M⁺ + 1) |
| 236 | 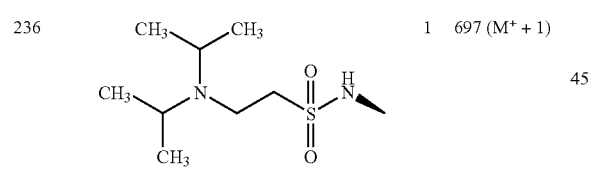 | 1 | 697 (M⁺ + 1) |
| 237 | 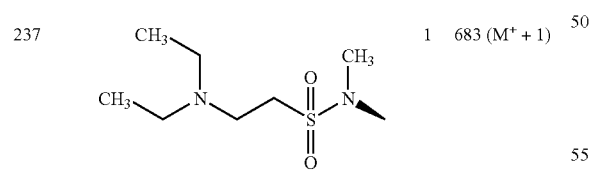 | 1 | 683 (M⁺ + 1) |
| 238 | 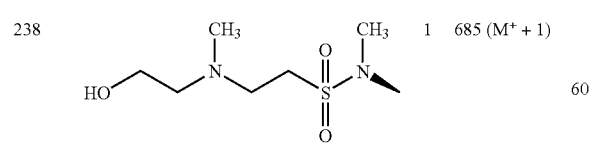 | 1 | 685 (M⁺ + 1) |
TABLE 70
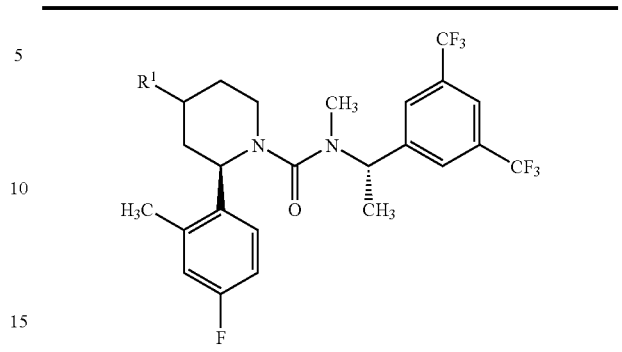
| Example No. | R¹ | MS |
|---|---|---|
| 239 |  | 618 (M⁺ + 1) |
| 240 | 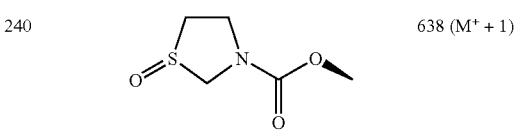 | 638 (M⁺ + 1) |
| 241 | 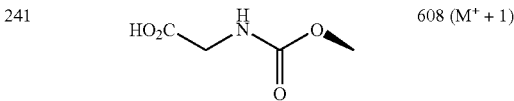 | 608 (M⁺ + 1) |
| 242 | 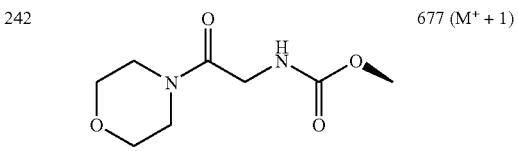 | 677 (M⁺ + 1) |
| 243 | 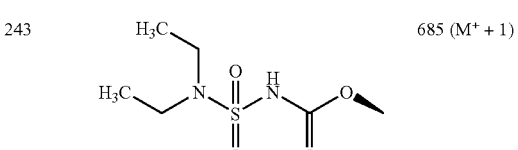 | 685 (M⁺ + 1) |

TABLE 71
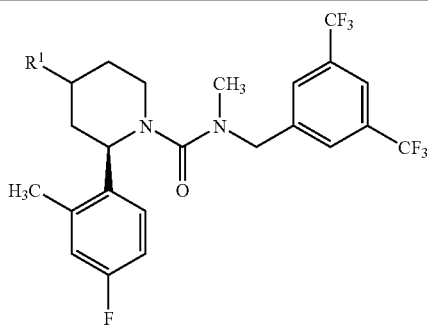
| Example No. | R[1] | MS |
|---|---|---|
| 244 | (5-oxopyrrolidine-2-carboxylic acid methyl ester) | 604 (M⁺ + 1) |
| 245 (a) | (pyridin-2-ylamino-methyl) | 569 (M⁺ + 1) |
TABLE 71-continued
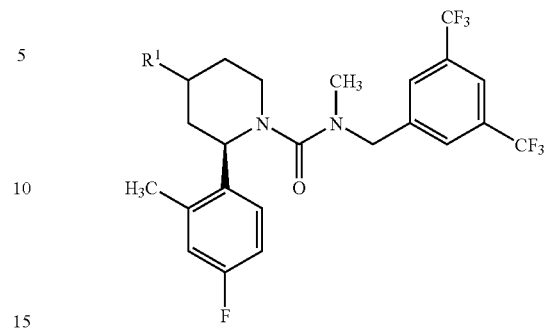
| Example No. | R[1] | MS |
|---|---|---|
| 245 (b) | (pyridin-2-ylamino) | 569 (M⁺ + 1) |
| 246 | (N-methyl-pyridin-2-ylamino) | 583 (M⁺ + 1) |
TABLE 72
| Example No. | Structural Formula | MS |
|---|---|---|
| 247 | | 660 (M⁺ + 1) |

TABLE 72-continued
| Example No. | Structural Formula | MS |
| --- | --- | --- |
| 248 | 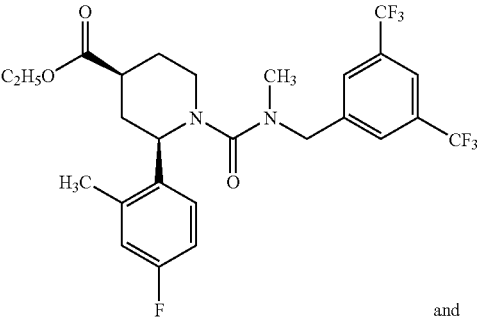 and 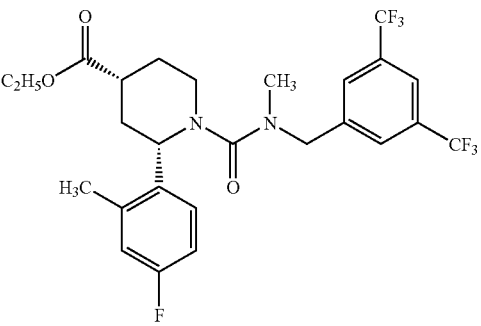 | 549 (M+ + 1) |
| 249 (a) | 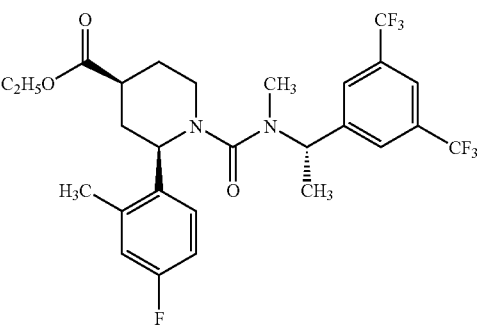 | 563 (M+ + 1) |
| 249 (b) | 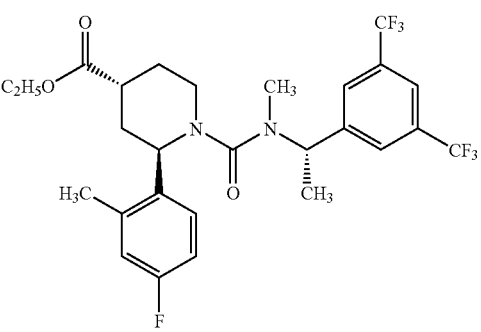 | 563 (M+ + 1) |

TABLE 73

| Example No. | Structural Formula | MS |
|---|---|---|
| 249 (c) | (structure) | 563 (M⁺ + 1) |
| 250 (2) | (structure) | 534 (M⁺ + 1) |
| 251 | (structure) | 578 (M⁺ + 1) |
| 252 | (structure) | 534 (M⁺ + 1) |

TABLE 73-continued
| Example No. | Structural Formula | MS |
|---|---|---|
| 253 | 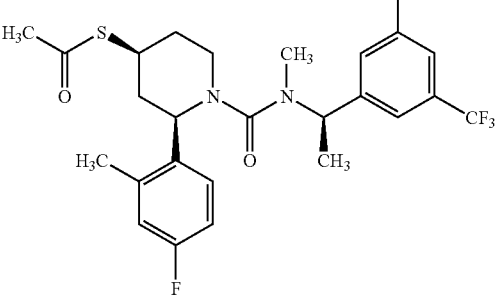 | 578 (M+ + 1) |
TABLE 74
| Example No. | Structural Formula | MS |
|---|---|---|
| 254 (2) | 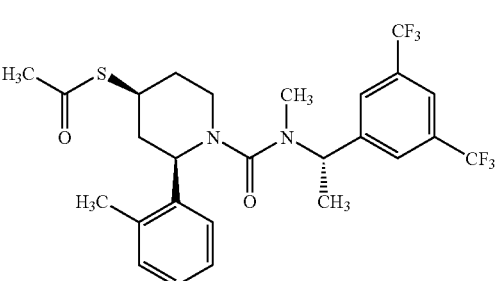 | 565 (M+ + 1) |
| 255 | 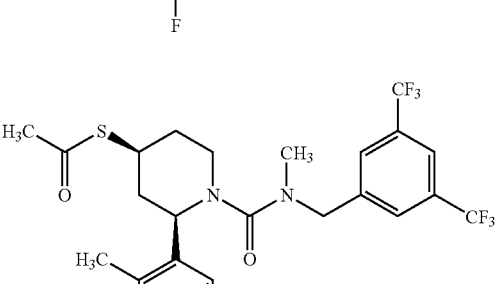 | 565 (M+ + 1) |
| 256 | | 551 (M+ + 1) |

TABLE 74-continued
| Example No. | Structural Formula | MS |
|---|---|---|
| 257 | | 537 (M⁺ + 1) |
| 258 | | 567 (M⁺ + 1) |
| 259 | | 581 (M⁺ + 1) |
TABLE 75
| Example No. | Structural Formula | MS |
|---|---|---|
| 260 | 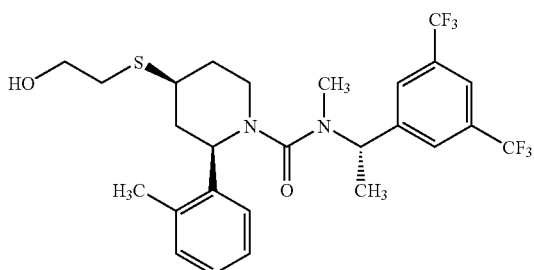 | 567 (M⁺ + 1) |

TABLE 75-continued

| Example No. | Structural Formula | MS |
|---|---|---|
| 261 | | 523 (M+ + 1) |
| 262 | | 553 (M+ + 1) |
| 263 | | 567 (M+ + 1) |

TABLE 76

| Example No. | Structural Formula | MS |
|---|---|---|
| 264 | | 610 (M+ + 1) |

TABLE 76-continued

| Example No. | Structural Formula | MS |
| --- | --- | --- |
| 265 | | 553 (M⁺ + 1) |
| 266 | | 583 (M⁺ + 1) |
| 267 | | 583 (M⁺ + 1) |
| 268 | | 539 (M⁺ + 1) |

TABLE 77

| Example No. | Structural Formula | MS |
|---|---|---|
| 269 | | 569 (M⁺ + 1) |
| 270 | | 597 (M⁺ + 1) |

TABLE 78

| Example No. | Structural Formula | MS |
|---|---|---|
| 271 | | 626 (M⁺ + 1) |
| 272 | | 569 (M⁺ + 1) |

TABLE 78-continued

| Example No. | Structural Formula | MS |
|---|---|---|
| 273 | | 599 (M⁺ + 1) |
| 274 | | 613 (M⁺ + 1) |
| 275 | | 599 (M⁺ + 1) |

TABLE 79

| Example No. | Structural Formula | MS |
|---|---|---|
| 276 | | 555 (M⁺ + 1) |

TABLE 79-continued

| Example No. | Structural Formula | MS |
|---|---|---|
| 277 | (structure) | 585 (M⁺ + 1) |
| 278 | (structure) | 613 (M⁺ + 1) |

TABLE 80

| Example No. | Structural Formula | MS |
|---|---|---|
| 279 | (structure) | 604 (M⁺ + 1) |

TABLE 81
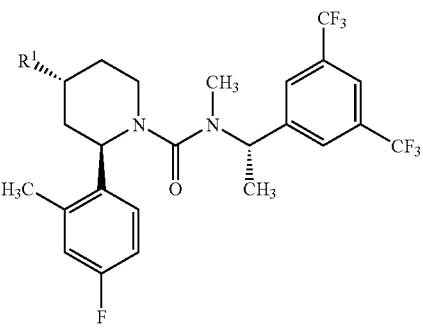
| Example No. | R¹ | MS |
|---|---|---|
| 280 | 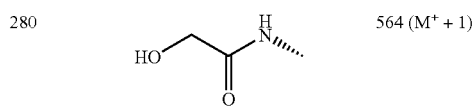 | 564 (M⁺ + 1) |
| 281 | 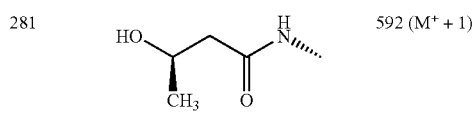 | 592 (M⁺ + 1) |
TABLE 82
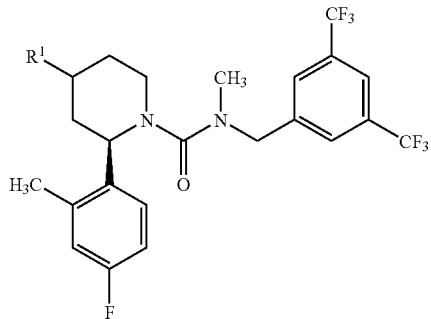
| Example No. | R¹ | MS |
|---|---|---|
| 282 | 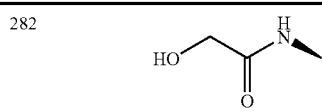 | 550 (M⁺ + 1) |
| 283 | 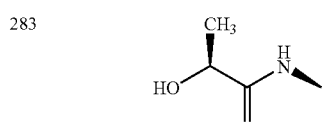 | 564 (M⁺ + 1) |
| 284 |  | 564 (M⁺ + 1) |
| 285 | 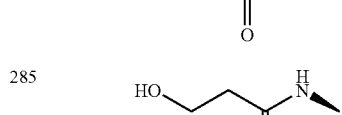 | 578 (M⁺ + 1) |
TABLE 82-continued
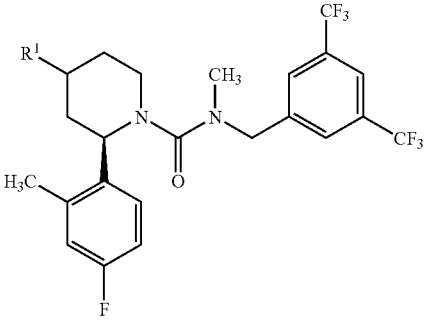
| Example No. | R¹ | MS |
|---|---|---|
| 286 | 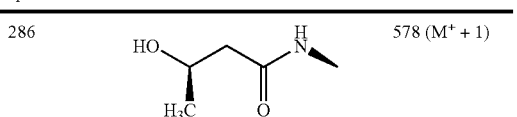 | 578 (M⁺ + 1) |
| 287 | 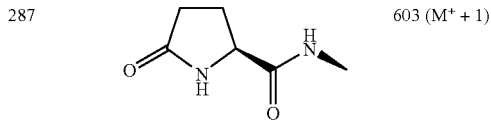 | 603 (M⁺ + 1) |
| 288 | 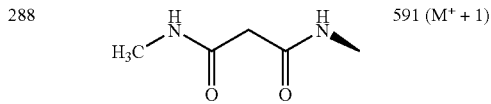 | 591 (M⁺ + 1) |
| 289 | 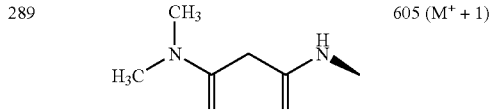 | 605 (M⁺ + 1) |
TABLE 83
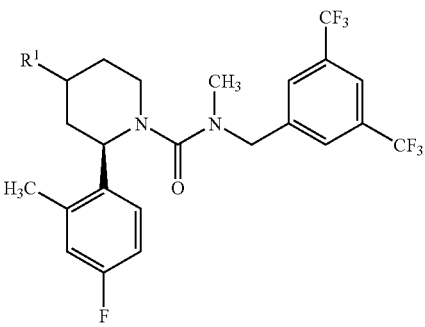
| Example No. | R¹ | MS |
|---|---|---|
| 290 | 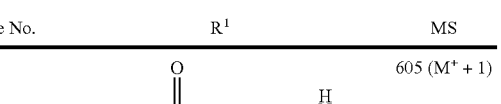 | 605 (M⁺ + 1) |
| 291 | 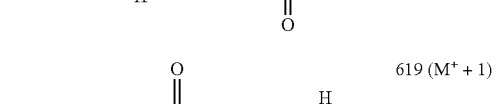 | 619 (M⁺ + 1) |

TABLE 83-continued
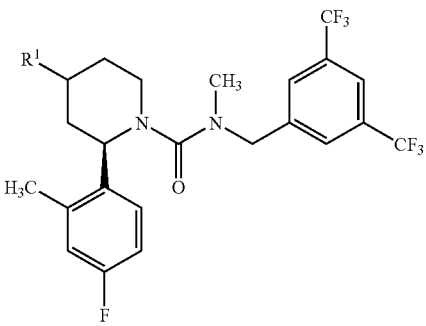
| Example No. | R¹ | MS |
|---|---|---|
| 292 | 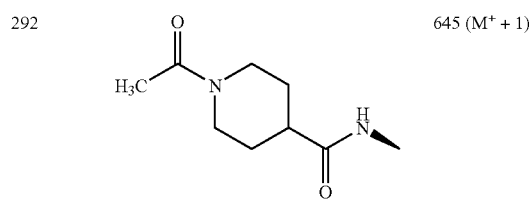 | 645 (M⁺ + 1) |
| 293 | | 552 (M⁺ + 1) |
| 294 | | 617 (M⁺ + 1) |
| 295 | | 646 (M⁺ + 1) |
| 296 | | 663 (M⁺ + 1) |
TABLE 84
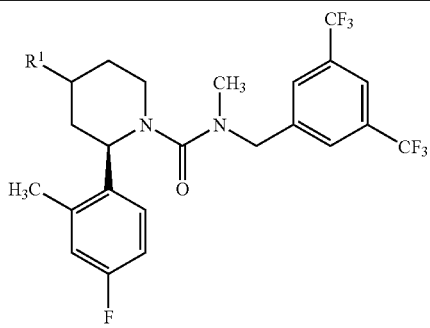
| Example No. | R¹ | MS |
|---|---|---|
| 297 | | 706 (M⁺ + 1) |
| 298 | | 795 (M⁺ + 1) |
| 299 | | 668 (M⁺ + 1) |
| 300 | | 566 (M⁺ + 1) |
| 301 | | 605 (M⁺ + 1) |
| 302 | | 619 (M⁺ + 1) |
TABLE 85
| Example No. | R¹ | MS |
|---|---|---|
| 303 | | 619 (M⁺ + 1) |

TABLE 85-continued
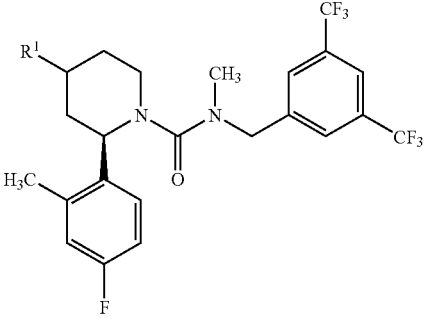
| Example No. | R¹ | MS |
|---|---|---|
| 304 | 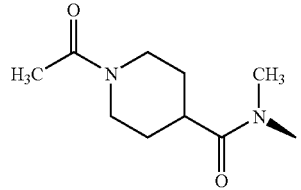 | 633 (M⁺ + 1) |
| 305 | 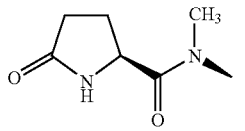 | 659 (M⁺ + 1) |
| 306 | 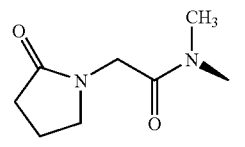 | 617 (M⁺ + 1) |
| 307 | 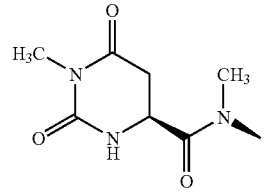 | 631 (M⁺ + 1) |
| 308 | 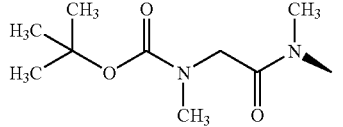 | 660 (M⁺ + 1) |
| 309 | 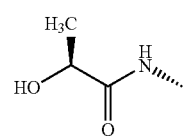 | 677 (M⁺ + 1) |
TABLE 86
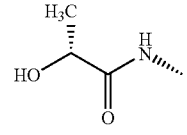
| Example No. | R¹ | MS |
|---|---|---|
| 310 | 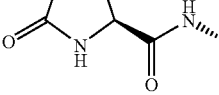 | 564 (M⁺ + 1) |
| 311 | 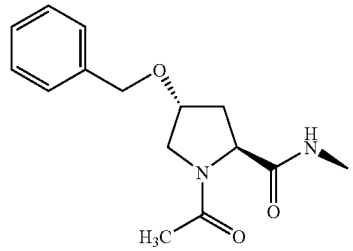 | 564 (M⁺ + 1) |
| 312 | 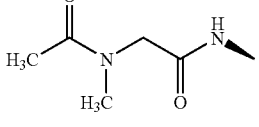 | 603 (M⁺ + 1) |
| 313 | 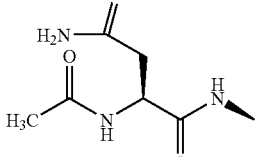 | 737 (M⁺ + 1) |
| 314 | | 605 (M⁺ + 1) |
| 315 | | 648 (M⁺ + 1) |

TABLE 87
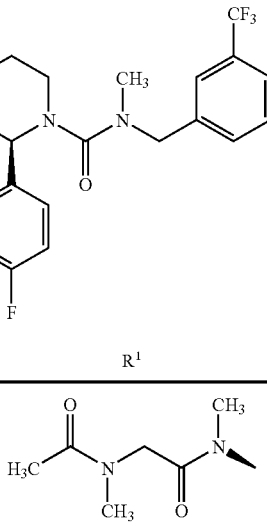
| Example No. | R¹ | MS |
|---|---|---|
| 316 | 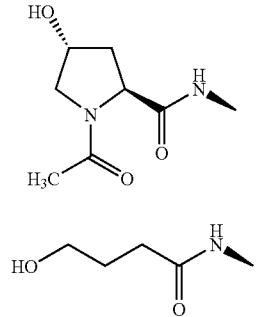 | 619 (M⁺ + 1) |
| 317 | 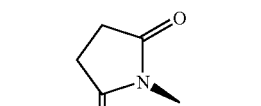 | 647 (M⁺ + 1) |
| 318 | 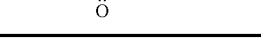 | 578 (M⁺ + 1) |
| 319 | 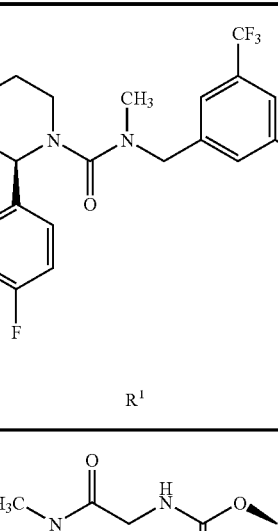 | 574 (M⁺ + 1) |
TABLE 88
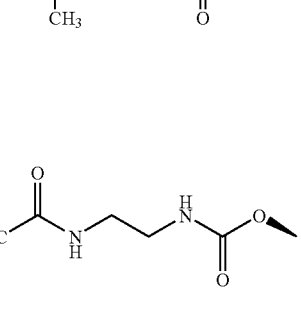
| Example No. | R¹ | MS |
|---|---|---|
| 320 | 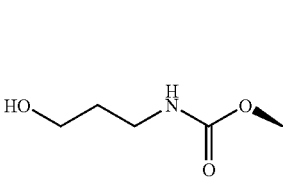 | 607 (M⁺ + 1) |
| 321 | 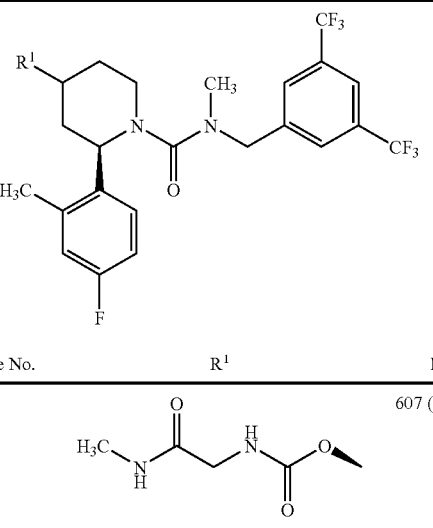 | 621 (M⁺ + 1) |
| 322 | 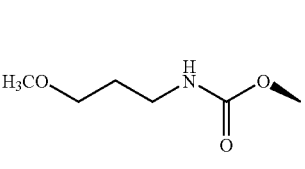 | 621 (M⁺ + 1) |
| 323 | 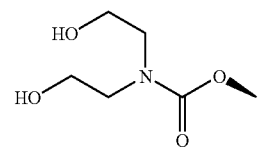 | 594 (M⁺ + 1) |
| 324 | 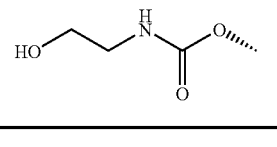 | 608 (M⁺ + 1) |
| 325 | | 624 (M⁺ + 1) |
| 326 | | 580 (M⁺ + 1) |

TABLE 89
| Example No. | Structural Formula | MS |
|---|---|---|
| 327 | | 510 (M⁺ + 1) |
| 328 | | 576 (M⁺ + 1) |
TABLE 90
| Example No. | Structural Formula | MS |
|---|---|---|
| 329 | | 576 (M⁺ + 1) |
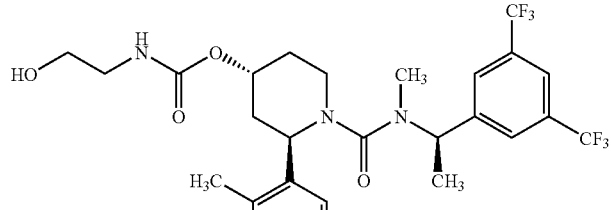

TABLE 90-continued

| Example No. | Structural Formula | MS |
|---|---|---|
| 330 | | 548 (M⁺ + 1) |

TABLE 91

| Example No. | R¹ | MS |
|---|---|---|
| 331 | | 563 (M⁺ + 1) |
| 332 | | 521 (M⁺ + 1) |
| 333 | | 570 (M⁺ + 1) |
| 334 | | 584 (M⁺ + 1) |
| 335 (3) | | 506 (M⁺ + 1) |
| 336 (2) | | 521 (M⁺ + 1) |
| 337 | | 578 (M⁺ + 1) |
| 338 | | 604 (M⁺ + 1) |

TABLE 91-continued
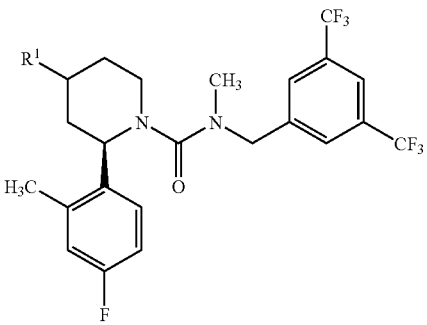
| Example No. | R[1] | MS |
|---|---|---|
| 339 | 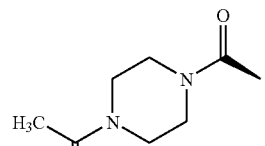 | 631 (M+ + 1) |
| 340 | 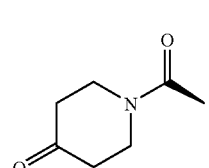 | 602 (M+ + 1) |
TABLE 92
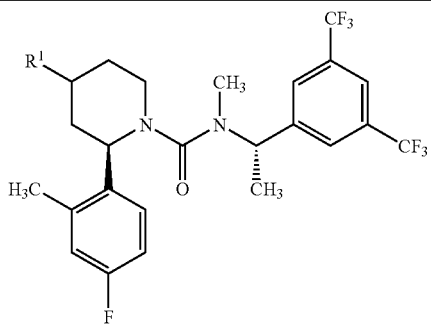
| Example No. | R[1] | MS |
|---|---|---|
| 341 (2) | 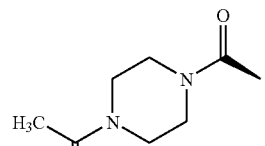 | 535 (M+ + 1) |
| 342 | 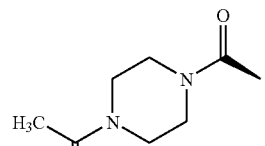 | 548 (M+ + 1) |
| 343 | 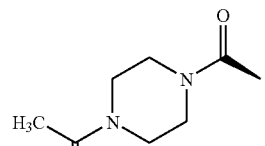 | 592 (M+ + 1) |
TABLE 92-continued
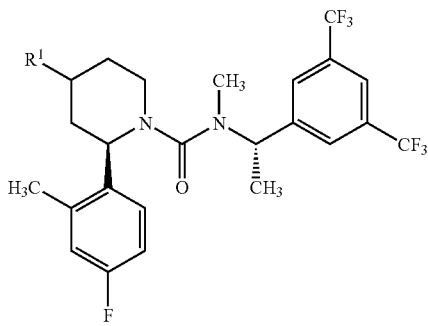
| Example No. | R[1] | MS |
|---|---|---|
| 344 | 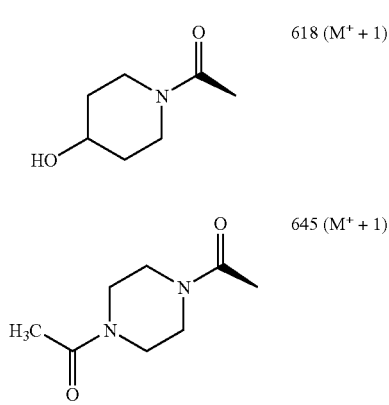 | 592 (M+ + 1) |
| 345 | 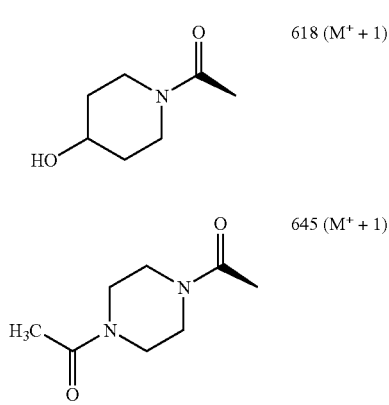 | 604 (M+ + 1) |
| 346 | 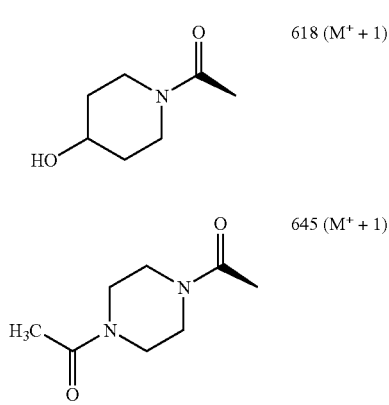 | 620 (M+ + 1) |
| 347 | 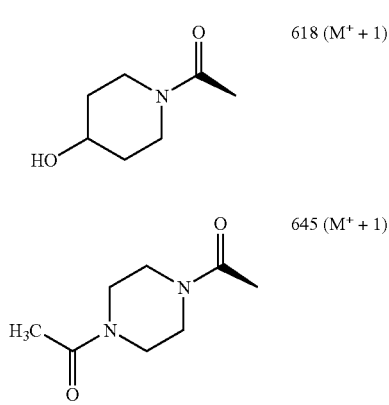 | 618 (M+ + 1) |
| 348 | 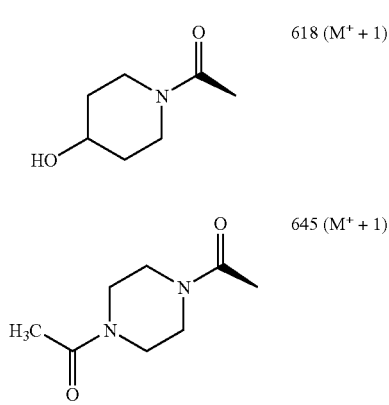 | 645 (M+ + 1) |
| 349 | 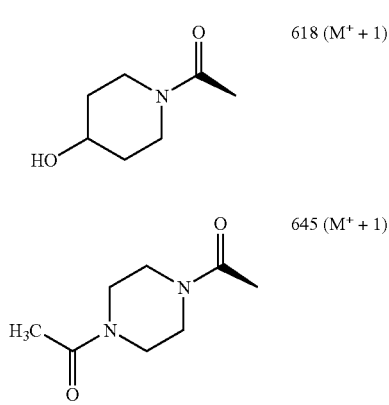 | 622 (M+ + 1) |

TABLE 93

[Structure: R¹-substituted piperidine with 2-(2-methyl-4-fluorophenyl) group, N-carboxamide with N-methyl-N-[(1S)-1-(3,5-bis(trifluoromethyl)phenyl)ethyl] group]

| Example No. | R¹ | MS |
|---|---|---|
| 350 | HO–CH₂–CH(CH₃)– | 521 (M⁺ + 1) |
| 351 | HO–CH₂CH₂–NH–C(O)–O–Et | 608 (M⁺ + 1) |
| 352 | HO–CH₂CH₂CH₂–NH–C(O)–O–Et | 622 (M⁺ + 1) |

TABLE 94

[Same core structure]

| Example No. | R¹ | MS |
|---|---|---|
| 353 | HO–C(O)–CH₂– | 535 (M⁺ + 1) |
| 354 | (R)-HO–CH₂–CH(CH₃)–NH–C(O)–CH₃ | 592 (M⁺ + 1) |
| 355 | (S)-HO–CH₂–CH(CH₃)–NH–C(O)–CH₃ | 592 (M⁺ + 1) |
| 356 | HO–CH₂CH₂–N(Et)–C(O)–CH₃ | 606 (M⁺ + 1) |

TABLE 94-continued

| Example No. | R¹ | MS |
|---|---|---|
| 357 | HO–CH₂CH₂–N(CH₃)–C(O)–CH₃ | 592 (M⁺ + 1) |
| 358 | 4-hydroxy-1-acetylpiperidin-yl | 618 (M⁺ + 1) |
| 359 | 1,4-diacetylpiperazin-yl | 645 (M⁺ + 1) |

TABLE 95

[Same core structure]

| Example No. | R¹ | MS |
|---|---|---|
| 360 | 4-acetyl-1-(ethylsulfonyl)piperazin-yl | 695 (M⁺ + 1) |

TABLE 95-continued
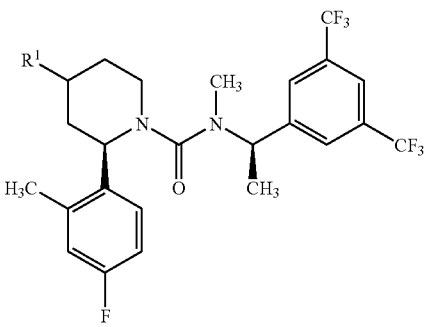
| Example No. | R¹ | MS |
|---|---|---|
| 361 | (1-acetyl-4-oxopiperidinyl) | 616 (M⁺ + 1) |
| 362 | (4-acetyl-1-(pyrimidin-2-yl)piperazinyl) | 681 (M⁺ + 1) |
| 363 | (4-acetyl-1-(pyrazin-2-yl)piperazinyl) | 681 (M⁺ + 1) |
| 364 | N,N-bis(2-hydroxyethyl)acetamido | 622 (M⁺ + 1) |
| 365 | (S)-1-acetyl-2-(hydroxymethyl)pyrrolidinyl | 618 (M⁺ + 1) |
TABLE 96
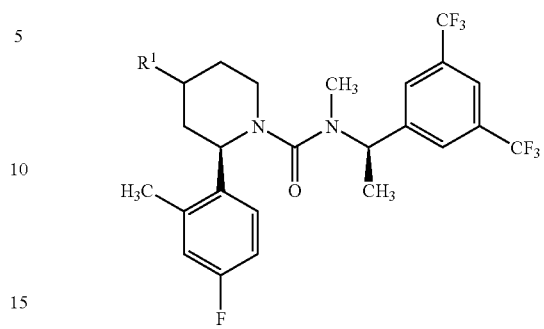
| Example No. | R¹ | MS |
|---|---|---|
| 366 | N-(pyrazin-2-yl)acetamido | 612 (M⁺ + 1) |
| 367 | HO–CH₂– | 521 (M⁺ + 1) |
TABLE 97
| Example No. | R¹ | MS |
|---|---|---|
| 368 | H₃C-C(=O)-O-CH₂-S-CH₃ | 581 (M⁺ + 1) |
| 369 | H₃C-C(=O)-O-CH₂-S(=O)₂-CH₃ | 613 (M⁺ + 1) |
| 370 | HO-S(=O)-CH₃ | 553 (M⁺ − 1) |
| 371 | (CH₃)₃S⁺ I⁻ | 537 (M−I) |

TABLE 98

Structure with R¹ substituent on piperidine, 2-(4-fluoro-2-methylphenyl), N-(3,5-bis(trifluoromethyl)benzyl), N-(3-acetoxypropyl) urea

| Example No. | R¹ | MS |
|---|---|---|
| 372 | HO− | 579 (M⁺ + 1) |
| 373 | H₃C−NH−C(O)−O− | 636 (M⁺ + 1) |
| 374 | morpholine-N−C(O)−O− | 692 (M⁺ + 1) |
| 375 | thiomorpholine-N−C(O)−O− | 708 (M⁺ + 1) |
| 376 | H₃C−CH₂−NH−C(O)−O− | 650 (M⁺ + 1) |

TABLE 99

Structure with R¹ substituent on piperidine, 2-(4-fluoro-2-methylphenyl), N-(3,5-bis(trifluoromethyl)benzyl), N-(3-hydroxypropyl) urea

| Example No. | R¹ | MS |
|---|---|---|
| 377 | H₃C−CH₂−NH−C(O)−O− | 608 (M⁺ + 1) |
| 378 | HO− | 537 (M⁺ + 1) |
| 379 | H₃C−NH−C(O)−O− | 594 (M⁺ + 1) |
| 380 | morpholine-N−C(O)−O− | 650 (M⁺ + 1) |
| 381 | thiomorpholine-N−C(O)−O− | 666 (M⁺ + 1) |
| 382 | S-oxide thiomorpholine-N−C(O)−O− | 682 (M⁺ + 1) |
| 383 (3) | (H₃C)₂CH−S(O)− | 611 (M⁺ + 1) |
| 384 | (H₃C)₂CH−S(O)₂− | 627 (M⁺ + 1) |

TABLE 100
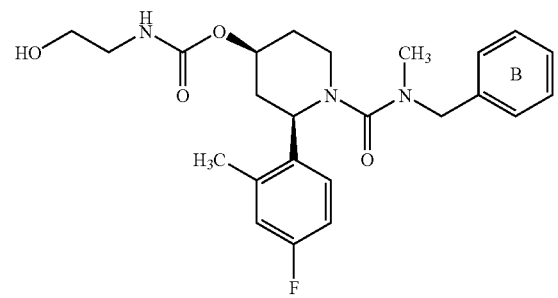
| Example No. | Ring B | MS |
| --- | --- | --- |
| 385 | 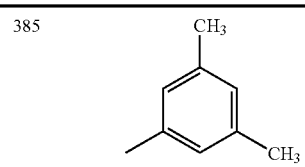 | 472 (M+ + 1) |
TABLE 100-continued
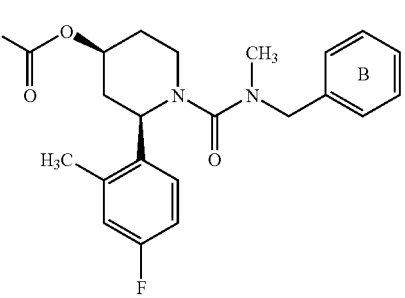
| Example No. | Ring B | MS |
| --- | --- | --- |
| 386 | 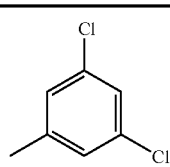 | 512 (M+ + 1) |
TABLE 101
| Example No. | Structural Formula | MS |
| --- | --- | --- |
| 387 | | 652 (M+ + 1) |

TABLE 101-continued

| Example No. | Structural Formula | MS |
|---|---|---|
| 388 | | 610 (M⁺ + 1) |

TABLE 102

| Example No. | R¹ | MS |
|---|---|---|
| 389 (2) | ethyl piperidine-1,4-dicarboxylate (methyl ester on N) | 676 (M⁺ + 1) |
| 390 | 1-(methoxycarbonyl)piperidine-4-carboxylic acid | 648 (M⁺ + 1) |
| 391 | methyl 4-[(2-hydroxyethyl)carbamoyl]piperidine-1-carboxylate | 691 (M⁺ + 1) |
| 392 | methyl 4-{[(2S)-2-hydroxypropyl]carbamoyl}piperidine-1-carboxylate | 705 (M⁺ + 1) |

TABLE 102-continued

[Structure: piperidine with R¹ at 4-position, 2-(4-fluoro-2-methylphenyl), N-methyl-N-(3,5-bis(trifluoromethyl)benzyl)carboxamide]

| Example No. | R¹ | MS |
|---|---|---|
| 393 | (S)-HOCH(CH₃)CH₂NH-C(O)-[4-piperidinyl]-N-C(O)OCH₃ | 705 (M⁺ + 1) |
| 394 | HO(CH₂)₃NH-C(O)-[4-piperidinyl]-N-C(O)OCH₃ | 705 (M⁺ + 1) |

TABLE 103

[Structure: piperidine with R¹ at 4-position, 2-(4-fluoro-2-methylphenyl), N-methyl-N-(3,5-bis(trifluoromethyl)benzyl)carboxamide]

| Example No. | R¹ | MS |
|---|---|---|
| 395 | H₃CO(CH₂)₃NH-C(O)-[4-piperidinyl]-N-C(O)OCH₃ | 719 (M⁺ + 1) |
| 396 | HOCH₂C(CH₃)₂CH₂NH-C(O)-[4-piperidinyl]-N-C(O)OCH₃ | 733 (M⁺ + 1) |
| 397 | H₃CS(CH₂)₃NH-C(O)-[4-piperidinyl]-N-C(O)OCH₃ | 735 (M⁺ + 1) |
| 398 | H₃CS(CH₂)₂NH-C(O)-[4-piperidinyl]-N-C(O)OCH₃ | 721 (M⁺ + 1) |

TABLE 104
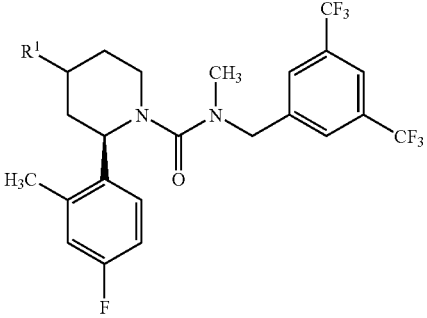
| Example No. | R¹ | MS |
|---|---|---|
| 399 | 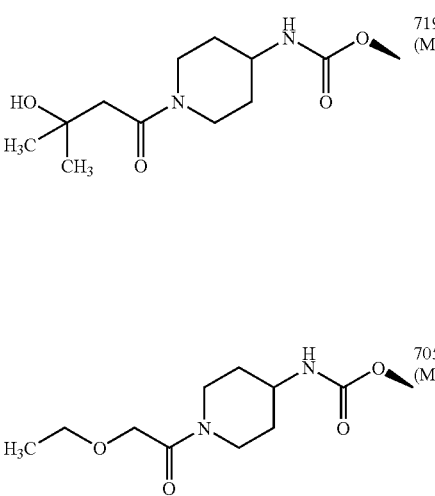 | 719 (M⁺ + 1) |
| 400 | 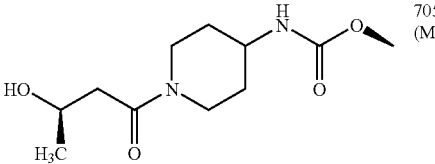 | 705 (M⁺ + 1) |
| 401 | 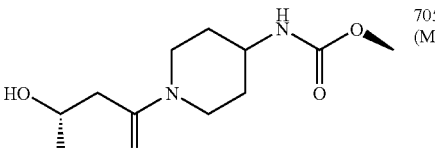 | 705 (M⁺ + 1) |
| 402 | 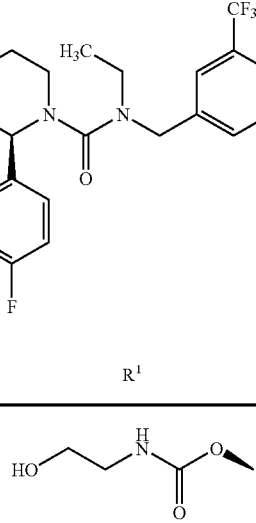 | 705 (M⁺ + 1) |
TABLE 105
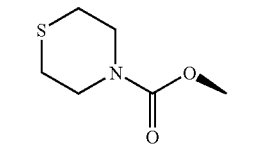
| Example No. | R¹ | MS |
|---|---|---|
| 403 | 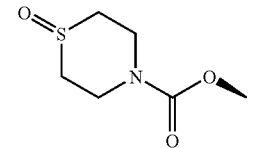 | 594 (M⁺ + 1) |
| 404 | 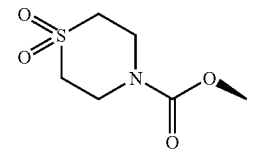 | 636 (M⁺ + 1) |
| 405 | 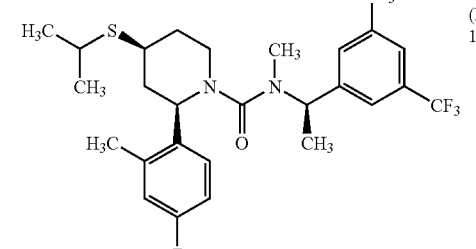 | 652 (M⁺ + 1) |
| 406 | 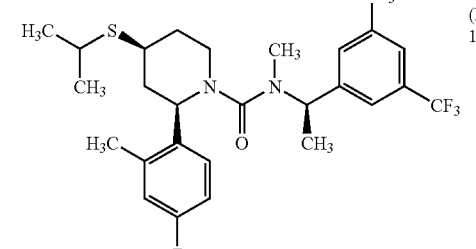 | 668 (M⁺ + 1) |
TABLE 106
| Example No. | Structural Formula | MS |
|---|---|---|
| 407 | 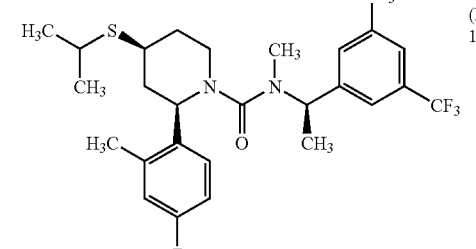 | 565 (M⁺ + 1) |

TABLE 107

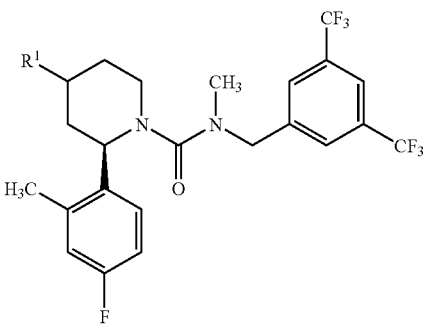

| Example No. | R¹ | MS |
|---|---|---|
| 408 | HO~~~S— (3-hydroxypropylthiomethyl) | 567 (M⁺ + 1) |
| 409 | (S)-HO-CH(CH₃)-CH₂-S— | 567 (M⁺ + 1) |
| 410 | (R)-HO-CH(CH₃)-CH₂-S— | 567 (M⁺ + 1) |
| 411 | H₃C-NH-C(O)-CH₂-S— | 580 (M⁺ + 1) |
| 412 | (CH₃)₂N-C(O)-CH₂-S— | 594 (M⁺ + 1) |
| 413 | H₃C-NH-C(O)-CH₂CH₂-S— | 594 (M⁺ + 1) |
| 414 | (CH₃)₃C-O-C(O)-NH-CH₂CH₂-S— | 652 (M⁺ + 1) |
| 415 (2) | HO-CH₂-C(O)-NH-CH₂CH₂-S— | 610 (M⁺ + 1) |

TABLE 108

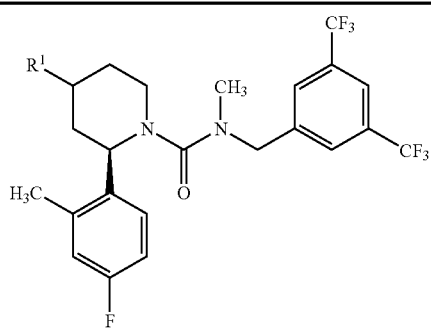

| Example No. | R¹ | MS |
|---|---|---|
| 416 | (S)-HO-CH(CH₃)-C(O)-NH-CH₂CH₂-S— | 624 (M⁺ + 1) |
| 417 | HO-C(CH₃)₂-C(O)-NH-CH₂CH₂-S— | 638 (M⁺ + 1) |
| 418 | HO-CH₂-C(CH₃)₂-C(O)-NH-CH₂CH₂-S— | 652 (M⁺ + 1) |
| 419 | (CH₃)₂C(OH)-CH₂-C(O)-NH-CH₂CH₂-S— | 652 (M⁺ + 1) |
| 420 | morpholine-4-C(O)-NH-CH₂CH₂-S— | 665 (M⁺ + 1) |
| 421 | HO-CH₂CH₂-NH-C(O)-NH-CH₂CH₂-S— | 639 (M⁺ + 1) |
| 422 | CH₃-S(O)-CH₂CH₂-NH-C(O)-[piperidine-4-yl]-N-C(O)-OCH₃ | 737 (M⁺ + 1) |
| 423 | CH₃-S(O)₂-CH₂CH₂CH₂-NH-C(O)-[piperidine-4-yl]-N-C(O)-OCH₃ | 767 (M⁺ + 1) |

TABLE 109

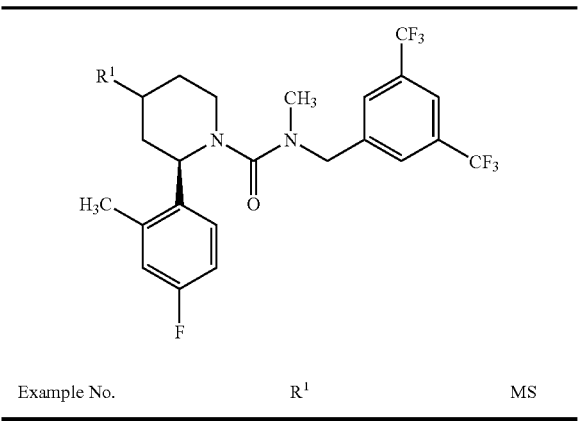

| Example No. | R¹ | MS |
|---|---|---|
| 424 | H₃CS–CH₂CH₂–NH–C(=O)–O–CH₃ | 610 (M⁺ + 1) |
| 425 | H₃CS–(CH₂)₃–NH–C(=O)–O–CH₃ | 624 (M⁺ + 1) |
| 426 | H₃C–S(=O)₂–CH₂CH₂–NH–C(=O)–O–CH₃ | 642 (M⁺ + 1) |
| 427 | H₃C–S(=O)₂–(CH₂)₃–NH–C(=O)–O–CH₃ | 656 (M⁺ + 1) |

TABLE 110

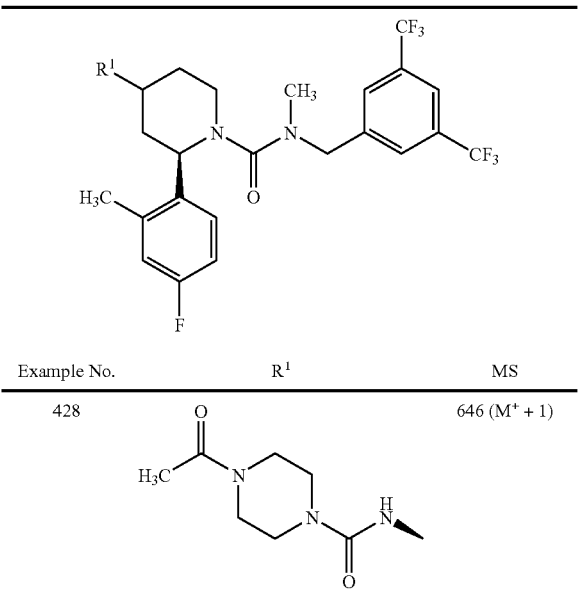

| Example No. | R¹ | MS |
|---|---|---|
| 428 | H₃C–C(=O)–piperazine–C(=O)–NH–CH₃ | 646 (M⁺ + 1) |

TABLE 110-continued

| Example No. | R¹ | MS |
|---|---|---|
| 429 | thiomorpholine–C(=O)–NH–CH₃ | 621 (M⁺ + 1) |
| 430 | H₃C–C(=O)–piperazine–C(=O)–N(CH₃)₂ | 660 (M⁺ + 1) |
| 431 | thiomorpholine–C(=O)–N(CH₃)H | 635 (M⁺ + 1) |

TABLE 111

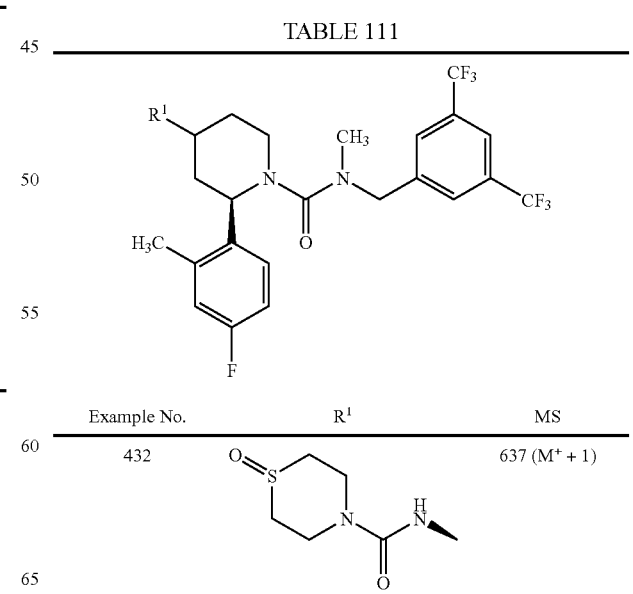

| Example No. | R¹ | MS |
|---|---|---|
| 432 | S-oxide thiomorpholine–C(=O)–NH–CH₃ | 637 (M⁺ + 1) |

TABLE 111-continued

| Example No. | R¹ | MS |
|---|---|---|
| 433 | (1-oxo-thiomorpholine-4-carboxylic acid methylamide) | 651 (M⁺ + 1) |
| 434 | (1,1-dioxo-thiomorpholine-4-carboxylic acid amide) | 653 (M⁺ + 1) |
| 435 | (1,1-dioxo-thiomorpholine-4-carboxylic acid methylamide) | 667 (M⁺ + 1) |

TABLE 112

| Example No. | Structural Formula | MS |
|---|---|---|
| 436 | (structure shown) | 624 (M⁺ + 1) |
| 437 | (structure shown) | 596 (M⁺ + 1) |

TABLE 112-continued

| Example No. | Structural Formula | MS |
|---|---|---|
| 438 | | 562 (M⁺ + 1) |
| 439 | | 548 (M⁺ + 1) |

TABLE 113

| Example No. | R¹ | MS |
|---|---|---|
| 440 | HO— | 493 (M⁺ + 1) |
| 441 | HO-CH₂CH₂-NH-C(O)-O— | 580 (M⁺ + 1) |
| 442 (a) | (CH₃)₃C-O-C(O)-NH— | 592 (M⁺ + 1) |
| 442 (b) | (CH₃)₃C-O-C(O)-NH— | 592 (M⁺ + 1) |
| 443 | H₂N— | 492 (M⁺ + 1) |

TABLE 114

| Example No. | R¹ | MS |
|---|---|---|
| 444 | 3-pyridyl-C(O)-NH— | 597 (M⁺ + 1) |
| 445 | 6-hydroxy-3-pyridyl-C(O)-NH— | 613 (M⁺ + 1) |
| 446 | 6-methyl-3-pyridyl-C(O)-NH— | 611 (M⁺ + 1) |

TABLE 114-continued

[Structure: piperidine with R¹ at 4-position, 2-(2-methyl-4-fluorophenyl), N-methyl-N-(3,5-bis(trifluoromethyl)benzyl)carboxamide]

| Example No. | R¹ | MS |
|---|---|---|
| 447 | 3-pyridyl-C(O)N(CH₃)₂ | 611 (M⁺ + 1) |
| 448 | 6-hydroxy-3-pyridyl-C(O)N(CH₃)₂ | 627 (M⁺ + 1) |
| 449 | 6-methyl-3-pyridyl-C(O)N(CH₃)₂ | 625 (M⁺ + 1) |
| 450 | HOCH₂-CH(CH₃)-NH-C(O)-OCH₃ (S) | 594 (M⁺ + 1) |
| 451 | HOCH₂-CH(CH₃)-NH-C(O)-OCH₃ (R) | 594 (M⁺ + 1) |

TABLE 115

[Structure: piperidine with R¹ at 4-position, 2-(2-methyl-4-fluorophenyl), N-methyl-N-(1-(3,5-bis(trifluoromethyl)phenyl)ethyl)carboxamide]

| Example No. | R¹ | MS |
|---|---|---|
| 452 | HO-(CH₂)₃-NH-C(O)CH₃ | 592 (M⁺ + 1) |
| 453 | HO-CH(CH₃)-CH₂-NH-C(O)CH₃ | 592 (M⁺ + 1) |
| 454 | 4-pyrimidinyl-NH-C(O)CH₃ | 612 (M⁺ + 1) |
| 455 | 4-pyrimidinyl-N(CH₃)-C(O)CH₃ | 626 (M⁺ + 1) |
| 456 | HOCH₂-C(CH₃)₂-NH-C(O)CH₃ | 606 (M⁺ + 1) |
| 457 | 1-methyl-2-oxo-4-acetylpiperazine | 631 (M⁺ + 1) |
| 458 | 3-pyridyl-NH-C(O)CH₃ | 611 (M⁺ + 1) |
| 459 | 2-pyrazinyl-N(CH₃)-C(O)CH₃ | 626 (M⁺ + 1) |

TABLE 116
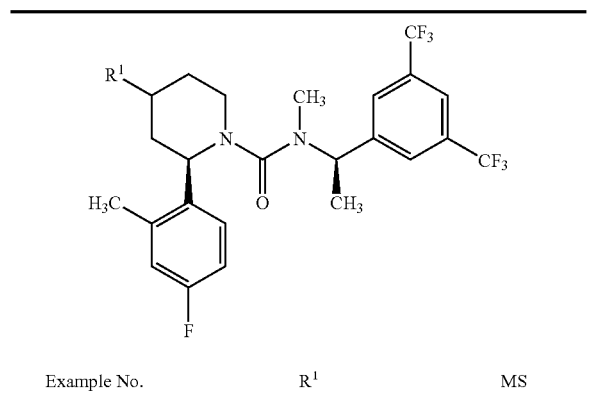
| Example No. | R¹ | MS |
|---|---|---|
| 460 | HO-pyridine-NHC(O)- | 627 (M⁺ + 1) |
| 461 | 1-methyl-2-oxo-pyridinyl-N(CH₃)C(O)- | 655 (M⁺ + 1) |
| 462 | 3-oxopiperazinyl-C(O)- | 617 (M⁺ + 1) |
TABLE 116-continued
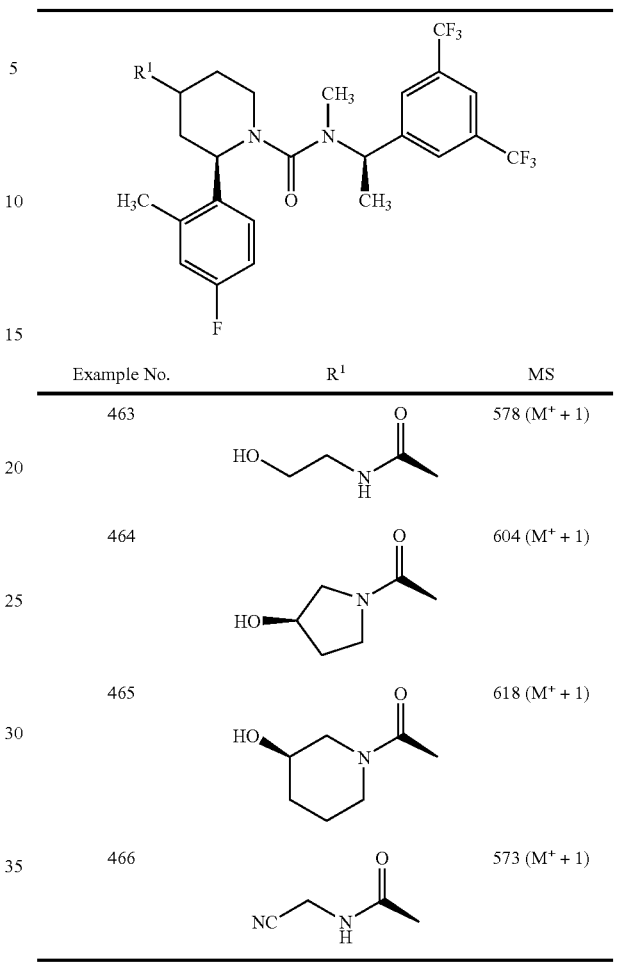
| Example No. | R¹ | MS |
|---|---|---|
| 463 | HOCH₂CH₂NHC(O)- | 578 (M⁺ + 1) |
| 464 | (3-hydroxy)pyrrolidinyl-C(O)- | 604 (M⁺ + 1) |
| 465 | (3-hydroxy)piperidinyl-C(O)- | 618 (M⁺ + 1) |
| 466 | NCCH₂NHC(O)- | 573 (M⁺ + 1) |
TABLE 117
| Example No. | Structural Formula | MS |
|---|---|---|
| 467 | 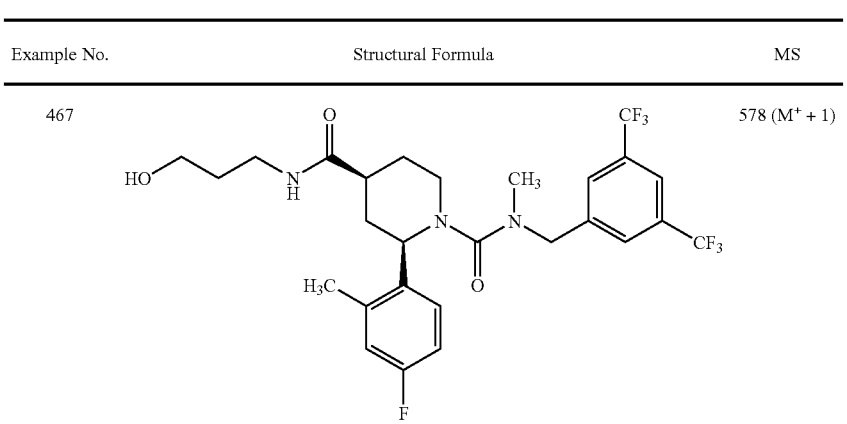 | 578 (M⁺ + 1) |

TABLE 117-continued
| Example No. | Structural Formula | MS |
|---|---|---|
| 468 | | 620 (M⁺ + 1) |
| 469 | | 592 (M⁺ + 1) |
TABLE 118
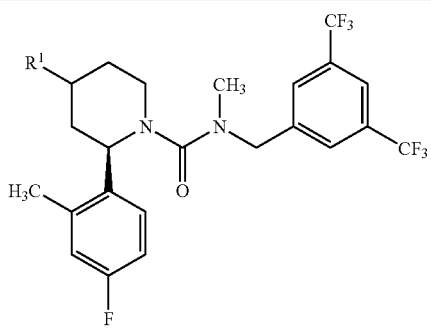
| Example No. | R¹ | MS |
|---|---|---|
| 470 | | 579 (M⁺ + 1) |
| 471 | | 593 (M⁺ + 1) |
| 472 | | 593 (M⁺ + 1) |
TABLE 118-continued
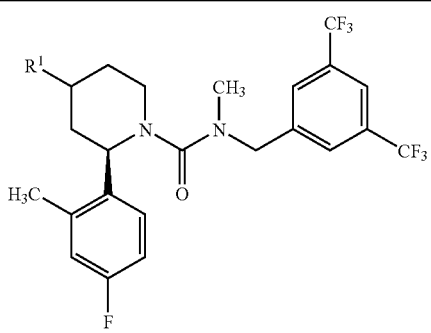
| Example No. | R¹ | MS |
|---|---|---|
| 473 | | 593 (M⁺ + 1) |
| 474 | | 593 (M⁺ + 1) |
| 475 | | 593 (M⁺ + 1) |

TABLE 118-continued

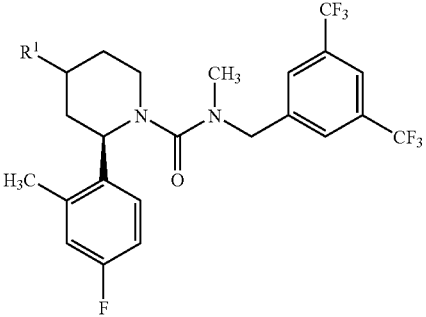

| Example No. | R¹ | MS |
|---|---|---|
| 476 | HO—(CH₂)₃—NH—C(=O)—NH—CH₃ | 593 (M⁺ + 1) |

TABLE 119

| Example No. | R¹ | MS |
|---|---|---|
| 477 | HO—CH₂CH₂—N(CH₃)—C(=O)—NH—CH₃ | 607 (M⁺ + 1) |
| 478 | HO—CH₂—CH(CH₃)—NH—C(=O)—NH—CH₃ (S) | 607 (M⁺ + 1) |
| 479 | HO—CH₂—CH(CH₃)—NH—C(=O)—NH—CH₃ (R) | 607 (M⁺ + 1) |
| 480 | HO—(CH₂)₃—NH—C(=O)—NH—CH₃ | 607 (M⁺ + 1) |

TABLE 120

| Example No. | R¹ | MS |
|---|---|---|
| 481 (a) | HO-CH₂CH₂-imidazolidinone-N-CH₃ | 605 (M⁺ + 1) |
| 481 (b) | HO-CH₂CH₂-imidazolidinone-N-CH₃ (stereo) | 605 (M⁺ + 1) |
| 482 | HO-CH₂CH₂-tetrahydropyrimidinone-N-CH₃ | 619 (M⁺ + 1) |

TABLE 121

| Example No. | R¹ | MS |
|---|---|---|
| 483 | HO-CH₂CH₂-imidazolidinone-N-CH₃ | 619 (M⁺ + 1) |
| 484 | HO-CH₂CH₂-tetrahydropyrimidinone-N-CH₃ | 633 (M⁺ + 1) |

TABLE 122
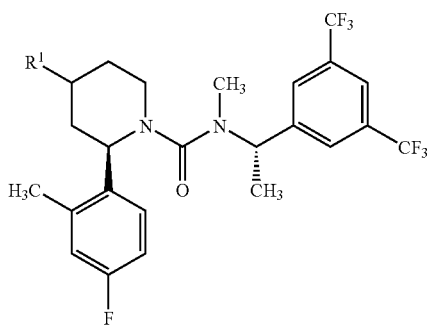
| Example No. | R[1] | MS |
|---|---|---|
| 485 | (hydroxyethyl-methyl-imidazolidinone) | 619 (M+ + 1) |
TABLE 122-continued
| Example No. | R[1] | MS |
|---|---|---|
| 486 | (hydroxyethyl-methyl-tetrahydropyrimidinone) | 633 (M+ + 1) |
TABLE 123
| Example No. | Structural Formula | MS |
|---|---|---|
| 487 | | 580 (M+ + 1) |
TABLE 124
| Example No. | Structural Formula | MS |
|---|---|---|
| 488 (2) | | 610 (M+ + 1) |

TABLE 125

| Reference Example No. | Structural Formula | MS |
|---|---|---|
| 1 | | 450 (M⁺ + 1) |
| 2 | | 342 (M⁺ + 1) |
| 3 | | 388 (M⁺ + 1) |
| 4 | | 254 (M⁺ + 1) |
| 5 | | 254 (M⁺ + 1) |

TABLE 126

| Reference Example No. | Structural Formula | MS |
|---|---|---|
| 6 | | 505 (M⁺ + 1) |
| 7 | | 491 (M⁺ + 1) |
| 8 | | 505 (M⁺ + 1) |
| 9 | | 505 (M⁺ + 1) |

TABLE 126-continued

| Reference Example No. | Structural Formula | MS |
|---|---|---|
| 10 | (4-oxo-piperidine with 2-(2-methyl-4-fluorophenyl), N-carboxamide-N-methyl-N-[(1S)-1-(3,5-bis(trifluoromethyl)phenyl)ethyl]) | 505 (M⁺ + 1) |
| 11 (1) | (4-oxo-piperidine with 2-(2-methyl-4-fluorophenyl), N-carboxamide-N-methyl-N-(3,5-bis(trifluoromethyl)benzyl)) | 491 (M⁺ + 1) |

TABLE 127

| Reference Example No. | Structural Formula | MS |
|---|---|---|
| 11 (2) | (4-oxo-piperidine with 2-(2-methyl-4-fluorophenyl), N-carboxamide-N-ethyl-N-(3,5-bis(trifluoromethyl)benzyl)) | 505 (M⁺ + 1) |

TABLE 127-continued

| Reference Example No. | Structural Formula | MS |
|---|---|---|
| 12 (a) | (4-propionylamino-piperidine with 2-(2-methyl-4-fluorophenyl), N-benzyloxycarbonyl) — two diastereomers shown | 399 (M⁺ + 1) |
| 12 (b) | (4-propionylamino-piperidine with 2-(2-methyl-4-fluorophenyl), N-benzyloxycarbonyl) — two diastereomers shown | 399 (M⁺ + 1) |

TABLE 128

| Reference Example No. | Structural Formula | MS |
|---|---|---|
| 13 (a) | isobutyramide-piperidine-(2-methyl-4-fluorophenyl)-N-Cbz (stereoisomer) and isobutyramide-piperidine-(2-methyl-4-fluorophenyl)-N-Cbz (stereoisomer) | 413 (M⁺ + 1) |
| 13 (b) | isobutyramide-piperidine-(2-methyl-4-fluorophenyl)-N-Cbz (stereoisomer) and isobutyramide-piperidine-(2-methyl-4-fluorophenyl)-N-Cbz (stereoisomer) | 413 (M⁺ + 1) |

TABLE 129

| Reference Example No. | Structural Formula | MS |
|---|---|---|
| 14 | propanamide-piperidine-(2-methyl-4-fluorophenyl) (stereoisomer) and propanamide-piperidine-(2-methyl-4-fluorophenyl) (stereoisomer) | 265 (M⁺ + 1) |
| 15 | propanamide-piperidine-(2-methyl-4-fluorophenyl) (stereoisomer) and propanamide-piperidine-(2-methyl-4-fluorophenyl) (stereoisomer) | 265 (M⁺ + 1) |

TABLE 130
| Reference Example No. | Structural Formula | MS |
|---|---|---|
| 16 | 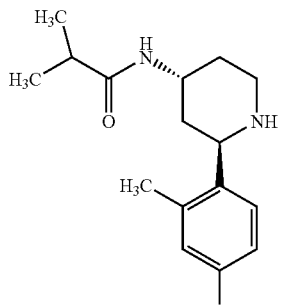 and | 279 (M⁺ + 1) |
TABLE 130-continued
| Reference Example No. | Structural Formula | MS |
|---|---|---|
| 17 | 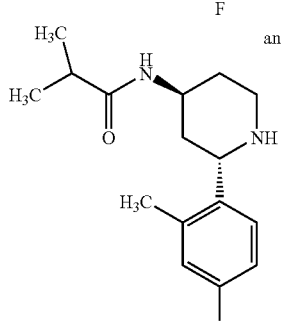 and | 279 (M⁺ + 1) |
TABLE 131
| Reference Example No. | Structural Formula | MS |
|---|---|---|
| 18 (a) | 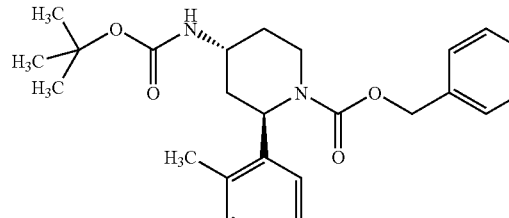 and | 443 (M⁺ + 1) |

TABLE 131-continued
| Reference Example No. | Structural Formula | MS |
|---|---|---|
| 18 (b) | 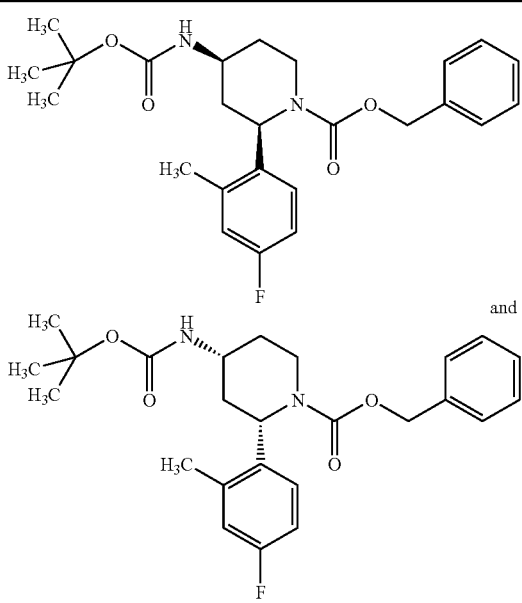 and 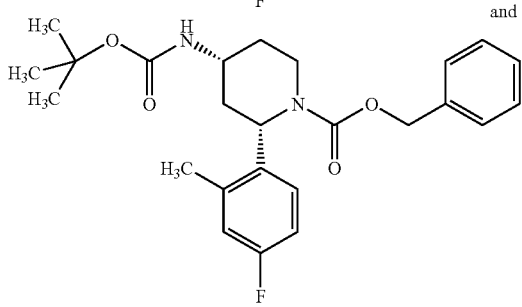 | 443 (M⁺ + 1) |
TABLE 132
| Reference Example No. | Structural Formula | MS |
|---|---|---|
| 19 | 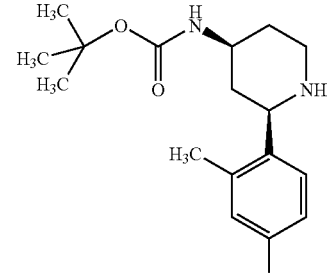 and 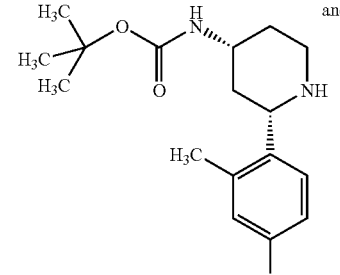 | 309 (M⁺ + 1) |
| 20 | 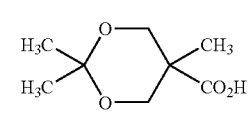 | 173 (M⁺ + 1) |
| 21 | 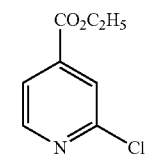 | 186 (M⁺ + 1) |

TABLE 132-continued

| Reference Example No. | Structural Formula | MS |
|---|---|---|
| 22 | | 260 (M⁺ + 1) |
| 23 | ...and... | 266 (M⁺ + 1) |

TABLE 133

| Reference Example No. | Structural Formula | MS |
|---|---|---|
| 24 (2) | | 266 (M⁺ + 1) |
| 25 (3) | | 535 (M⁺ + 1) |
| 26 (5) | | 297 (M⁺ + 1) |
| 27 | | 288 (M⁺ + 1) |
| 28 (2) | | 396 (M⁺ + 1) |

TABLE 134

| Reference Example No. | Structural Formula | MS |
|---|---|---|
| 29 (5) | 2-methoxy-4-fluorophenyl piperidine carbamate with hydroxyethyl | 313 (M⁺ + 1) |
| 30 (5) | phenyl piperidine carbamate with hydroxyethyl | 265 (M⁺ + 1) |
| 31 (2) | 1-(3,5-bis(trifluoromethyl)phenyl)ethyl imidazole carboxylate | 353 (M⁺ + 1) |
| 32 | tert-butyl 2-(2-methyl-4-fluorophenyl)-4-oxo-3,4-dihydropyridine-1(2H)-carboxylate | 306 (M⁺ + 1) |
| 33 | 2-(2-methyl-4-fluorophenyl)-4-hydroxypiperidine | 210 (M⁺ + 1) |
| 34 | N-methyl-N-(3,5-bis(trifluoromethyl)benzyl)carbamoyl chloride | 319 (M⁺ + 1) |

TABLE 135

| Reference Example No. | Structural Formula | MS |
|---|---|---|
| 35 | N-ethyl-3,5-bis(trifluoromethyl)benzylamine | 272 (M⁺ + 1) |
| 36 (4) | 2-(2-methylphenyl)piperidin-4-yl (2-hydroxyethyl)carbamate | 279 (M⁺ + 1) |
| 37 (4) | 2-(4-fluorophenyl)piperidin-4-yl (2-hydroxyethyl)carbamate (two stereoisomers) | 283 (M⁺ + 1) |

TABLE 136

| Reference Example No. | Structural Formula | MS |
|---|---|---|
| 38 | 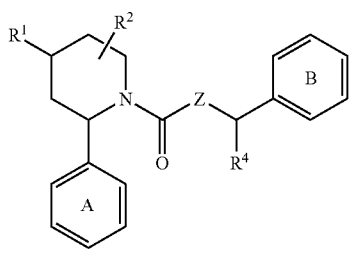 | 210 (M⁺ + 1) |
| 39 | | 288 (M⁺ + 1) |

INDUSTRIAL APPLICABILITY

The compound of the present invention of a salt thereof has an excellent tachykinin receptor antagonistic action. Further, the compound of the present invention or a salt thereof is excellent in terms of safety, absorption, transportability into brain, metabolic stability, concentration in blood and sustainability, so that it has excellent pharmaceutical effects.

The invention claimed is:

1. A piperidine compound represented by the formulas [I]:

[I]

wherein Ring A is a benzene ring of the formula:

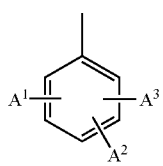

and Ring B is a benzene ring of the formula:

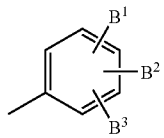

wherein
$A^1$, $A^2$ and $A^3$ are the same or different, and each is hydrogen atom, a halogen atom, an alkyl group, a hydroxyl group, hydroxyl group is substituted by benzyl group, phenethyl group, tert-butyldimethylsilyl group, tert-butyldiphenylsilyl group, acetyl group, propionyl group, malonyl group, acryloyl group or benzoyl group, or an alkoxy group, $B^1$, $B^2$ and $B^3$ are the same or different, and each is hydrogen atom, a trihalogenoalkyl group, a halogen atom, a cyano group, a phenyl group, tetrazolyl group, an alkyl group, a hydroxyl group is optionally substituted by benzyl group, phenethyl group, tert-butyldimethylsilyl group, tertbutyldiphenylsilyl group, acetyl group, propionyl group, malonyl group, acryloyl group or benzoyl group, or an alkoxy group, $R^1$ represents a hydroxyl group is substituted by
(1) a carbonyl group is substituted by a group selected from
an alkyl group optionally substituted by hydroxyl group,
an alkoxy group optionally substituted by an alkoxy group hydroxyl group or a halogen atom,
an amino group substituted by an alkyl group substituted by a group selected from a halogen atom, a dialkylamino group, piperidinyl group, morpholino group, a carboxyl group, a morpholinocarbonyl group, a dialkylaminocarbonyl group, a $C_{1-6}$-alkylaminocarbonyl group, an alkanoylamino group, an alkylthio group, an alkoxy group, an alkylsulfonyl group, an alkanoyloxy group and hydroxyl group; piperidinyl group substituted by a hydroxyalkanoyl group or an alkoxyalkanoyl group; or a dialkylaminosulfonyl group, and
an optionally substituted monocyclic heterocyclic group selected from morpholino group, piperazinyl group, imidazolyl group, thiomorpholino group, piperidino group, furyl group, tetrahydrothiazolinyl group or pirrolidinyl group (the substitutent of the monocyclic heterocyclic group is an alkyl group optionally substituted by hydroxyl group, an alkoxycarbonyl group, a carboxyl group, a hydroxyalkylaminocarbonyl group, an alkoxyalkylaminocarbonyl group, an alkylthioalkylaminocarbonyl group, an alkylsulfinylalkylaminocarbonyl group, an alkylsulfonylalkylaminocarbonyl group or a morpholino group; an oxo group; or hydroxyl group.),
(2) a sulfinyl group is substituted by a group selected from
an alkyl group, and
a thienyl group,
(3) a sulfonyl group is substituted by a group selected from
an alkyl group, and
a thienyl group,
(4) an alkyl group is substituted by a group selected from
a hydroxyl group optionally substituted by an alkyl group, an alkylsulfonyl group or tetrahydropyranyl group,
a dialkylamino group, and
an optionally substituted monocyclic heterocyclic group is selected from pyridyl group, piperidinyl group, morpholino group, isoxazolyl group, triazolyl group, tetrazolyl group and pirrolidinyl group (the substituent of the monocyclic hetrocyclic group is an alkyl group or phenyl group), R² represents hydrogen atom, a hydroxy group optionally substituted by an alkyl group,
an amino group optionally substituted by an alkyl group,
an alkyl group optionally substituted by an alkoxy group,
a carbonyl group substituted by hydroxyl group, an nalkoxy group or an alkylamino group, or a halogen atom,
Z represents oxygen atom or a group represented by —N(R³)—, wherein R³ represents hydrogen atom or an alkyl group optionally substituted by hydroxy group, analkanoyl group, a halogen atom, an alkoxy group or an alkylamino group and
R⁴ represents hydrogen atom or an alkyl group optionally substituted by a halogen atom, an alkoxy group or an alkylamino group, or a pharmaceutically acceptable salt thereof.

2. The compound according to claim 1, wherein Ring A is a benzene ring of the formula:

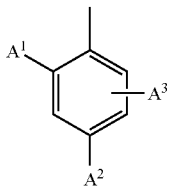

and Ring B is a benzene ring of the formula:

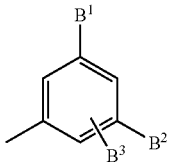

wherein A¹ is an alkyl group, hydrogen atom, a halogen atom or an alkoxy group, A² is hydrogen atom or a halogen atom, A³ is hydrogen atom, B¹ is a trihalogenoalkyl group, a halogen atom or an alkyl group, B² is a trihalogenoalkyl group, a halogen atom or an alkyl group, B³ is hydrogen atom, R¹ an alkoxy group optionally substituted by hydroxyl group, an alkylsulfonyloxy group, a tetrahydropyranyloxy group, a dialkylamino group, pyridyl group, a triazolyl group, a tetrazolyl group optionally substituted by an alkyl group, piperidino group, morpholino group, pyrrolidino group or an alkoxy group; morpholinocarbonyloxy group; alkyl piperazinocarbonyloxy group; imidazolylcarbonyloxy group; peridinoalkylaminocarbonyloxy group; morphol inoalkylaminocarbonyloxy group; an alkylaminocarbonyloxy group wherein the alkyl moiety thereof is optionally substituted by hydroxyl group, a morpholinocarbonyl group, a dialkylaminocarbonyl group, an alkylaminocarbonyl group an alkanoylamino group, an alkylthio group, an alkoxy group, an alkylsulfonyl group, an alkanoyloxy group or a carboxyl group; dialkylaminoalkylaminocarbonyl group; a piperidinocarbonyloxy group substituted by hydroxyl group, an alkoxycarbonyl group, a carboxyl group, a hydroxyalkylaminocarbonyl group, an alkoxyalkylaminocarbonyl group, an alkylthioalkylaminocarbonyl group, an alkylsulfinylalkylaminocarbonyl group, an alkylsulfonylalkylaminocarbonyl group or hydroxyalkyl group; dialkylaminocarbonyloxy group optionally substituted by hydroxyl group; a piperidinylaminocarbonyloxy group substituted by a hydroxyalkanoyl group or an alkoxyalkanoyl group; a thiomorpholinocarbonyloxy group wherein the sulfur atom is optionally substituted by an oxo group; oxoyrrol idinylcarbonyloxy group; oxotetrahydrothiazolinylcarbonyloxy group; dialkylaminosulfonylaminocarbonyloxy group; a carboxyl group;
R² is hydrogen atom, Z is an oxygen atom or a group represented by —N(R³)—, R³ is an alkyl group optionally substituted by hydroxyl group or an alkanoyl group, R⁴ is hydrogen atom or an alkyl group optionally substituted by hydroxyl group.

3. The compound according to claim 1, wherein R¹ is a hydroxyalkylcarbonyloxy group, an alkoxyalkoxycarbonyloxy group, a hydroxyalkoxycarbonyloxy group, a halogenoalkoxycarbonyloxy group, a halogenoalkylaminocarbonyloxy group, a dialkylaminoalkylaminocarbonyloxy group, a piperidinylalkylaminocarbonyloxy group, a morpholinoalkylaminocarbonyloxy group, a carboxylalkylaminocarbonyloxy group, a morpholinocarbonylalkylaminocarbonyloxy group, a dialkylaminocarbonylalkylaminocarbonyloxy group, an alkanoylaminoalkylaminocarbonyloxy group, an alkylthioalkylaminocarbonyloxy group, an alkylsulfonylalkylaminocarbonyloxy group, an alkanoyloxyalkylaminocarbonyloxy group, hydroxyalkylaminocarbonyloxy group, a hydroxyalkanoylpiperidinylaminocarbonyloxy group, an alkoxyalkanoylpeperidinylaminocarhonyloxy group, a dialkylaminosulfonylaminocarbonyloxy group, morpholinocarbonyloxy group, a piperazinylcarbonyloxy group, an imidazolylcarbonyloxy group, thiomorpholinocarbonyloxy group, piperidinocarbonyloxy group, a furylcarbonyloxy group, a tetrahydrothiazolinylcarbonyloxy group, an irrolidinylcarbonyloxy group, an alkylsulfinyloxy group, a thienylsulfinyloxy group, an alkylsulfonyloxy group, a thienylsulfonyloxy group, an alkoxyalkyloxy group, an alkylsulfonyloxyalkoxy group, a tetrahydropyranyloxyalkoxy group, dialkylaminoalkyloxy group, a pyridylalkoxy group, a piperidinylalkoxy group, morholinoalkoxy group, an isoxazolylalkoxy group, a triazolylalkoxy group, a tetrazolylalkoxy group, or a pirrolidinylalkoxy group.

4. A compound selected from the following (A) to (I),
(A) (2R,4S)-1-{N-(3,5-bistrifluoromethylberizyl)-N-methyl}-aminocarbonyl-2-(4-filuoro-2-methylphenyl)-4-(2-hydroxyethoxy)-piperidine,
(B) (2R,4S)-1-{N-{1-(R)-(3,5-bistrifluoromethylphenyl)ethyl}-N-methyl]aminocarbonyl-2-(4-fluoro-2-methylphenyl)-4-{2-(2-tetrahydropyranyloxy)ethoxy}piperidine,
(C) (2R,4S)-1-[N-{1-(S)-(3,5-bistrifluoromethylphenyl)ethyl}-N-methyl]aminocarbonyl-2-)4-fluoro-2-methylphenyl)-4-methoxy-acetylaminopiperidine,
(D) (2R,4S)-1-[N-{1-(S)-(3,5-bistrifluoroethylphenyl)ethyl}-N-methyl]aminocarbonyl-2-(4-fluoro-2-methylphenyl)-4-methoxy-carbonylaminopiperidine,
(E) (2R,4S)-1-[N-{1-(S)-(3,5-bistrifluoroethylphenyl)ethyl}-N-methyl]aminocarbonyl-2-(4-fluoro-2-methylphenyl)-4-(2-hydroxyethoxy) piperidine,
(F) (2R,4S)-1-[N-{1-(R)-(3,5-bistrifiluoromethylphenyl)ethyl}-N-methyl]aminocarbonyl-2-(4-fluoro-2-methylphenyl)-4-(3-hydroxypropoxy) piperidine,
(G) (2R,4S)-1-{N-(3,5-bistrifuoromethylbenzyl)-N-methyl}-aminocarbonyl-2-(4-fluoro-2-methylphenyl)-4-(2-hydroxyethyl-aminocarbonyloxy) piperidine, (H) (2R,4S)-1-[N-{1-(R)-3,5-bistrifluoromethylphenyl)ethyl}-N-methyl]aminocarbonyl-2-(4-fluoro-2-methylphenyl)-4-(2-hydroxyethylaminocarbonyloxy) piperidine, or (I) (2R,4S)-I-{N-(3,5,-bistrifluoroethylbenzyl)-N-methyl}-aminocarbonyl-2-(4-fluoro-2-methylphenyl)-4-(1-oxothio-morpholinocarbonyloxy)piperidine.

5. A pharmacetucial composition comprising the compound according to any one of claims 3, 2 or 4 in a clinically effective dose, and a pharmaceutically acceptable carrier.

6. A method for preparing a piperidine compound of the formula [I']:

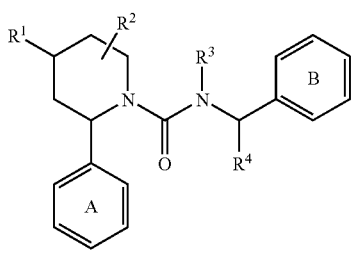

wherein Ring A is a benzene ring of the formula:

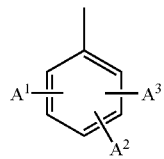

and Ring B is a benzene ring of the formula:

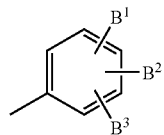

wherein $A^1$, $A^2$ and $A^3$ are the same or different, and each is hydrogen atom, a halogen atom, an alkyl group, a hydroxyl group, hydroxyl group is substituted by benzyl group, phenethyl group, tert-butyldimethylsilyl group, tert-butyldiphenylsilyl group, acetyl group, propionyl group, malonyl group, acryloyl group or benzoyl group, or an aikoxy group, $B^1$, $B^2$ and $B^3$ are the same or different, and each is hydrogen atom, a trihalogenoalkyl group, a halogen atom, a cyano group, a phenyl group, tetrazolyl group, an alkyl group, a hydroxyl group is optionally substituted by benzyl group, phenethyl group, tert-butyldimethylsilyl group, tert-butyldiphenylsilyl group, acetyl group, propionyl group, malonyl group, acryloyl group or benzoyl group, or an alkoxy group, $R^1$ represents a hydroxyl group is substituted by (1) a carbonyl group is substituted by a group selected from an alkyl group optionally substituted by hydroxyl group, an alkoxy group optionally substituted by an alkoxy group hydroxyl group or a halogen atom, an amino group substituted by an alkyl group substituted by a group selected from a halogen atom, a dialkylamino group, piperidinyl group, morpholino group, a carboxyl group, a morpholinocarbonyl group, a dialkylaminocarbonyl group, a $C_{1-6}$-alkylaminocarbonyl group, an alkanoylamino group, an alkylthio group, an alkoxy group, an alkylsulfonyl group, an alkanoyloxy group and hydroxyl group; piperidinyl group substituted by a hydroxyalkanoyl group or an alkoxyalkanoyl group; or a dialkylaminosulfonyl group, and an optionally substituted monocyclic heterocyclic group selected from morpholino group, piperazinyl group, imidazolyl group, thiomorpholino group, piperidino group, furyl group, tetrahydrothiazolinyl group or pirrolidinyl group (the substitutent of the monocyclic hetrocyclic group is an alkyl group optionally substituted by hydroxyl group, an alkoxycarbonyl group, a carboxyl group, a hydroxyalkylaminocarbonyl group, an alkoxyalkylaminocarbonyl group, an alkylthioalkylaminocarbonyl group, an alkylsulfinylalkylaminocarbonyl group, an alkylsulfonylalkylaminocarbonyl group or a morpholino group; an oxo group; or hydroxyl group.)

(2) a sulfinyl group is substituted by a group selected from an alkyl group, and
a thienyl group, (3) a sulfonyl group is substituted by a group selected from an alkyl group, and
a thienyl group, (4) an alkyl group is substituted by a group selected from
a hydroxyl group optionally substituted by an alkyl group, an alkylsulfonyl group or tetrahydropyranyl group,
a dialkylamino group, and
an optionally substituted mono cyclic hotorocyclic group is selected from pyridyl group, piperidinyl group, morpholino group, isoxazolyl group, triazolyl group, tetrazolyl group and pirrolidinyl group (the substituent of the monocyclic hetrocyclic group is an alkyl group or phenyl group.), $R^2$ represents hydrogen atom, a hydroxy group optionally substituted by an alkyl group,
an amino group optionally substituted by an alkyl group,
an alkyl group optionally substituted by an alkoxy group,
a carbonyl group substituted by hydroxyl group, an nalkoxy group or an alkylamino group, or a halogen atom, $R^3$ represents hydrogen atom or an alkyl group optionally substituted by hydroxy group, analkanoyl group, a halogen atom, an alkoxy group or an alkylamino group and $R^4$ represents hydrogen atom or an alkyl group optionally substituted by a halogen atom, an alkoxy group or an alkylamino group, or a pharmaceutically acceptable salt thereof, comprising reacting a compound of the formula [II]:

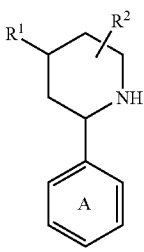

wherein Ring A, R¹ and R² have the same meanings as defined above, with a compound of the formula [III']

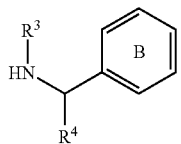

wherein Ring B, and R⁴ have the same meanings as defined above, in the presence of a urea bond forming agent, and if desired, converting into a pharmaceutically acceptable salt thereof.

7. A method for preparing a piperidine compound of the formula [I"]:

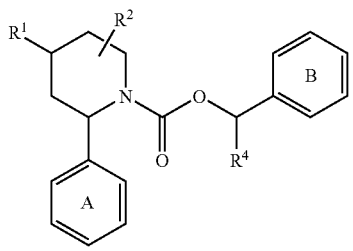

wherein Ring A is a benzene ring of the formula:

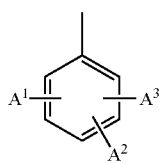

and Ring B is a benzene ring of the formula:

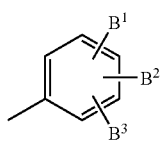

wherein
A¹, A² and A³ are the same or different, and each is hydrogen atom, a halogen atom, an alkyl group, a hydroxyl group, hydroxyl group is substituted by benzyl group, phenethyl group, tert-butyldimethylsilyl group, tert-butyldiphenylsilyl group, acetyl group, propionyl group, malonyl group, acryloyl group or benzoyl group, or an alkoxy group, B¹, B² and B³ are the same or different, and each is hydrogen atom, a trihalogenoalkyl group, a halogen atom, a cyano group, a phenyl group, tetrazolyl group, an alkyl group, a hydroxyl group is optionally substituted by benzyl group, phenethyl group, tert-butyldimethylsilyl group, tert-butyldiphenylsilyl group, acetyl group, propionyl group, malonyl group, acryloyl group or benzoyl group, or an alkoxy group, R¹ represents a hydroxyl group is substituted by
(1) a carbonyl group is substituted by a group selected from
an alkyl group optionally substituted by hydroxyl group,
an alkoxy group optionally substituted by an alkoxy group hydroxyl group or a halogen atom,
an amino group substituted by an alkyl group substituted by a group selected from a halogen atom, a dialkylamino group, piperidinyl group, morpholino group, a carboxyl group, a morpholinocarbonyl group, a dialkylaminocarbonyl group, a $C_{1-6}$-alkylaminocarbonyl group, an alkanoylamino group, an alkylthio group, an alkoxy group, an alkylsulfonyl group, an alkanoyloxy group and hydroxyl group; piperidinyl group substituted by a hydroxyalkanoyl group or an alkoxyalkanoyl group; or a dialkylaminosulfonyl group, and
an optionally substituted monocyclic heterocyclic group selected from morpholino group, piperazinyl group, imidazolyl group, thiomorpholino group, piperidino group, furyl group, tetrahydrothiazolinyl group or pirrolidinyl group (the substitutent of the monocyclic hetrocyclic group is an alkyl group optionally substituted by hydroxyl group, an alkoxycarbonyl group, a carboxyl group, a hydroxyalkylaminocarbonyl group, an alkoxyalkylaminocarbonyl group, an alkylthioalkylaminocarbonyl group, an alkylsulfinylalkylaminocarbonyl group, an alkylsulfonylalkylaminocarbonyl group or a morpholino group;
an oxo group; or hydroxyl group.)
(2) a sulfinyl group is substituted by a group selected from
an alkyl group, and
a thienyl group,
(3) a sulfonyl group is substituted by a group selected from
an alkyl group, and
a thienyl group,
(4) an alkyl group is substituted by a group selected from
a hydroxyl group optionally substituted by an alkyl group, an alkylsulfonyl group or tetrahydropyranyl group
a dialkylamino group, and
an optionally substituted monocyclic heterocyclic group is selected from pyridyl group, piperidinyl group, morpholino group, isoxazolyl group, triazolyl group, tetrazolyl group and pirrolidinyl group (the substituent of the monocyclic hetrocyclic group is an alkyl group or phenyl group.), R² represents hydrogen atom, a hydroxy group optionally substituted by an alkyl group,
an amino group optionally substituted by an alkyl group,
an alkyl group optionally substituted by an aikoxy group,
a carbonyl group substituted by hydroxyl group, an nalkoxy group or an alkylamino group, or a halogen atom, R³ represents hydrogen atom or an alkyl group optionally substituted by hydroxy group, analkanoy group, a halogen atom, an alkoxy group or an alkylamino group, and
R⁴ represents hydrogen atom or an alkyl group optionally substituted by a halogen atom, an alkoxy group or an alkylamino group, or a pharmaceutically acceptable salt thereof, comprising reacting a compound of the formula [II]

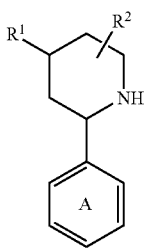

[II]

Wherein Ring A, R¹ and R² have the same meaning as defined above, with a compound of the formula [III']:

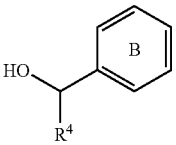

[III']

Wherein Ring B, R³ and R⁴ have the same meanings as defined above, in the presence of a urea bond forming agent, and if desired, converting into a pharmaceutically acceptable salt thereof.

* * * * *

UNITED STATES PATENT AND TRADEMARK OFFICE
CERTIFICATE OF CORRECTION

PATENT NO. : 7,619,092 B2  Page 1 of 1
APPLICATION NO. : 10/515845
DATED : November 17, 2009
INVENTOR(S) : Masami Takahashi et al.

It is certified that error appears in the above-identified patent and that said Letters Patent is hereby corrected as shown below:

On the Title page,

[*] Notice: Subject to any disclaimer, the term of this patent is extended or adjusted under 35 U.S.C. 154(b) by 559 days.

Delete the phrase "by 559 days" and insert -- by 920 days --

Signed and Sealed this

Thirty-first Day of August, 2010

David J. Kappos
*Director of the United States Patent and Trademark Office*